(12) United States Patent
Pfeifer, III et al.

(10) Patent No.: US 9,045,785 B2
(45) Date of Patent: Jun. 2, 2015

(54) EICOSAPENTAENOIC ACID-PRODUCING MICROORGANISMS, FATTY ACID COMPOSITIONS, AND METHODS OF MAKING AND USES THEREOF

(75) Inventors: Joseph W. Pfeifer, III, Westminster, MD (US); Jon Milton Hansen, West Friendship, MD (US); Jose R. Garcia, Lorton, VA (US); Xiao Daniel Dong, Woodstock, MD (US); Paul Warren Behrens, Ellicott City, MD (US); Kirk E. Apt, Ellicott City, MD (US)

(73) Assignee: DSM IP Assets B.V., Heerlen (NL)

( * ) Notice: Subject to any disclaimer, the term of this patent is extended or adjusted under 35 U.S.C. 154(b) by 69 days.

(21) Appl. No.: 13/554,975

(22) Filed: Jul. 20, 2012

(65) Prior Publication Data

US 2013/0172590 A1    Jul. 4, 2013

Related U.S. Application Data

(60) Provisional application No. 61/510,464, filed on Jul. 21, 2011.

(51) Int. Cl.
| | |
|---|---|
| C12P 7/64 | (2006.01) |
| C12R 1/89 | (2006.01) |
| C12N 1/12 | (2006.01) |

(52) U.S. Cl.
CPC ............... *C12P 7/6427* (2013.01); *C12R 1/89* (2013.01); *C12N 1/12* (2013.01)

(58) Field of Classification Search
CPC ........... C12P 7/00; C12P 7/64; C12P 7/6409; C12P 7/6427; C12N 1/00; C12N 1/10; C12N 2310/00; C12N 2521/00; C11B 1/00; C11B 1/025; C11B 1/10; C11B 1/06; C12R 1/00; C12R 1/90
See application file for complete search history.

(56) References Cited

U.S. PATENT DOCUMENTS

| 6,607,900 B2 | 8/2003 | Bailey et al. | |
|---|---|---|---|
| 7,005,280 B2 | 2/2006 | Barclay | |
| 2009/0064567 A1* | 3/2009 | Lippmeier et al. | 44/308 |
| 2009/0087890 A1* | 4/2009 | Pyle et al. | 435/167 |
| 2010/0285105 A1 | 11/2010 | Radianingtyas | |

OTHER PUBLICATIONS

Burja, A.M. et al. 2006. Isolation and characterization of polyunsaturated fatty acids producing *Thraustochytrium* species: screening of strains and optimization of omega-3 production. Applied Microbiology and Biotechnology 72:1161-1169. specif. pp. 1161, 1163, 1165-1166, 1168.*

Ramaiah, N. 2006. A review on fungal diseases of algae, marine fishes, shrimps and corals. indian Journal of Marine Sciences 35(4): 380-387. specif. p. 384.*

Barclay et al., Heterotrophic Production of Long Chain Omega 3 Fatty Acids Utilizing Algae and Algae-like Microorganisms; J. Appl. Phycology; Apr. 1994; vol. 6 No. 2; pp. 123-129. Especially p. 125 col. 1 para 3, p. 126 col. 2 para 2.

Yazawa et al., Production of Eicosapentaenoic Acid from Marine Baceria; Lipids; Mar. 1996; vol. 31 Suppl; p. S297-300. Especially abstract, p. S299 fig 3.

Yongmanitchai et al., Growth of and Omega-3 Fatty Acid Production by *Phaeodactylum tricornutum* under Different Culture Conditions; Appl. Environ. Microiol; Feb. 1991; vol. 57, No. 2 pp. 419-425. Especially p. 421 col. 2 para 3, p. 422, table 9.

* cited by examiner

*Primary Examiner* — John S Brusca
*Assistant Examiner* — Sharon M Papciak
(74) *Attorney, Agent, or Firm* — Xi Chen; Shannon McGarrah

(57) ABSTRACT

The present invention is directed to isolated microorganisms as well as strains and mutants thereof, biomasses, microbial oils, compositions, and cultures; methods of producing the microbial oils, biomasses, and mutants; and methods of using the isolated microorganisms, biomasses, and microbial oils.

3 Claims, 25 Drawing Sheets

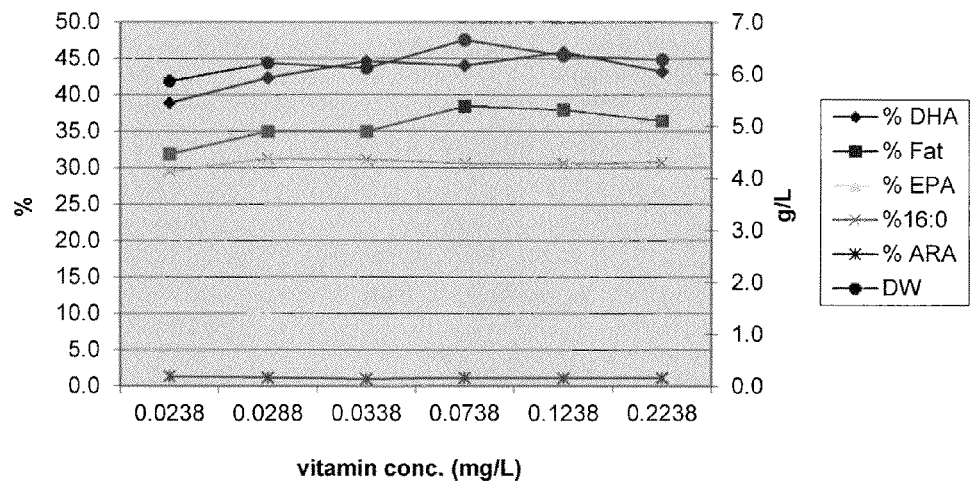
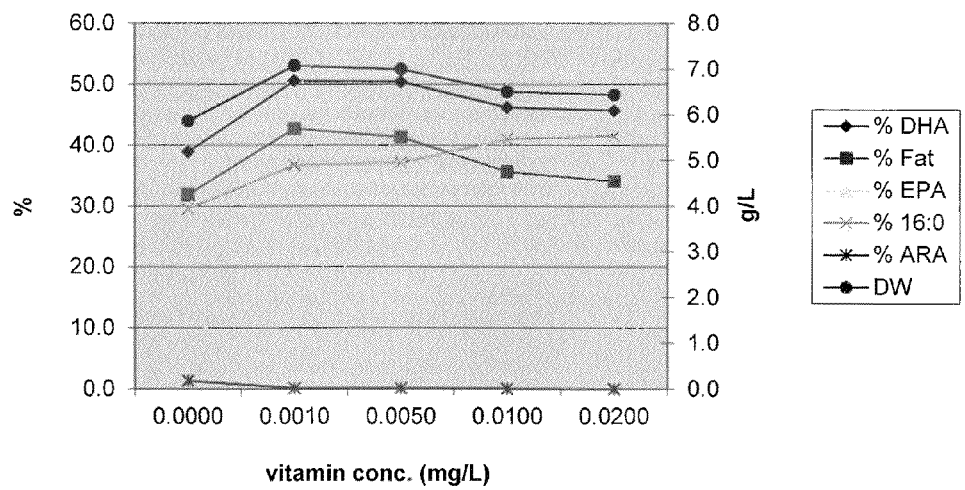

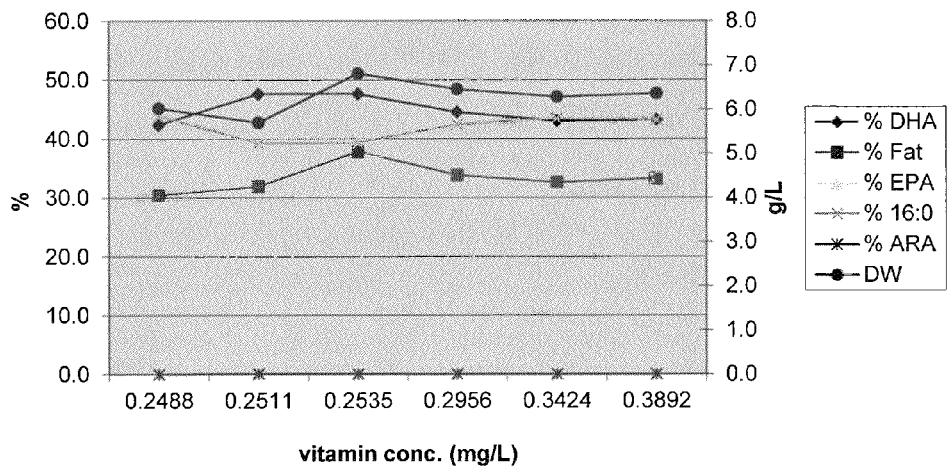
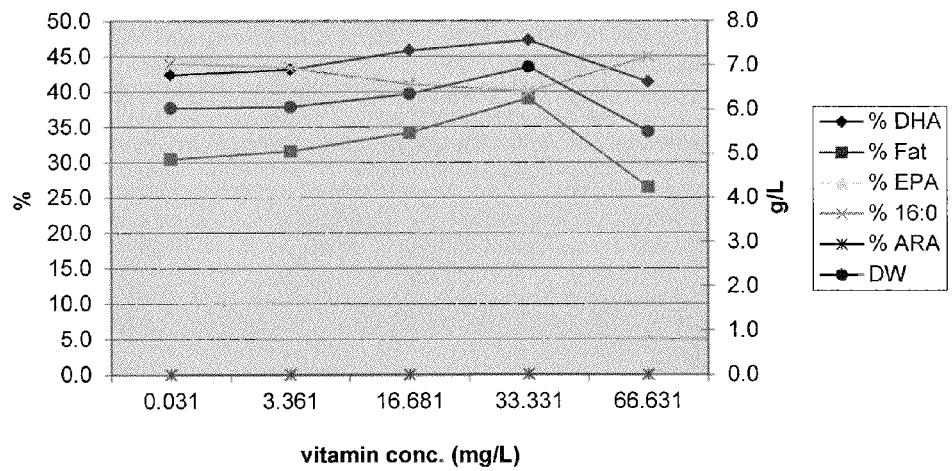

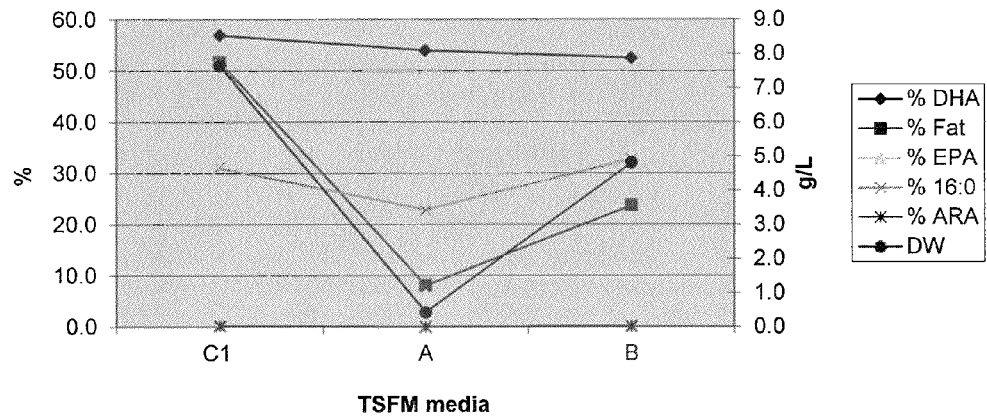
Figure 5. Performance of PTA-9695 in standard TSFM (C1) with 2g/L tastone and 1x thiamine and 1x B12, Tastone-free TSFM without any vitamins (A), and in Tastone-free with 1x thiamine and B12 (B)
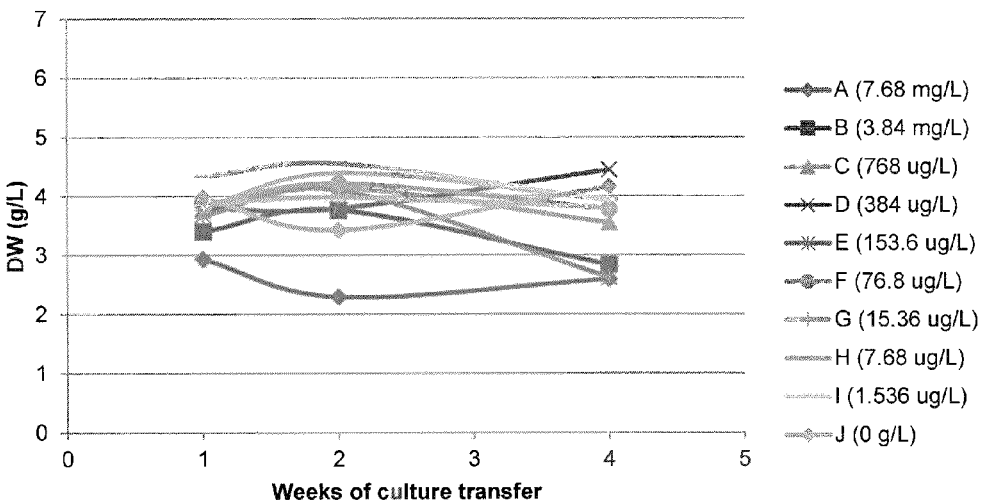
Figure 6. Dry weight of PTA-9695 in Defined SDFM-B with variuos concentrations of vitamin B12 at 10% CO2 condition

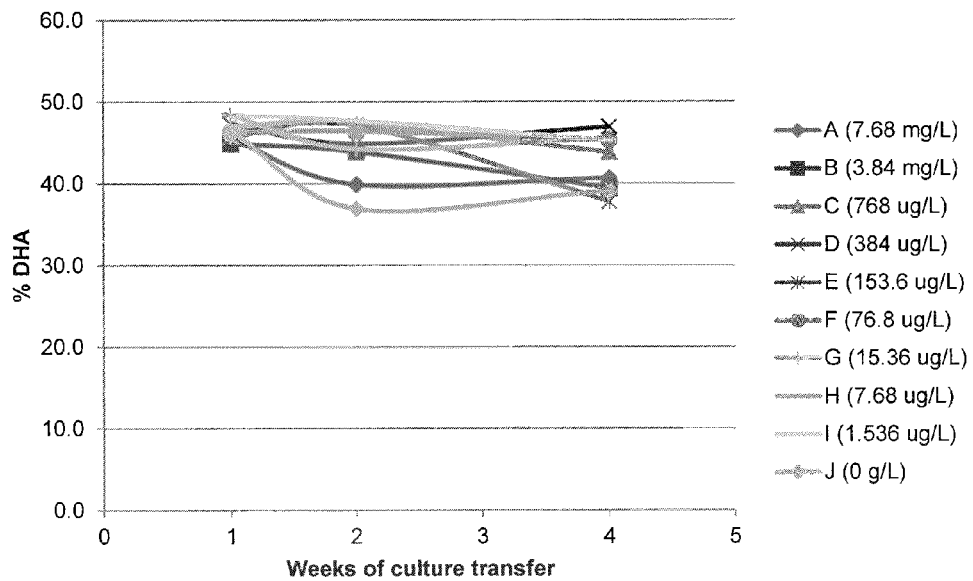
Figure 7. % DHA of PTA-9695 in Defined SDFM-B with variuos concentrations of vitamin B12 at 10% CO2 condition
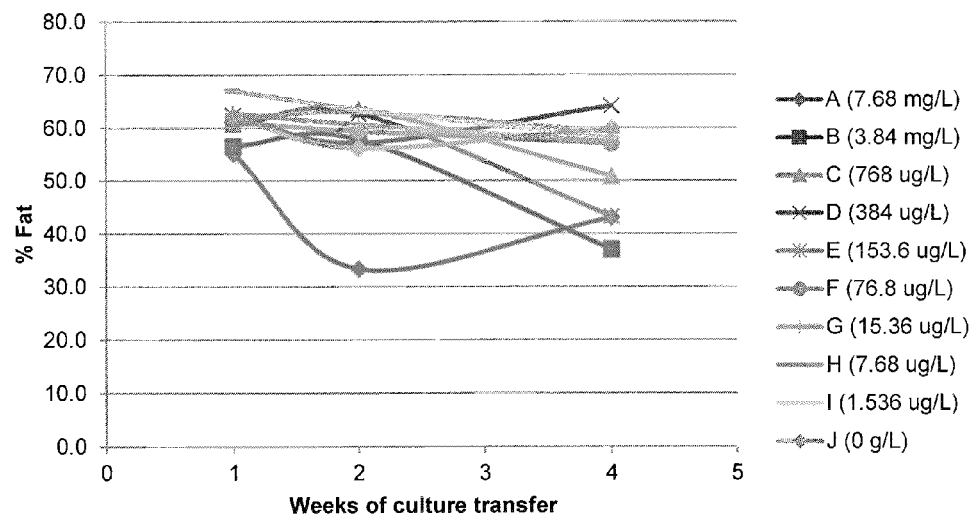
Figure 8. % Fat of PTA-9695 in Defined SDFM-B with variuos concentrations of vitamin B12 at 10% CO2 condition

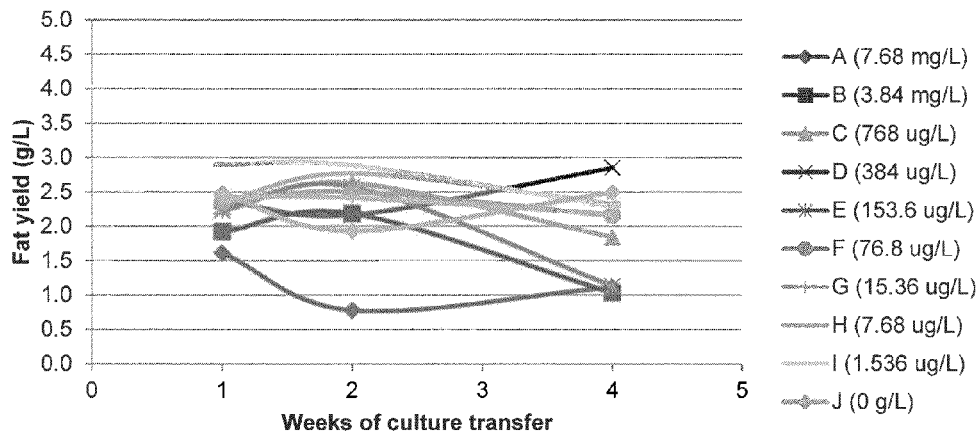
Figure 9. Fat yield (g/L) of PTA-9695 in Defined SDFM-B with variuos concentrations of vitamin B12 at 10% CO2 condition
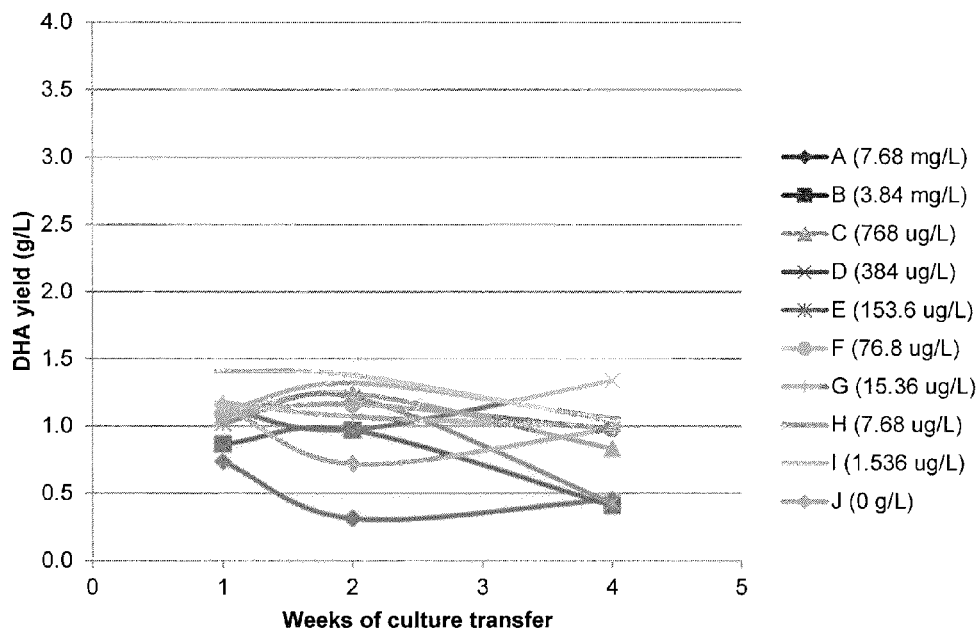
Figure 10. DHA yield (g/L) of PTA-9695 in Defined SDFM-B with variuos concentrations of vitamin B12 at 10% CO2 condition

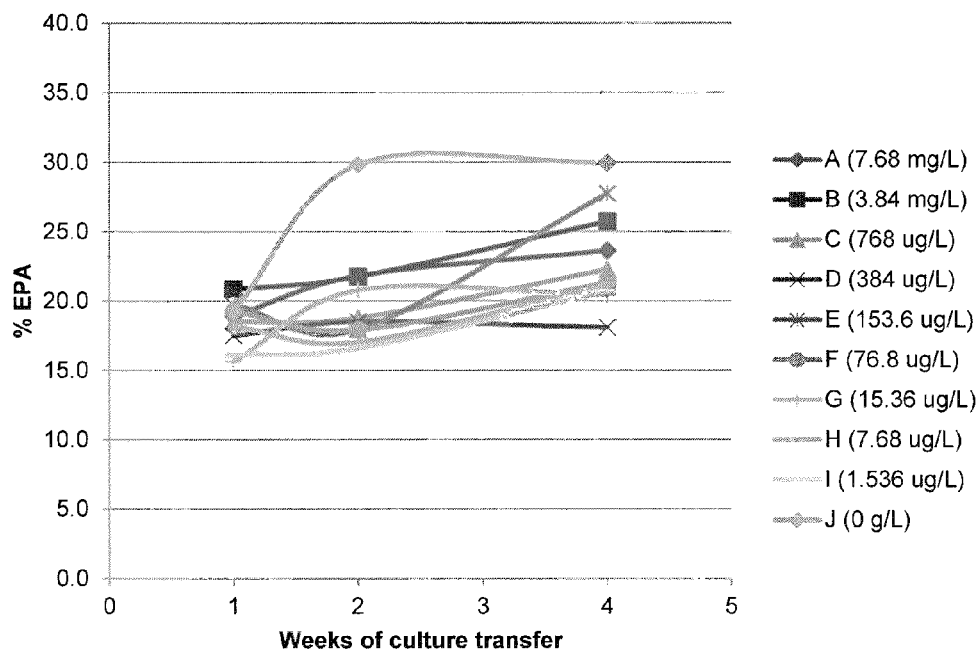
Figure 11. % EPA of PTA-9695 in Defined SDFM-B with variuos concentrations of vitamin B12 at 10% CO2 condition
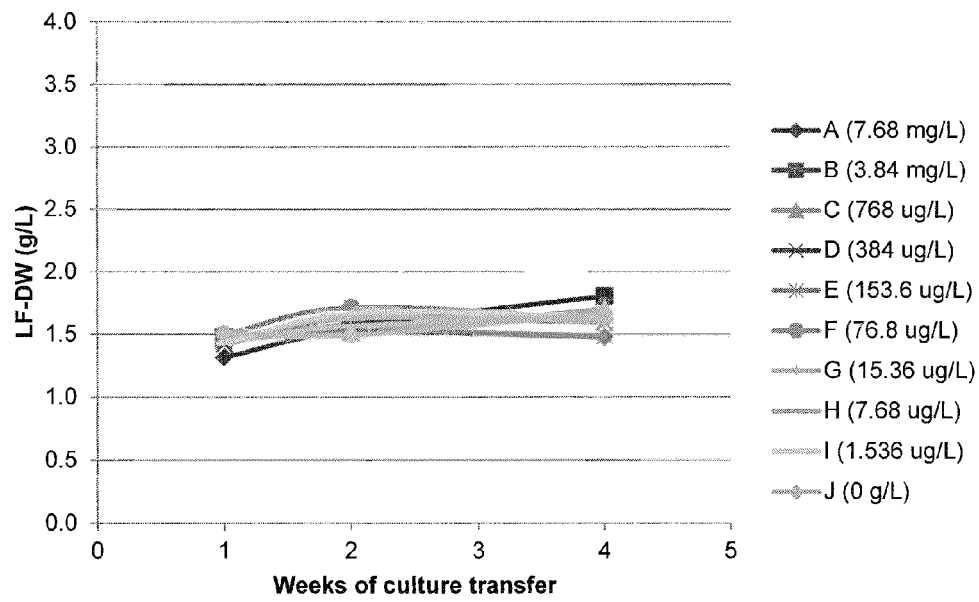
Figure 12. Lipid-free dry weight of PTA-9695 in Defined SDFM-B with variuos concentrations of vitamin B12 at 10% CO2 condition

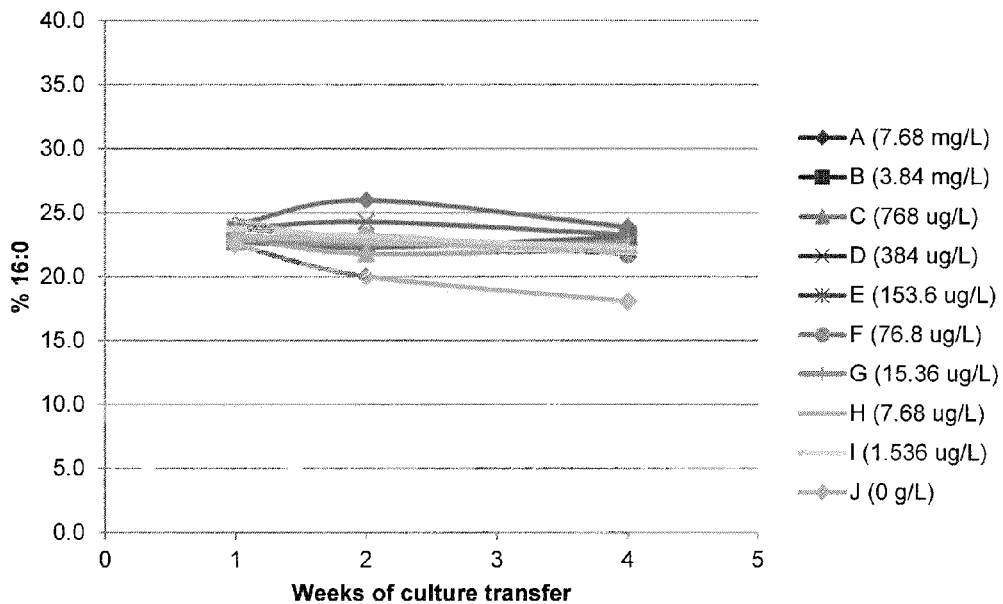
Figure 13. % 16:0 of PTA-9695 in Defined SDFM-B with variuos concentrations of vitamin B12 at 10% $CO_2$ condition
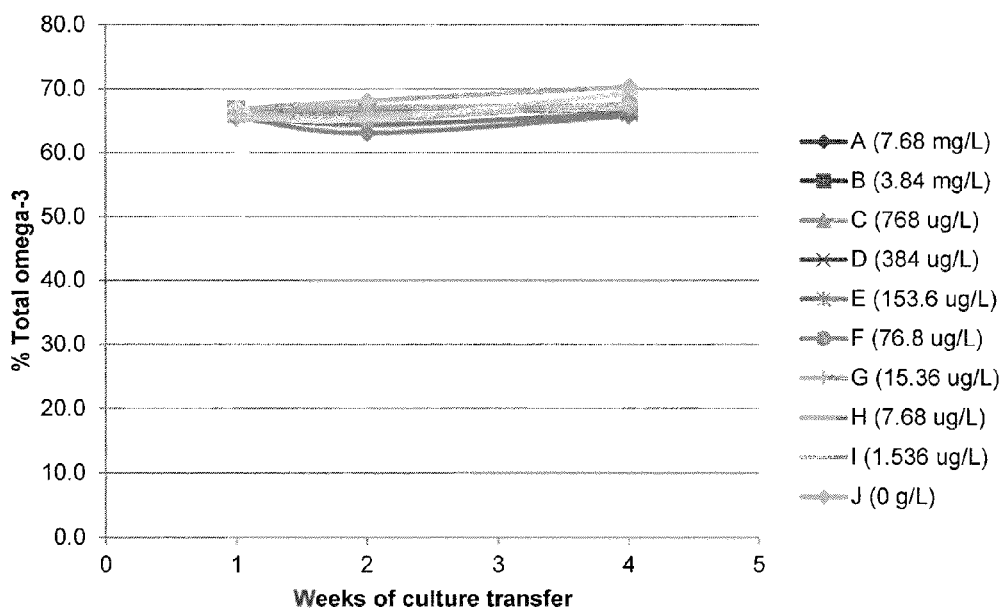
Figure 14. % Total omega-3 of PTA-9695 in Defined SDFM-B with variuos concentrations of vitamin B12 at 10% $CO_2$ condition

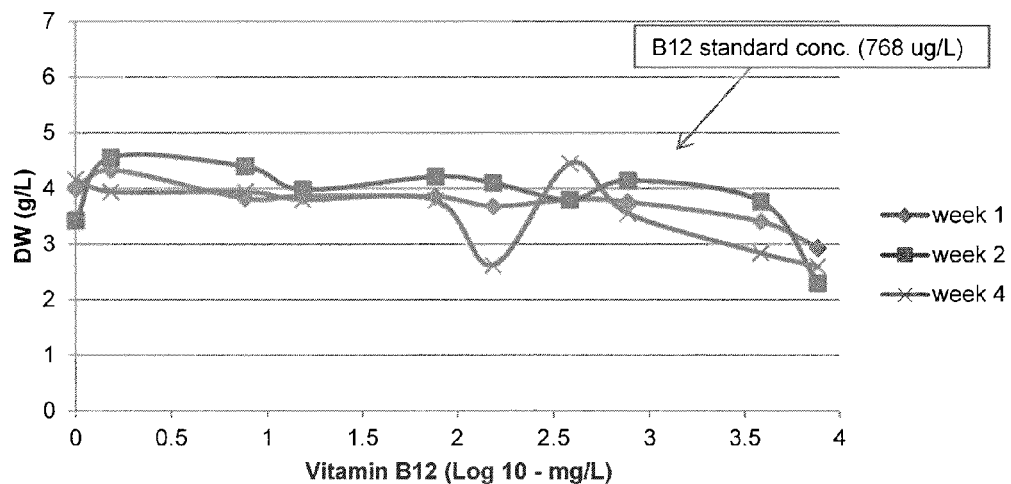
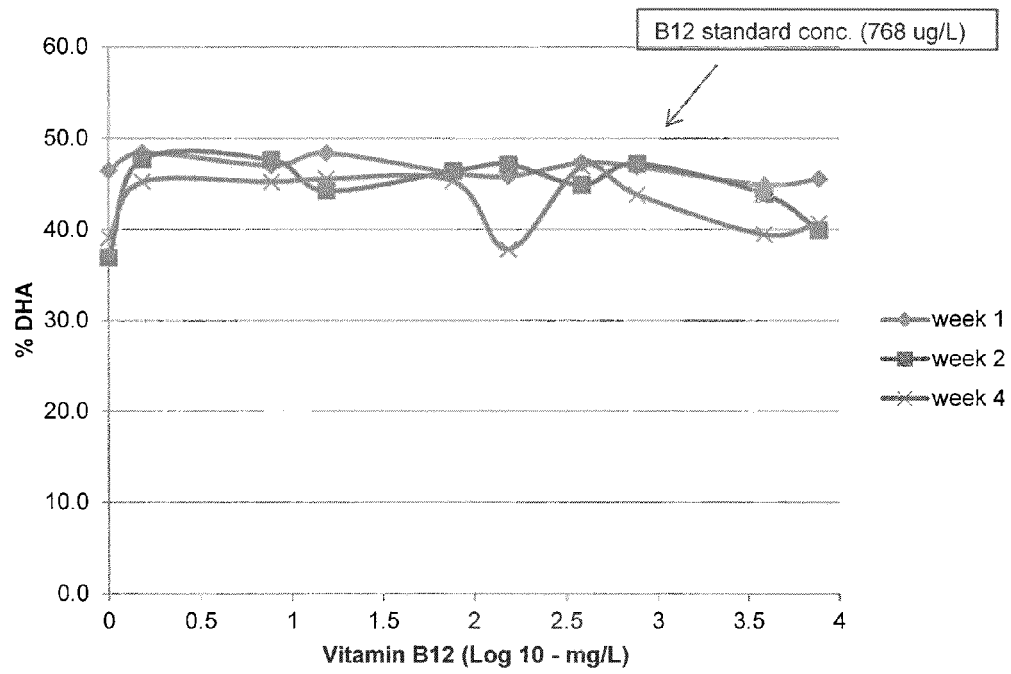

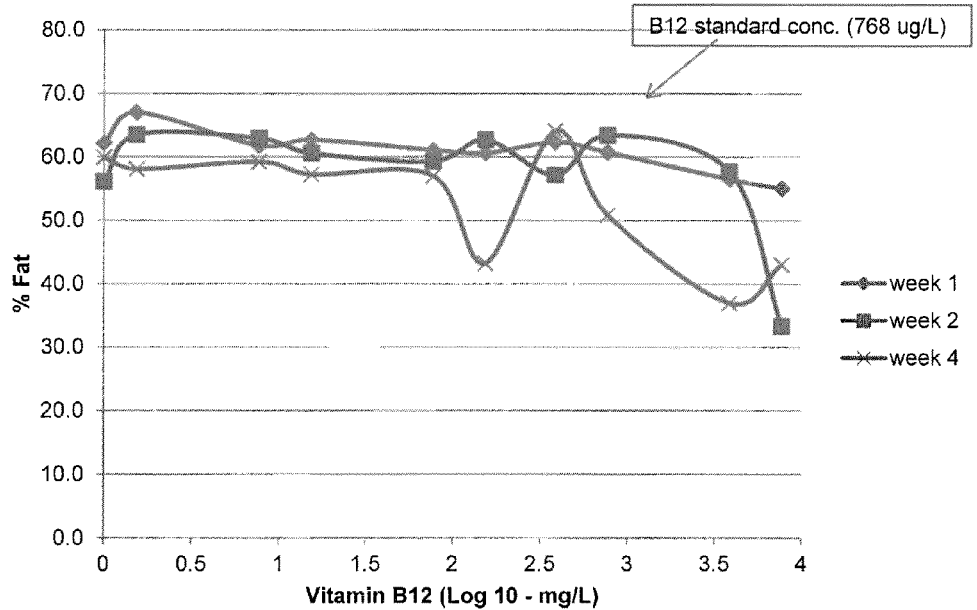
Figure 17. % Fat PTA-9695 as a function of various concentrations of vitamin B12 in defined SDFM-B at 10% $CO_2$
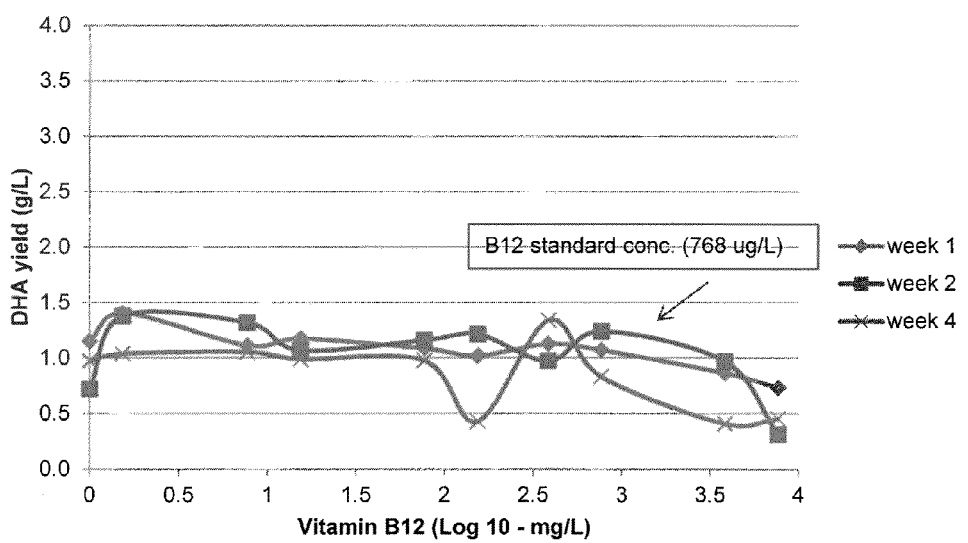
Figure 18. DHA yield of PTA-9695 as a function of various concentrations of vitamin B12 in defined SDFM-B at 10% $CO_2$

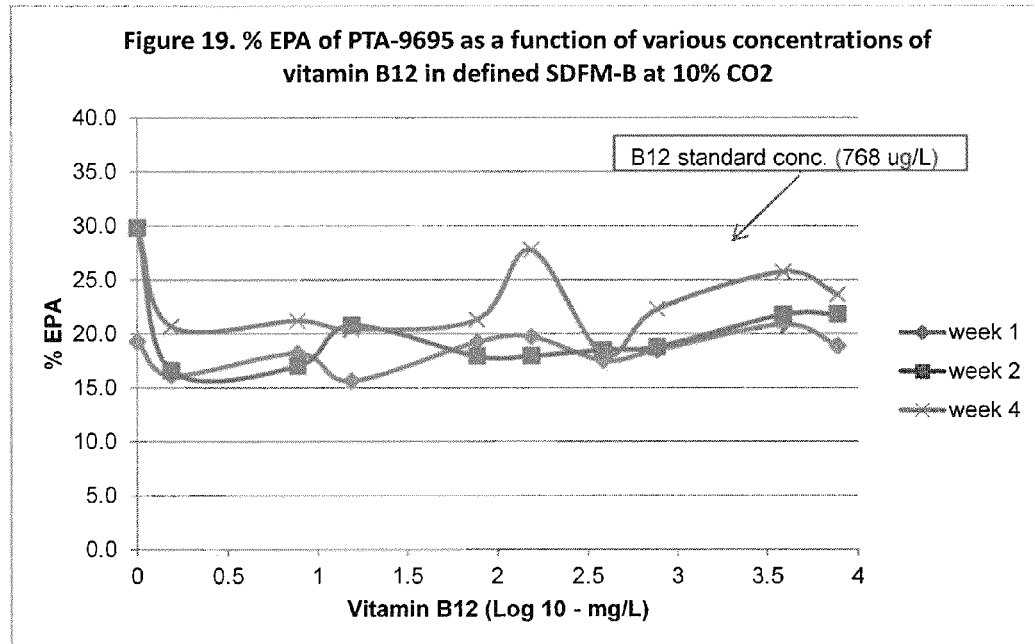
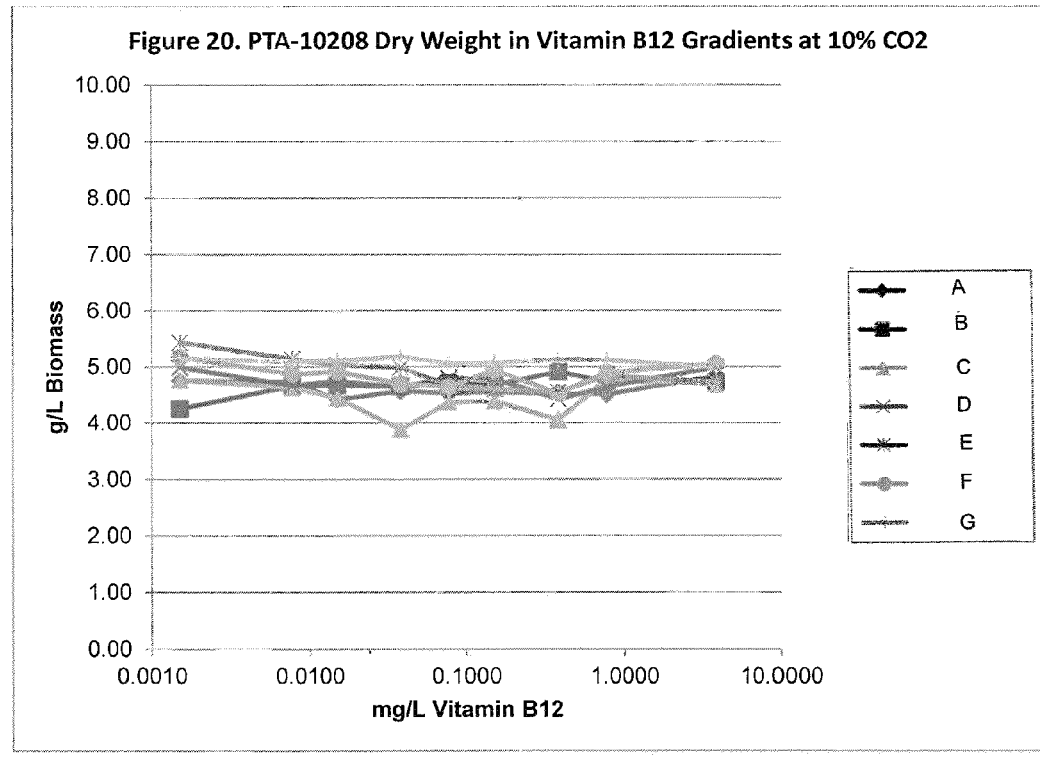

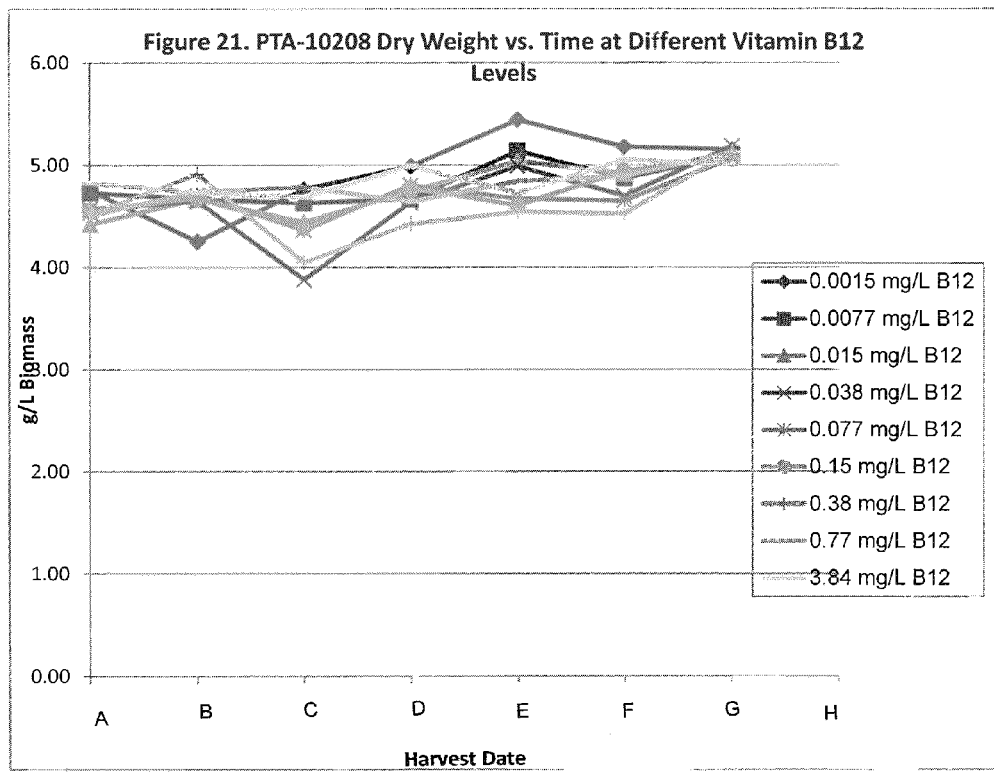
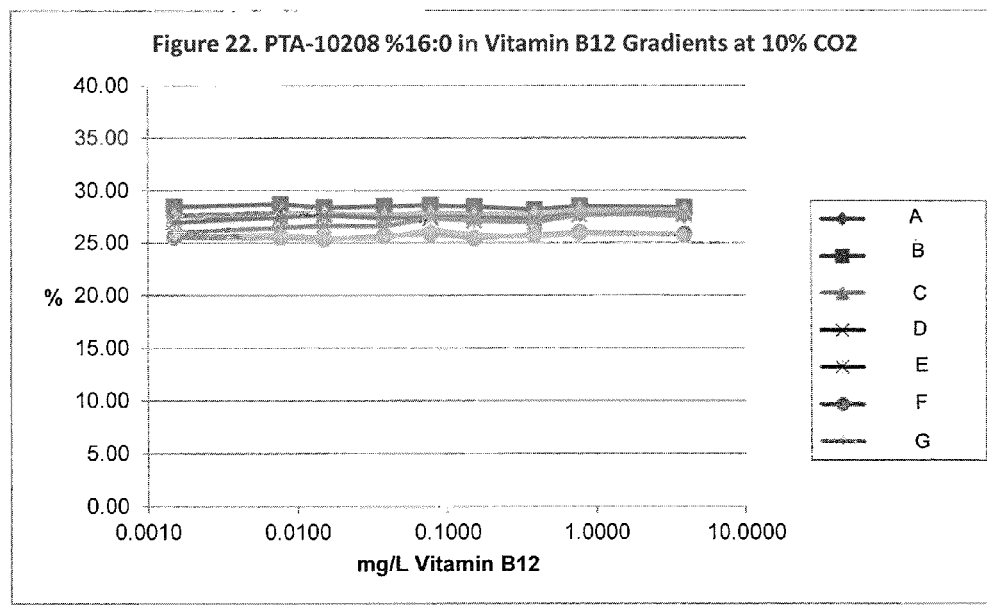

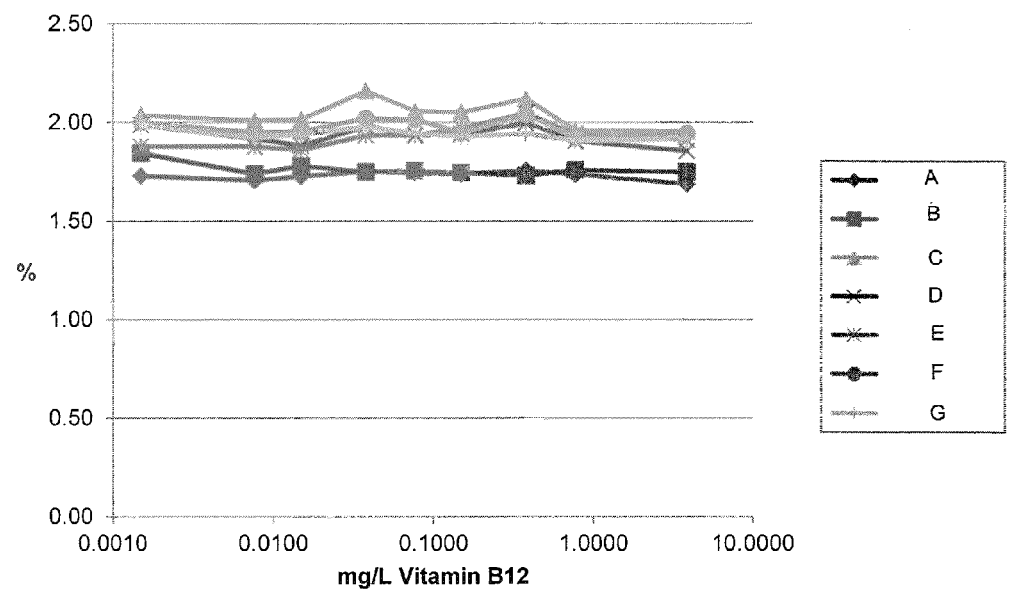
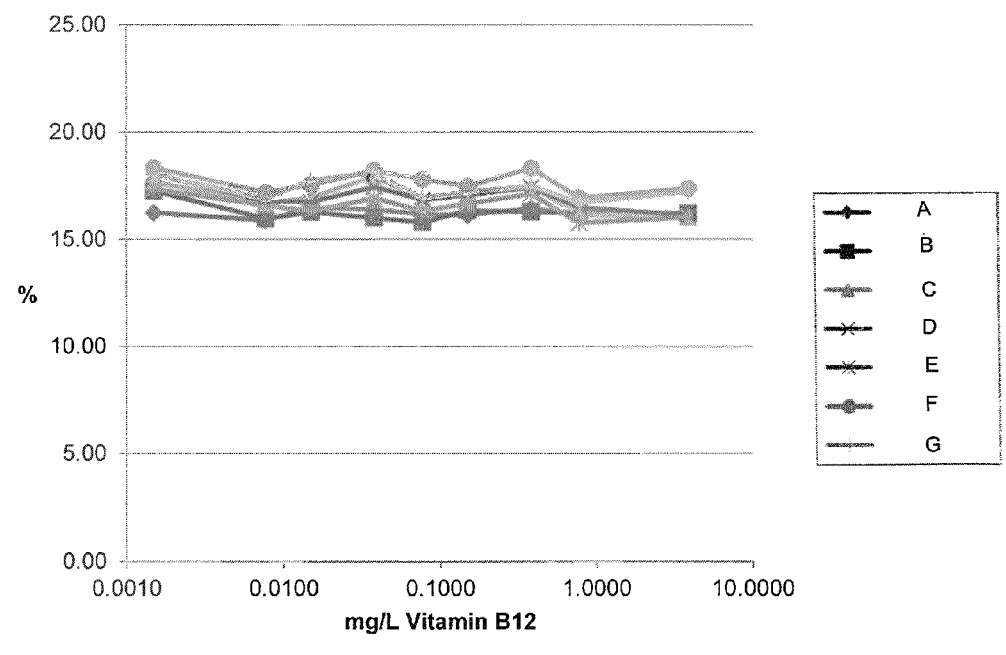

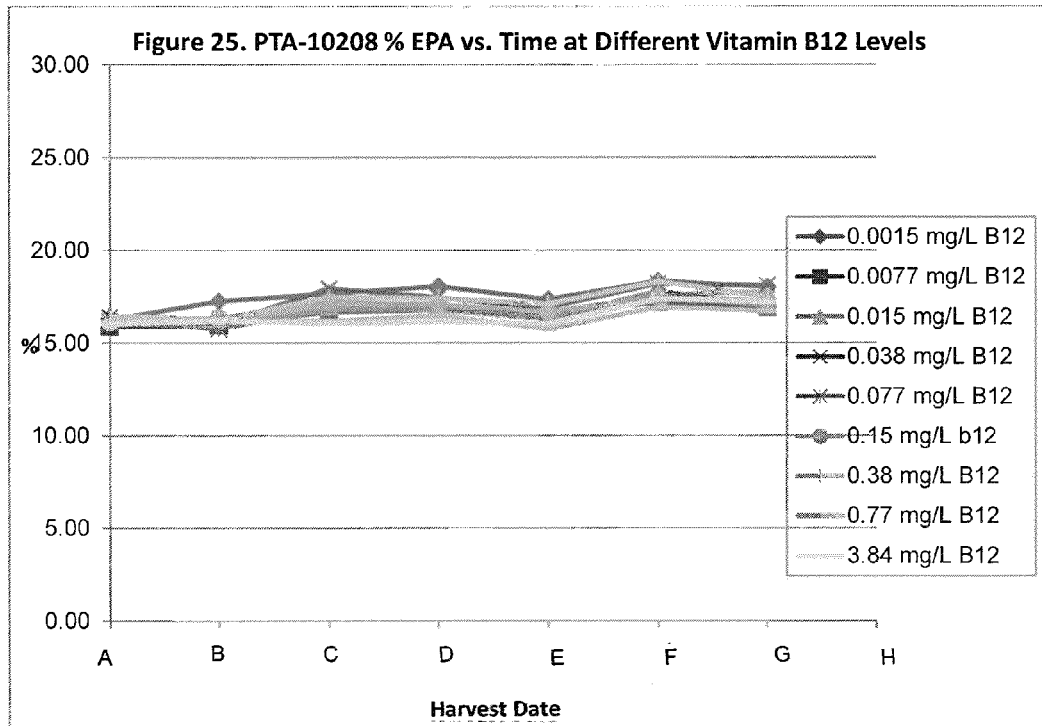
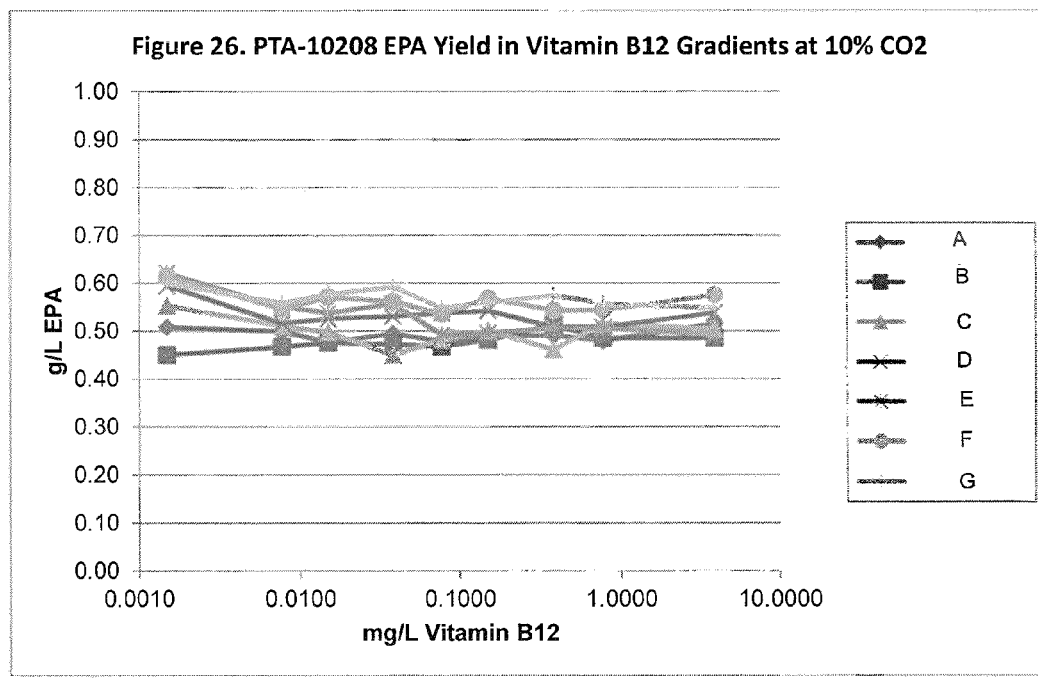

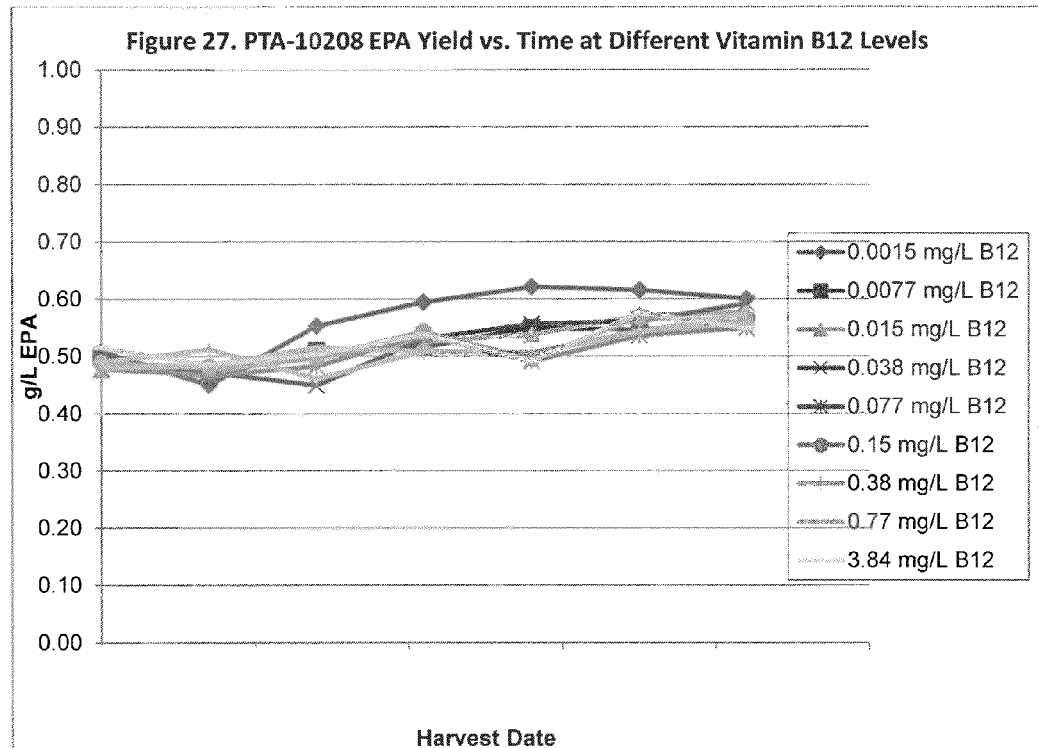
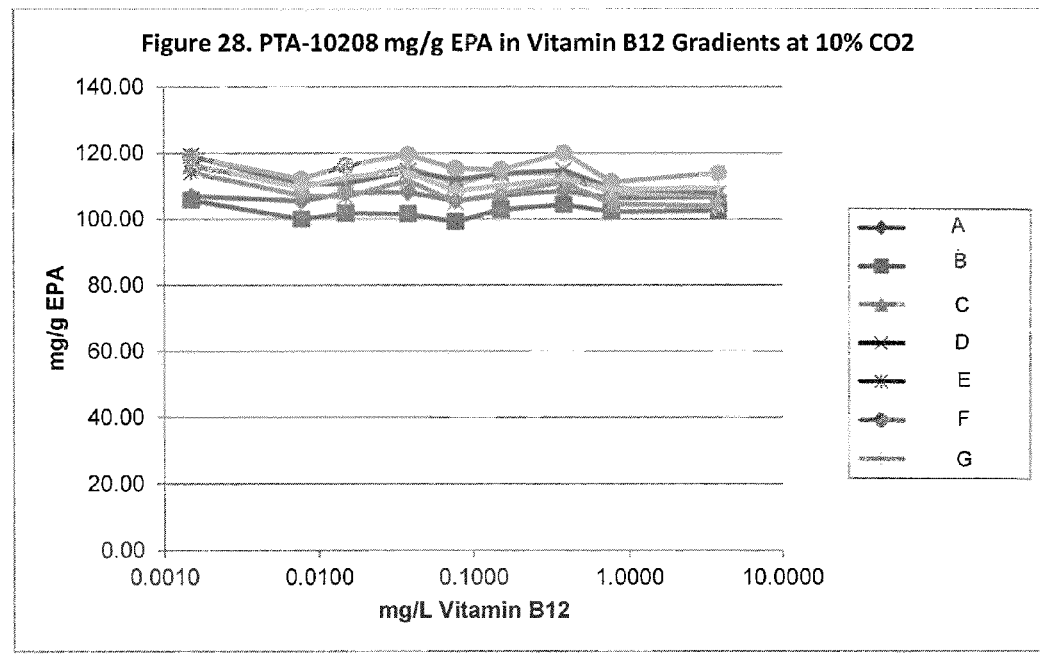

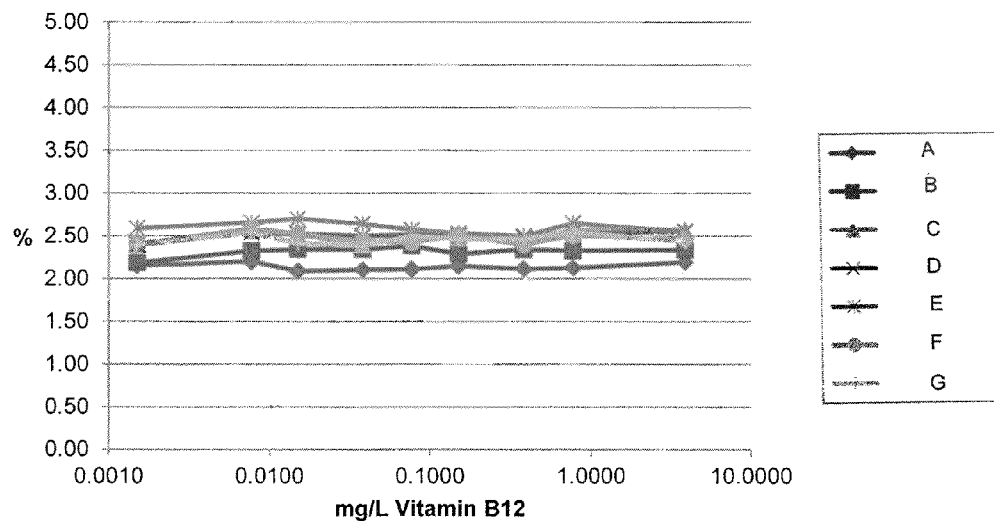
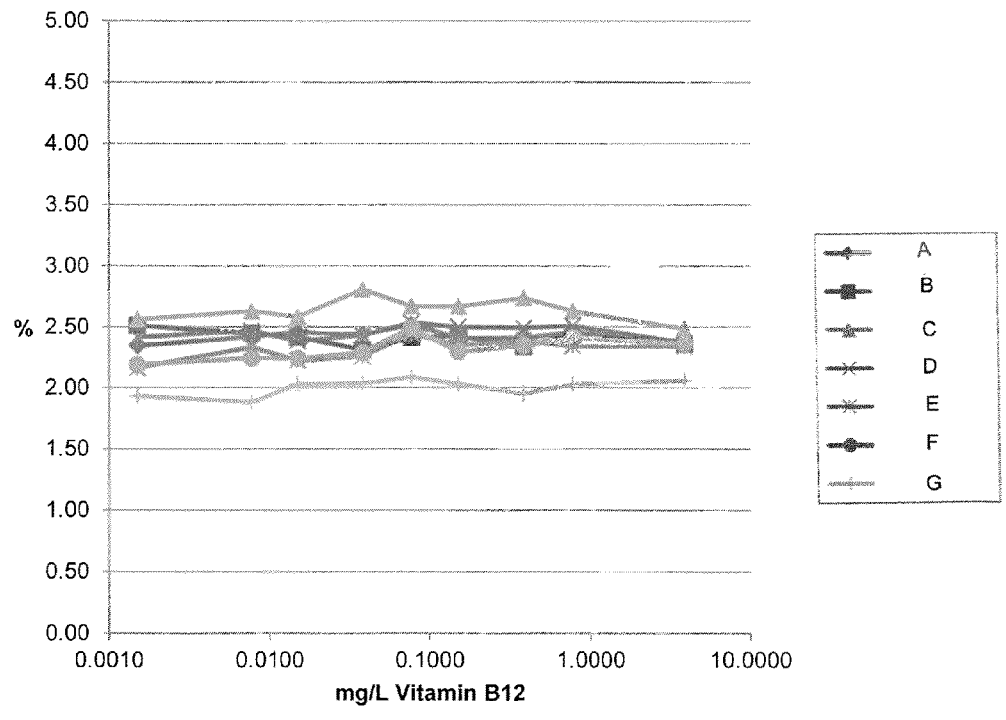

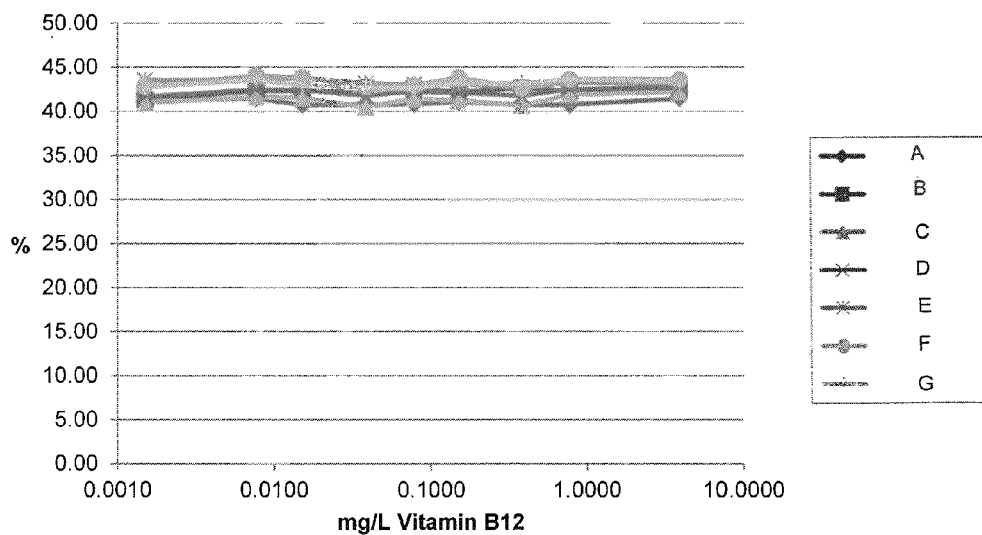
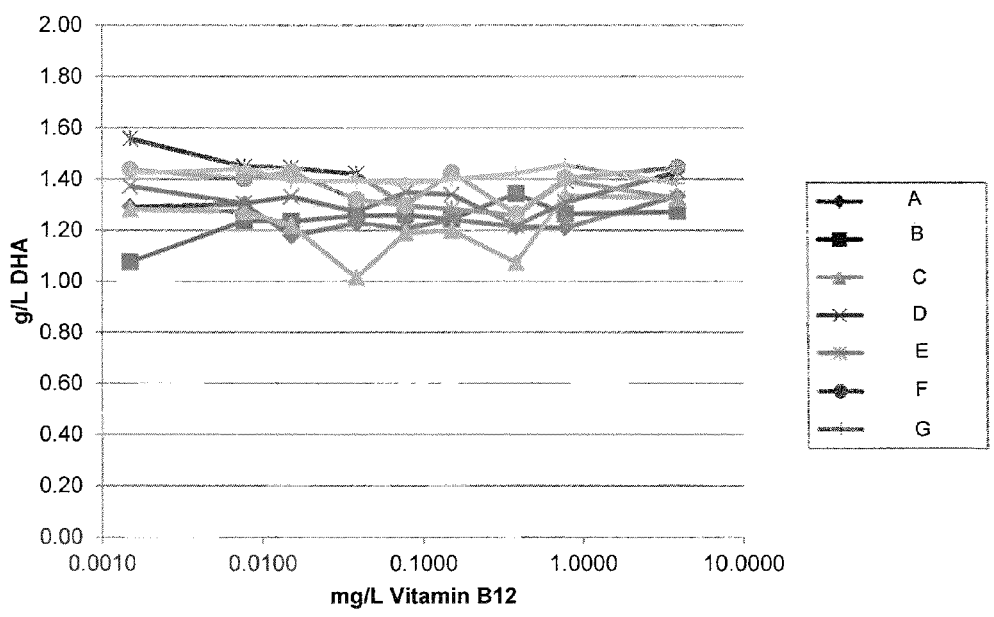

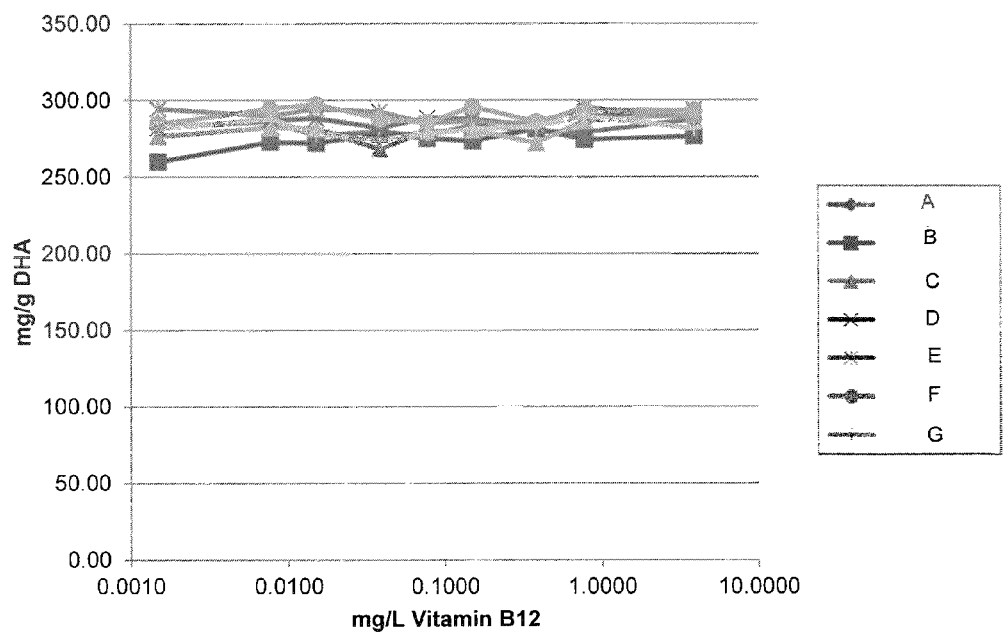
Figure 33. PTA-10208 mg/g DHA in Vitamin B12 Gradients at 10% CO2
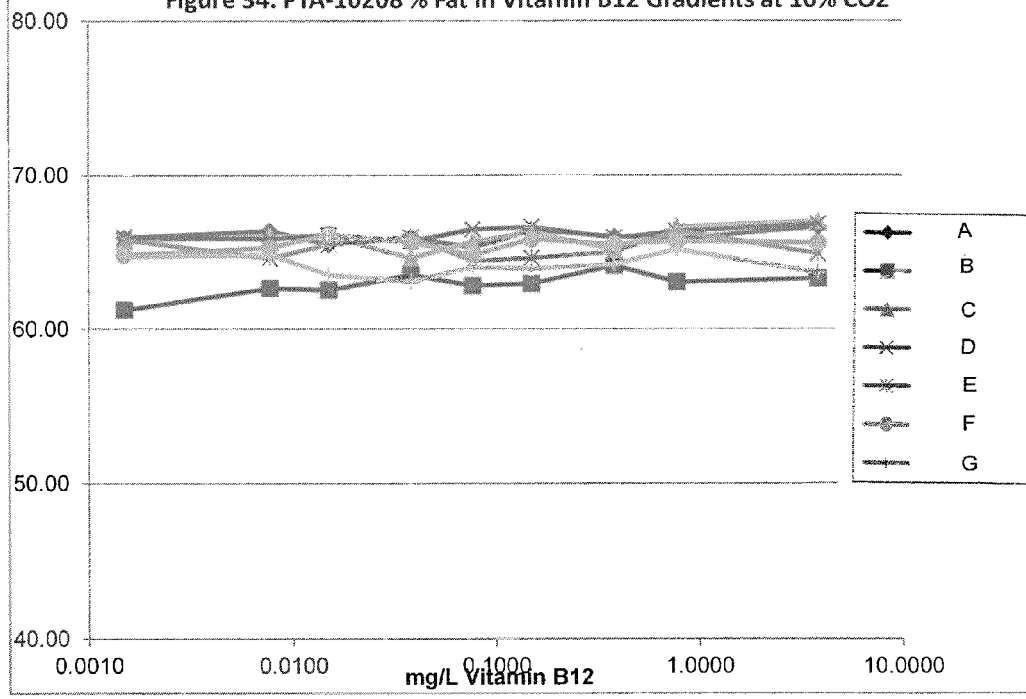
Figure 34. PTA-10208 % Fat in Vitamin B12 Gradients at 10% CO2

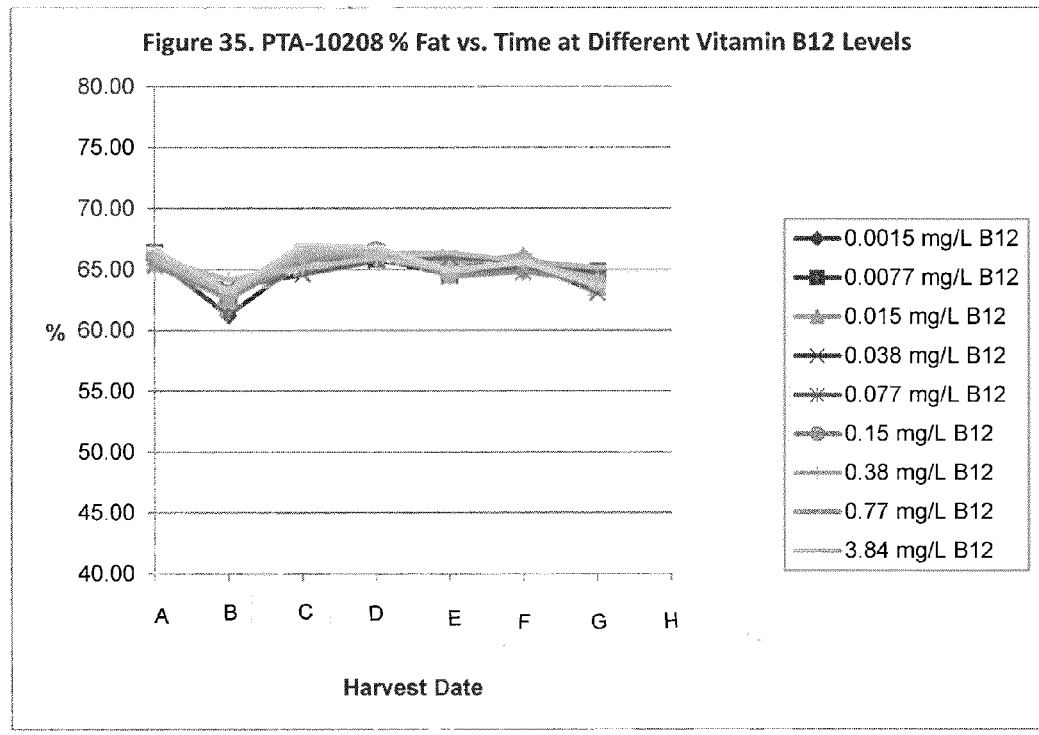
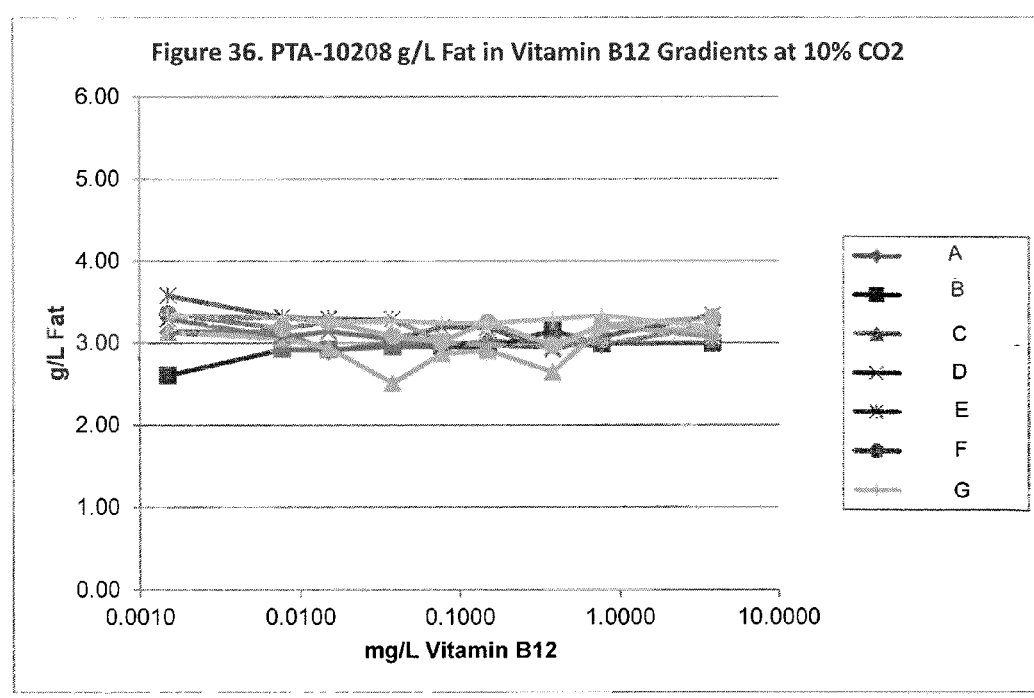

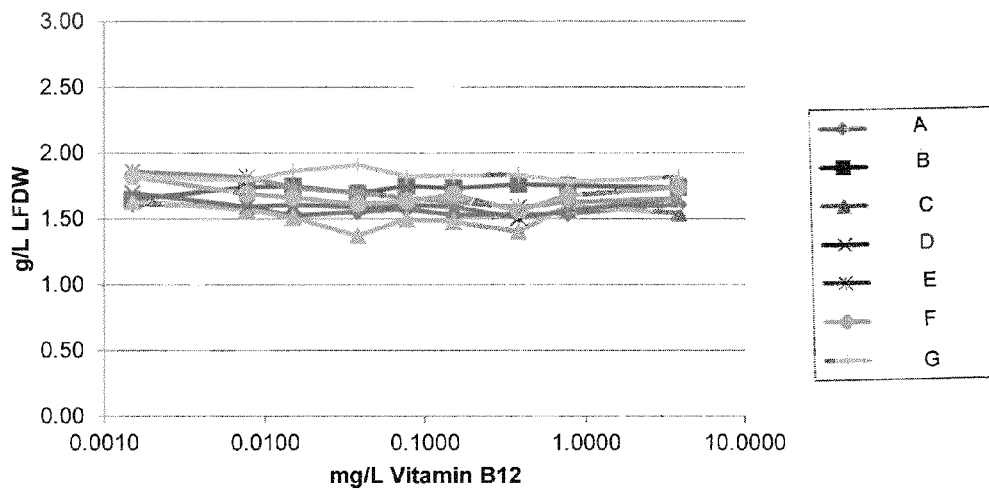
Figure 37. PTA-10208 Lipid Free Dry Weight in Vitamin B12 Gradients at 10% CO2
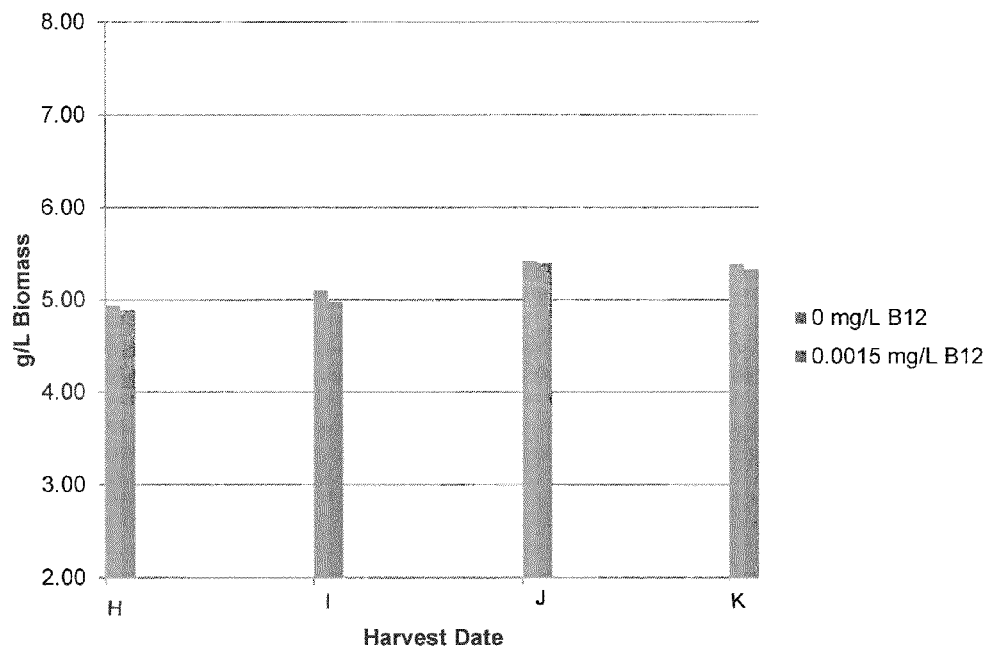
Figure 38. PTA-10208 Dry Weight with 0.0015 mg/L and 0 mg/L Vitamin B12 at 10% CO2

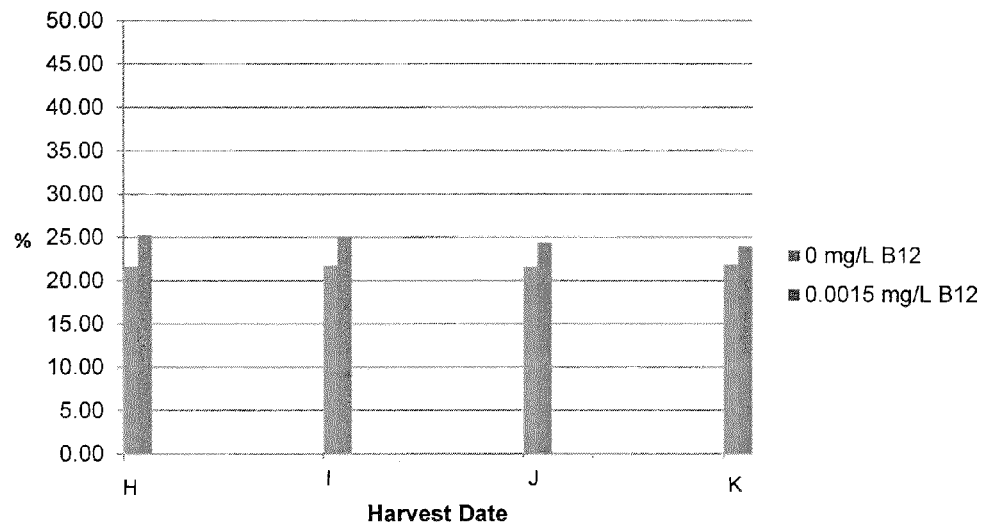
Figure 39. PTA-10208 %16:0 with 0.0015 mg/L and 0 mg/L Vitamin B12 at 10% CO2
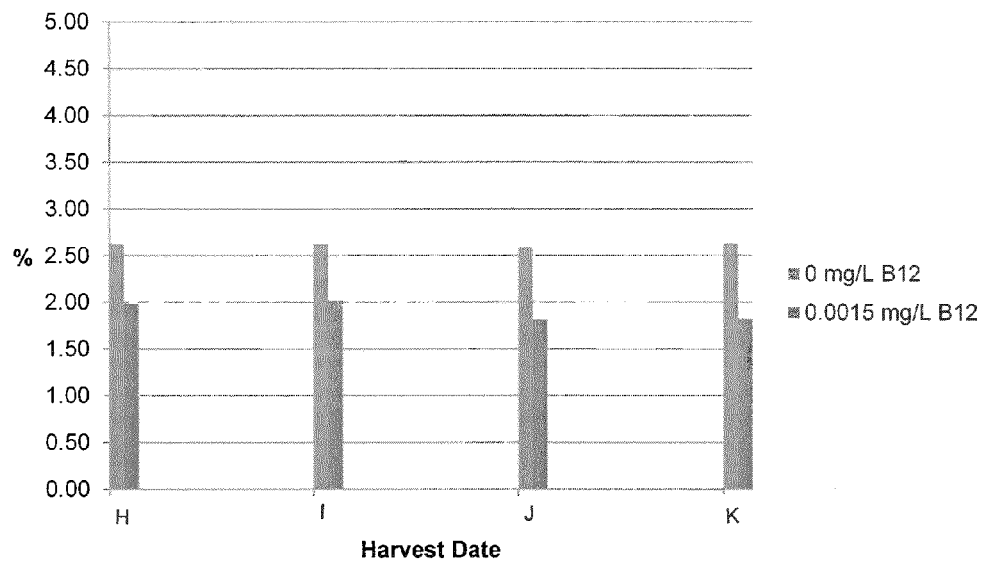
Figure 40. PTA-10208 %ARA with 0.0015 mg/L and 0 mg/L Vitamin B12 at 10% CO2

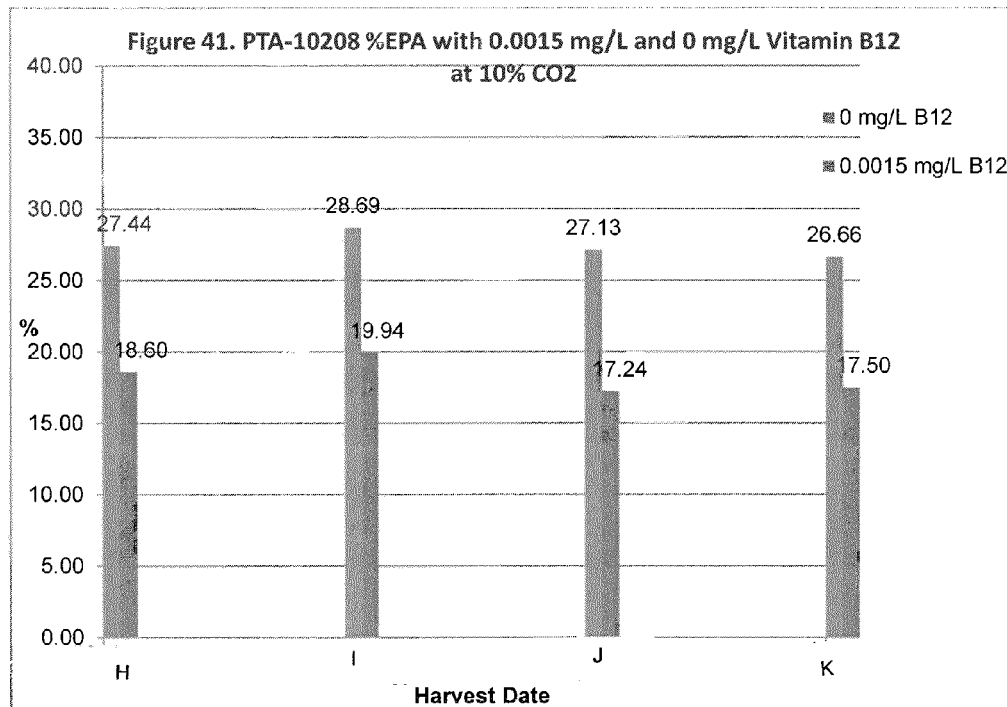
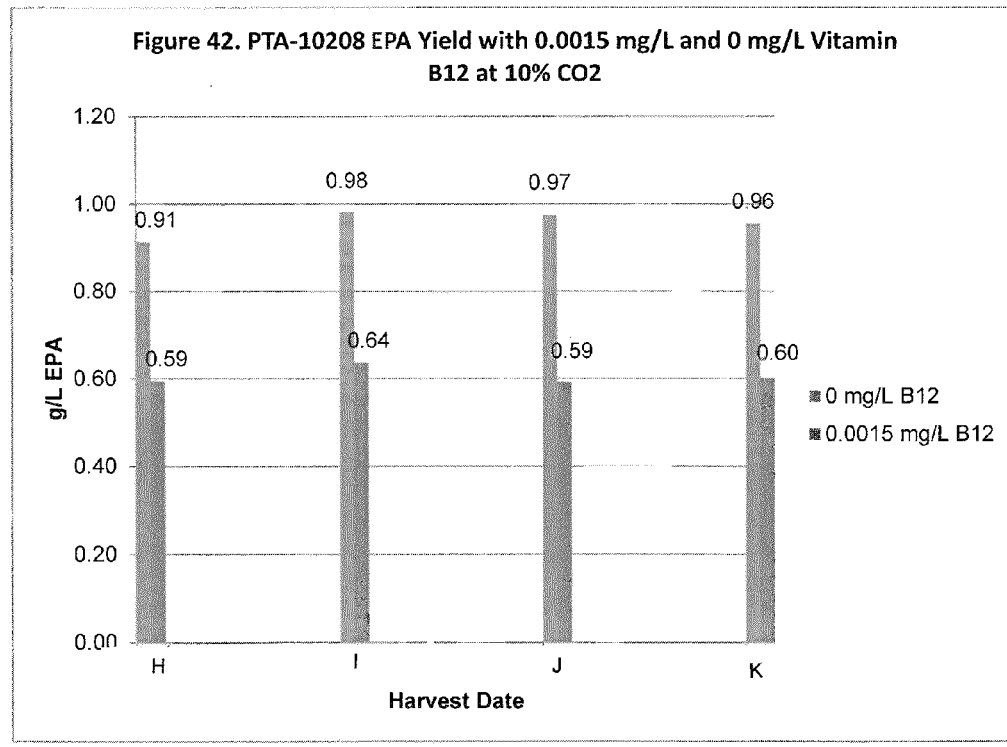

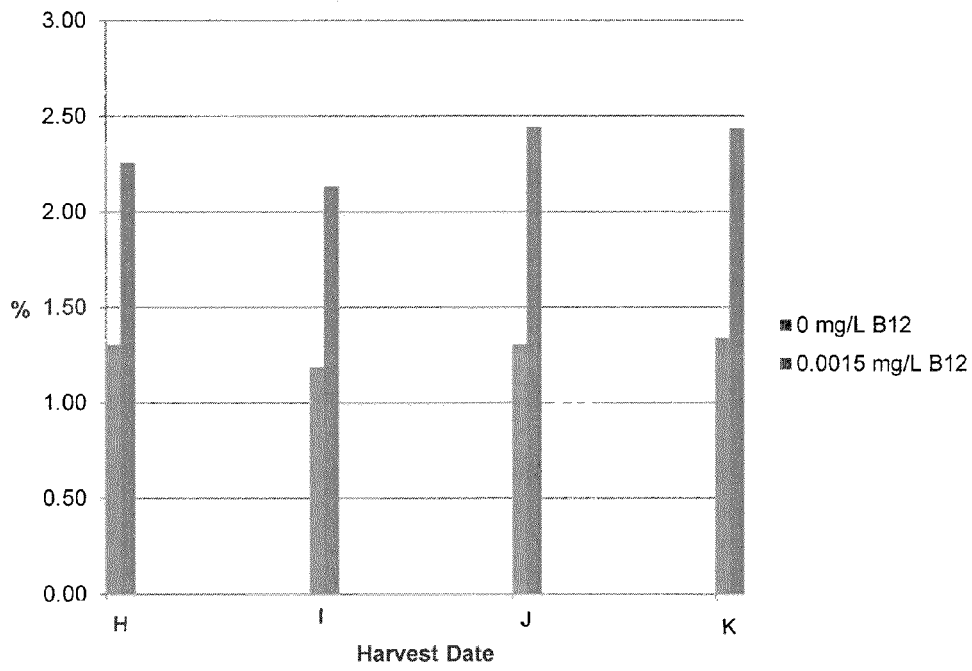
Figure 43. PTA-10208 %DPA (n-6) with 0.0015 mg/L and 0 mg/L Vitamin B12 at 10% CO2
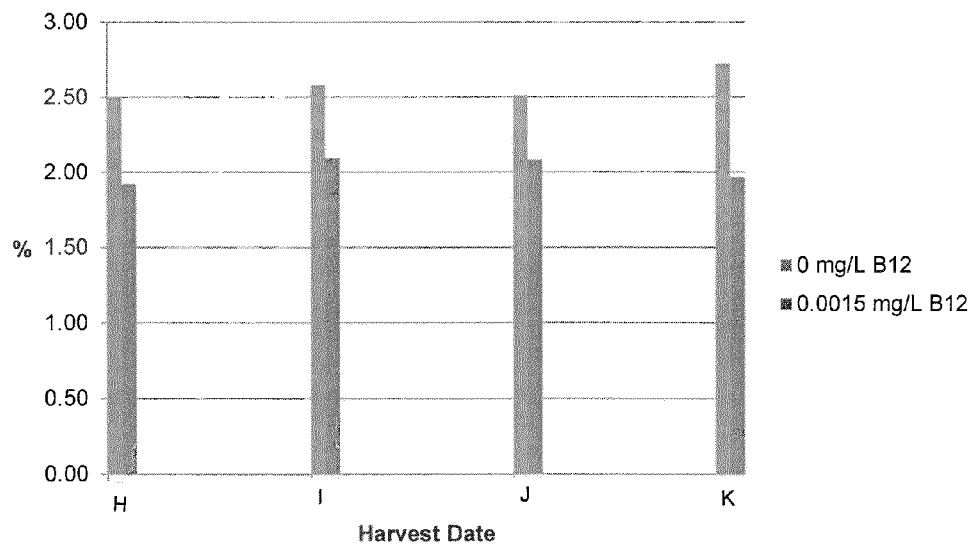
Figure 44. PTA-10208 %DPA (n-3) with 0.0015 mg/L and 0 mg/L Vitamin B12 at 10% CO2

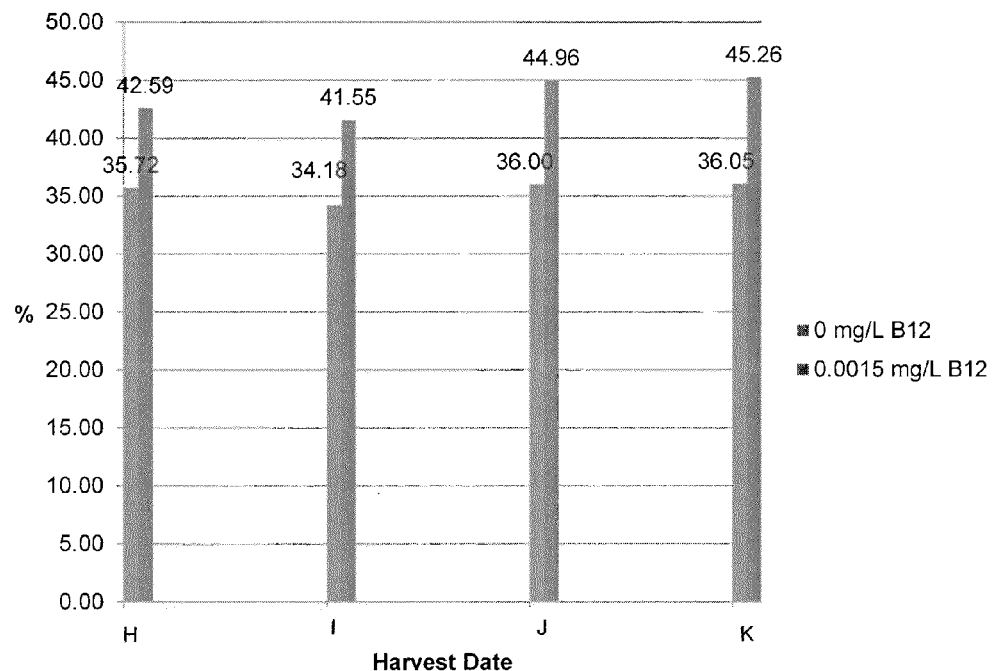
Figure 45. PTA-10208 %DHA with 0.0015 mg/L and 0 mg/L Vitamin B12 at 10% CO2
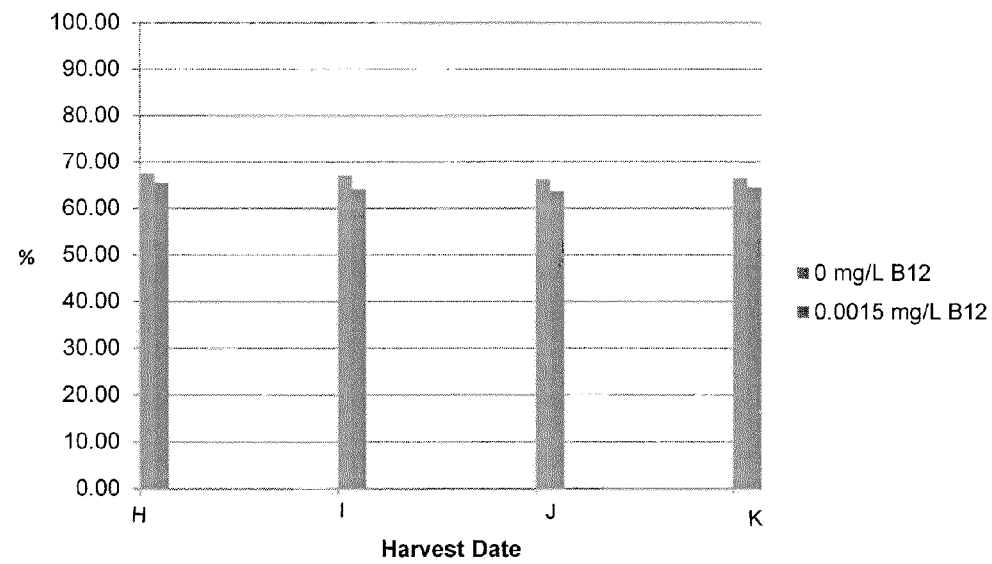
Figure 46. PTA-10208 %Fat with 0.0015 mg/L and 0 mg/L Vitamin B12 at 10% CO2

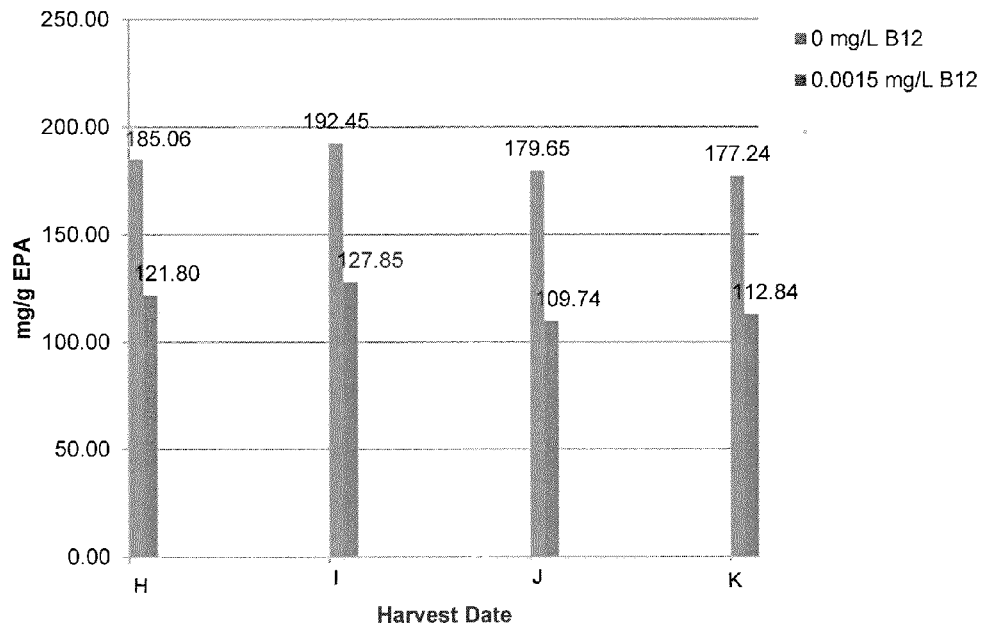
Figure 47. PTA-10208 mg/g EPA with 0.0015 mg/L and 0 mg/L Vitamin B12 at 10% CO2
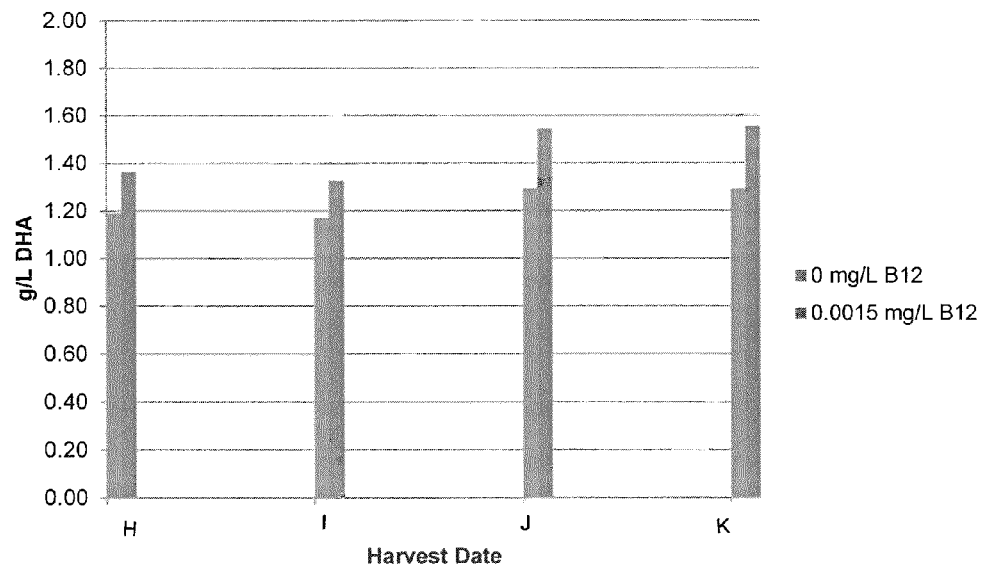
Figure 48. PTA-10208 DHA Yield with 0.0015 mg/L and 0 mg/L Vitamin B12 at 10% CO2

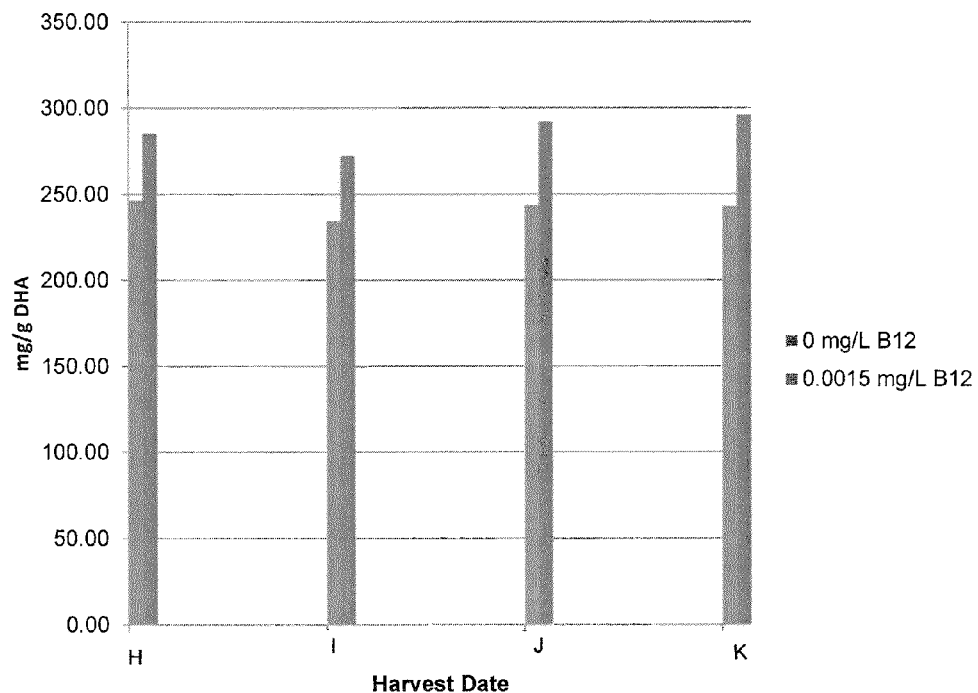

EICOSAPENTAENOIC ACID-PRODUCING MICROORGANISMS, FATTY ACID COMPOSITIONS, AND METHODS OF MAKING AND USES THEREOF

BACKGROUND OF THE INVENTION

1. Field of the Invention

The present invention is directed to isolated microorganisms as well as strains and mutants thereof, biomasses, microbial oils, compositions, and cultures; methods of producing the microbial oils, biomasses, and mutants; and methods of using the isolated microorganisms, biomasses, and microbial oils.

2. Background Art

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

Polyunsaturated fatty acids (PUFAs) are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 long chain polyunsaturated fatty acid (LC-PUFA) with a chain length of 22 carbons and 6 double bonds, often designated as "22:6 n-3." Other omega-3 LC-PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 LC-PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., *Proc. Nutr. Soc.* 58: 397-401 (1999). DHA, for example, accounts for approximately 15%-20% of lipids in the human cerebral cortex, 30%-60% of lipids in the retina, is concentrated in the testes and sperm, and is an important component of breast milk. Bergé, J. P., and Barnathan, G. *Adv. Biochem. Eng. Biotechnol.* 96:49-125 (2005). DHA accounts for up to 97% of the omega-3 fatty acids in the brain and up to 93% of the omega-3 fatty acids in the retina. Moreover, DHA is essential for both fetal and infant development as well as maintenance of cognitive functions in adults. Id. Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Thraustochytrids are microorganisms of the order Thraustochytriales. Thraustochytrids include members of the genus *Schizochytrium* and *Thraustochytrium* and have been recognized as an alternative source of omega-3 fatty acids, including DHA and EPA. See U.S. Pat. No. 5,130,242. Oils produced from these marine heterotrophic microorganisms often have simpler polyunsaturated fatty acid profiles than corresponding fish or microalgal oils. Lewis, T. E., *Mar. Biotechnol.* 1: 580-587 (1999). Strains of thraustochytrid species have been reported to produce omega-3 fatty acids as a high percentage of the total fatty acids produced by the organisms. U.S. Pat. No. 5,130,242; Huang, J. et al., *J. Am. Oil. Chem. Soc.* 78: 605-610 (2001); Huang, J. et al., *Mar. Biotechnol.* 5: 450-457 (2003). However, isolated thraustochytrids vary in the identity and amounts of LC-PUFAs produced, such that some previously described strains can have undesirable levels of omega-6 fatty acids and/or can demonstrate low productivity in culture. As such, a continuing need exists for the isolation of microorganisms demonstrating high productivity and desirable LC-PUFA profiles.

BRIEF SUMMARY OF THE INVENTION

The applicants have found that the amount of EPA and DHA, produced by a Thraustochytrid that produces a biomass having at least 3% EPA, can be modulated by varying the amounts of dissolved carbon dioxide ($CO_2$) in an aqueous phase of a fermentation broth during the fermentation of the microorganism. Provided herein is a method of making a biomass of a microorganism having fatty acids and a concentration of EPA, comprising: fermenting the microorganism in a fermentor vessel having a dissolved gas in a fermentation broth to produce a biomass, wherein the microorganism comprises a Thraustochytrid that produces a biomass having at least 3% EPA of the total weight of the fatty acids; and adjusting the dissolved $CO_2$ levels in the dissolved gas. In one embodiment, the dissolved $CO_2$ levels may be adjusted to attain a desired EPA and/or DHA level in the biomass. In a further embodiment the amount of dissolved $CO_2$ in the aqueous phase of a fermentation broth ranges from about 38 to about 600 ppm of the total dissolved gas, and particularly from about 38 to about 135 ppm of the total dissolved gas.

Further provided herein is a method of making a biomass of a microorganism having fatty acids and a concentration of EPA, comprising: fermenting the microorganism in a fermentor vessel, comprising a gas, to produce a biomass wherein the microorganism comprises a Thraustochytrid that produces a biomass having at least 3% EPA of the total weight of the fatty acids; and supplementing the gas with $CO_2$. Supplementing means to add to or charge the vessels with $CO_2$ in an amount additional to the amount produced by the fermentation of the cells or an amount at ambient conditions. In one embodiment the $CO_2$ is supplemented to the vessel to attain a desired EPA and/or DHA amount in the biomass.

Also provided herein is a method of making a biomass of a microorganism having fatty acids and a concentration of EPA, comprising: fermenting the microorganism in a fermentor vessel to produce a biomass wherein the microorganism comprises a Thraustochytrid that produces a biomass having at least 3% EPA of the total weight of the fatty acids; and adjusting the amount of the biomass in the vessel. In an embodiment of the invention the biomass is adjusted to attain a desired EPA or DHA level in the biomass.

A method of making a microorganism having fatty acids and a concentration of EPA, comprising: fermenting the microorganism in a fermentor vessel to produce a biomass wherein the microorganism comprises a Thraustochytrid that produces a biomass having at least 3% EPA of the total weight of the fatty acids; and adjusting the pressure on the biomass, for example, but not limited to, controlling the back pressure of the vessel. In one embodiment the pressure is adjusted to attain a desired EPA or DHA level in the biomass.

In another embodiment provided herein is a method of making a microorganism having fatty acids and a concentration of EPA, comprising: fermenting the microorganism in a fermentor vessel to produce a fermentation broth and a biomass wherein the microorganism comprises a Thraustochytrid that produces a biomass having at least 3% EPA of the total weight of the fatty acids; and adjusting the temperature in the broth. In one embodiment the temperature is adjusted to attain a desired EPA and/or DHA level in the biomass.

In various embodiments, the amounts of EPA and DHA can also be modulated by adjusting the amount of dissolved $CO_2$ in an aqueous phase or fermentation broth of the vessel by increasing or decreasing the amount of $CO_2$ in the vessel. The amount of dissolved $CO_2$ can be adjusted by additionally adjusting the amount of the biomass fermented. For example, by fermenting the cells in flasks and larger fermentation vessels. The EPA and DHA can also be varied according to embodiments provided herein by varying the temperature. The amount of dissolved $CO_2$ can be additionally adjusted for example by adjusting the temperature in the vessel. For example, lower vessel temperatures will produce higher concentrations of EPA and lower concentrations of DHA. The amount of dissolved $CO_2$ can further be adjusted by adjusting the pressure in the vessel. For example, increasing pressure will likely increase dissolved $CO_2$ which will increase the amount of EPA and decrease the amount of DHA in the biomass. Each of the above described adjustments, e.g., supplemented $CO_2$, increase or decrease in biomass, increase or decrease in temperature, or increase or decrease in pressure, can each be combined with any of the other adjustments to attain a desired EPA and DHA level in the biomass and any oil extracted from the biomass. Dissolved $CO_2$ can also be adjusted by a change in pH.

In some embodiments, the total amount of EPA and DHA remains relatively constant compared to the amount, by weight, of the total weight of the fatty acids and omega-3 fatty acids.

In further embodiments, the EPA or DHA content of the biomass is measured prior to making an adjustment to the amount of the supplemented $CO_2$, pressure, temperature, or biomass.

While not wishing to be bound to any theory, it is hypothesized that the increase and decrease in the amounts of the EPA or DHA is directly related to the amount of dissolved $CO_2$ in the aqueous phase of the fermentation broth and that the above described adjustments of $CO_2$, of pressure, and of temperature, vary the amount of dissolved $CO_2$ in the biomass.

In some embodiments, the invention provides a method of making a biomass of a microorganism having increased concentration of EPA, the method comprising growing the microorganism in a culture medium comprising less than 0.1 mg/L vitamin B12 to produce a biomass. In some embodiments, the culture medium comprises less than 0.01 mg/L vitamin B12. In some embodiments, the culture medium comprises less than 0.001 mg/L vitamin B12. In further embodiments, the culture medium comprises less than 0.0001 mg/L vitamin B12. In some embodiments, the culture medium contains no vitamin B12.

In some embodiments, the culture medium further comprises less than 1 g of yeast extract per 50 g of lipid-free biomass. In some embodiments, the culture medium further comprises less than 0.5 g of yeast extract per 50 g of lipid-free biomass. In further embodiments, the culture medium further comprises less than 0.1 g of yeast extract per 50 g of lipid-free biomass.

In some embodiments, the EPA concentration is increased by at least 400% compared to the EPA concentration in a biomass obtained from the microorganism grown in a culture medium comprising greater than 0.1 mg/L vitamin B12. In some embodiments, the EPA concentration is increased by at least 300% compared to the EPA concentration in a biomass from a microorganism grown in a culture medium comprising greater than 0.01 mg/L vitamin B12. In further embodiments, the EPA concentration is increased by at least 200% compared to the EPA concentration in a biomass from a microorganism grown in a culture medium comprising greater than 0.001 mg/L vitamin B12. In some embodiments, the EPA concentration is increased by at least 100% compared to the EPA concentration in a biomass from a microorganism grown in a culture medium comprising greater than 0.0001 mg/L vitamin B 12.

In some embodiments, the invention provides a method of making a biomass of a microorganism having increased concentration of EPA, comprising growing the microorganism in a culture medium comprising less than 0.1 mg/L cobalt to produce a biomass. In some embodiments, the culture medium comprises less than 0.01 mg/L cobalt. In some embodiments, the culture medium comprises less than 0.001 mg/L cobalt. In further embodiments, the culture medium comprises less than 0.0001 mg/L cobalt. In some embodiments, the culture medium contains no cobalt.

In some embodiments, the microorganism is a Thraustochytrid. In some embodiments, the microorganism produces at least 3% EPA of the total weight of the fatty acids.

In some embodiments, the culture medium has a dissolved $CO_2$ level of at least 5%. In further embodiments, the culture medium has a dissolved $CO_2$ level of at least 10%. In some embodiments, the culture medium has a dissolved $CO_2$ level of at least 15%.

The invention also provides an isolated biomass, and a microbial oil extracted from the biomass of any of the methods herein.

BRIEF DESCRIPTION OF DRAWINGS

The various embodiments of the invention can be more fully understood from the following detailed description, the figures, and the accompanying sequence descriptions, which form a part of this application.

FIG. 1 shows the performance of PTA-9695 in a thiamine gradient.

FIG. 2 shows the performance of PTA-9695 in a vitamin B12 gradient.

FIG. 3 shows the performance of PTA-9695 in a biotin gradient.

FIG. 4 shows the performance of PTA-9695 in a Ca-pantothenate gradient.

FIG. 5 shows the performance of PTA-9695 in TSFM standards.

FIG. 6-FIG. 19 show the performance of PTA-9695 in a vitamin B12 gradient at 10% $CO_2$.

FIG. 20-FIG. 49 show the performance of PTA-10208 in a vitamin B12 gradient at 10% $CO_2$.

DETAILED DESCRIPTION OF THE INVENTION

The methods and compositions provided herein are particularly applicable to a Thraustochytrid that produces a biomass having at least 3% EPA of the total weight of the fatty acids it produces. A particular Thraustochytrid that produces a biomass having at least 3% EPA provided herein is an isolated microorganism of the species deposited under ATCC Accession No. PTA-10212. The isolated microorganism associated with ATCC Accession No. PTA-10212 was deposited under the Budapest Treaty on Jul. 14, 2009 at the American Type Culture Collection, Patent Depository, 10801 University Boulevard, Manassas, Va. 20110-2209.

A particular Thraustochytrid that produces a biomass having at least 3% EPA is selected from an isolated microorganism deposited under ATCC Accession No. PTA-10212, PTA-10213, PTA-10214, PTA-10215, PTA-10208, PTA-10209, PTA-10210, or PTA-10211.

A particular embodiment provided here is directed to an isolated microorganism comprising an 18s rRNA comprising a polynucleotide sequence of SEQ ID NO:1 or a polynucleotide sequence having at least 94% identity to SEQ ID NO:1.

A particular embodiment provided here is directed to an isolated microorganism comprising an 18s rRNA polynucleotide sequence that has at least 94% identity to an 18s rRNA polynucleotide sequence of the microorganism deposited under ATCC Accession No. PTA-10212.

A particular Thraustochytrid that produces a biomass having at least 3% EPA provided herein is directed to an isolated microorganism of the species deposited under ATCC Accession No. PTA-10208

A particular embodiment provided here is directed to an isolated microorganism of the species deposited under ATCC Accession No. PTA-10208, wherein the total fatty acids produced by the microorganism comprises more than about 10% by weight eicosapentaenoic acid.

A particular Thraustochytrid that produces a biomass having at least 3% EPA he present invention is directed to an isolated microorganism having the characteristics of the species deposited under ATCC Accession No. PTA-10208, wherein the total fatty acids produced by the microorganism comprises more than about 10% by weight eicosapentaenoic acid. A particular Thraustochytrid that produces a biomass having at least 3% EPA provided herein is selected from an isolated microorganism selected from the a mutant strain deposited under ATCC Accession No. PTA-10209, PTA-10210, or PTA-10211. The microorganisms associated with ATCC Accession Nos. PTA-10209, PTA-10210, and PTA-10211 were deposited under the Budapest Treaty on Sep. 25, 2009 at the American Type Culture Collection, Patent Depository, 10801 University Boulevard, Manassas, Va. 20110-2209.

Embodiments provided herein are directed to the microorganisms described, above, their mutant strains and the microorganisms identified in U.S. patent application Ser. No. 12/729,013 incorporated by reference herein in its entirety.

An embodiment provided herein is directed to an isolated microorganism that produces a triacylglycerol fraction, wherein eicosapentaenoic acid content of the triacylglycerol fraction is at least about 12% by weight.

An embodiment provided herein is directed to an isolated biomass, wherein at least about 20% by weight of a dry cell weight of the biomass are fatty acids, wherein more than about 10% by weight of fatty acids is eicosapentaenoic acid, and wherein the fatty acids comprise less than about 5% by weight each of arachidonic acid and docosapentaenoic acid n-6. In some embodiments, at least about 25% by weight of the fatty acids is docosahexaenoic acid.

In some embodiments, the present invention is directed to an isolated biomass comprising triacylglycerol, wherein at least about 12% by weight of triacylglycerol is eicosapentaenoic acid.

In some embodiments, the present invention is directed to any of the isolated biomasses of the invention wherein the fatty acids further comprise less than about 5% by weight each of oleic acid, linoleic acid, linolenic acid, eicosenoic acid, and erucic acid.

The present invention is directed to an isolated thraustochytrid microorganism of the thraustochytrid species deposited under ATCC Accession No. PTA-9695 or a strain derived therefrom, wherein the total fatty acids produced by said microorganism or strain derived therefrom comprise about 10% or less by weight eicosapentaenoic acid. An embodiment provided herein is direct to the microorganism describe above or a strain therefrom and other related microorganism describe in U.S. Patent Application Publication No. US 2010/0239533 incorporated by reference herein in its entirety.

Also provided herein is a method of increasing the concentration of EPA in a biomass of a microorganism having fatty acids and a concentration of EPA comprising: fermenting the microorganism in a fermentor vessel, comprising a gas, to produce a biomass wherein the microorganism comprises a Thraustochytrid that produces a biomass having at least 3% EPA of the total weight of the fatty acids; and supplementing the gas with $CO_2$ in an amount sufficient to increase the concentration of the EPA in the biomass. The increase in the concentration of the EPA can be compared for example to the concentration of EPA similarly fermented microorganism not supplemented with $CO_2$ or when compared to a similarly fermented microorganism at ambient conditions.

In another embodiment, the amount of $CO_2$ sufficient to increase the concentration of the EPA is greater than or equal to 2% of the total gas in the vessel. In another embodiment, the amount of the $CO_2$ in the vessel is greater than or equal to about 5% up to about 20% of the total gas in the vessel. In another embodiment, the amount of the $CO_2$ in the vessel is greater than or equal to about 5% up to about 15% of the total gas in the vessel.

In a further embodiment, the amount of $CO_2$ supplemented is greater than or equal to 2% of the total gas in the vessel to increase the concentration of the EPA in the biomass to greater than about 4%, by weight, of the total weight of the fatty acids, more particularly from about greater than 4% up to about 45%, by weight, of the total weight of the fatty acids, more particularly, from about greater than 4% up to about 40% of the total weight of the fatty acids.

In a further embodiment, the amount of $CO_2$ supplemented is sufficient to increase the EPA levels from about 4% to a range of about 6 to 30%, by weight, of the total weight of the fatty acids. In another embodiment, the amount of $CO_2$ provided is sufficient to increase the concentration of the EPA from about 15% up to about 40%, by weight of the total weight of the fatty acids. In another embodiment, the amount of $CO_2$ provided is sufficient to increase the concentration of the EPA to greater than 20%, by weight, of the total weight of the fatty acids. In another embodiment, the $CO_2$ is provided in an amount sufficient to increase the concentration of the EPA from about 20% up to about 25%.

In another embodiment, provided herein is a method of increasing the concentration of EPA in a biomass of a microorganism having fatty acids and a concentration of EPA comprising: fermenting the microorganism in a fermentor vessel to produce a biomass; providing a pressure on the biomass sufficient to increase the concentration of the EPA in the biomass. The increase in the concentration of the EPA can be compared for example to the concentration of EPA similarly fermented microorganism not provided with the pressure or when compared to a similarly fermented microorganism at ambient conditions. In further embodiment, the pressure provided on the biomass is about 0.5 psi above atmospheric pressure. In another embodiment, the vessel has a head pressure (or back pressure) of greater than or equal to about 0.4 psi, more particularly from about 0.4 psi up to about 30 psi, even more particularly of from about 1 up to about 30 psi. In another embodiment, the vessel has a head pressure of from about 1 up to about 20 psi. In another embodiment the pressure provided is provided for a time sufficient to adjust the amount of EPA in the biomass, particularly for a time up to 120 hours.

In another embodiment provided herein is a method of making a biomass of a microorganism producing fatty acids and a concentration of EPA comprising fermenting the microorganism in a fermentor vessel to produce a biomass wherein the microorganism comprises a Thraustochytrid that produces a biomass having at least 3% EPA of the total weight of the fatty acids at a temperature sufficient to increase the concentration of the EPA in the biomass. In some embodiments, the temperature sufficient to increase the EPA levels is less than about 30° C., more particularly is less than or equal to about 22° C., and more particularly the temperature is at less than or equal to about 21° C. The increase in the concentration of the EPA can be compared for example to the concentration of EPA in a similarly fermented microorganism where the temperature is not adjusted or when compared to a similarly fermented microorganism at ambient conditions.

In a further embodiment, the methods provided herein vary the amounts of EPA generated during fermentation to produce a biomass, and an oil extracted, wherein the amount of EPA provided is greater than 4%, particularly from about greater than 4% up to about 45%, more particularly from about greater than 4% up to about 40% by weight, of the total weight of the fatty acids. In another embodiment the amount of EPA produced by a method provided herein is in an amount from about 6% up to about 30% by weight of the total weight of the fatty acids. In a further embodiment the amount of EPA produced by a method provided herein is in an amount of from about 15% up to about 40% by weight of the total weight of the fatty acids. In a further embodiment the amount of EPA produced by a method provided herein is in an amount of greater than about 20%, more particularly from about 20% up to about 25% by weight of the total weight of the fatty acids.

In a further embodiment, the desired EPA level provided is greater than 4%, particularly from about greater than 4% up to about 45%, more particularly from about greater than 4% up to about 40% by weight, of the total weight of the fatty acids. In another embodiment the desired EPA level produced by a method provided herein is in an amount from about 6% up to about 30% by weight of the total weight of the fatty acids. In a further embodiment the desired EPA level produced by a method provided herein is in an amount of from about 15% up to about 40% by weight of the total weight of the fatty acids. In a further embodiment the desired EPA level produced by a method provided herein is in an amount of greater than about 20%, more particularly from about 20% up to about 25% by weight of the total weight of the fatty acids.

A method of increasing the concentration of EPA in a biomass of a microorganism having fatty acids and a concentration of EPA comprising: fermenting the microorganism in a fermentor vessel to produce a biomass wherein the microorganism a Thraustochytrid that produces a biomass having at least 3% EPA of the total weight of the fatty acids; and increasing the biomass in an amount sufficient to increase the concentration of the EPA in the biomass. In some embodiments the amount of biomass sufficient to increase the concentration of the EPA has a density of greater than or equal to 10 g/l. In some embodiments the amount of biomass sufficient to increase the concentration of the EPA has a density of about 10 g/l up to about 250 g/l. The increase in the concentration of the EPA can be compared for example to the concentration of EPA in a similarly fermented microorganism wherein the biomass is not increased.

In some embodiments, the EPA concentration of the biomass grown in a culture medium comprising a higher $CO_2$ level (for example, in a vessel comprising $CO_2$ in an amount of greater than or equal to 2%, greater than or equal to 5%, greater than or equal to 10%, greater than or equal to 15%, greater than or equal to 20%, 5% to 20%, or 5% to 15% of the total gas in the vessel) is at least 10%, at least 50%, at least 100%, at least 250%, at least 500%, at least 750%, at least 1000%, at least 1100%, at least 1200%, at least 1300%, at least 1400%, at least 1500%, at least 1600%, at least 1700%, at least 1800%, at least 1900%, or at least 2000% higher than the EPA concentration in a biomass obtained from the microorganism grown in a culture medium comprising lower $CO_2$ levels (for example, in a vessel comprising $CO_2$ in an amount of less than 2%, less than 5%, less than 10%, less than 15%, less than 20%, 0% to 4%, or 1% to 3% of the total gas in the vessel, respectively). For example, the EPA concentration of the biomass grown in a culture medium comprising a higher $CO_2$ level (for example, in a vessel comprising $CO_2$ in an amount of greater than or equal to 2%, greater than or equal to 5%, greater than or equal to 10%, greater than or equal to 15%, greater than or equal to 20%, 5% to 20%, or 5% to 15% of the total gas in the vessel) is at least 10%, at least 50%, at least 100%, at least 250%, at least 500%, at least 750%, at least 1000%, at least 1100%, at least 1200%, at least 1300%, at least 1400%, at least 1500%, at least 1600%, at least 1700%, at least 1800%, at least 1900%, or at least 2000% higher than the EPA concentration in a biomass obtained from the microorganism grown in a vessel at an ambient $CO_2$ level.

Vitamin B12 in Culture Medium

The term "vitamin B 12" as used herein refers to a class of chemically related compounds in both naturally occurring and synthetic forms, including, but not limited to, vitamin B12, cobalamin, cyanocobalamin, and hydroxocobalamin. In some embodiments, the invention provides methods of increasing the EPA concentration in the biomass of a microorganism that produces EPA by growing the microorganism in a culture medium having low levels of vitamin B 12 or in a culture medium having no vitamin B12. In some embodiments, the invention provides methods of making a biomass of a microorganism having increased concentration of EPA, comprising growing the microorganism in a culture medium comprising less than 0.1 mg/L vitamin B12 to produce a biomass. In some embodiments, the culture medium comprises less than 0.05 mg/L, less than 0.01 mg/L, less than 0.005 mg/L, less than 0.001 mg/L, less than 0.0005 mg/L, less than 0.0001 mg/L, or no vitamin B12.

In some embodiments, the culture medium comprises less than 1 g of sources of vitamin B12 (such as yeast extract, corn steep solids, soy flour, and other complex nitrogen sources) per 50 g of lipid-free biomass. In some embodiments, the culture medium comprises less than 0.8 g, less than 0.5 g, less than 0.3 g, less than 0.1 g, less than 0.05 g, or less than 0.01 g of such sources of vitamin B12 per 50 g of lipid-free biomass. In some embodiments, the culture medium further comprises less than 1 g of yeast extract per 50 g of lipid-free biomass, less than 0.8 g of yeast extract per 50 g of lipid-free biomass, less than 0.5 g of yeast extract per 50 g of lipid-free biomass, less than 0.3 g of yeast extract per 50 g of lipid-free biomass, less than 0.1 g of yeast extract per 50 g of lipid-free biomass, less than 0.05 g of yeast extract per 50 g of lipid-free biomass, or less than 0.01 g of yeast extract per 50 g of lipid-free biomass. As used herein, the term "lipid-free biomass" refers to the target fat-free dry cell weight of the microorganism after cultivation.

In some embodiments, the EPA concentration of the biomass grown in a culture medium comprising a lower vitamin B12 level (for example, in a culture medium comprising less than 0.1 mg/L, less than 0.05 mg/L, less than 0.01 mg/L, less than 0.005 mg/L, less than 0.001 mg/L, less than 0.0005 mg/L, less than 0.0001 mg/L, or no vitamin B12) is at least 10%, at least 25%, at least 50%, at least 75%, at least 100%, at least 150%, at least 200%, at least 250%, at least 300%, at least 350%, at least 400%, at least 450%, at least 500%, at least 550%, at least 600%, at least 650%, or at least 700% higher than the EPA concentration in a biomass obtained from the microorganism grown in a culture medium comprising higher vitamin B 12 levels (for example, in a culture medium comprising at least 0.1 mg/L, at least 0.05 mg/L, at least 0.01 mg/L, at least 0.005 mg/L, at least 0.001 mg/L, at least 0.0005 mg/L, at least 0.0001 mg/L, or at least 0.00005 mg/L vitamin B12, respectively). For example, the EPA concentration of the biomass grown in a culture medium containing no vitamin B12 is at least 10%, at least 25%, at least 50%, at least 75%, at least 100%, at least 150%, at least 200%, at least 250%, at least 300%, at least 350%, at least 400%, at least 450%, at least 500%, at least 550%, at least 600%, at least 650%, or at least 700% higher than the EPA concentration in a biomass obtained from the microorganism grown in a culture medium comprising vitamin B12 (such as at least 0.0001 mg/L vitamin B12).

In some embodiments, the EPA concentration of the biomass grown in a culture medium comprising lower vitamin B 12 levels (for example, in a culture medium comprising less than 0.1 mg/L, less than 0.05 mg/L, less than 0.01 mg/L, less than 0.005 mg/L, less than 0.001 mg/L, less than 0.0005 mg/L, less than 0.0001 mg/L, or no vitamin B12) under an ambient $CO_2$ level is at least 100%, at least 200%, at least 300%, at least 400%, or at least 500% higher than the EPA concentration in a biomass obtained from the microorganism grown in a culture medium comprising higher vitamin B 12 levels (for example, in a culture medium comprising at least 0.1 mg/L, at least 0.05 mg/L, at least 0.01 mg/L, at least 0.005 mg/L, at least 0.001 mg/L, at least 0.0005 mg/L, at least 0.0001 mg/L, or at least 0.00005 mg/L vitamin B12, respectively) under an ambient $CO_2$ level. In some embodiments, the EPA concentration of the biomass grown in a culture medium comprising lower vitamin B12 levels under an ambient $CO_2$ level is 100% to 700%, 150% to 650%, 200% to 600%, 250% to 550%, or 300% to 500% higher than the EPA concentration in a biomass obtained from the microorganism grown in a culture medium comprising higher vitamin B12 levels under an ambient $CO_2$ level. In some embodiments, the EPA concentration of the biomass grown in a culture medium comprising lower vitamin B12 levels under high $CO_2$ level (for example, a dissolved $CO_2$ level of at least 5%, at least 10%, at least 15%, or at least 20%) is at least 5%, at least 10%, at least 15%, at least 20%, at least 25%, at least 30%, at least 40%, at least 50%, at least 60%, at least 70%, at least 80%, at least 90%, or at least 100% higher than the EPA concentration in a biomass obtained from the microorganism grown in a culture medium comprising higher vitamin B12 levels under a high $CO_2$ level. In some embodiments, the EPA concentration of the biomass grown in a culture medium comprising lower vitamin B12 levels under high $CO_2$ level (for example, a dissolved $CO_2$ level of at least 5%, at least 10%, at least 15%, or at least 20%) is 5% to 200%, 10% to 175%, 15% to 150%, 20% to 125%, or 25% to 100% higher than the EPA concentration in a biomass obtained from the microorganism grown in a culture medium comprising higher vitamin B 12 levels under a high $CO_2$ level. For example, the EPA concentration of the biomass grown in a culture medium comprising no vitamin B12 under an ambient $CO_2$ level is at least 100%, at least 200%, at least 300%, at least 400%, or at least 500% higher than the EPA concentration in a biomass obtained from the microorganism grown in a culture medium comprising vitamin B12 (such as at least 0.0001 mg/L vitamin B12) under an ambient $CO_2$ level. As another example, the EPA concentration of the biomass grown in a culture medium comprising no vitamin B12 under a dissolved $CO_2$ level of at least 10% is at least 5%, at least 10%, at least 15%, at least 20%, at least 25%, at least 30%, at least 40%, at least 50%, at least 60%, at least 70%, at least 80%, at least 90%, or at least 100% higher than the EPA concentration in a biomass obtained from the microorganism grown in a culture medium comprising vitamin B12 (such as at least 0.0001 mg/L vitamin B12) under a dissolved $CO_2$ level of at least 10%.

In some embodiments, the EPA concentration is increased by at least 100%, at least 200%, at least 300%, at least 400%, or at least 500% in the biomass of a microorganism grown in a culture medium having less than 0.1 mg/L vitamin B12 compared to the same microorganism grown in a culture medium having greater than 0.1 mg/L vitamin B12. In some embodiments, the EPA concentration is increased by at least 100%, at least 200%, at least 300%, at least 400%, or at least 500% in the biomass of a microorganism grown in a culture medium having less than 0.01 mg/L vitamin B12 compared to the same microorganism grown in a culture medium having greater than 0.01 mg/L vitamin B12. In some embodiments, the EPA concentration is increased by at least 100%, at least 200%, at least 300%, at least 400%, or at least 500% in the biomass of a microorganism grown in a culture medium having less than 0.001 mg/L vitamin B12 compared to the same microorganism grown in a culture medium having greater than 0.001 mg/L vitamin B12. In further embodiments, the EPA concentration is increased by at least 100%, at least 200%, at least 300%, at least 400%, or at least 500% in the biomass of a microorganism grown in a culture medium having less than 0.0001 mg/L vitamin B12 compared to the same microorganism grown in a culture medium having greater than 0.0001 mg/L vitamin B12. In some embodiments, the EPA concentration is increased by at least 100%, at least 200%, at least 300%, at least 400%, or at least 500% in the biomass of a microorganism grown in a culture medium having no vitamin B12 compared to the same microorganism grown in a culture medium containing an amount of vitamin B12. The determination of the increase in EPA concentration in the biomass can be made by growing a microorganism in a culture medium having higher amounts of vitamin B12, growing the same microorganism in a culture medium having lower amounts of vitamin B12, and comparing the EPA concentration in the biomass resulting from each culture. In this determination, the content of the culture media having lower or higher amounts of vitamin B12 are the same except for their level of vitamin B12.

In some embodiments, the EPA concentration of the biomass of the microorganism grown in a culture medium comprising at least 0.1 mg/L, at least 0.05 mg/L, at least 0.01 mg/L, at least 0.005 mg/L, at least 0.001 mg/L, at least 0.0005 mg/L, or at least 0.0001 mg/L vitamin B12 is at least 1%, at least 2%, at least 3%, at least 4%, or at least 5% EPA by weight of the total fatty acids. In some embodiments, the EPA concentration of the biomass of the microorganism grown in a culture medium comprising at least 0.1 mg/L, at least 0.05 mg/L, at least 0.01 mg/L, at least 0.005 mg/L, at least 0.001 mg/L, at least 0.0005 mg/L, or at least 0.0001 mg/L vitamin B12 is 1% to 50%, 1% to 40%, 1% to 30%, 1% to 20%, 2% to 50%, 2% to 40%, 2% to 30%, or 2% to 20% EPA by weight of the total fatty acids.

Cobalt in Culture Medium

In some embodiments, the invention provides methods of making a biomass of a microorganism having increased concentration of EPA, comprising growing the microorganism in a culture medium comprising less than 0.1 mg/L cobalt to produce a biomass. In some embodiments, the culture medium comprises less than 0.05 mg/L, less than 0.01 mg/L, less than 0.005 mg/L, less than 0.001 mg/L, less than 0.0005 mg/L, less than 0.0001 mg/L, or no cobalt.

In some embodiments, the culture medium further comprises less than 1 g of yeast extract per 50 g of lipid-free biomass, less than 0.8 g of yeast extract per 50 g of lipid-free biomass, less than 0.5 g of yeast extract per 50 g of lipid-free biomass, less than 0.3 g of yeast extract per 50 g of lipid-free biomass, less than 0.1 g of yeast extract per 50 g of lipid-free biomass, less than 0.05 g of yeast extract per 50 g of lipid-free biomass, or less than 0.01 g of yeast extract per 50 g of lipid-free biomass.

In some embodiments, the EPA concentration of the biomass grown in a culture medium comprising a lower cobalt level (for example, in a culture medium comprising less than 0.1 mg/L, less than 0.05 mg/L, less than 0.01 mg/L, less than 0.005 mg/L, less than 0.001 mg/L, less than 0.0005 mg/L, less than 0.0001 mg/L, or no cobalt) is at least 10%, at least 25%, at least 50%, at least 75%, at least 100%, at least 150%, at least 200%, at least 250%, at least 300%, at least 350%, at least 400%, at least 450%, at least 500%, at least 550%, at least 600%, at least 650%, or at least 700% higher than the EPA concentration in a biomass obtained from the microorganism grown in a culture medium comprising higher cobalt levels (for example, in a culture medium comprising at least 0.1 mg/L, at least 0.05 mg/L, at least 0.01 mg/L, at least 0.005 mg/L, at least 0.001 mg/L, at least 0.0005 mg/L, at least 0.0001 mg/L, or at least 0.00005 mg/L cobalt, respectively). For example, the EPA concentration of the biomass grown in a culture medium containing no cobalt is at least 10%, at least 25%, at least 50%, at least 75%, at least 100%, at least 150%, at least 200%, at least 250%, at least 300%, at least 350%, at least 400%, at least 450%, at least 500%, at least 550%, at least 600%, at least 650%, or at least 700% higher than the EPA concentration in a biomass obtained from the microorganism grown in a culture medium comprising cobalt (such as at least 0.0001 mg/L cobalt).

In some embodiments, the EPA concentration of the biomass grown in a culture medium comprising lower cobalt levels (for example, in a culture medium comprising less than 0.1 mg/L, less than 0.05 mg/L, less than 0.01 mg/L, less than 0.005 mg/L, less than 0.001 mg/L, less than 0.0005 mg/L, less than 0.0001 mg/L, or no cobalt) under an ambient $CO_2$ level is at least 100%, at least 200%, at least 300%, at least 400%, or at least 500% higher than the EPA concentration in a biomass obtained from the microorganism grown in a culture medium comprising higher cobalt levels (for example, in a culture medium comprising at least 0.1 mg/L, at least 0.05 mg/L, at least 0.01 mg/L, at least 0.005 mg/L, at least 0.001 mg/L, at least 0.0005 mg/L, at least 0.0001 mg/L, or at least 0.00005 mg/L cobalt, respectively) under an ambient $CO_2$ level. In some embodiments, the EPA concentration of the biomass grown in a culture medium comprising lower cobalt levels under an ambient $CO_2$ level is 100% to 700%, 150% to 650%, 200% to 600%, 250% to 550%, or 300% to 500% higher than the EPA concentration in a biomass obtained from the microorganism grown in a culture medium comprising higher cobalt levels under an ambient $CO_2$ level. In some embodiments, the EPA concentration of the biomass grown in a culture medium comprising lower cobalt levels under high $CO_2$ level (for example, a dissolved $CO_2$ level of at least 5%, at least 10%, at least 15%, or at least 20%) is at least 5%, at least 10%, at least 15%, at least 20%, at least 25%, at least 30%, at least 40%, at least 50%, at least 60%, at least 70%, at least 80%, at least 90%, or at least 100% higher than the EPA concentration in a biomass obtained from the microorganism grown in a culture medium comprising higher cobalt levels under a high $CO_2$ level. In some embodiments, the EPA concentration of the biomass grown in a culture medium comprising lower cobalt levels under high $CO_2$ level (for example, a dissolved $CO_2$ level of at least 5%, at least 10%, at least 15%, or at least 20%) is 5% to 200%, 10% to 175%, 15% to 150%, 20% to 125%, or 25% to 100% higher than the EPA concentration in a biomass obtained from the microorganism grown in a culture medium comprising higher cobalt levels under a high $CO_2$ level. For example, the EPA concentration of the biomass grown in a culture medium comprising no cobalt under an ambient $CO_2$ level is at least 100%, at least 200%, at least 300%, at least 400%, or at least 500% higher than the EPA concentration in a biomass obtained from the microorganism grown in a culture medium comprising cobalt (such as at least 0.0001 mg/L cobalt) under an ambient $CO_2$ level. As another example, the EPA concentration of the biomass grown in a culture medium comprising no cobalt under a dissolved $CO_2$ level of at least 10% is at least 5%, at least 10%, at least 15%, at least 20%, at least 25%, at least 30%, at least 40%, at least 50%, at least 60%, at least 70%, at least 80%, at least 90%, or at least 100% higher than the EPA concentration in a biomass obtained from the microorganism grown in a culture medium comprising cobalt (such as at least 0.0001 mg/L cobalt) under a dissolved $CO_2$ level of at least 10%.

In some embodiments, the EPA concentration is increased by at least 100%, at least 200%, at least 300%, at least 400%, or at least 500% in the biomass of a microorganism grown in a culture medium having less than 0.1 mg/L cobalt compared to the same microorganism grown in a culture medium having greater than 0.1 mg/L cobalt. In some embodiments, the EPA concentration is increased by at least 100%, at least 200%, at least 300%, at least 400%, or at least 500% in the biomass of a microorganism grown in a culture medium having less than 0.01 mg/L cobalt compared to the same microorganism grown in a culture medium having greater than 0.01 mg/L cobalt. In some embodiments, the EPA concentration is increased by at least 100%, at least 200%, at least 300%, at least 400%, or at least 500% in the biomass of a microorganism grown in a culture medium having less than 0.001 mg/L cobalt compared to the same microorganism grown in a culture medium having greater than 0.001 mg/L cobalt. In further embodiments, the EPA concentration is increased by at least 100%, at least 200%, at least 300%, at least 400%, or at least 500% in the biomass of a microorganism grown in a culture medium having less than 0.0001 mg/L cobalt compared to the same microorganism grown in a culture medium having greater than 0.0001 mg/L cobalt. In some embodiments, the EPA concentration is increased by at least 100%, at least 200%, at least 300%, at least 400%, or at least 500% in the biomass of a microorganism grown in a culture medium having no cobalt compared to the same microorganism grown in a culture medium containing an amount of cobalt. The determination of the increase in EPA concentration in the biomass can be made by growing a microorganism in a culture medium having higher amounts of cobalt, growing the same microorganism in a culture medium having lower amounts of cobalt, and comparing the EPA concentration in the biomass resulting from each culture. In this determination, the content of the culture media having lower or higher amounts of cobalt are the same except for their level of cobalt.

In some embodiments, the EPA concentration of the biomass of the microorganism grown in a culture medium comprising at least 0.1 mg/L, at least 0.05 mg/L, at least 0.01 mg/L, at least 0.005 mg/L, at least 0.001 mg/L, at least 0.0005 mg/L, or at least 0.0001 mg/L cobalt is at least 1%, at least 2%, at least 3%, at least 4%, or at least 5% EPA by weight of the total fatty acids. In some embodiments, the EPA concentration of the biomass of the microorganism grown in a culture medium comprising at least 0.1 mg/L, at least 0.05 mg/L, at least 0.01 mg/L, at least 0.005 mg/L, at least 0.001 mg/L, at least 0.0005 mg/L, or at least 0.0001 mg/L cobalt is 1% to 50%, 1% to 40%, 1% to 30%, 1% to 20%, 2% to 50%, 2% to 40%, 2% to 30%, or 2% to 20% EPA by weight of the total fatty acids.

The culture medium containing low amounts of vitamin B 12, yeast extract, and/or cobalt could further comprise a dissolved $CO_2$ level of at least 5%, at least 10%, at least 15%, or at least 20%. The present invention is directed to an isolated biomass of the methods disclosed herein, as well as to a microbial oil extracted from the biomass of the methods.

The present invention is directed to an isolated culture comprising any of the microorganisms of the invention or mixtures thereof.

The present invention is directed to a food product, cosmetic, or pharmaceutical composition for a non-human animal or human, comprising any of the microorganisms or biomasses of the invention or mixtures thereof.

The present invention is directed to a microbial oil comprising at least about 20% by weight eicosapentaenoic acid and less than about 5% by weight each of arachidonic acid, docosapentaenoic acid n-6, oleic acid, linoleic acid, linolenic acid, eicosenoic acid, erucic acid, and stearidonic acid. In some embodiments, the microbial oil further comprises at least about 25% by weight docosahexaenoic acid.

The present invention is directed to a microbial oil comprising a triacylglycerol fraction of at least about 10% by weight, wherein at least about 12% by weight of the fatty acids in the triacylglycerol fraction is eicosapentaenoic acid, wherein at least about 25% by weight of the fatty acids in the triacylglycerol fraction is docosahexaenoic acid, and wherein less than about 5% by weight of the fatty acids in the triacylglycerol fraction is arachidonic acid.

The present invention is directed to a food product, cosmetic, or pharmaceutical composition for a non-human animal or human, comprising any of the microbial oils of the invention. In some embodiments, the food product is an infant formula. In some embodiments, the infant formula is suitable for premature infants. In some embodiments, the food product is a milk, a beverage, a therapeutic drink, a nutritional drink, or a combination thereof. In some embodiments, the food product is an additive for the non-human animal or human food. In some embodiments, the food product is a nutritional supplement. In some embodiments, the food product is an animal feed. In some embodiments, the animal feed is an aquaculture feed. In some embodiments, the animal feed is a domestic animal feed, a zoological animal feed, a work animal feed, a livestock feed, or a combination thereof.

The present invention is directed to a method for producing a microbial oil comprising omega-3 fatty acids, the method comprising: growing any of the isolated microorganisms of the invention or mixtures thereof in a culture to produce an oil comprising omega-3 fatty acids. In some embodiments, the method further comprises extracting the oil.

The present invention is directed to a method for producing a microbial oil comprising omega-3 fatty acids, the method comprising extracting an oil comprising omega-3 fatty acids from any of the biomasses of the invention. In some embodiments, the microbial oil is extracted using an organic solvent extraction process, for example hexane extraction. In some embodiments, the microbial oil is extracted using a solventless extraction process.

The present invention is directed to a microbial oil produced by a method of the invention.

The present invention is directed to a method for producing a biomass of the invention, comprising: growing any of the isolated microorganisms of the invention or mixtures thereof in a culture to produce a biomass.

The present invention is directed to a biomass produced by a method of the invention.

The present invention is directed to a method for producing a mutant strain of the invention, comprising: mutagenizing any of the microorganisms of the invention, and isolating the mutant strain.

The present invention is directed to use of any of the isolated microorganisms, biomasses, or microbial oils of the invention, or mixtures thereof, for the manufacture of a medicament for treatment of inflammation or a condition related thereto.

The present invention is directed to use of any of the isolated microorganisms, biomasses, or microbial oils of the invention, or mixtures thereof, for treatment of inflammation or a condition related thereto.

The present invention is directed to any of the isolated microorganisms, biomasses, or microbial oils of the invention, or mixtures thereof, for use in treatment of inflammation or a condition related thereto.

The present invention is directed to a method for treating inflammation or a condition related thereto in a subject in need thereof, comprising administering to the subject any of the isolated microorganisms, biomasses, or microbial oils of the invention, or mixtures thereof, and a pharmaceutically acceptable carrier.

The present invention is directed to methods of producing microbial oils, and biomasses, from the microorganisms of the invention, and methods of using the microorganisms, biomasses, and microbial oils.

Microorganisms

In some embodiments, a microbial cell for use with the present invention is a microorganism of the phylum Labyrinthulomycota. In some embodiments, a microbial cell of the phylum Labyrinthulomycota is a thraustochytrid, such as a *Schizochytrium* or *Thraustochytrium*. According to the present invention, the term "thraustochytrid" refers to any member of the order Thraustochytriales, which includes the family Thraustochytriaceae, and the term "labyrinthulid" refers to any member of the order Labyrinthulales, which includes the family Labyrinthulaceae.

Members of the family Labyrinthulaceae were previously considered to be members of the order Thraustochytriales, but in more recent revisions of the taxonomic classification of such organisms, the family Labyrinthulaceae is now considered to be a member of the order Labyrinthulales. Both Labyrinthulales and Thraustochytriales are considered to be members of the phylum Labyrinthulomycota. Taxonomic theorists now generally place both of these groups of microorganisms with the algae or algae-like protists of the Stramenopile lineage. The current taxonomic placement of the thraustochytrids and labyrinthulids can be summarized as follows:

Realm: Stramenopila (Chromista)
Phylum: Labyrinthulomycota (Heterokonta)
    Class: Labyrinthulomycetes (Labyrinthulae)
        Order: Labyrinthulales
            Family: Labyrinthulaceae
        Order: Thraustochytriales
            Family: Thraustochytriaceae For purposes of the present invention, strains of microbial cells described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum*, and *striatum*), *Ulkenia* (Species: sp., *amoeboidea, kerguelensis, minuta, profunda, radiata, sailens, sarkariana, schizochytrops, visurgensis, yorkensis*, and sp. BP-5601), *Schizochytrium* (Species: sp., *aggregatum, limnaceum, mangrovei, minutum*, and *octosporum*), *Japonochytrium* (Species: sp., *marinum*), *Aplanochytrium* (Species: sp., *haliotidis, kerguelensis, profunda*, and *stocchinoi*), *Althornia* (Species: sp., *crouchii*), or *Elina* (Species: sp., *marisalba*, and *sinorifica*). For the purposes of this invention, species described within *Ulkenia* will be considered to be members of the genus *Thraustochytrium*. *Aurantiacochytrium* and *Oblogospora* are two additional genuses encompassed by the phylum Labyrinthulomycota in the present invention. In some embodiments, a microbial cell is of the genus *Thraustochystrium*, *Schizochytrium*, and mixtures thereof.

The invention is directed to isolated microorganisms and strains derived therefrom. A strain that is "derived" from an isolated microorganism of the invention can be a natural or artificial derivative such as, for example, a mutant, variant, or recombinant strain. The term "isolated" as used herein does not necessarily reflect the extent to which an isolate has been purified, but indicates isolation or separation from a native form or native environment. An isolate can include, but is not limited to, an isolated microorganism, an isolated biomass, an isolated culture, an isolated microbial oil, and an isolated sequence (such as an isolated polynucleotide sequence disclosed herein). The term "microorganism" as used herein includes, but is not limited to, the terms "microalgae," "thraustochytrid," and taxonomic classifications associated with any of the deposited microorganisms described herein. The terms "Thraustochytriales," "thraustochytrid," "*Schizochytrium*," and "*Thraustochytrium*" as used in reference to any of the microorganisms of the invention, including the deposited microorganisms described herein, are based on present taxonomic classifications including available phylogenetic information and are not intended to be limiting in the event that the taxonomic classifications are revised after the filing date of the present application.

In some embodiments, the invention is directed to an isolated microorganism of the species deposited under ATCC Accession No. PTA-10212. The isolated microorganism associated with ATCC Accession No. PTA-10212 is also known herein as *Thraustochytrium* sp. ATCC PTA-10212. The isolated microorganism associated with ATCC Accession No. PTA-10212 was deposited under the Budapest Treaty on Jul. 14, 2009 at the American Type Culture Collection, Patent Depository, 10801 University Boulevard, Manassas, Va. 20110-2209. In some embodiments, the invention is directed to an isolated strain deposited under ATCC Accession No. PTA-10212. In some embodiments the invention is directed to an isolated microorganism deposited under ATCC Accession No. PTA-10212, PTA-10213, PTA-10214, PTA-10215, PTA-10208, PTA-10209, PTA-10210, or PTA-10211.

In some embodiments, the invention is directed to an isolated microorganism having the characteristics of the species deposited under ATCC Accession No. PTA-10212 or a strain derived therefrom. The characteristics of the species deposited under ATCC Accession No. PTA-10212 can include its growth and phenotypic properties (examples of phenotypic properties include morphological and reproductive properties), its physical and chemical properties (such as dry weights and lipid profiles), its gene sequences, and combinations thereof, in which the characteristics distinguish the species over previously identified species. In some embodiments, the invention is directed to an isolated microorganism having the characteristics of the species deposited under ATCC Accession No. PTA-10212, wherein the characteristics include an 18s rRNA comprising the polynucleotide sequence of SEQ ID NO:1 or a polynucleotide sequence having at least 94%, 95%, 96%, 97%, 98%, or 99% identity to SEQ ID NO:1, the morphological and reproductive properties of the species deposited under ATCC Accession No. PTA-10212, and the fatty acid profiles of the species deposited under ATCC Accession No. PTA-10212. In some embodiments, isolated microorganisms of the invention have phenotypic properties substantially identical to those of the microorganism deposited under ATCC Accession No. PTA-10212. In some embodiments, isolated microorganisms of the invention have growth properties substantially identical to those of the microorganism deposited under ATCC Accession No. PTA-10212. In some embodiments, the invention is directed to an isolated microorganism comprising an 18s rRNA comprising the polynucleotide sequence of SEQ ID NO:1 or a polynucleotide sequence having at least 94%, 95%, 96%, 97%, 98%, or 99% identity to SEQ ID NO:1. In some embodiments, the invention is directed to an isolated microorganism comprising an 18s rRNA polynucleotide sequence that has at least 94% identity to the 18s rRNA polynucleotide sequence of the microorganism deposited under ATCC Accession No. PTA-10212.

In some embodiments, the invention is directed to a mutant strain of the microorganism deposited under ATCC Accession No. PTA-10212. In further embodiments, the mutant strain is a strain deposited under ATCC Accession No. PTA-10213, PTA-10214, or PTA-10215. The microorganisms associated with ATCC Accession Nos. PTA-10213, PTA-10214, and PTA-10215 were deposited under the Budapest Treaty on Jul. 14, 2009 at the American Type Culture Collection, Patent Depository, 10801 University Boulevard, Manassas, Va. 20110-2209.

In some embodiments, the invention is directed to an isolated microorganism of the species deposited under ATCC Accession No. PTA-10208. The isolated microorganism associated with ATCC Accession No. PTA-10208 is also known herein as *Schizochytrium* sp. ATCC PTA-10208. The microorganism associated with ATCC Accession No. PTA-10208 was deposited under the Budapest Treaty on Jul. 14, 2009 at the American Type Culture Collection, Patent Depository, 10801 University Boulevard, Manassas, Va. 20110-2209. In some embodiments, the invention is directed to an isolated strain deposited under ATCC Accession No. PTA-10208.

In some embodiments, the invention is directed to an isolated microorganism of the species deposited under ATCC Accession No. PTA-10208, wherein the total fatty acids produced by the microorganism comprises more than about 10%, more than about 11%, more than about 12%, more than about 13%, more than about 14%, more than about 15%, more than about 16%, more than about 17%, more than about 18%, more than about 19%, or more than about 20% by weight EPA. In some embodiments, the invention is directed to an isolated microorganism of the species deposited under ATCC Accession No. PTA-10208, wherein the total fatty acids produced by the microorganism comprises about 10% to about 55%, about 10% to about 50%, about 10% to about 45%, about 10% to about 40%, about 10% to about 35%, about 10% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, about 20% to about 40%, about 20% to about 35%, or about 20% to about 30% by weight EPA.

In some embodiments, the invention is directed to an isolated microorganism having the characteristics of the species deposited under ATCC Accession No. PTA-10208, wherein the total fatty acids produced by the microorganism comprises more than about 10% by weight eicosapentaenoic acid. The characteristics of the microorganism deposited under ATCC Accession No. PTA-10208 include its growth and phenotypic properties (examples of phenotypic properties include morphological and reproductive properties), its physical and chemical properties (such as dry weights and lipid profiles), its gene sequences, and combinations thereof, in which the characteristics distinguish the species over previously identified species. In some embodiments, the invention is directed to an isolated microorganism having the characteristics of the species deposited under ATCC Accession No. PTA-10212, wherein the characteristics include an 18s rRNA comprising the polynucleotide sequence of SEQ ID NO:2, the morphological and reproductive properties of the species deposited under ATCC Accession No. PTA-10208, and the fatty acid profiles of the species deposited under ATCC Accession No. PTA-10208. In some embodiments, isolated microorganisms of the invention have physical and chemical properties substantially identical to those of the microorganism deposited under ATCC Accession No. PTA-10208.

In some embodiments, the invention is directed to a mutant strain of the microorganism deposited under ATCC Accession No. PTA-10208. In further embodiments, the mutant strain is a strain deposited under ATCC Accession No. PTA-10209, PTA-10210, or PTA-10211. The microorganisms associated with ATCC Accession Nos. PTA-10209, PTA-10210, and PTA-10211 were deposited under the Budapest Treaty on Sep. 25, 2009 at the American Type Culture Collection, Patent Depository, 10801 University Boulevard, Manassas, Va. 20110-2209.

In some embodiments, the invention is directed to an isolated microorganism of the invention that produces a triacylglycerol fraction, wherein the EPA content of the triacylglycerol fraction is at least about 12%, at least about 13%, at least about 14%, at least about 15%, at least about 16%, at least about 17%, at least about 18%, at least about 19%, or at least about 20% by weight. In some embodiments, the invention is directed to an isolated microorganism that produces a triacylglycerol fraction, wherein the EPA content of the triacylglycerol fraction is about 12% to about 55%, about 12% to about 50%, about 12% to about 45%, about 12% to about 40%, about 12% to about 35%, about 12% to about 30%, about 15% to about 45%, about 15% to about 40%, about 15% to about 35%, about 15% to about 30%, or about 20% to about 30% by weight.

In some embodiments, the invention is directed to a mutant, variant, or recombinant of an isolated microorganism of the invention that produces a triacylglycerol fraction, wherein the EPA content of the triacylglycerol fraction is at least about 10%, at least about 11%, at least about 12%, at least about 13%, at least about 14%, at least about 15%, at least about 16%, at least about 17%, at least about 18%, at least about 19%, or at least about 20% by weight. In some embodiments, the invention is directed to a mutant, variant, or recombinant of an isolated microorganism of the invention that produces a triacylglycerol fraction, wherein the EPA content of the triacylglycerol fraction is about 12% to about 55%, about 12% to about 50%, about 12% to about 45%, about 12% to about 40%, about 12% to about 35%, about 12% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, about 20% to about 40%, about 20% to about 35%, or about 20% to about 30% by weight. Mutant strains can be produced by well-known procedures. Common procedures include irradiation, treatment at high temperatures, and treatment with a mutagen. Variant strains can be other naturally occurring isolates and/or sub-isolates of the species described herein. Recombinant strains can be produced by any well-known methods in molecular biology for the expression of exogenous genes or alteration of endogenous gene function or expression. In some embodiments, the mutant, variant, or recombinant strain produces a higher amount of omega-3 fatty acids, particularly EPA, than the wild-type strain. In some embodiments, the mutant, variant, or recombinant strain produces a lower amount of one or more fatty acids, such as lower amounts of DHA, ARA, DPA n-6, or combinations thereof. In some embodiments, the mutant, variant, or recombinant strain produces a larger dry cell weight per liter of culture than the wild-type strain. Such mutant, variant, or recombinant strains are examples of strains derived from an isolated microorganism of the invention.

The present invention is also directed to an isolated thraustochytrid microorganism having the characteristics of the thraustochytrid species deposited under ATCC Accession No. PTA-9695, wherein the total fatty acids produced by said microorganism or strain derived therefrom comprise about 10% or less by weight eicosapentaenoic acid.

The present invention is also directed to an isolated thraustochytrid microorganism, or a strain derived therefrom, comprising a triglyceride fraction, wherein the docosahexaenoic acid content of the triglyceride fraction is at least about 40% by weight, wherein the docosapentaenoic acid n-6 content of the triglyceride fraction is from at least about 0.5% by weight to about 6% by weight, and wherein the total fatty acids produced by said microorganism or strain derived therefrom comprise about 10% or less by weight eicosapentaenoic acid.

The present invention is also directed to an isolated thraustochytrid microorganism of the same species as the thraustochytrid deposited under ATCC Accession No. PTA-9695, or a strain derived therefrom, wherein the total fatty acids produced by said microorganism or strain derived therefrom comprise about 10% or less by weight eicosapentaenoic acid.

In some embodiments, the strain derived from the isolated thraustochytrid microorganism of the invention is a mutant strain.

The present invention is also directed to an isolated microorganism deposited under ATCC Accession No. PTA-9695, PTA-9696, PTA-9697, or PTA-9698.

The present invention is also directed to a thraustochytrid biomass comprising any one of the thraustochytrid microorganisms of the invention or mixtures thereof.

The present invention is also directed to an isolated thraustochytrid biomass, wherein at least about 50% by weight of the dry cell weight of the biomass are fatty acids, and wherein at least about 50% by weight of the fatty acids are omega-3 fatty acids. In some embodiments, at least about 50% by weight of the fatty acids is docosahexaenoic acid. The present invention is also directed to an isolated thraustochytrid biomass, wherein at least about 25% by weight of the dry cell weight of the biomass is docosahexaenoic acid.

In some embodiments, the present invention is also directed to an isolated thraustochytrid biomass wherein about 10% or less by weight of the fatty acids is eicosapentaenoic acid, and wherein the weight ratio of docosahexaenoic acid to eicosapentaenoic acid is at least about 5:1.

In some embodiments, the present invention is also directed to an isolated thraustochytrid biomass wherein about 1.5% or less by weight of the fatty acids is arachidonic acid, and wherein the weight ratio of docosahexaenoic acid to arachidonic acid is at least about 20:1.

In some embodiments, the present invention is also directed to an isolated thraustochytrid biomass comprising docosahexaenoic acid and docosapentaenoic acid n-6 in a weight ratio of at least about 10:1. In some embodiments, the invention is directed to a thraustochytrid of the species deposited under ATCC Accession No. PTA-9695. The isolated thraustochytrid is also known herein as *Schizochytrium* sp. ATCC PTA-9695. The thraustochytrid associated with ATCC Accession No. PTA-9695 was deposited under the Budapest Treaty on Jan. 7, 2009 at the American Type Culture Collection, Patent Depository, 10801 University Boulevard, Manassas, Va. 20110-2209.

In some embodiments, the invention is directed to an isolated thraustochytrid strain deposited under ATCC Accession No. PTA-9695. In some embodiments, the invention is directed to an isolated thraustochytrid microorganism of the same species as the thraustochytrid deposited under ATCC Accession No. PTA-9695.

In some embodiments, the invention is directed to an isolated thraustochytrid having the characteristics of the species deposited under ATCC Accession No. PTA-9695 or a strain derived therefrom. The characteristics of the thraustochytrid species deposited under ATCC Accession No. PTA-9695 include its growth and phenotypic properties (examples of phenotypic properties include morphological and reproductive properties), its physical and chemical properties (such as dry weights and lipid profiles), and its gene sequences. In some embodiments, the isolated thraustochytrids of the invention have substantially identical phenotypic properties of the thraustochytrid deposited under ATCC Accession No. PTA-9695. In some embodiments, the isolated thraustochytrids of the invention have substantially identical growth properties of the thraustochytrid deposited under ATCC Accession No. PTA-9695.

In some embodiments, the invention is directed to a mutant, variant, or recombinant of an isolated thraustochytrid of the invention, wherein the total fatty acids produced by the mutant, variant, or recombinant comprise about 10% or less by weight eicosapentaenoic acid. Mutant strains can be produced by well-known procedures. Common procedures include irradiation; treatment at high temperatures; and treatment with a mutagen. Variant strains can be other naturally occurring isolates and/or subisolates of the species described herein. Recombinant strains can be produced by any well-known methods in molecular biology for the expression of exogenous genes or the alteration of endogenous gene function or expression. In some embodiments, the mutant, variant, or recombinant strain produces a higher amount of omega-3 fatty acids, including DHA and/or EPA, than the wild-type strain. In some embodiments, the mutant, variant, or recombinant strain produces a lower amount of one or more fatty acids, such as lower amounts of EPA, ARA, DPA n-6, or combinations thereof. In some embodiments, the mutant, variant, or recombinant strain produces a larger dry cell weight per liter of culture than the wild-type strain. Such mutant, variant, or recombinant strains are examples of strains derived from an isolated thraustochytrid of the invention.

In some embodiments, the invention is directed to a mutant strain of the thraustochytrid deposited under ATCC Accession No. PTA-9695. In further embodiments, the mutant strain is a strain deposited under ATCC Accession Nos. PTA-9696, PTA-9697, or PTA-9698. The thraustochytrid strains associated with ATCC Accession Nos. PTA-9696, PTA-9697, and PTA-9698 were deposited under the Budapest Treaty on Jan. 7, 2009 at the American Type Culture Collection, Patent Depository, University Boulevard, Manassas, Va. 20110-2209. These deposited mutant strains are derivatives of the thraustochytrid deposited under ATCC Accession No. PTA-9695.

In some embodiments, an isolated thraustochytrid of the invention, including mutants, variants, or recombinants thereof, comprises a fatty acid profile in one or more fractions isolated from the thraustochytrid. The one or more fractions isolated from the thraustochytrid includes the total fatty acid fraction, the sterol esters fraction, the triglyceride fraction, the free fatty acid fraction, the sterol fraction, the diglyceride fraction, the polar fraction (including the phospholipid fraction), and combinations thereof.

The present invention is also directed to an isolated thraustochytrid culture comprising any one of the thraustochytrid microorganisms of the invention or mixtures thereof. In some embodiments, the culture comprises at least about 5% dissolved oxygen.

The present invention is also directed to a food product, cosmetic, or pharmaceutical composition for animals or humans comprising any one of the thraustochytrid microorganisms or biomasses of the invention or mixtures thereof.

The present invention is also directed to a microbial oil comprising a triglyceride fraction of at least about 70% by weight, wherein the docosahexaenoic acid content of the triglyceride fraction is at least about 50% by weight, and wherein the docosapentaenoic acid n-6 content of the triglyceride fraction is from about 0.5% by weight to about 6% by weight. In some embodiments, the microbial oil further comprises an arachidonic acid content of the triglyceride fraction of about 1.5% or less by weight.

The present invention is also directed to a microbial oil comprising a triglyceride fraction of at least about 70% by weight, wherein the docosahexaenoic acid content of the triglyceride fraction is at least about 40% by weight, wherein the docosapentaenoic acid n-6 content of the triglyceride fraction is from at least about 0.5% by weight to about 6% by weight, and wherein the ratio of docosahexaenoic acid to docosapentaenoic acid n-6 is greater than about 6:1.

The present invention is also directed to a microbial oil comprising a triglyceride fraction of at least about 70% by weight, wherein the docosahexaenoic acid content of the triglyceride fraction is at least about 60% by weight.

In some embodiments, at least about 20% of the triglycerides in the triglyceride fraction of the microbial oil contain docosahexaenoic acid at two positions in the triglyceride selected from any two of the sn-1, sn-2, and sn-3 positions. In some embodiments, at least about 5% of the triglycerides in the triglyceride fraction of the microbial oil contain docosahexaenoic acid at all three of the sn-1, sn-2, and sn-3 positions in the triglyceride.

In some embodiments, an isolated microorganism of the invention, including mutants, variants, and recombinants thereof, comprises a fatty acid profile in one or more fractions isolated from the microorganism. The one or more fractions isolated from the microorganism include the total fatty acid fraction, the sterol esters fraction, the triacylglycerol fraction, the free fatty acid fraction, the sterol fraction, the diacylglycerol fraction, the polar fraction (including the phospholipid fraction), and combinations thereof. The fatty acid profile for a specific fraction can include any of the fatty acid profiles associated with the specific fraction as disclosed herein.

The invention is directed to a method of producing a mutant comprising mutagenizing any of the microorganisms of the invention and isolating the mutant strain.

Cultures and Isolated Biomasses

The invention is directed to a culture comprising one or more isolated microorganisms of the invention. Various fermentation parameters for inoculating, growing, and recovering microflora, such as microalgae and thraustochytrids, are known in the art. See, e.g., U.S. Pat. No. 5,130,242, incorporated by reference herein in its entirety. Liquid or solid media can contain natural or artificial sea water. Carbon sources for heterotrophic growth include, but are not limited to, glucose, fructose, xylose, saccharose, maltose, soluble starch, molasses, fucose, glucosamine, dextran, fats, oils, glycerol, sodium acetate, and mannitol. Nitrogen sources include, but are not limited to, peptone, yeast extract, polypeptone, malt extract, meat extract, casamino acid, corn steep liquor, organic nitrogen sources, sodium glutamate, urea, inorganic nitrogen sources, ammonium acetate, ammonium sulfate, ammonium chloride, and ammonium nitrate.

A typical media for growth of the microorganism deposited under ATCC Accession No. PTA-10212 is shown in Table 1:

TABLE 1

| PTA-10212 Vessel Media | | | |
|---|---|---|---|
| Ingredient | | concentration | ranges |
| $Na_2SO_4$ | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| $MgSO_4 \cdot 7H_2O$ | g/L | 5.0 | 0-10, 2-8, or 3-6 |
| $(NH_4)_2SO_4$ | g/L | 0.44 | 0-10, 0.25-5, or 0.05-3 |
| $MSG \cdot 1H_2O$ | g/L | 6.0 | 0-10, 4-8, or 5-7 |
| $CaCl_2$ | g/L | 0.29 | 0.1-5, 0.15-3, or 0.2-1 |
| T 154 (yeast extract) | g/L | 6.0 | 0-20, 0.1-10, or 1-7 |
| $KH_2PO_4$ | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| $FeSO_4 \cdot 7H_2O$ | mg/L | 10.30 | 0.1-100, 1-50, or 5-25 |
| $MnCl_2 \cdot 4H_2O$ | mg/L | 3.10 | 0.1-100, 1-50, or 2-25 |
| $ZnSO_4 \cdot 7H_2O$ | mg/L | 3.10 | 0.01-100, 1-50, or 2-25 |
| $CoCl_2 \cdot 6H_2O$ | mg/L | 0.04 | 0-1, 0.001-0.1, or 0.01-0.1 |
| $Na_2MoO_4 \cdot 2H_2O$ | mg/L | 0.04 | 0.001-1, 0.005-0.5, or 0.01-0.1 |
| $CuSO_4 \cdot 5H_2O$ | mg/L | 2.07 | 0.1-100, 0.5-50, or 1-25 |
| $NiSO_4 \cdot 6H_2O$ | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B12 | mg/L | 0.16 | 0.01-100, 0.05-5, or 0.1-1 |
| Ca½-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |
| Nitrogen Feed: | | | |
| Ingredient | Concentration | | |
| $MSG \cdot 1H_2O$ | g/L | 17 | 0-150, 10-100, or 15-50 |

Typical cultivation conditions would include the following:

pH about 6.5-about 9.5, about 6.5-about 8.0, or about 6.8-about 7.8;

temperature: about 15-about 30 degrees Celsius, about 18-about 28 degrees Celsius, or about 21 to about 23 degrees Celsius;

dissolved oxygen: about 0.1-about 100% saturation, about 5-about 50% saturation, or about 10-about 30% saturation; and/or glycerol controlled @: about 5-about 50 g/L, about 10-about 40 g/L, or about 15-about 35 g/L.

In some embodiments, the microorganism deposited under ATCC Accession No. PTA-10212, or a mutant, variant, or recombinant thereof, grows heterotrophically on glycerol as the carbon source but does not grow on glucose as the carbon source.

A typical media for growth of the microorganism deposited under ATCC Accession No. PTA-10208 is shown in Table 2:

TABLE 2

PTA-10208 Vessel Media

| Ingredient | | concentration | ranges |
|---|---|---|---|
| $Na_2SO_4$ | g/L | 8.8 | 0-25, 2-20, or 3-10 |
| NaCl | g/L | 0.625 | 0-25, 0.1-10, or 0.5-5 |
| KCl | g/L | 1.0 | 0-5, 0.25-3, or 0.5-2 |
| $MgSO_4 \cdot 7H_2O$ | g/L | 5.0 | 0-10, 2-8, or 3-6 |
| $(NH_4)_2SO_4$ | g/L | 0.42 | 0-10, 0.25-5, or 0.05-3 |
| $CaCl_2$ | g/L | 0.29 | 0.1-5, 0.15-3, or 0.2-1 |
| T 154 (yeast extract) | g/L | 1.0 | 0-20, 0.1-10, or 0.5-5 |
| $KH_2PO_4$ | g/L | 1.765 | 0.1-10, 0.5-5, or 1-3 |
| Post autoclave (Metals) | | | |
| Citric acid | mg/L | 46.82 | 0.1-5000, 10-3000, or 40-2500 |
| $FeSO_4 \cdot 7H_2O$ | mg/L | 10.30 | 0.1-100, 1-50, or 5-25 |
| $MnCl_2 \cdot 4H_2O$ | mg/L | 3.10 | 0.1-100, 1-50, or 2-25 |
| $ZnSO_4 \cdot 7H_2O$ | mg/L | 9.3 | 0.01-100, 1-50, or 2-25 |
| $CoCl_2 \cdot 6H_2O$ | mg/L | 0.04 | 0-1, 0.001-0.1, or 0.01-0.1 |
| $Na_2MoO_4 \cdot 2H_2O$ | mg/L | 0.04 | 0.001-1, 0.005-0.5, or 0.01-0.1 |
| $CuSO_4 \cdot 5H_2O$ | mg/L | 2.07 | 0.1-100, 0.5-50, or 1-25 |
| $NiSO_4 \cdot 6H_2O$ | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| $Ca^{1/2}$-pantothenate | mg/L | 3.33 | 0.1-100, 0.1-50, or 1-10 |
| Biotin | mg/L | 3.58 | 0.1-100, 0.1-50, or 1-10 |
| Post autoclave (Carbon) | | | |
| Glucose | g/L | 30.0 | 5-150, 10-100, or 20-50 |
| Nitrogen Feed: | | | |
| Ingredient | Concentration | | |
| $NH_4OH$ | mL/L | 23.6 | 0-150, 10-100, or 15-50 |

Typical cultivation conditions would include the following:
pH about 6.5-about 8.5, about 6.5-about 8.0, or about 7.0-about 8.0;
temperature: about 17-about 30 degrees Celsius, about 20-about 28 degrees Celsius, or about 22 to about 24 degrees Celsius;
dissolved oxygen: about 2-about 100% saturation, about 5-about 50% saturation, or about 7-about 20% saturation; and/or
glucose controlled @: about 5-about 50 g/L, about 10-about 40 g/L, or about-20-about 35 g/L.

In some embodiments, the fermentation volume (volume of culture) is at least about 2 liters, at least about 10 liters, at least about 50 liters, at least about 100 liters, at least about 200 liters, at least about 500 liters, at least about 1000 liters, at least about 10,000 liters, at least about 20,000 liters, at least about 50,000 liters, at least about 100,000 liters, at least about 150,000 liters, at least about 200,000 liters, or at least about 250,000 liters. In some embodiments, the fermentation volume is about 2 liters to about 300,000 liters, about 2 liters, about 10 liters, about 50 liters, about 100 liters, about 200 liters, about 500 liters, about 1000 liters, about 10,000 liters, about 20,000 liters, about 50,000 liters, about 100,000 liters, about 150,000 liters, about 200,000 liters, about 250,000 liters, or about 300,000 liters.

In some embodiments, the invention is directed to an isolated biomass comprising a fatty acid profile of the invention. In some embodiments, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the dry cell weight of the biomass are fatty acids. In some embodiments, greater than about 20%, greater than about 25%, greater than about 30%, greater than about 35%, greater than about 40%, greater than about 45%, greater than about 50%, greater than about 55%, or greater than about 60% of the dry cell weight of the biomass are fatty acids. In some embodiments, about 20% to about 55%, about 20% to about 60%, about 20% to about 70%, about 20% to about 80%, about 30% to about 55%, about 30% to about 70%, about 30% to about 80%, about 40% to about 60%, about 40% to about 70%, about 40% to about 80%, about 50% to about 60%, about 50% to about 70%, about 50% to about 80%, about 55% to about 70%, about 55% to about 80%, about 60% to about 70%, or about 60% to about 80% by weight of the dry cell weight of the biomass are fatty acids. In some embodiments, the biomass comprises more than about 10%, at least about 12%, at least about 15%, at least about 20%, at least about 25%, at least about 30%, about least about 35%, at least about 40%, or at least about 45% by weight of the fatty acids as EPA. In some embodiments, the biomass comprises about 10% to about 55%, about 12% to about 55%, about 15% to about 55%, about 20% to about 55%, about 20% to about 40%, or about 20% to about 30% by weight of the fatty acids as EPA. In some embodiments, the biomass comprises a triacylglycerol fraction, wherein at least about 12%, at least about 13%, at least about 14%, at least about 15%, at least about 16%, at least about 17%, at least about 18%, at least about 19%, or at least about 20% by weight of the triacylglycerol fraction is EPA. In some embodiments, the biomass comprises a triacylglycerol fraction, wherein the EPA content of the triacylglycerol fraction is from at least about 12% to about 55%, about 12% to about 50%, about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, at least about 20% to about 40%, at least about 20% to about 35%, or about 20% to about 30% by weight. In some embodiments, at least about 20%, at least about 25%, at least about 30%, at least about 35%, at least about 40%, at least about 50%, or at least about 60% by weight of the dry cell weight of the biomass is DHA. In some embodiments, about 20% to about 60%, about 25% to about 60%, about 25% to about 50%, about 25% to about 45%, about 30% to about 50%, or about 35% to about 50% by weight of the dry cell weight of the biomass is DHA. In some embodiments, the biomass comprises about 10% or less, about 9% or less, about 8% or less, about 7% or less, about 6% or less, about 5% or less, about 4% or less, about 3% or less, about 2% or less, or about 1% or less by weight of the fatty acids as DHA. In some embodiments, the biomass comprises about 1% to about 10%, about 1% to about 5%, about 2% to about 5%, about 3% to about 5%, or about 3% to about 10% by weight of the fatty acids as DHA. In some embodiments, the biomass is substantially free of DHA. In some embodiments, the biomass comprises about 0.1% to less than about 5%, about 0.1% to about 4%, about 0.1% to about 3%, about 0.1% to about 2%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight of the fatty acids as ARA. In some embodiments, the biomass comprises less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight of the fatty acids as ARA. In some embodiments, the biomass is substantially free of ARA. In some embodiments, the biomass comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight of the fatty acids as DPA n-6. In some embodiments, the biomass comprises about 5% or less, less than about 5%, about 4% or less, about 3% or less, about 2% or less, about 1% or less, about 0.75% or less, about 0.6% or less, or about 0.5% or less by weight of the fatty acids as DPA n-6. In some embodiments, the biomass is substantially free of DPA n-6. In some embodiments, the biomass comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), or combinations thereof.

The characteristics of an isolated biomass of the invention are associated with endogenous or native properties of the isolated biomass rather than exogenously introduced materials. In some embodiments, the isolated biomass does not contain polyvinylpyrrolidone or is not isolated from a culture containing polyvinylpyrrolidone.

The present invention is directed to a method of producing a biomass. In some embodiments, the method for producing a biomass of the invention comprises growing any of the isolated microorganisms of the invention or mixtures thereof in a culture to produce a biomass. The present invention is directed to a biomass produced by the method.

In some embodiments the biomass comprises fatty acids wherein the fatty acids further comprises omega-3 polyunsaturated fatty acids wherein the omega-3 polyunsaturated fatty acids comprise DHA and EPA in an amount of about ≥90%, by weight, of the total amount of omega-3 polyunsaturated fatty acids and the amount of EPA, by weight, is from about 6% up to about 65% of the total amount of EPA and DHA. Particularly provided is a biomass wherein the amount of EPA, by weight, is from about 6% up to about 28% of the total amount of EPA and DHA. Further provided herein is a biomass wherein the amount of EPA, by weight, is from about 36% up to about 65 of the total amount of the EPA and DHA. More particularly provided is a biomass wherein the amount of EPA, by weight, is from about 28% to about 36% of the total amount of EPA and DHA.

Some embodiments provided herein comprise a biomass comprising fatty acids wherein the fatty acids further comprise DHA and EPA and the amount of EPA, by weight, is from about 15 up to about 60% of the total weight of EPA and DHA.

Some embodiments of the invention are further directed to a culture comprising a thraustochytrid, or a mutant strain, deposited under ATCC Accession No. PTA-9695. Various fermentation parameters for inoculating, growing, and recovering microflora are known in the art, such as described in U.S. Pat. No. 5,130,242. Any conventional medium for growth of thraustochytrids can be used. Liquid or solid mediums can contain natural or artificial sea water. Carbon sources include, but are not limited to, glucose, fructose, xylose, saccharose, maltose, soluble starch, molasses, fucose, glucosamine, dextran, fats, oils, glycerol, sodium acetate, and mannitol. Nitrogen sources include, but are not limited to, peptone, yeast extract, polypeptone, malt extract, meat extract, casamino acid, corn steep liquor, organic nitrogen sources, sodium glutamate, urea, inorganic nitrogen sources, ammonium acetate, ammonium sulfate, ammonium chloride, ammonium nitrate, sodium sulfate. A typical media is shown in Table 3:

TABLE 3

PTA-9695 Vessel Media

| Ingredient | concentration | | ranges |
|---|---|---|---|
| NaCl | g/L | 12.5 | 0-25, 5-20, or 10-15 |
| KCl | g/L | 1.0 | 0-5, 0.25-3, or 0.5-2 |
| MgSO$_4$•7H$_2$O | g/L | 5.0 | 0-10, 2-8, or 3-6 |
| (NH$_4$)$_2$SO$_4$ | g/L | 0.6 | 0-10, 0.25-5, or 0.5-3 |
| CaCl$_2$ | g/L | 0.29 | 0.1-5, 0.15-3, or 0.2-1 |

TABLE 3-continued

| PTA-9695 Vessel Media | | | |
|---|---|---|---|
| T 154 (yeast extract) | g/L | 6.0 | 0-20, 1-15, or 5-10 |
| KH$_2$PO$_4$ | g/L | 1.2 | 0.1-10, 0.5-5, or 1-3 |
| Post autoclave (Metals) | | | |
| Citric acid | mg/L | 3.5 | 0.1-100, 1-50, or 2-25 |
| FeSO$_4$•7H$_2$O | mg/L | 10.30 | 0.1-100, 1-50, or 5-25 |
| MnCl$_2$•4H$_2$O | mg/L | 3.10 | 0.1-100, 1-50, or 2-25 |
| ZnSO$_4$•7H$_2$O | mg/L | 3.10 | 0.1-100, 1-50, or 2-25 |
| CoCl$_2$•6H$_2$O | mg/L | 0.04 | 0.001-1, 0.005-0.5, or 0.01-0.1 |
| Na$_2$MoO$_4$•2H$_2$O | mg/L | 0.04 | 0.001-1, 0.005-0.5, or 0.01-0.1 |
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine** | mg/L | 9.75 | 0.1-100, 1-50, or 5-25 |
| Vitamin B12** | mg/L | 0.16 | 0.1-100, 0.1-10, or 0.1-1 |
| Ca½-pantothenate** | mg/L | 3.33 | 0.1-100, 0.1-50, or 1-10 |
| Post autoclave (Carbon) | | | |
| Glucose | g/L | 30.0 | 5-150, 10-100, or 20-50 |
| Nitrogen Feed: | | | |
| Ingredient | Concentration | | |
| NH$_4$OH | mL/L | 21.6 | 0-150, 10-100, or 15-50 |

**Filter sterilized

Typical cultivation conditions would include the following:
pH about 6.5-about 8.5, about 6.5-about 8.0, or about 7.0-about 7.5
temperature: about 17-about 30 degrees Celsius, about 20-about 25 degrees Celsius, or about 22 to about 23 degrees Celsius
dissolved oxygen: about 5-about 100% saturation, about 10-about 80% saturation, or about 20-about 50% saturation
glucose controlled @: about 5-about 50 g/L, about 10-about 40 g/L, or about 20-about 35 g/L.

In some embodiments, the culture medium comprises at least about 5%, at least about 10%, at least about 20%, at least about 30%, at least about 40%, at least about 50%, at least about 60%, at least about 70%, at least about 80%, or at least about 90% dissolved oxygen, as a percentage of saturation level. In some embodiments, the culture medium comprises from about 5% to about 20%, about 5% to about 50%, about 5% to about 100%, about 10% to about 20%, about 10% to about 50%, about 10% to about 100%, about 20% to about 50%, or about 20% to about 100% dissolved oxygen, as a percentage of saturation level.

The invention is further directed to an isolated biomass of a thraustochytrid of the invention. An isolated thraustochytrid biomass of the invention is a harvested cellular biomass obtained by any conventional method for the isolation of a thraustochytrid biomass, such as described in U.S. Pat. No. 5,130,242 and U.S. Appl. Publ. No. 2002/0001833.

In some embodiments, the dry cell weight of the biomass isolated from each liter of culture is at least about 50 g, at least about 60 g, at least about 70 g, at least about 80 g, at least about 100 g, at least about 120 g, at least about 140 g, at least about 160 g, at least about 180 g, or at least about 200 g after growing for about 7 days at about 17° C. to about 30° C. in a culture medium of about pH 6.5 to about 8.5 comprising sources of carbon, nitrogen, and nutrients, and about 950 ppm to about 8500 ppm chloride ions. In some embodiments, the dry cell weight of the biomass isolated from each liter of culture is at least about 50 g, at least about 60 g, at least about 70 g, at least about 80 g, at least about 100 g, at least about 120 g, at least about 140 g, at least about 160 g, at least about 180 g, or at least about 200 g after growing for about 7 days at about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, or about pH 8.5 comprising sources of carbon, nitrogen, and nutrients, and about 950 ppm to about 8500 ppm chloride ions. In some embodiments, the dry cell weight of the biomass isolated from each liter of culture is from about 50 g to about 200 g after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions. In some embodiments, the dry cell weight of the biomass isolated from each liter of culture is from about 50 g to about 200 g after growing for about 7 days at about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, or about pH 8.5 comprising sources of carbon, nitrogen, and nutrients, and about 950 ppm to about 8500 ppm chloride ions.

In some embodiments, the isolated thraustochytrid culture has an omega-3 fatty acid productivity of at least about 2 g/L/day, at least about 4 g/L/day, or at least about 8 g/L/day after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions. In some embodiments, the isolated thraustochytrid culture has an omega-3 fatty acid productivity of between about 1 g/L/day to about 20 g/L/day, about 2 g/L/day to about 15 g/L/day, about 2 g/L/day to about 10 g/L/day, about 3 g/L/day to about 10 g/L/day, or about 4 g/L/day to about 9 g/L/day, after growing for about 7 days at about 17° C. to about 30° C. in a culture medium of about pH 6.5 to about pH 8.5 comprising sources of carbon, nitrogen, and nutrients, and about 950 ppm to about 8500 ppm chloride ions.

In some embodiments, the fermentation volume (volume of culture) is at least about 2 liters, at least about 10 liters, at least about 50 liters, at least about 100 liters, at least about 200 liters, at least about 500 liters, at least about 1000 liters, at least about 10,000 liters, at least about 20,000 liters, at least about 50,000 liters, at least about 100,000 liters, at least about 150,000 liters, at least about 200,000 liters, or at least about 250,000 liters. In some embodiments, the fermentation volume is about 2 liters to about 300,000 liters, about 2 liters, about 10 liters, about 50 liters, about 100 liters, about 200 liters, about 500 liters, about 1000 liters, about 10,000 liters, about 20,000 liters, about 50,000 liters, about 100,000 liters, about 150,000 liters, about 200,000 liters, about 250,000 liters, or about 300,000 liters.

In some embodiments, the invention is directed to an isolated thraustochytrid biomass comprising a fatty acid profile of the invention. In some embodiments, at least about 50%, at least about 60%, at least about 70%, or at least about 80% of the dry cell weight of the biomass are fatty acids. In some embodiments, greater than about 50%, greater than about 55%, or greater than about 60% of the dry cell weight of the biomass are fatty acids. In some embodiments, from about 50% to about 60%, about 50% to about 70%, about 50% to about 80%, about 55% to about 70%, about 55% to about 80%, about 60% to about 70%, or about 60% to about 80% by weight of the dry cell weight of the biomass are fatty acids. In some embodiments, the biomass comprises at least about 50%, at least about 60%, at least about 70%, or at least about 80% by weight of the fatty acids as omega-3 fatty acids. In some embodiments, the biomass comprises from about 50% to about 60%, about 50% to about 70%, about 50% to about 80% by weight of the fatty acids as omega-3 fatty acids. In some embodiments, the biomass comprises at least about 50%, at least about 55%, at least about 60%, at least about 65%, at least about 70%, at least about 75%, or at least about 80% by weight of the fatty acids as DHA. In some embodiments, the biomass comprises from about 50% to about 60%, about 50% to about 70%, or about 50% to about 80% by weight of the fatty acids as DHA. In some embodiments, at least about 25%, at least about 30%, at least about 40%, or at least about 50%, or at least about 60% by weight of the dry cell weight of the biomass is docosahexaenoic acid. In some embodiments, about 25% to about 65%, about 25% to about 50%, about 30% to about 40%, or about 25% to about 35% by weight of the dry cell weight of the biomass is docosahexaenoic acid. In some embodiments, the biomass comprises about 10% or less, about 9% or less, about 8% or less, about 7% or less, about 6% or less, about 5% or less, about 4% or less, about 3% or less, about 2% or less, or about 1% or less by weight of the fatty acids as EPA. In some embodiments, the biomass comprises from about 1% to about 10%, about 1% to about 5%, about 2% to about 5%, about 3% to about 5%, or about 3% to about 10% by weight of the fatty acids as EPA. In some embodiments, the biomass is substantially free of EPA. In some embodiments, the biomass comprises a weight ratio of DHA to EPA of at least about 5:1, at least about 7:1, at least about 10:1, at least about 11:1, at least about 14:1, at least about 15:1, at least about 17:1, at least about 20:1, at least about 25:1, at least about 50:1, or at least about 100:1, wherein the biomass comprises about 10% or less by weight of the fatty acids as EPA. In some embodiments, the biomass comprises from about 0.1% to about 0.2%, about 0.1% to about 0.3%, about 0.1% to about 0.4%, about 0.1% to about 0.5%, or about 0.1% to about 1.5% by weight of the fatty acids as ARA. In some embodiments, the biomass comprises about 1.5% or less, about 1% or less, about 0.5% or less, about 0.4% or less, about 0.3% or less, about 0.2% or less, or about 0.1% or less by weight of the fatty acids as ARA. In some embodiments, the biomass is substantially free of ARA. In some embodiments, the biomass comprises a weight ratio of DHA to ARA of at least about 20:1, at least about 40:1, at least about 60:1, at least about 80:1, at least about 100:1, at least about 150:1, at least about 200:1, at least about 250:1, or at least about 300:1. In some embodiments, the biomass comprises from about 0.5% to about 1%, about 0.5% to about 2%, about 0.5% to about 5%, about 0.5% to about 6%, about 1% to about 5%, about 1% to about 6%, about 2% to about 5%, or about 2% to about 6% by weight of the fatty acids as DPA n-6. In some embodiments, the biomass comprises about 6% or less, about 5% or less, about 2% or less, about 1% or less, or about 0.5% or less by weight of the fatty acids as DPA n-6. In some embodiments, the biomass is substantially free of DPA n-6. In some embodiments, the biomass comprises a weight ratio of DHA to DPA n-6 of greater than about 6:1, at least about 8:1, at least about 10:1, at least about 15:1, at least about 20:1, at least about 25:1, at least about 50:1, or at least about 100:1. In some embodiments, the biomass comprises fatty acids with about 5% or less, about 4% or less, about 3% or less, or about 2% or less by weight each of linoleic acid (18:2 n-6), linolenic acid (18:3 n-3), eicosenoic acid (20:1 n-9), and erucic acid (22:1 n-9).

In another embodiment provided herein is a biomass comprising fatty acids wherein the fatty acids further comprises omega-3 polyunsaturated fatty acids wherein the omega-3 polyunsaturated fatty acids comprise DHA and EPA in an amount of about greater than or equal to about 58-68%, particularly about 60%, by weight, of the total amount of omega-3 polyunsaturated fatty acids and the amount of EPA, by weight, is from about 5% up to about 60% of the total amount of the total weight of the EPA and DHA.

The characteristics of an isolated biomass of the invention are associated with endogenous or native properties of the isolated biomass rather than exogenously introduced material.

Microbial Oils

Provided herein are oils, particular microbial oils, made by the methods described above.

In some embodiments the microbial oil comprises fatty acids wherein the fatty acids further comprises omega-3 polyunsaturated fatty acids wherein the omega-3 polyunsaturated fatty acids comprise DHA and EPA in an amount of about ≥90%, by weight, of the total amount of omega-3 polyunsaturated fatty acids and the amount of EPA, by weight, is from about 6% up to about 65% of the total amount of EPA and DHA. Particularly provided is a microbial oil wherein the amount of EPA, by weight, is from about 6% up to about 28% of the total amount of EPA and DHA. Further provided herein is a microbial oil wherein the amount of EPA, by weight, is from about 36% up to about 65 of the total amount of the EPA and DHA. More particularly provided is a microbial oil wherein the amount of EPA, by weight, is from about 28% to about 36% of the total amount of EPA and DHA.

In a further embodiment provided herein comprise a microbial oil comprising fatty acids wherein the fatty acids further comprise DHA and EPA and the amount of EPA, by weight, is from about 15 up to about 60% of the total weight of EPA and DHA.

In another embodiment provided herein is a microbial oil comprising fatty acids wherein the fatty acids further comprises omega-3 polyunsaturated fatty acids wherein the omega-3 polyunsaturated fatty acids comprise DHA and EPA in an amount of about greater than or equal to about 58-68%, particularly about 60%, by weight, of the total amount of omega-3 polyunsaturated fatty acids and the amount of EPA, by weight, is from about 5% up to about 60% of the total amount of the total weight of the EPA and DHA.

The invention is directed to a microbial oil comprising a fatty acid profile of the invention. A microbial oil of the invention is a "crude oil" or a "refined oil" comprising a triacylglycerol fraction of at least about 35% by weight. A "crude oil" is an oil that is extracted from the biomass of the microorganism without further processing. A "refined oil" is an oil that is obtained by treating a crude oil with standard processing of refining, bleaching, and/or deodorizing. See, e.g., U.S. Pat. No. 5,130,242, incorporated by reference herein in its entirety. A microbial oil also includes a "final oil" as described herein, which is a refined oil that has been diluted with a vegetable oil. In some embodiments, a final oil is a refined oil that has been diluted with high oleic sunflower oil. The term "microbial" as used herein includes, but is not limited to, the terms "microalgal," "thraustochytrid," and taxonomic classifications associated with any of the deposited microorganisms described herein. The terms "Thraustochytriales," "thraustochytrid," "*Schizochytrium*," and "*Thraustochytrium*" as used in reference to any of the microbial oils of the deposited microorganisms described herein are based on present taxonomic classifications including available phylogenetic information and are not intended to be limiting in the event that the taxonomic classifications are revised after the filing date of the present application.

In some embodiments, a fatty acid as described herein can be a fatty acid ester. In some embodiments, a fatty acid ester includes an ester of an omega-3 fatty acid, omega-6 fatty acid, and combinations thereof. In some embodiments, the fatty acid ester is a DHA ester, an EPA ester, or a combination thereof. In some embodiments, an oil or fraction thereof as described herein is esterified to produce an oil or fraction thereof comprising fatty acid esters. The term "ester" refers to the replacement of the hydrogen in the carboxylic acid group of the fatty acid molecule with another substituent. Typical esters are known to those in the art, a discussion of which is provided by Higuchi, T. and V. Stella in Pro-drugs as Novel Delivery Systems, Vol. 14, A.C.S. Symposium Series, Bioreversible Carriers in Drug Design, Ed. Edward B. Roche, American Pharmaceutical Association, Pergamon Press, 1987, and Protective Groups in Organic Chemistry, McOmie ed., Plenum Press, New York, 1973. Examples of esters include methyl, ethyl, propyl, butyl, pentyl, t-butyl, benzyl, nitrobenzyl, methoxybenzyl, benzhydryl, and trichloroethyl. In some embodiments, the ester is a carboxylic acid protective ester group, esters with aralkyl (e.g., benzyl, phenethyl), esters with lower alkenyl (e.g., allyl, 2-butenyl), esters with lower-alkoxy-lower-alkyl (e.g., methoxymethyl, 2-methoxyethyl, 2-ethoxyethyl), esters with lower-alkanoyloxy-lower-alkyl (e.g., acetoxymethyl, pivaloyloxymethyl, 1-pivaloyloxyethyl), esters with lower-alkoxycarbonyl-lower-alkyl (e.g., methoxycarbonylmethyl, isopropoxycarbonylmethyl), esters with carboxy-lower alkyl (e.g., carboxymethyl), esters with lower-alkoxycarbonyloxy-lower-alkyl (e.g., 1-(ethoxycarbonyloxy)ethyl, 1-(cyclohexyloxycarbonyloxy)ethyl), esters with carbamoyloxy-lower alkyl (e.g., carbamoyloxymethyl), and the like. In some embodiments, the added substituent is a linear or cyclic hydrocarbon group, e.g., a C1-C6 alkyl, C1-C6 cycloalkyl, C1-C6 alkenyl, or C1-C6 aryl ester. In some embodiments, the ester is an alkyl ester, e.g., a methyl ester, ethyl ester or propyl ester. In some embodiments, the ester substituent is added to the free fatty acid molecule when the fatty acid is in a purified or semi-purified state. Alternatively, the fatty acid ester is formed upon conversion of a triacylglycerol to an ester.

The present invention is directed to methods of producing microbial oils. In some embodiments, the method comprises growing any of the isolated microorganisms of the invention or mixtures thereof in a culture to produce a microbial oil comprising omega-3 fatty acids. In some embodiments, the method further comprises extracting the microbial oil. In some embodiments, the method comprises extracting a microbial oil comprising omega-3 fatty acids from any of the biomasses of the invention or mixtures thereof. In some embodiments, the method comprises heterotrophically growing the isolated microorganism, wherein the culture comprises a carbon source as described herein. The microbial oil can be extracted from a freshly harvested biomass or can be extracted from a previously harvested biomass that has been stored under conditions that prevent spoilage. Known methods can be used to culture a microorganism of the invention, to isolate a biomass from the culture, to extract a microbial oil from the biomass, and to analyze the fatty acid profile of oils extracted from the biomass. See, e.g., U.S. Pat. No. 5,130,242, incorporated by reference herein in its entirety. The invention is directed to a microbial oil produced by any of the methods of the invention.

In some embodiments, the microbial oil is extracted by an enzyme extraction method. In some embodiments, the microbial oil is extracted by a mechanical extraction method. In some embodiments, the mechanical extraction method comprises one or more of: (1) processing a pasteurized fermentation broth through a homogenizer to assist in cell lysis and release of oil from cells; (2) adding isopropyl alcohol to the fermentation broth following homogenization to break the oil and water emulsion; (3) centrifuging the mixture to recover the oil phase; and (4) drying under vacuum with addition of antioxidants. In some embodiments, the crude oil is purified. In some embodiments, purification of the crude oil comprises one or more of: (1) pumping the crude oil into a refining tank and heating the oil, followed by adding an acid solution with mixing; (2) adding a caustic solution to the oil after acid treatment; (3) reheating the crude oil and then centrifuging to separate the heavy phase from the refined oil; (4) removing the remaining polar compounds, trace metals, and oxidation products from the refined oil by using, for example, acid, TriSyl®, clay, and/or filtration; (5) chill filtering the bleached oil to further remove high melting point components from the oil to achieve the desired level of clarity; (6) heating the oil, after which the oil is then cooled and held for a period of time causing the high melting triglycerides and waxes to crystallize; (7) adding a filter aid to the chilled oil and then removing crystallized solids by filtration; (8) using a deodorizer after chill filtration, operated under high temperature and vacuum, to remove, for example, peroxides and any remaining low molecular weight compounds that can cause off-odor and flavors; (9) transferring the oil to the deodorizer feed tank, deaerating, and deodorizing, for example, in a packed column deodorizer; and (10) cooling, for example, under a nitrogen blanket at the end of the deodorization cycle and adding suitable antioxidants to the deodorized oil to provide oxidative stability.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of about 5% or less, about 4% or less, about 3% or less, about 2% or less, about 1% or less, about 0.5% or less, about 0.3% or less, about 0.2% or less, about 0.5% or less, about 0.4% or less, about 0.3% or less, or about 0.2% or less by weight.

In some embodiments, the microbial oil comprises a triacylglycerol fraction of at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some embodiments, the microbial oil comprises a triacylglycerol fraction of about 35% to about 98%, about 35% to about 90%, about 35% to about 80%, about 35% to about 70%, about 35% to about 70%, about 35% to about 65%, about 40% to about 70%, about 40% to about 65%, about 40% to about 55%, about 40% to about 50%, about 65% to about 95%, about 75% to about 95%, about 75% to about 98%, about 80% to about 95%, about 80% to about 98%, about 90% to about 96%, about 90% to about 97%, about 90% to about 98%, about 90%, about 95%, about 97%, or about 98% by weight.

In some embodiments, the microbial oil comprises a diacylglycerol fraction of at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 10% to about 45%, about 10% to about 40%, about 10% to about 35%, about 10% to about 30%, about 15% to about 40%, about 15% to about 35%, or about 15% to about 30% by weight. In some embodiments, the microbial oil comprises a 1,2-diacylglycerol fraction of at least about 0.2%, at least about 0.3%, at least about 0.4%, at least about 0.5%, at least about 1%, at least about 5%, at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 0.2% to about 45%, about 0.2% to about 30%, about 0.2% to about 20%, about 0.2% to about 10%, about 0.2% to about 5%, about 0.2% to about 1%, about 0.2% to about 0.8%, about 0.4% to about 45%, about 0.4% to about 30%, about 0.4% to about 20%, about 0.4% to about 10%, about 0.4% to about 5%, about 0.4% to about 1%, about 0.4% to about 0.8%, about 0.5% to about 1%, about 0.5% to about 0.8%, about 10% to about 45%, about 10% to about 40%, about 10% to about 35%, about 10% to about 30%, about 15% to about 40%, about 15% to about 35%, about 15% to about 30%, or about 15% to about 25% by weight. In some embodiments, the microbial oil comprises a 1,3-diacylglycerol fraction of at least about 0.1%, at least about 0.2%, at least about 0.5%, at least about 1%, at least about 2%, at least about 2.5%, or at least about 3% by weight. In some embodiments, the microbial oil comprises a sterol fraction of at least about 0.3%, at least about 0.4%, at least about 0.5%, at least about 1%, at least about 1.5%, at least about 2%, or at least about 5% by weight.

In some embodiments, the microbial oil comprises a sterol fraction of about 0.3% to about 5%, about 0.3% to about 2%, about 0.3% to about 1.5%, about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of about 5% or less, about 4% or less, about 3% or less, about 2% or less, about 1.5% or less, or about 1% or less by weight.

In some embodiments, the microbial oil comprises a phospholipid fraction of at least about 2%, at least about 5%, or at least about 8% by weight. In some embodiments, the microbial oil comprises a phospholipid fraction of about 2% to about 25%, about 2% to about 20%, about 2% to about 15%, about 2% to about 10%, about 5% to about 25%, about 5% to about 20%, about 5% to about 20%, about 5% to about 10%, or about 7% to about 9% by weight. In some embodiments, the microbial oil comprises a phospholipid fraction of less than about 20%, less than about 15%, less than about 10%, less than about 9%, or less than about 8% by weight. In some embodiments, the microbial oil is substantially free of phospholipids. In some embodiments, the microbial oil comprises unsaponifiables of less than about 2%, less than about 1.5%, less than about 1%, or less than about 0.5% by weight of the oil. The lipid classes present in the microbial oil, such as a triacylglycerol fraction, can be separated by flash chromatography and analyzed by thin layer chromatography (TLC), or separated and analyzed by other methods known in the art.

In some embodiments, the microbial oil and/or one or more fractions thereof selected from the triacylglycerol fraction, the free fatty acid fraction, the sterol fraction, the diacylglycerol fraction, and combinations thereof, comprises at least about 5%, at least about 10%, more than about 10%, at least about 12%, at least about 13%, at least about 14%, at least about 15%, at least about 16%, at least about 17%, at least about 18%, at least about 19%, at least about 20%, at least about 25%, at least about 30%, about least about 35%, at least about 40%, or at least about 45% by weight EPA. In some embodiments, the microbial oil and/or one or more fractions thereof selected from the triacylglycerol fraction, the free fatty acid fraction, the sterol fraction, the diacylglycerol fraction, and combinations thereof, comprises about 5% to about 55%, about 5% to about 50%, about 5% to about 45%, about 5% to about 40%, about 5% to about 35%, about 5% to about 30%, about 10% to about 55%, about 10% to about 50%, about 10% to about 45%, about 10% to about 40%, about 10% to about 35%, about 10% to about 30%, at least about 12% to about 55%, at least about 12% to about 50%, at least about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 15% to about 25%, about 15% to about 20%, about 20% to about 55%, about 20% to about 50%, about 20% to about 45%, about 20% to about 40%, or about 20% to about 30% by weight EPA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises at least about 5%, at least about 10%, at least about 15%, at least about 20%, at least about 25%, at least about 30%, at least about 35%, at least about 40%, at least about 50%, or at least about 60% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% to about 60%, about 5% to about 55%, about 5% to about 50%, about 5% to about 40%, about 10% to about 60%, about 10% to about 50%, about 10% to about 40%, about 20% to about 60%, about 25% to about 60%, about 25% to about 50%, about 25% to about 45%, about 30% to about 50%, about 35% to about 50%, or about 30% to about 40% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 10% or less, about 9% or less, about 8% or less, about 7% or less, about 6% or less, about 5% or less, about 4% or less, about 3% or less, about 2% or less, or about 1% or less by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 1% to about 10%, about 1% to about 5%, about 2% to about 5%, about 3% to about 5%, or about 3% to about 10% by weight of the fatty acids as DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.1% to about 5%, about 0.1% to less than about 5%, about 0.1% to about 4%, about 0.1% to about 3%, about 0.1% to about 2%, about 0.2% to about 5%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% or less, less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5%, less than about 5%, about 4% or less, about 3% or less, about 2% or less, about 1% or less, about 0.75% or less, about 0.6% or less, or about 0.5% or less by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), stearidonic acid (18:4 n-3), or combinations thereof.

The triacylglycerol molecule contains 3 central carbon atoms (C(sn-1)$H_2$R1-(sn-2)$H_2$R2-C(sn-3)$H_2$R3), allowing for formation of different positional isomers. In some embodiments, the microbial oil comprises a triacylglycerol fraction in which at least about 2%, at least about 3%, at least about 5%, at least about 10%, at least about 15%, at least about 20%, at least about 30%, at least about 35%, or at least about 40% of the triacylglycerols in the triacylglycerol fraction contain DHA at two positions in the triacylglycerol (di-substituted DHA) selected from any two of the sn-1, sn-2, and sn-3 positions, based on the relative area percent of peaks on an HPLC chromatograph. In some embodiments, the microbial oil comprises a triacylglycerol fraction in which about 2% to about 55%, about 2% to about 50%, about 2% to about 45%, about 2% to about 40%, about 2% to about 35%, about 2% to about 30%, about 2% to about 25%, about 5% to about 55%, about 5% to about 50%, about 5% to about 45%, about 5% to about 40%, about 5% to about 35%, about 5% to about 30%, about 5% to about 25%, about 10% to about 55%, about 10% to about 50%, about 10% to about 45%, about 10% to about 40%, about 10% to about 35%, about 10% to about 30%, about 10% to about 25%, about 10% to about 20%, about 20% to about 40%, about 20% to about 35%, or about 20% to about 25% of the triacylglycerols in the triacylglycerol fraction contain EPA at two positions in the triacylglycerol selected from any two of the sn-1, sn-2, or sn-3 positions, based on the relative area percent of peaks on an HPLC chromatograph. In some embodiments, the microbial oil comprises a triacylglycerol fraction in which at least about 0.5%, at least about 1%, at least about 1.5%, or at least about 2% of the triacylglycerols in the triacylglycerol fraction contain DHA at all of the sn-1, sn-2, and sn-3 positions (tri-substituted DHA), based on the relative area percent of peaks on an HPLC chromatograph. In some embodiments, the microbial oil comprises a triacylglycerol fraction in which about 0.5% to about 5%, about 0.5% to about 3%, about 0.5% to about 2.5%, about 0.5% to about 2%, about 1% to about 5%, about 1% to about 3%, or about 1% to about 2% of the triacylglycerols in the triacylglycerol fraction contain DHA at all of the sn-1, sn-2, and sn-3 positions, based on the relative area percent of peaks on an HPLC chromatograph. In some embodiments, the microbial oil comprises a triacylglycerol fraction in which at least about 10%, at least about 15%, at least about 20%, at least about 25%, at least about 30%, at least about 35%, at least about 40%, at least about 45%, at least about 50%, at least about 55%, or at least about 60% of the triacylglycerols in the triacylglycerol fraction contain DHA at one position in the triacylglycerol selected from any one of the sn-1, sn-2, or sn-3 positions, based on the relative area percent of peaks on an HPLC chromatograph. In some embodiments, the microbial oil comprises a triacylglycerol fraction in which about 10% to about 80%, about 10% to about 70%, about 10% to about 60%, about 15% to about 80%, about 15% to about 75%, about 15% to about 70%, about 15% to about 65%, about 15% to about 60%, about 35% to about 80%, about 35% to about 75%, about 35% to about 65%, about 35% to about 60%, about 40% to about 80%, about 40% to about 75%, about 40% to about 70%, about 40% to about 65%, about 40% to about 60%, or about 40% to about 55% of the triacylglycerols in the triacylglycerol fraction contain DHA at one position in the triacylglycerol selected from any one of the sn-1, sn-2, and sn-3 positions, based on the relative area percent of peaks on an HPLC chromatograph.

The present invention is further directed to methods of producing microbial oils. In some embodiments, the method comprises growing a thraustochytrid of the invention in a culture to produce a biomass and extracting an oil comprising omega-3 fatty acids from the biomass. The oil can be extracted from a freshly harvested biomass or can be extracted from a previously harvested biomass that has been stored under conditions that prevent spoilage. Known methods can be used to culture a thraustochytrid of the invention, to isolate a biomass from the culture, to extract a microbial oil from the biomass, and to analyze the fatty acid profile of oils extracted from the biomass. See, e.g., U.S. Pat. No. 5,130,242.

The invention is further directed to a microbial oil comprising a fatty acid profile of the invention. A microbial oil of the invention can be any oil derived from a microorganism, including, for example: a crude oil extracted from the biomass of the microorganism without further processing; a refined oil that is obtained by treating a crude microbial oil with further processing steps such as refining, bleaching, and/or deodorizing; a diluted microbial oil obtained by diluting a crude or refined microbial oil; or an enriched oil that is obtained, for example, by treating a crude or refined microbial oil with further methods of purification to increase the concentration of a fatty acid (such as DHA) in the oil.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of from about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of less than about 5%, less than about 4%, less than about 3%, or less than about 2% by weight. In some embodiments, the microbial oil comprises a triglyceride fraction of at least about 65%, at least about 70%, at least about 75%, at least about 80%, at least about 85%, or at least about 90% by weight. In some embodiments, the microbial oil comprises a triglyceride fraction of from about 65% to about 95%, about 75% to about 95%, or about 80% to about 95% by weight, or about 97% by weight, or about 98% by weight. In some embodiments, the microbial oil comprises a free fatty acid fraction of at least about 0.5%, at least about 1%, at least about 1.5%, at least about 2%, at least about 2.5%, or at least about 5% by weight. In some embodiments, the microbial oil comprises a free fatty acid fraction of from about 0.5% to about 5%, about 0.5% to about 2.5%, about 0.5% to about 2%, about 0.5% to about 1.5%, about 0.5% to about 1%, about 1% to about 2.5%, about 1% to about 5%, about 1.5% to about 2.5%, about 2% to about 2.5%, or about 2% to about 5% by weight. In some embodiments, the microbial oil comprises a free fatty acid fraction of less than about 5%, less than about 4%, less than about 3%, less than about 2%, or less than about 1% by weight. In some embodiments, the microbial oil comprises a sterol fraction of at least about 0.5%, at least about 1%, at least about 1.5%, at least about 2%, or at least about 5% by weight. In some embodiments, the microbial oil comprises a sterol fraction of from about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of less than about 5%, less than about 4%, less than about 3%, less than about 2%, or less than about 1% by weight. In some embodiments, the microbial oil comprises a diglyceride fraction of at least about 1.5%, at least about 2%, at least about 2.5%, at least about 3%, at least about 3.5%, or at least about 5% by weight. In some embodiments, the microbial oil comprises a diglyceride fraction of from about 1.5% to about 3%, about 2% to about 3%, about 1.5% to about 3.5%, about 1.5% to about 5%, about 2.5% to about 3%, about 2.5% to about 3.5%, or about 2.5% to about 5% by weight. In some embodiments, the microbial oil comprises unsaponifiables of less than about 2%, less than about 1.5%, less than about 1%, or less than about 0.5% by weight of the oil. The lipid classes present in the microbial oil, such as the triglyceride fraction, can be separated by flash chromatography and analyzed by thin layer chromatography (TLC), or separated and analyzed by other methods know in the art.

In some embodiments, the microbial oil and/or one or more fractions thereof selected from the triglyceride fraction, the free fatty acid fraction, the sterol fraction, the diglyceride fraction, and combinations thereof, comprises at least about 40%, at least about 45%, at least about 50%, at least about 55%, at least about 60%, at least about 65%, at least about 70%, at least about 75%, or at least about 80% by weight DHA. In some embodiments, the microbial oil and/or one or more fractions thereof selected from the triglyceride fraction, the free fatty acid fraction, the sterol fraction, the diglyceride fraction, and combinations thereof, comprises from about 40% to about 45%, about 40% to about 50%, about 40% to about 60%, about 50% to about 60%, about 55% to about 60%, about 40% to about 65%, about 50% to about 65%, about 55% to about 65%, about 40% to about 70%, about 40% to about 80%, about 50% to about 80%, about 55% to about 80%, about 60% to about 80%, or about 70% to about 80% by weight DHA. In some embodiments, the microbial oil comprises a sterol esters fraction comprising about 45% or less, about 40% or less, about 35% or less, about 30% or less, about 25% or less, about 20% or less, about 15% or less, or about 13% or less by weight DHA. In some embodiments, the microbial oil and/or one or more fractions thereof selected from the triglyceride fraction, the free fatty acid fraction, the sterol fraction, the diglyceride fraction, and combinations thereof, comprises about 10% or less, about 9% or less, about 8% or less, about 7% or less, about 6% or less, about 5% or less, about 4% or less, about 3% or less, about 2% or less, or about 1% or less by weight EPA. In some embodiments, the microbial oil and/or one or more fractions thereof selected from the triglyceride fraction, the free fatty acid fraction, the sterol fraction, the diglyceride fraction, and combinations thereof, comprises from about 2% to about 3%, about 2% to about 3.5%, about 2.5% to about 3.5%, about 2% to about 6%, about 2.5% to about 6%, about 3.0% to about 6%, about 3.5% to about 6%, about 5% to about 6%, or about 2% to about 10% by weight EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to EPA of at least about 5:1, at least about 7:1, at least about 9:1, at least about 10:1, at least about 15:1, at least about 20:1, at least about 25:1, at least about 30:1, or at least about 50:1, wherein the microbial oil and/or one or more fractions thereof comprises 10% or less by weight of EPA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to EPA of at least about 5:1, but less than about 20:1. In some embodiments, the weight ratio of DHA to EPA is from about 5:1 to about 18:1, from about 7:1 to about 16:1, or from about 10:1 to about 15:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof comprises from about 0.1% to about 0.25%, about 0.2% to about 0.25%, about 0.1% to about 0.5%, or about 0.1% to about 1.5% by weight ARA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 1.5% or less, about 1% or less, about 0.5% or less, about 0.2% or less, or about 0.1% or less by weight ARA. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of ARA. In some embodiments, the microbial oil and/or one or more fractions thereof selected from the sterol esters fraction, the triglyceride fraction, the free fatty acid fraction, the diglyceride fraction, the polar fraction (including the phospholipid fraction), and combinations thereof, comprises a weight ratio of DHA to ARA of at least about 20:1, at least about 30:1, at least about 35:1, at least about 40:1, at least about 60:1, at least about 80:1, at least about 100:1, at least about 150:1, at least about 200:1, at least about 250:1, or at least about 300:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises from about 0.5% to about 1%, about 0.5% to about 2%, about 0.5% to about 2.5%, about 0.5% to about 3%, about 0.5% to about 3.5%, about 0.5% to about 5%, about 0.5% to about 6%, about 1% to about 2%, about 2% to about 3%, about 2% to about 3.5%, about 1% to about 2.5%, about 1% to about 3%, about 1% to about 3.5%, about 1% to about 5%, or about 1% to about 6% by weight DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 6% or less, about 5% or less, about 3% or less, about 2.5% or less, about 2% or less, about 1% or less, or about 0.5% or less by weight DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, is substantially free of DPA n-6. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises a weight ratio of DHA to DPA n-6 of greater than about 6:1, of at least about 8:1, at least about 10:1, at least about 15:1, at least about 20:1, at least about 25:1, at least about 50:1, or at least about 100:1. In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 5% or less, about 4% or less, about 3% or less, about 2% or less, about 1.5% or less, about 1% or less, or about 0.5% or less by weight each of linoleic acid (18:2 n-6), linolenic acid (18:3 n-3), eicosenoic acid (20:1 n-9), and erucic acid (22:1 n-9). In some embodiments, the microbial oil and/or one or more fractions thereof selected from the sterol esters fraction, the triglyceride fraction, the free fatty acid fraction, the sterol fraction, the diglyceride fraction, the polar fraction (including the phospholipid fraction), and combinations thereof, comprises about 5% or less, about 4% or less, about 3% or less, about 2% or less, about 1.5% or less, or about 1% or less by weight of heptadecanoic acid (17:0). In some embodiments, the microbial oil and/or one or more fractions thereof comprise about 0.01% to about 5% by weight, about 0.05% to about 3% by weight, or about 0.1% to about 1% by weight of heptadecanoic acid.

The triglyceride molecule contains 3 central carbon atoms ($C_{sn-1}H_2R1$-$C_{sn-2}H_2R2$-$C_{sn-3}H_2R3$), allowing for formation of different positional isomers. In some embodiments, the microbial oil comprises a triglyceride fraction in which at least about 20%, at least about 30%, at least about 35%, or at least about 40% of the triglycerides in the triglyceride fraction contain DHA at two positions in the triglyceride (di-substituted DHA) selected from any two of the sn-1, sn-2, and sn-3 positions, based on the relative area percent of peaks on an HPLC chromatograph. In some embodiments, the microbial oil comprises a triglyceride fraction in which from about 20% to about 40%, about 20% to about 35%, about 30% to about 40%, or about 30% to about 35% of the triglycerides in the triglyceride fraction contain DHA at two positions in the triglyceride selected from any two of the sn-1, sn-2, or sn-3 positions, based on the relative area percent of peaks on an HPLC chromatograph. In some embodiments, the microbial oil comprises a triglyceride fraction in which at least about 5%, at least about 10%, at least about 15%, or at least about 20% of the triglycerides in the triglyceride fraction contain DHA at all of the sn-1, sn-2, and sn-3 positions (tri-substituted DHA), based on the relative area percent of peaks on an HPLC chromatograph. In some embodiments, the microbial oil comprises a triglyceride fraction in which from about 5% to about 20%, about 5% to about 15%, about 10% to about 20%, or about 10% to about 15% of the triglycerides in the triglyceride fraction contain DHA at all of the sn-1, sn-2, and sn-3 positions, based on the relative area percent of peaks on an HPLC chromatograph. In contrast, the TAG species reported in U.S. Pat. No. 6,582,941 does not contain DHA at all three positions. In some embodiments, the microbial oil comprises a triglyceride fraction in which at least about 50%, at least about 55%, at least about 60%, at least about 65%, at least about 70%, or at least about 75% of the triglycerides in the triglyceride fraction contain DHA at one position in the triglyceride selected from any one of the sn-1, sn-2, or sn-3 positions, based on the relative area percent of peaks on an HPLC chromatograph. In some embodiments, the microbial oil comprises a triglyceride fraction in which from about 50% to about 75%, about 50% to about 70%, about 50% to about 65%, about 60% to about 75%, about 60% to about 70%, or about 60% to about 65% of the triglycerides in the triglyceride fraction contain DHA at one position in the triglyceride selected from any one of the sn-1, sn-2, and sn-3 positions, based on the relative area percent of peaks on an HPLC chromatograph.

Compositions

The invention is directed to compositions comprising a microorganism of the invention, an isolated biomass of the invention, a microbial oil of the invention, or combinations thereof.

A microorganism, biomass, or microbial oil of the invention can be further chemically or physically modified or processed based on the requirements of the composition by any known technique.

Microorganism cells or biomasses can be dried prior to use in a composition by methods including, but not limited to, freeze drying, air drying, spray drying, tunnel drying, vacuum drying (lyophilization), and a similar process. Alternatively, a harvested and washed biomass can be used directly in a composition without drying. See, e.g., U.S. Pat. Nos. 5,130,242 and 6,812,009, each of which is incorporated by reference herein in its entirety.

Microbial oils of the invention can be used as starting material to more efficiently produce a product enriched in a fatty acid such as EPA. For example, the microbial oils of the invention can be subjected to various purification techniques known in the art, such as distillation or urea adduction, to produce a higher potency product with higher concentrations of EPA or another fatty acid. The microbial oils of the invention can also be used in chemical reactions to produce compounds derived from fatty acids in the oils, such as esters and salts of EPA or another fatty acid.

A composition of the invention can include one or more excipients. As used herein, "excipient" refers to a component, or mixture of components, that is used in a composition of the present invention to give desirable characteristics to the composition, including foods as well as pharmaceutical, cosmetic, and industrial compositions. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with tissues of human beings and non-human animals without excessive toxicity, irritation, allergic response, or other problematic complications over the desired duration of contact commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, 21$^{st}$ ed. (2005). Inclusion of an excipient in a particular classification herein (e.g., "solvent") is intended to illustrate rather than limit the role of the excipient. A particular excipient can fall within multiple classifications.

Compositions of the invention include, but are not limited to, food products, pharmaceutical compositions, cosmetics, and industrial compositions.

In some embodiments, the composition is a food product. A food product is any food for non-human animal or human consumption, and includes both solid and liquid compositions. A food product can be an additive to animal or human foods. Foods include, but are not limited to, common foods; liquid products, including milks, beverages, therapeutic drinks, and nutritional drinks; functional foods; supplements; nutraceuticals; infant formulas, including formulas for premature infants; foods for pregnant or nursing women; foods for adults; geriatric foods; and animal foods.

In some embodiments, a microorganism, biomass, or microbial oil of the invention can be used directly as or included as an additive within one or more of: an oil, shortening, spread, other fatty ingredient, beverage, sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, and a finished or semi-finished powdered food product. In some embodiments, the nutritional supplement is in the form of a vegetarian capsule that is not formed from and does not contain any components from an animal source.

A partial list of food compositions that can include a microbial oil of the invention includes, but is not limited to, soya based products (milks, ice creams, yogurts, drinks, creams, spreads, whiteners); soups and soup mixes; doughs, batters, and baked food items including, for example, fine bakery wares, breakfast cereals, cakes, cheesecakes, pies, cupcakes, cookies, bars, breads, rolls, biscuits, muffins, pastries, scones, croutons, crackers, sweet goods, snack cakes, pies, granola/snack bars, and toaster pastries; candy; hard confectionery; chocolate and other confectionery; chewing gum; liquid food products, for example milks, energy drinks, infant formula, carbonated drinks, teas, liquid meals, fruit juices, fruit-based drinks, vegetable-based drinks; multivitamin syrups, meal replacers, medicinal foods, and syrups; powdered beverage mixes; pasta; processed fish products; processed meat products; processed poultry products; gravies and sauces; condiments (ketchup, mayonnaise, etc.); vegetable oil-based spreads; dairy products; yogurt; butters; frozen dairy products; ice creams; frozen desserts; frozen yogurts; semi-solid food products such as baby food; puddings and gelatin desserts; processed and unprocessed cheese; pancake mixes; food bars including energy bars; waffle mixes; salad dressings; replacement egg mixes; nut and nut-based spreads; salted snacks such as potato chips and other chips or crisps, corn chips, tortilla chips, extruded snacks, popcorn, pretzels, potato crisps, and nuts; and specialty snacks such as dips, dried fruit snacks, meat snacks, pork rinds, health food bars and rice/corn cakes.

In some embodiments, a microbial oil of the invention can be used to supplement infant formula. Infant formula can be supplemented with a microbial oil of the invention alone or in combination with a physically refined oil derived from an arachidonic acid (ARA)-producing microorganism. An ARA-producing microorganism, for example, is *Mortierella alpina* or *Mortierella* sect. *schmuckeri*. Alternatively, infant formulas can be supplemented with a microbial oil of the invention in combination with an oil rich in ARA, including ARASCO® (Martek Biosciences, Columbia, Md.).

In some embodiments, the composition is an animal feed. An "animal" includes non-human organisms belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; or rodents such as mice, rats, hamsters and guinea pigs; and so on. An animal feed includes, but is not limited to, an aquaculture feed, a domestic animal feed including pet feed, a zoological animal feed, a work animal feed, a livestock feed, and combinations thereof.

In some embodiments, the composition is a feed or feed supplement for any animal whose meat or products are consumed by humans, such as any animal from which meat, eggs, or milk is derived for human consumption. When fed to such animals, nutrients such as LC-PUFAs can be incorporated into the flesh, milk, eggs or other products of such animals to increase their content of these nutrients.

In some embodiments, the composition is a spray-dried material that can be crumbled to form particles of an appropriate size for consumption by zooplankton, artemia, rotifers, and filter feeders. In some embodiments, the zooplankton, artemia, or rotifers fed by the composition are in turn fed to fish larvae, fish, shellfish, bivalves, or crustaceans.

In some embodiments, the composition is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an anti-depressant, an anti-convulsant, an anti-*Helicobacter pylori* drug, a drug for treatment of neurodegenerative disease, a drug for treatment of degenerative liver disease, an antibiotic, a cholesterol lowering composition, and a triacylglycerol lowering composition. In some embodiments, the composition is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

In some embodiments, the microbial oil can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the microbial oil can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinylpyrrolidone, agar, or alginic acid or a salt thereof such as sodium alginate. Pharmaceutical preparations that can be used orally include, but are not limited to, push-fit capsules made of gelatin, as well as soft, sealed capsules made of gelatin and a plasticizer, such as glycerol or sorbitol. In some embodiments, the dosage form is a vegetarian dosage form, in which the dosage form is not formed from and does not contain any components from an animal source. In some embodiments, the vegetarian dosage form is a vegetarian capsule.

In some embodiments, the composition is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

In some embodiments, the composition is an industrial composition. In some embodiments, the composition is a starting material for one or more manufactures. A manufacture includes, but is not limited to, a polymer; a photographic photosensitive material; a detergent; an industrial oil; or an industrial detergent. For example, U.S. Pat. No. 7,259,006 describes use of DHA-containing fat and oil for production of behenic acid and production of photographic sensitive materials using behenic acid.

Methods of Using the Compositions

In some embodiments, the compositions can be used in the treatment of a condition in humans or non-human animals. In some embodiments, the compositions can be used for nutrition in humans or non-human animals.

The terms "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation or elimination of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In some embodiments, the composition is used to treat a condition, disease, or disorder such as acne, acute inflammation, age related maculopathy, allergy, Alzheimer's, arthritis, asthma, atherosclerosis, autoimmune disease, blood lipid disorder, breast cysts, cachexia, cancer, cardiac restenosis, cardiovascular diseases, chronic inflammation, coronary heart disease, cystic fibrosis, degenerative disorder of the liver, diabetes, eczema, gastrointestinal disorder, heart disease, high triacylglycerol levels, hypertension, hyperactivity, immunological diseases, inhibiting tumor growth, inflammatory conditions, intestinal disorders, kidney dysfunction, leukemia, major depression, multiple sclerosis, neurodegenerative disorder, osteoarthritis, osteoporosis, peroxisomal disorder, preeclampsia, preterm birth, psoriasis, pulmonary disorder rheumatoid arthritis, risk of heart disease, or thrombosis.

In some embodiments, the composition is used to increase the length of gestation of a fetus in the third trimester.

In some embodiments, the composition is used to control blood pressure.

In some embodiments, the composition is used to improve or maintain cognitive function.

In some embodiments, the composition is used to improve or maintain memory.

The composition or dosage form can be administered into the body of a subject by any route compatible with the composition or dosage form. A substance is considered to be "administered" if the substance is introduced into the body of the subject by the subject, or if another person, a machine, or a device introduces the substance into the body of the subject. "Administering," therefore, includes, e.g., self-administration, administration by others, and indirect administration. The term "continuous" or "consecutive," as used herein in reference to "administration," means that the frequency of administration is at least once daily. Note, however, that the frequency of administration can be greater than once daily and still be "continuous" or "consecutive," e.g., twice or even three times daily, as long as the dosage levels as specified herein are not exceeded. The means and methods for administration are known in the art and an artisan can refer to various pharmacologic references for guidance. For example, "Modern Pharmaceutics," Banker & Rhodes, Informa Healthcare, USA, 4th ed. (2002); and "Goodman & Gilman's The Pharmaceutical Basis of Therapeutics," McGraw-Hill Companies, Inc., New York, 10th ed. (2001) can be consulted.

By "subject," "individual," or "patient" is meant any subject, whether human or non-human, for whom diagnosis, prognosis, therapy, or administration of the composition or dosage form is desired. Mammalian subjects include, but are not limited to, humans; domestic animals; farm animals; zoo animals; sport animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. The term subject also encompasses model animals, e.g., disease model animals. In some embodiments, the term subject includes valuable animals, either economically or otherwise, e.g., economically important breeding stock, racing animals, show animals, heirloom animals, rare or endangered animals, or companion animals. In certain embodiments, the subject is a human subject. In certain embodiments, the subject is a non-human subject.

The composition can be administered as a "nutritional amount," "therapeutically effective amount," a "prophylactically effective amount," a "therapeutic dose," or a "prophylactic dose." A "nutritional amount" refers to an amount effective, at dosages and for periods of time necessary, to achieve a desired nutritional result. A nutritional result can be, e.g., increased levels of a desirable fatty acid component in a subject. A "therapeutically effective amount" or "therapeutic dose" refers to an amount effective, at dosages and for periods of time necessary, to achieve a desired therapeutic result. A therapeutic result can be, e.g., lessening of symptoms, prolonged survival, improved mobility, and the like. A therapeutic result need not be a "cure." A "prophylactically effective amount" or "prophylactic dose" refers to an amount effective, at dosages and for periods of time necessary, to achieve the desired prophylactic result. Typically, since a prophylactic dose is used in subjects prior to or at an earlier stage of disease, a prophylactically effective amount will be less than a therapeutically effective amount for treatment of an advanced stage of disease.

Various dosage amounts of the composition, dosage form, or pharmaceutical composition can be administered to a subject, based on the amount of EPA or other fatty acid component of the microorganism, biomass, or microbial oil to be administered to the subject. The terms "daily dosage," "daily dosage level," and "daily dosage amount" refer herein to the total amount of EPA or other fatty acid component administered per day (per 24 hour period). Thus, for example, administration of EPA to a subject at a daily dosage of 2 mg means that the subject receives a total of 2 mg of EPA on a daily basis, whether the EPA is administered as a single dosage form comprising 2 mg EPA, or alternatively, four dosage forms comprising 0.5 mg EPA each (for a total of 2 mg EPA). In some embodiments, the daily amount of EPA is administered in a single dosage form, or in two dosage forms. The dosage forms of the present invention can be taken in a single application or multiple applications. For example, if four tablets are taken daily, each tablet comprising 0.5 mg EPA, then all four tablets can be taken once daily, or 2 tablets can be taken twice daily, or 1 tablet can be taken every 6 hours. In some embodiments, the daily dosage is about 100 mg to about 15 g of EPA. In some embodiments, the daily dosage is about 0.5 mg to about 250 mg, about 100 mg to about 250 mg, about 100 mg to about 500 mg, about 100 mg to about 1 g, about 1 g to about 2.5 g, about 1 g to about 5 g, about 1 g to about 10 g, about 1 g to about 15 g, about 5 g to about 10 g, about 5 g to about 15 g, about 10 g to about 15 g, about 100 mg to about 10 g, about 100 mg to about 5 g, or about 100 mg to about 2.5 g of EPA, DHA, or a combination thereof. In some embodiments, the composition is a dosage form that comprises about 0.5 mg to about 250 mg, 100 mg to about 250 mg, about 0.5 mg to about 500 mg, about 100 mg to about 500 mg, about 0.5 mg to about 1 g, or about 100 mg to about 1 g of EPA, DHA, or a combination thereof per dosage form.

Administration of the compositions or dosage forms of the present invention can be achieved using various regimens. For example, in some embodiments, administration occurs daily on consecutive days, or alternatively, occurs every other day (bi-daily). Administration can occur on one or more days.

Administration of the compositions and dosage forms can be combined with other regimens used for treatment of the condition. For example, the method of the present invention can be combined with diet regimens (e.g., low carbohydrate diets, high protein diets, high fiber diets, etc.), exercise regimens, weight loss regimens, smoking cessation regimens, or combinations thereof. The method of the present invention can also be used in combination with other pharmaceutical products in the treatment of the condition. The compositions or dosage forms of the present invention can be administered before or after other regimens or pharmaceutical products.

Kits Comprising the Compositions

The invention is directed to kits or packages containing one or more units of a composition of the invention. Kits or packages can include units of a food product, pharmaceutical composition, cosmetic, or industrial composition comprising the microorganism, biomass, or microbial oil of the invention, or combinations thereof. Kits or packages can also include an additive comprising the microorganism, biomass, or microbial oil of the invention, or combinations thereof for preparation of a food, cosmetic, pharmaceutical composition, or industrial composition.

In some embodiments, the kit or package contains one or more units of a pharmaceutical composition to be administered according to the methods of the present invention. The kit or package can contain one dosage unit, or more than one dosage unit (i.e., multiple dosage units). If multiple dosage units are present in the kit or package, the multiple dosage units can be optionally arranged for sequential administration.

The kits of the present invention can optionally contain instructions associated with the units or dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the units or dosage forms in the kit according to the methods of the invention. For example, the instructions can be in the form of printed matter, or in the form of a pre-recorded media device.

In the course of examination of a patient, a medical professional can determine that administration of one of the methods of the present invention is appropriate for the patient, or the physician can determine that the patient's condition can be improved by the administration of one of the methods of the present invention. Prior to prescribing any regimen, the physician can counsel the patient, for example, on the various risks and benefits associated with the regimen. The patient can be provided full disclosure of all known and suspected risks associated with the regimen. Such counseling can be provided verbally, as well as in written form. In some embodiments, the physician can provide the patient with literature materials on the regimen, such as product information, educational materials, and the like.

The present invention is directed to methods of educating consumers about the methods of treatment, the method comprising distributing the dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the dosage forms according to the methods of the present invention, appropriate age use, indication, contraindications, appropriate dosing, warnings, telephone number or website address. In some embodiments, the method further comprises providing professional information to relevant persons in a position to answer consumer questions regarding use of the disclosed regimens according to the methods of the present invention. The term "professional information" includes, but is not limited to, information concerning the regimen when administered according to the methods of the present invention that is designed to enable a medical professional to answer costumer questions. A "medical professional," includes, for example, a physician, physician assistant, nurse, nurse practitioner, pharmacist and customer service representative.

Having generally described this invention, a further understanding can be obtained by reference to the examples provided herein. These examples are for purposes of illustration only and are not intended to be limiting.

EXAMPLE 1

In this example, *Schizochytrium* sp. was cultivated in 250 ml Erlenmeyer shake flasks containing 50 mls of culture medium. An inoculum was prepared in the same medium which consisted of 0.625 g NaCl, 1.0 g KCl, 5 g $MgSO_4.7H_2O$, 0.1 g $(NH_4)_2SO_4$, 0.29 g $CaCl_2.2H_2O$, 1.0 g monosodium glutamate monohydrate, 1.0 g yeast extract, and 23.8 g HEPES buffer dissolved in approximately 900 mls of distilled water. The medium was brought to pH 7 using NaOH. The final volume of the medium was brought to 896 mls, and the medium was sterilized by autoclaving. After autoclaving the following components were sterilely added to the medium: 0.89 ml of 56.5 g/l $KH_2PO_4$, 100 ml of 500 g/l glucose, 2 ml of trace metal stock solution, and 1 ml of vitamin stock solution. The trace metal stock solution contained the following: 90 g citric acid, 5.15 g $FeSO_4.7H_2O$, 1.55 g $MnCl_2.4H_2O$, 0.965 g $ZnSO_4.7H_2O$, 0.02 g $CoCl_2.6H_2O$, 0.02 g $Na_2MoO_4.2H_2O$, 1.035 g $CuSO_4.5H_2O$, 1.035 g $NiSO_4.6H_2O$ dissolved in one liter of distilled water and pH'ed to 2.5 with HCl. The vitamin stock solution contained the following: 0.16 g vitamin B12, 9.75 g thiamine, and 3.33 g calcium pantothenate dissolved in one liter of distilled water. The shake flasks were inoculated with 1 ml of inoculum. Triplicate flasks were placed in a $CO_2$ incubator set to maintain an atmosphere of either 5, 10 or 15% $CO_2$ in air. Another set of triplicate flasks were placed in an incubator at ambient $CO_2$ levels. All sets of flasks were shaken at 200 rpm and all incubators were set at 22.5 C. After seven days of growth the biomass was collected from the shake flasks by centrifugation, the biomass was freeze dried and the fatty acid profile of the biomass was determined using standard methyl esterification procedures. Elevated $CO_2$ levels produced significant changes in the biomass, % Fat and the fatty acid profiles. Notable was the change produced in the % EPA and % DHA values between $CO_2$ conditions and ambient conditions. Furthermore, the changes in these fatty acids became more pronounced as the $CO_2$ level increased. The results are presented in Table 4.

TABLE 4

| SAMPLE | Biomass (g/l) | % 16:0 | % EPA | % DHA | % Fat |
|---|---|---|---|---|---|
| Ambient (1) | 3.43 | 33.55 | 4.24 | 54.15 | 54.55 |
| Ambient (2) | 3.35 | 33.29 | 4.30 | 54.42 | 52.67 |

TABLE 4-continued

| SAMPLE | Biomass (g/l) | % 16:0 | % EPA | % DHA | % Fat |
|---|---|---|---|---|---|
| Ambient (3) | 3.27 | 33.29 | 4.29 | 54.38 | 50.62 |
| 15% CO2 (1) | 2.96 | 28.41 | 26.12 | 29.52 | 53.31 |
| 15% CO2 (2) | 2.94 | 28.13 | 26.20 | 29.98 | 55.46 |
| 15% CO2 (3) | 2.80 | 28.12 | 26.61 | 29.46 | 53.20 |
| Ambient (1) | 3.89 | 35.34 | 3.95 | 52.31 | 60.21 |
| Ambient (2) | 3.85 | 34.74 | 4.00 | 53.03 | 58.33 |
| Ambient (3) | 3.91 | 34.76 | 4.04 | 52.95 | 58.18 |
| 10% CO2 (1) | 4.91 | 33.35 | 12.94 | 41.13 | 69.98 |
| 10% CO2 (2) | 5.03 | 33.28 | 12.99 | 41.15 | 69.58 |
| 10% CO2 (3) | 4.95 | 33.46 | 12.84 | 41.02 | 69.08 |
| Ambient (1) | 3.51 | 29.95 | 3.00 | 45.06 | 58.48 |
| Ambient (2) | 3.69 | 30.57 | 2.97 | 44.92 | 54.87 |
| Ambient (3) | 3.43 | 29.98 | 3.13 | 45.20 | 53.29 |
| 5% CO2 (1) | 4.18 | 32.03 | 5.59 | 40.55 | 42.89 |
| 5% CO2 (2) | 4.16 | 31.87 | 5.85 | 40.36 | 43.47 |
| 5% CO2 (3) | 4.14 | 31.58 | 6.13 | 40.43 | 44.13 |

EXAMPLE 2

In this example, *Schizochytrium* sp. was cultivated in 250 ml Erlenmeyer shake flasks containing 50 mls of culture medium. An inoculum was prepared in the same medium which consisted of 0.625 g NaCl, 1.0 g KCl, 5 g MgSO4.7H2O, 0.1 g (NH4)2SO4, 0.29 g CaCl2.2H2O, 1.0 g monosodium glutamate monohydrate, 1.0 g yeast extract, and 23.8 g HEPES buffer dissolved in approximately 900 mls of distilled water. The medium was brought to pH 7 using NaOH. The final volume of the medium was brought to 896 mls, and the medium was sterilized by autoclaving. After autoclaving the following components were sterilely added to the medium: 0.89 ml of 56.5 g/l KH2PO4, 100 ml of 500 g/l glucose, 2 ml of trace metal stock solution, and 1 ml of vitamin stock solution. The trace metal stock solution contained the following: 90 g citric acid, 5.15 g FeSO4.7H2O, 1.55 g MnCl2.4H2O, 0.965 g ZnSO4.7H2O, 0.02 g CoCl2.6H2O, 0.02 g Na2MoO4.2H2O, 1.035 g CuSO4.5H2O, 1.035 g NiSO4.6H2O dissolved in one liter of distilled water and pH'ed to 2.5 with HCl. The vitamin stock solution contained the following: 0.16 g vitamin B12, 9.75 g thiamine, and 3.33 g calcium pantothenate dissolved in one liter of distilled water. The shake flasks were inoculated with 1 ml of inoculum. Duplicate flasks were placed in a $CO_2$ incubator set to maintain an atmosphere of either 5, 10 or 15% $CO_2$ in air. Another set of duplicate flasks were placed in an incubator at ambient $CO_2$ levels. All sets of flasks were shaken at 200 rpm and all incubators were set at 22.5 C. After seven days of growth the biomass was collected from the shake flasks by centrifugation, the biomass was freeze dried and the fatty acid profile of the biomass was determined using standard methyl esterification procedures. Elevated $CO_2$ levels produced significant changes in the biomass, % Fat and the fatty acid profiles. Notable was the change produced in the % EPA and % DHA values between $CO_2$ conditions and ambient conditions. Furthermore, the changes in these fatty acids became more pronounced as the $CO_2$ level increased. The results are provide in Table 5 below.

TABLE 5

| SAMPLE | Biomass (g/l) | % 16:0 | % EPA | % DHA | % Fat |
|---|---|---|---|---|---|
| Ambient (1) | 5.81 | 28.22 | 3.88 | 58.69 | 60.86 |
| Ambient (2) | 6.03 | 26.54 | 3.89 | 60.87 | 66.74 |
| 15% CO2 (1) | 4.38 | 14.67 | 36.12 | 35.84 | 62.44 |

TABLE 5-continued

| SAMPLE | Biomass (g/l) | % 16:0 | % EPA | % DHA | % Fat |
|---|---|---|---|---|---|
| 15% CO$_2$ (2) | 4.44 | 14.31 | 36.09 | 36.59 | 63.00 |
| 10% CO$_2$ (1) | 5.36 | 21.44 | 19.88 | 46.40 | 64.94 |
| 10% CO$_2$ (2) | 5.63 | 21.39 | 19.88 | 46.74 | 65.82 |
| 5% CO$_2$ (1) | 6.40 | 24.71 | 11.56 | 54.04 | 77.16 |
| 5% CO$_2$ (2) | 6.33 | 24.62 | 11.74 | 54.36 | 67.94 |

EXAMPLE 3

In this example, *Thrasutochytrium* sp. was cultivated in 250 ml Erlenmeyer shake flasks containing 50 mls of culture medium. An inoculum was prepared in the same medium which consisted of 42 g Na$_2$SO$_4$, 0.625 g NaCl, 1.0 g KCl, 5 g MgSO$_4$.7H$_2$O, 0.1 g (NH$_4$)$_2$SO$_4$, 0.29 g CaCl$_2$.2H$_2$O, 1.0 g monosodium glutamate monohydrate, 1.0 g yeast extract, and 23.8 g HEPES buffer dissolved in approximately 900 mls of distilled water. The medium was brought to pH 7 using NaOH. The final volume of the medium was brought to 961 mls, and the medium was sterilized by autoclaving. After autoclaving the following components were sterilely added to the medium: 0.89 ml of 56.5 g/l KH$_2$PO$_4$, 35 ml of 500 g/l glycerol, 2 ml of trace metal stock solution, and 1 ml of vitamin stock solution. The trace metal stock solution contained the following: 9 g citric acid, 5.15 g FeSO$_4$.7H$_2$O, 1.55 g MnCl$_2$.4H$_2$O, 0.965 g ZnSO$_4$.7H$_2$O, 0.02 g CoCl$_2$.6H$_2$O, 0.02 g Na$_2$MoO$_4$.2H$_2$O, 1.035 g CuSO$_4$.5H$_2$O, 1.035 g NiSO$_4$.6H$_2$O dissolved in one liter of distilled water and pH'ed to 2.5 with HCl. The vitamin stock solution contained the following: 0.16 g vitamin B12, 9.75 g thiamine, and 3.33 g calcium pantothenate dissolved in one liter of distilled water. The shake flasks were inoculated with 1 ml of inoculum. Triplicate flasks were placed in a $CO_2$ incubator set to maintain an atmosphere of 15% $CO_2$ in air. Another set of triplicate flasks were placed in an incubator at ambient $CO_2$ levels. Both sets of flasks were shaken at 200 rpm and both incubators were set at 22.5 C. After seven days of growth the biomass was collected from the shake flasks by centrifugation, the biomass was freeze dried and the fatty acid profile of the biomass was determined using standard methyl esterification procedures. An atmosphere of 15% $CO_2$ in air produced substantial changes in the *Thraustochytrium* culture. At high $CO_2$ the biomass and the % fat were lower than under ambient conditions. The %16:0 and % DHA were lower and the % EPA was significantly higher than under ambient conditions. The results are presented in Table 6 below.

TABLE 6

| Atmosphere | Biomass (g/l) | % 16:0 | % EPA | % DHA | % Fat |
|---|---|---|---|---|---|
| Ambient (1) | 3.39 | 31.74 | 11.61 | 44.65 | 53.32 |
| Ambient (2) | 3.42 | 30.88 | 11.95 | 44.99 | 53.30 |
| Ambient (3) | 3.39 | 32.13 | 11.46 | 44.19 | 53.93 |
| 15% CO$_2$ (1) | 2.23 | 22.12 | 36.94 | 19.04 | 38.73 |
| 15% CO$_2$ (2) | 2.05 | 21.40 | 37.14 | 18.57 | 39.34 |
| 15% CO$_2$ (3) | 2.11 | 21.68 | 36.83 | 18.52 | 40.86 |

EXAMPLE 4

In this example [NBx0614et10], *Schizochytrium* species (ATCC PTA-10208) was cultivated in four 100-liter New Brunswick Scientific BioFlo 6000 fermentors at a target final (recipe) volume of 80-liters with a carbon (glucose) and nitrogen (ammonium hydroxide) fed-batch process at various over pressure conditions to evaluate the sensitivity of the culture to increased dissolved carbon dioxide. The fermentations were each inoculated with 8 liters of culture. For inoculum propagation, an 80-liter New Brunswick Scientific BioFlo 5000 fermentor was utilized. The inoculum medium consisted of 65-liters of medium prepared in six separate groups. Group 1 consisted of 585 g MSG*1H2O, 65 g KCl, 325 g MgSO4*7H2O, 24.05 g (NH4)2SO4, 40.625 g of NaCl, 390 g of T154 (yeast extract), and 13 mL Dow 1520US (antifoam). Group 1 was batch sterilized at 121 degrees in the inoculum fermentor at a volume of approximately 60 liters. Group 2 consisted of 18.85 g CaCl2*2H2O. Group 3 consisted of 33.8 g KH2PO4. Groups 2 and 3 were each autoclaved in separate solutions for approximately 45-60 minutes and added to group 1 aseptically post-sterilization. Group 4 consisted of 201.5 mg MnCl2*4H2O, 201.5 mg ZnSO4*7H2O, 2.6 mg CoCl2*6H2O, 2.6 mg Na2MoO4*2H2O, 134.6 mg CuSO4*5H2O, 134.6 mg NiSO4*6H2O, 669.4 mg FeSO4*7H2O and 1.522 g citric acid. Group 4 was autoclaved in the same manner as groups 2 and 3. Group 5 consisted of 633.75 mg Thiamine-HCl, 10.4 mg vitamin B12, and 216.5 mg pantothenic acid hemi-calcium salt. Group 5 was dissolved in RO water and then filter-sterilized. Group 6 consisted of 3250 g glucose dissolved in a volume of 3000 mL RO water. After the inoculum fermentor was cooled to 22.5 degrees Celsius, groups 2, 3, 4, 5, and 6 were added to the fermentor. Using sodium hydroxide and sulfuric acid, the fermentor was pH adjusted to 7 and the dissolved oxygen was spanned to 100% prior to inoculation. The inoculum fermentor was inoculated with 1300 mL of a smaller fermentation culture (The smaller fermentation culture was prepared and cultivated in the same manner as the 65-liter inoculum culture.) and cultivated at 22.5 degrees Celsius, pH 7, 180 rpm agitation, and 32.5 lpm of air for a period of 37 hours, at which point 8 liters of inoculum broth was transferred to each 100-liter fermentor. Each 100-liter fermentor contained 80-liters of fermentation media. The fermentation media was prepared in a similar fashion to the inoculum fermentor. For each 100-liter fermentor, the fermentation media consisted of 6 batched media groups. For vessels NB5, NB6, and NB7, group 1 contained 704 g Na2SO4, 50 g NaCl, 80 g KCl, 400 g MgSO4*7H2O, 33.6 g (NH4)2SO4, 80 g T154 yeast extract, and 8 mL Dow 1520-US antifoam. Group 1 was steam sterilized at 122 degrees Celsius for 60 minutes in the 100-liter fermentors at a volume of approximately 35 liters. Group 2 contained 23.2 g CaCl2*2H2O in a volume of approximately 300 mL. Group 3 contained 141.2 g KH2PO4 dissolved in RO water. Group 4 contained 248 mg MnCl2*4H2O, 744 mg ZnSO4*7H2O, 3.2 mg Na2MoO4*2H2O, 165.6 mg CuSO4*5H2O, and 165.6 mg NiSO4*6H2O, 824 mg FeSO4*7H2O and 80 g citric acid all dissolved in RO water. Group 5 contained 780 mg Thiamine-HCl, 266.4 mg pantothenic acid hemi-calcium salt, and 286.4 ug of biotin, all dissolved and filter sterilized in RO water. Group 6 contained 2400 g of glucose in approximately 3 liters of RO water. Groups 2, 3, 4, 5, and 6 were combined and added to the fermentor after the fermentor reached an operating temperature of 22.5 degrees Celsius. For vessel NB8, all of the groups were the same as the other three conditions with the exception of the citric acid. In NB8, group 4 only contained ~3.75 g of citric acid. Each fermentor volume prior to inoculation was approximately 52-53 liters. Each fermentor was inoculated with 8 liters of broth from the inoculum fermentation described above. The fermentation was pH controlled utilizing a 7.3 liter solution of 4N ammonium hydroxide at a pH of 7 until nitrogen exhaustion at which point 4N sodium hydroxide and 4N sulfuric acid were utilized for pH control. The dissolved oxygen was controlled to maintain a target of 20% throughout the fermentation using agitation from 180 to 480 rpm and airflow from 40 LPM to 80 LPM. Each of these vessels was controlled at a different head pressure (NB5=2, NB6=15, and NB7=20 PSI) to evaluate the sensitivity of the organism to increased dissolved carbon dioxide. Throughout the fermentation, an 850 g/L solution of 95% dextrose (corn syrup) was fed to maintain a glucose concentration less than 50 g/L. After 8 days, the dry cell weight and omega-3 titer of each 80-liter fermentor was similar with NB5 at 110.1 g/L DCW and 44.37 g/L omega-3; NB6 at 117.7 g/L DCW and 45.78 g/L omega-3; NB7 at 114.1 g/L DCW and 48.43 g/L omega-3; NB8 at 119.5 g/L DCW and 43.55 g/L omega-3. As the pressure was increased, the % DHA/FAME decreased, the % EPA/FAME increased, and the ratio of DHA to EPA decreased. When comparing the final fatty acid content of 2 PSI to 20 PSI, the % DHA/FAME decreased from 50.48% to 41.26% and the % EPA/FAME increased from 18.95% to 23.28%. The results are presented in Table 7.

TABLE 7

| hours | NB5 (2 PSI) | NB6 (15 PSI) | NB7 (20 PSI) | NB8 (20 PSI) |
|---|---|---|---|---|
| % EPA/FAME | | | | |
| 17.5 | 12.63 | 13.43 | 13.15 | 14.32 |
| 41.5 | 12.05 | 12.01 | 11.54 | 16.37 |
| 65.5 | 14.03 | 16.54 | 15.34 | 20.37 |
| 89.5 | 18.67 | 20.04 | 20.86 | 23.08 |
| 116.5 | 21.99 | 21.40 | 24.55 | 24.52 |
| 139.0 | 21.24 | 21.57 | 25.85 | 25.25 |
| 161.5 | 19.95 | 20.42 | 24.78 | 24.96 |
| 185.5 | 18.95 | 18.89 | 23.28 | 23.90 |
| % DHA/FAME | | | | |
| 17.5 | 48.66 | 52.94 | 52.56 | 49.15 |
| 41.5 | 52.62 | 52.38 | 52.98 | 43.43 |
| 65.5 | 45.69 | 41.45 | 44.05 | 35.17 |
| 89.5 | 40.35 | 39.22 | 34.81 | 31.87 |
| 116.5 | 42.26 | 39.77 | 34.14 | 32.42 |
| 139.0 | 45.70 | 41.83 | 34.92 | 33.31 |
| 161.5 | 48.55 | 44.96 | 38.09 | 35.65 |
| 185.5 | 50.48 | 47.52 | 41.26 | 38.38 |
| DHA:EPA Ratio | | | | |
| 17.5 | 3.85 | 3.94 | 4.00 | 3.43 |
| 41.5 | 4.37 | 4.36 | 4.59 | 2.65 |
| 65.5 | 3.26 | 2.51 | 2.87 | 1.73 |
| 89.5 | 2.16 | 1.96 | 1.67 | 1.38 |
| 116.5 | 1.92 | 1.86 | 1.39 | 1.32 |
| 139.0 | 2.15 | 1.94 | 1.35 | 1.32 |
| 161.5 | 2.43 | 2.20 | 1.54 | 1.43 |
| 185.5 | 2.66 | 2.52 | 1.77 | 1.61 |

EXAMPLE 5

In this example [Nx0719et10], *Schizochytrium* species (ATCC PTA-10208) was cultivated in four 14-liter New Brunswick Scientific BioFlo 310 fermentors at a target final (recipe) volume of 10-liters with a carbon (glucose) and nitrogen (ammonium hydroxide) fed-batch process. Three of the four fermentors were supplemented with carbon dioxide at different time points during the fermentation to evaluate the sensitivity of the culture to increased dissolved carbon dioxide. NBS1, NBS2, and NBS3 were supplemented with carbon dioxide beginning at log hour 12, 24, and 48 respectively. The fermentations were each inoculated with 1 liters of culture each. For inoculum propagation, a 14-liter Virtis fermentor was utilized. The inoculum medium consisted of 10-liters of medium prepared in four separate groups. Group 1 consisted of 90 g MSG*1H2O, 10 g KCl, 50 g MgSO4*7H2O, 3.3 g (NH4)2SO4, 6.25 g of NaCl, 60 g of T154 (yeast extract), 4.97 g KH2PO4, 2.9 g CaCl2*2H2O, and 2 mL Dow 1520US (antifoam). Group 1 was autoclaved at 121 degrees for 120 minutes at a volume of approximately 9.8 liters. Group 2 consisted of 500 g glucose dissolved in a volume of 800 mL RO water. Group 3 consisted of 31 mg MnCl2*4H2O, 31 mg ZnSO4*7H2O, 0.4 mg CoCl2*6H2O, 0.4 mg Na2MoO4*2H2O, 20.7 mg CuSO4*5H2O, 20.7 mg NiSO4*6H2O, 103 mg FeSO4*7H2O and 234.1 mg citric acid. Groups 2 and 3 were each autoclaved 60 minutes. Group 4 consisted of 97.5 mg Thiamine-HCl, 1.6 mg vitamin B12, and 33.3 mg pantothenic acid hemi-calcium salt. Group 4 was dissolved in RO water and then filter-sterilized. After the fermentor was cooled to 22.5 degrees Celsius, groups 2, 3, 4, and 5 were added to the fermentor. Using sodium hydroxide and sulfuric acid, the fermentor was pH adjusted to 7 and the dissolved oxygen was spanned to 100% prior to inoculation. The inoculum fermentor was inoculated with 150 mL of a smaller fermentation culture (The smaller fermentation culture was prepared and cultivated in the same manner as the 10-liter inoculum culture.) and cultivated at 22.5 degrees Celsius, pH 7, 433 rpm agitation, and 5 lpm of air for a period of 44.5 hours, at which point 1 liters of inoculum broth was transferred to each 14-liter fermentor. Each 14-liter fermentor contained 10-liters of fermentation media. The fermentation media was prepared in a similar fashion to the inoculum fermentor. For each 14-liter fermentor, the fermentation media consisted of 6 batched media groups. For all vessels, group 1 contained 60 g Na2SO4, 6.25 g NaCl, 10 g KCl, 50 g MgSO4*7H2O, 0.43 g (NH4)2SO4, 10 g T154 yeast extract, and 1 mL Dow 1520-US antifoam. Group 1 was autoclaved at 121 degrees Celsius for 120 minutes in the 14-liter fermentors at a volume of approximately 6.5 liters. Group 2 contained 2.9 g CaCl2*2H2O in a volume of approximately 20 mL RO water. Group 3 contained 17.61 g KH2PO4 dissolved in 100 mL of RO water. Group 4 contained 31 mg MnCl2*4H2O, 93 mg ZnSO4*7H2O, 0.4 mg Na2MoO4*2H2O, 20.7 mg CuSO4*5H2O, 20.7 mg NiSO4*6H2O, 103 mg FeSO4*7H2O and 10 g citric acid all dissolved in 50 mL of RO water. Group 5 contained 97.5 mg Thiamine-HCl, 33.3 mg pantothenic acid hemi-calcium salt, and 36.3 ug of biotin, all dissolved and filter sterilized in 10 mL RO water. Group 6 contained 300 g of glucose in approximately 0.5 liters of RO water. Groups 2, 3, 4, 5, and 6 were combined and added to the fermentor after the fermentor reached an operating temperature of 22.5 degrees Celsius. Each fermentor volume prior to inoculation was approximately 6.5 liters. Each fermentor was inoculated with 1 liter of broth from the inoculum fermentation described above. The fermentation was pH controlled utilizing a 0.85 liter solution of 4N ammonium hydroxide at a pH of 7 until nitrogen exhaustion at which point 4N sodium hydroxide and 3N sulfuric acid were utilized for pH control at a set-point of 7.5. The dissolved oxygen was controlled to maintain a target of 20% throughout the fermentation using agitation from 357 to 833 rpm and airflow from 7 LPM to 7 LPM. Vessels NBS1, NBS2, NBS3 were each supplemented with carbon dioxide for different timeframes to evaluate the sensitivity of the organism to increased dissolved carbon dioxide. Throughout the fermentation, an 850 g/L solution of 95% dextrose (corn syrup) was fed to maintain a glucose concentration less than 50 g/L. After 8 days, the dry cell weight and omega-3 titer of each 10-liter fermentor varied depending on the carbon dioxide supplementation conditions. At 183 hours, NBS1 was at 109.1 g/L DCW and 45.87 g/L omega-3; NBS1 was at 108.9 g/L DCW and 45.41 g/L omega-3; NBS3 was at 116.4 g/L DCW and 50.6 g/L omega-3; NBS4 was at 95.7 g/L DCW and 40.36 g/L omega-3. Shortly after the carbon dioxide supplementation was initiated, the % DHA/FAME decreased, the % EPA/FAME increased, and the ratio of DHA to EPA decreased. When comparing the maximum % EPA/FAME content of the carbon dioxide supplemented conditions and the ambient condition, there is 65% increase in the maximum EPA content under $CO_2$ supplemented conditions. The results are presented in Table 8.

TABLE 8

| | % EPA/FAME | | | |
| --- | --- | --- | --- | --- |
| hours | NBS1 (+CO2 @ 12 hours) | NBS2 (+CO2 @ 24 hours) | NBS3 (+CO2 @ 48 hours) | NBS4 (no CO2 added) |
| 15 | 12.29 | 10.67 | 10.22 | 10.14 |
| 39 | 22.82 | 19.32 | 10.37 | 9.85 |
| 63 | 23.79 | 24.58 | 19.77 | 15.09 |
| 87 | 23.69 | 23.71 | 23.83 | 14.09 |
| 114 | 27.85 | 27.55 | 26.91 | 16.98 |
| 137 | 29.47 | 27.94 | 26.76 | 17.81 |
| 159 | 29.13 | 27.20 | 26.52 | 17.81 |
| 183 | 27.62 | 25.50 | 25.62 | 17.09 |
| | % DHA/FAME | | | |
| hours | NBS1 | NBS2 | NBS3 | NBS4 |
| 15 | 43.27 | 44.69 | 46.34 | 45.91 |
| 39 | 33.34 | 43.14 | 39.54 | 38.81 |
| 63 | 32.18 | 33.65 | 36.22 | 47.31 |
| 87 | 26.33 | 26.65 | 27.82 | 45.79 |
| 114 | 23.99 | 24.36 | 28.09 | 44.13 |
| 137 | 25.43 | 27.47 | 31.11 | 46.47 |
| 159 | 28.54 | 30.59 | 33.70 | 48.59 |
| 183 | 31.83 | 33.70 | 35.98 | 50.98 |
| | DHA:EPA Ratio | | | |
| hours | NBS1 | NBS2 | NBS3 | NBS4 |
| 15 | 3.52 | 4.19 | 4.53 | 4.53 |
| 39 | 1.46 | 2.23 | 3.81 | 3.94 |
| 63 | 1.35 | 1.37 | 1.83 | 3.14 |
| 87 | 1.11 | 1.12 | 1.17 | 3.25 |
| 114 | 0.86 | 0.88 | 1.04 | 2.60 |
| 137 | 0.86 | 0.98 | 1.16 | 2.61 |
| 159 | 0.98 | 1.12 | 1.27 | 2.73 |
| 183 | 1.15 | 1.32 | 1.40 | 2.98 | carbon dioxide supplemented during highlighted timeframe

EXAMPLE 6

In this example [Nx0106et10], *Schizochytrium* species (ATCC PTA-10208) was cultivated in four 14-liter New Brunswick Scientific BioFlo 310 fermentors at a target final (recipe) volume of 10-liters with a carbon (glucose) and nitrogen (ammonium hydroxide) fed-batch process. The temperature was controlled throughout the fermentation run to maintain a target of 21.0° C., 22.5° C., 24.0° C., and 25.5° C. for NBS1, NBS2, NBS3, and NBS4 respectively. The fermentations were each inoculated with 1 liters of culture each. For inoculum propagation, a 14-liter Virtis fermentor was utilized. The inoculum medium consisted of 10-liters of medium prepared in four separate groups. Group 1 consisted of 90 g MSG*1H2O, 10 g KCl, 50 g MgSO4*7H2O, 3.7 g (NH4)2SO4, 6.25 g of NaCl, 60 g of T154 (yeast extract), 5.2 g KH2PO4, 2.9 g CaCl2*2H2O, and 2 mL Dow 1520US (antifoam). Group 1 was autoclaved at 121 degrees for 120 minutes at a volume of approximately 9.8 liters. Group 2 consisted of 500 g glucose dissolved in a volume of 800 mL RO water. Group 3 consisted of 31 mg MnCl2*4H2O, 31 mg ZnSO4*7H2O, 0.4 mg CoCl2*6H2O, 0.4 mg Na2MoO4*2H2O, 20.7 mg CuSO4*5H2O, 20.7 mg NiSO4*6H2O, 103 mg FeSO4*7H2O and 234.1 mg citric acid. Groups 2 and 3 were each autoclaved for 60 minutes. Group 4 consisted of 97.5 mg Thiamine-HCl, 1.6 mg vitamin B12, and 33.3 mg pantothenic acid hemi-calcium salt. Group 4 was dissolved in RO water and then filter-sterilized. After the fermentor was cooled to 22.5 degrees Celsius, groups 2, 3, 4, and 5 were added to the fermentor. Using sodium hydroxide and sulfuric acid, the fermentor was pH adjusted to 7 and the dissolved oxygen was spanned to 100% prior to inoculation. The inoculum fermentor was inoculated with 200 mL of a smaller fermentation culture (The smaller fermentation culture was prepared and cultivated in the same manner as the 10-liter inoculum culture.) and cultivated at 22.5 degrees Celsius, pH 7, 433 rpm agitation, and 5 lpm of air for a period of 42 hours, at which point 1 liters of inoculum broth was transferred to each 14-liter fermentor. Each 14-liter fermentor contained 10-liters of fermentation media. The fermentation media was prepared in a similar fashion to the inoculum fermentor. For each 14-liter fermentor, the fermentation media consisted of 4 batched media groups. For all vessels, group 1 contained 88 g Na2SO4, 6.25 g NaCl, 10 g KCl, 50 g MgSO4*7H2O, 4.2 g (NH4)2SO4, 2.9 g CaCl2*2H2O, 17.65 g KH2PO4, 10 g T154 yeast extract, and 1 mL Dow 1520-US antifoam. Group 1 was autoclaved at 121 degrees Celsius for 120 minutes in the 14-liter fermentors at a volume of approximately 7.0 liters. Group 2 contained 31 mg MnCl2*4H2O, 93 mg ZnSO4*7H2O, 0.4 mg Na2MoO4*2H2O, 20.7 mg CuSO4*5H2O, 20.7 mg NiSO4*6H2O, 103 mg FeSO4*7H2O and 468 mg of citric acid dissolved in 50 mL of RO water. Group 2 was autoclaved for 60 minutes. Group 3 contained 97.5 mg Thiamine-HCl, 33.3 mg pantothenic acid hemi-calcium salt, and 35.8 ug of biotin, all dissolved and filter sterilized in 10 mL RO water. Group 4 contained 300 g of glucose in approximately 0.5 liters of RO water and autoclaved for 60 minutes. Groups 2, 3, and 4 were combined and added to the fermentor after the fermentor reached an operating temperature of 22.5 degrees Celsius. Each fermentor volume prior to inoculation was approximately 6.5 liters. Each fermentor was inoculated with 1 liter of broth from the inoculum fermentation described above. The fermentation was pH controlled at 7.0 throughout the fermentation utilizing a 0.85 liter solution of 4N ammonium hydroxide until nitrogen exhaustion at which point 4N sodium hydroxide and 3N sulfuric acid were utilized for pH control at a set-point. The dissolved oxygen was controlled to maintain a target of 20% until nitrogen exhaustion. After nitrogen exhaustion, the dissolved oxygen was controlled to maintain a target of 10% until the end of the fermentation using agitation from 357 to 714 rpm and 8 LPM of airflow. Throughout the fermentation, an 850 g/L solution of 95% dextrose (corn syrup) was fed to maintain a glucose concentration less than 50 g/L. After 8 days, the dry cell weight or omega-3 titer varied slightly for the different temperatures evaluated; however, the lower fermentation temperatures resulted in higher % EPA/FAME. At 184 hours, NBS1 was at 85.2 g/L DCW and 29.9 g/L omega-3; NBS2 was at 92.0 g/L DCW and 35.0 g/L omega-3; NBS3 was at 86.8 g/L DCW and 31.7 g/L omega-3; NBS4 was at 84.2 g/L DCW and 29.4 g/L omega-3.

For NBS1, % EPA/FAME ranged from 12.36% to 19.02% from start to end of the fermentation run with a maximum of 21.57%. For NBS2, % EPA/FAME ranged from 11.72% to 18.11% from start to end of the fermentation run with a maximum of 20.21%. NBS3, % EPA/FAME ranged from 11.49% to 15.43% from start to end of the fermentation run with a maximum of 18.09%. NBS4, % EPA/FAME ranged from 11.65% to 13.65% from start to end of the fermentation run with a maximum of 15.70%. When comparing the maximum % EPA/FAME, the lowest fermentation temperature resulted in a 37% increase in the maximum EPA content over the highest fermentation temperature evaluated. The results are provided in Table 9 below.

TABLE 9

| Hours | NBS1 (21° C.) | NBS2 (22.5° C.) | NBS3 (24° C.) | NBS4 (25.5° C.) |
|---|---|---|---|---|
| % EPA/FAME | | | | |
| 24 | 12.36 | 11.72 | 11.49 | 11.65 |
| 40 | 14.17 | 13.61 | 12.21 | 13.04 |
| 64 | 14.48 | 14.94 | 14.23 | 13.62 |
| 89 | 19.52 | 18.45 | 17.42 | 15.70 |
| 112 | 21.57 | 20.21 | 18.09 | 15.69 |
| 136 | 21.05 | 20.11 | 17.15 | 14.82 |
| 160 | 19.90 | 18.88 | 16.15 | 13.98 |
| 184 | 19.02 | 18.11 | 15.43 | 13.65 |
| % DHA/FAME | | | | |
| 24 | 56.58 | 55.61 | 54.62 | 53.56 |
| 40 | 52.80 | 51.58 | 52.17 | 49.77 |
| 64 | 47.46 | 45.36 | 46.41 | 44.57 |
| 89 | 38.89 | 39.69 | 39.46 | 39.54 |
| 112 | 40.08 | 40.89 | 41.72 | 42.20 |
| 136 | 43.22 | 43.87 | 45.23 | 45.56 |
| 160 | 45.92 | 46.98 | 47.80 | 48.07 |
| 184 | 48.04 | 48.99 | 49.38 | 49.39 |
| DHA:EPA Ratio | | | | |
| 24 | 4.58 | 4.75 | 4.75 | 4.60 |
| 40 | 3.73 | 3.79 | 4.27 | 3.82 |
| 64 | 3.28 | 3.04 | 3.26 | 3.27 |
| 89 | 1.99 | 2.15 | 2.27 | 2.52 |
| 112 | 1.86 | 2.02 | 2.31 | 2.69 |
| 136 | 2.05 | 2.18 | 2.64 | 3.07 |
| 160 | 2.31 | 2.49 | 2.96 | 3.44 |
| 184 | 2.53 | 2.71 | 3.20 | 3.62 |

EXAMPLE 7

In this example [Nx0614et10], *Schizochytrium* species (ATCC PTA-10208) was cultivated in two 14-liter New Brunswick Scientific BioFlo 310 fermentors at a target final (recipe) volume of 10-liters with a carbon (glucose) and nitrogen (ammonium hydroxide) fed-batch process. One fermentor (NBS15) was sparged with air supplemented with 15% carbon dioxide from start to end of the fermentation run and the other fermentor (NBS17) was sparged with air only to evaluate the sensitivity of the culture to increased dissolved carbon dioxide. The fermentations were each inoculated with 1 liters of culture each. For inoculum propagation, a 14-liter Virtis fermentor was utilized. The inoculum medium consisted of 10-liters of medium prepared in four separate groups. Group 1 consisted of 90 g MSG*1H2O, 10 g KCl, 50 g MgSO4*7H2O, 3.3 g (NH4)2SO4, 6.25 g of NaCl, 60 g of T154 (yeast extract), 4.97 g KH2PO4, 2.9 g CaCl2*2H2O, and 2 mL Dow 1520US (antifoam). Group 1 was autoclaved at 121 degrees for 120 minutes at a volume of approximately 9.8 liters. Group 2 consisted of 500 g glucose dissolved in a volume of 800 mL RO water. Group 3 consisted of 31 mg MnCl2*4H2O, 31 mg ZnSO4*7H2O, 0.4 mg CoCl2*6H2O, 0.4 mg Na2MoO4*2H2O, 20.7 mg CuSO4*5H2O, 20.7 mg NiSO4*6H2O, 103 mg FeSO4*7H2O and 234.1 mg citric acid. Groups 2 and 3 were each autoclaved for 60 minutes. Group 4 consisted of 97.5 mg Thiamine-HCl, 1.6 mg vitamin B12, and 33.3 mg pantothenic acid hemi-calcium salt. Group 4 was dissolved in RO water and then filter-sterilized. After the fermentor was cooled to 22.5 degrees Celsius, groups 2, 3, 4, and 5 were added to the fermentor. Using sodium hydroxide and sulfuric acid, the fermentor was pH adjusted to 7 and the dissolved oxygen was spanned to 100% prior to inoculation. The inoculum fermentor was inoculated with 200 mL of a smaller fermentation culture (The smaller fermentation culture was prepared and cultivated in the same manner as the 10-liter inoculum culture.) and cultivated at 22.5 degrees Celsius, pH 7, 433 rpm agitation, and 5 lpm of air for a period of 40 hours, at which point 1 liters of inoculum broth was transferred to each 14-liter fermentor. Each 14-liter fermentor contained 10-liters of fermentation media. The fermentation media was prepared in a similar fashion to the inoculum fermentor. For each 14-liter fermentor, the fermentation media consisted of 6 batched media groups. For all vessels, group 1 contained 88 g Na2SO4, 6.25 g NaCl, 10 g KCl, 50 g MgSO4*7H2O, 4.2 g (NH4)2SO4, 10 g T154 yeast extract, and 1 mL Dow 1520-US antifoam. Group 1 was autoclaved at 121 degrees Celsius for 120 minutes in the 14-liter fermentors at a volume of approximately 6.5 liters. Group 2 contained 2.9 g CaCl2*2H2O in a volume of approximately 20 mL RO water. Group 3 contained 17.65 g KH2PO4 dissolved in 100 mL of RO water. Group 4 contained 31 mg MnCl2*4H2O, 93 mg ZnSO4*7H2O, 0.4 mg Na2MoO4*2H2O, 20.7 mg CuSO4*5H2O, 20.7 mg NiSO4*6H2O, 103 mg FeSO4*7H2O and 468 mg of citric acid dissolved in 50 mL of RO water. Groups 2, 3, and 4 were each autoclaved for 60 minutes. Group 5 contained 97.5 mg Thiamine-HCl, 33.3 mg pantothenic acid hemi-calcium salt, and 36.3 ug of biotin, all dissolved and filter sterilized in 10 mL RO water. Group 6 contained 300 g of glucose in approximately 0.5 liters of RO water and autoclaved for 60 minutes. Groups 2, 3, 4, 5, and 6 were combined and added to the fermentor after the fermentor reached an operating temperature of 22.5 degrees Celsius. Each fermentor volume prior to inoculation was approximately 6.5 liters. Each fermentor was inoculated with 1 liter of broth from the inoculum fermentation described above. The fermentation was pH controlled at 7.0 throughout the fermentation utilizing a 0.85 liter solution of 4N ammonium hydroxide until nitrogen exhaustion at which point 4N sodium hydroxide and 3N sulfuric acid were utilized for pH control at a set-point. The dissolved oxygen was controlled to maintain a target of 20% until nitrogen exhaustion. After nitrogen exhaustion, the dissolved oxygen was controlled to maintain a target of 10% until the end of the fermentation using agitation from 357 to 833 rpm and 8 LPM of airflow. Throughout the fermentation, an 850 g/L solution of 95% dextrose (corn syrup) was fed to maintain a glucose concentration less than 50 g/L. After 8 days, the dry cell weight and omega-3 titer of each 10-liter fermentor varied depending on the carbon dioxide supplementation conditions. At 188 hours, NBS15 was at 54.5 g/L DCW and 13.7 g/L omega-3; NBS17 was at 96.1 g/L DCW and 37.5 g/L omega-3. % EPA/FAME was higher in NBS15 ($CO_2$ supplemented condition throughout the run) than NBS17 (no $CO_2$ supplementation). For NBS15, % EPA/FAME ranged from 25.50% to 35.48% from start to end of the fermentation run with a maximum of 38.34%. For NBS 17, % EPA/FAME ranged from 12.31% to 19.80% from start to end of the fermentation run with a maximum of 22.29%. When comparing the maximum % EPA/FAME content of the carbon dioxide supplemented conditions and the ambient condition, there is 73% increase in the maximum EPA content under $CO_2$ supplemented conditions.

% DHA/FAME was lower for the $CO_2$ supplemented conditions than for the ambient condition throughout the fermentation run. The results are provided in Table 10 below.

TABLE 10

| Hours | NBS1 (21° C.) | NBS2 (22.5° C.) | NBS3 (24° C.) | NBS4 (25.5° C.) |
|---|---|---|---|---|
| % EPA/FAME | | | | |
| 24 | 12.36 | 11.72 | 11.49 | 11.65 |
| 40 | 14.17 | 13.61 | 12.21 | 13.04 |
| 64 | 14.48 | 14.94 | 14.23 | 13.62 |
| 89 | 19.52 | 18.45 | 17.42 | 15.70 |
| 112 | 21.57 | 20.21 | 18.09 | 15.69 |
| 136 | 21.05 | 20.11 | 17.15 | 14.82 |
| 160 | 19.90 | 18.88 | 16.15 | 13.98 |
| 184 | 19.02 | 18.11 | 15.43 | 13.65 |
| % DHA/FAME | | | | |
| 24 | 56.58 | 55.61 | 54.62 | 53.56 |
| 40 | 52.80 | 51.58 | 52.17 | 49.77 |
| 64 | 47.46 | 45.36 | 46.41 | 44.57 |
| 89 | 38.89 | 39.69 | 39.46 | 39.54 |
| 112 | 40.08 | 40.89 | 41.72 | 42.20 |
| 136 | 43.22 | 43.87 | 45.23 | 45.56 |
| 160 | 45.92 | 46.98 | 47.80 | 48.07 |
| 184 | 48.04 | 48.99 | 49.38 | 49.39 |
| DHA:EPA Ratio | | | | |
| 24 | 4.58 | 4.75 | 4.75 | 4.60 |
| 40 | 3.73 | 3.79 | 4.27 | 3.82 |
| 64 | 3.28 | 3.04 | 3.26 | 3.27 |
| 89 | 1.99 | 2.15 | 2.27 | 2.52 |
| 112 | 1.86 | 2.02 | 2.31 | 2.69 |
| 136 | 2.05 | 2.18 | 2.64 | 3.07 |
| 160 | 2.31 | 2.49 | 2.96 | 3.44 |
| 184 | 2.53 | 2.71 | 3.20 | 3.62 |

EXAMPLE 8

In this example [K019], *Schizochytrium* species (ATCC PTA-10208) was cultivated in 157,000-liter agitated fermentor at a target final (recipe) weight of 100,000 kg with a carbon (glucose) and nitrogen (anhydrous ammonia gas) fed-batch process. The fermentation was inoculated with 4500 kg of culture. For inoculum propagation, a 7500-liter agitated seed fermentor was utilized. The inoculum medium consisted of 4500 kg of medium prepared in four separate groups. Group 1 consisted of 40.5 kg MSG*1H2O, 4.5 kg KCl, 22.5 kg MgSO4*7H2O, 1.7 kg (NH4)2SO4, 2.81 kg of NaCl, 27 kg of T154 (yeast extract), 2 kg KH2PO4, 985 g CaCl2, and 0.9 kg Dow 1520US (antifoam) dissolved in process water with a total weight of 2300 kg. Group 2 consisted of 247.5 kg glucose.1H2O dissolved in process water with a total weight of 1500 kg. Group 1 was sterilized in the seed fermentor, and Group 2 was sterilized in a separate vessel, with steam-in-place at 122-123 degrees Celsius for 30 minutes. Group 3 consisted of 14 g MnCl2*4H2O, 14 g ZnSO4*7H2O, 180 mg CoCl2*6H2O, 180 mg Na2MoO4*2H2O, 9.3 g CuSO4*5H2O, 9.3 g NiSO4*6H2O, 46.4 g FeSO4*7H2O and 105.3 g citric acid dissolved in 5 L of distilled water. Group 3 were autoclaved at 121 degrees Celsius for 60 minutes. Group 4 consisted of 43.9 g Thiamine-HCl, 720 mg vitamin B12, and 15 g pantothenic acid hemi-calcium salts dissolved in 5 L distilled water and then filter-sterilized. After the seed fermentor was cooled to 22.5 degrees Celsius, groups 2, 3, 4 were added to the fermentor. Using sodium hydroxide and sulfuric acid, the fermentor was pH adjusted to 7 and the dissolved oxygen was spanned to 100% prior to inoculation. The seed fermentor was inoculated with 12 L of a smaller fermentation culture (The smaller fermentation culture was prepared and cultivated in the same manner as the seed culture) and cultivated at 22.5 degrees Celsius, pH 7, 90 rpm agitation, and 130-170 Nm3/hr of air for a period of 4-5 days to get a dry cell weight about 15 g/L. The fermentation media was prepared in a similar fashion to the inoculum fermentor. the fermentation media consisted of 5 groups. Group 1 contained 177 kg KH2PO4, 880 kg Na2SO4, 500 kg MgSO4*7H2O, 42 kg (NH4)2SO4, 100 kg T154 yeast extract, and 10 kg of Dow 1520-US antifoam in a 9,000 kg of solution. Group 2 contained 21.9 kg CaCl2, 62.5 kg NaCl, 100 kg KCl, in a 9,000 kg solution. Group 1 and 2 were pumped through a heat exchanger into the fermentor, followed by water to get 67,000 kg of weight in fermentor. Group 3 contained 310 g MnCl2*4H2O, 930 g ZnSO4*7H2O, 4 g Na2MoO4*2H2O, 207 g CuSO4*5H2O, 207 g NiSO4*6H2O, 1.03 kg FeSO4*7H2O and 4.68 kg citric acid dissolved in 1500 kg of process water. Group 4 contained 4300 kg of corn syrup (DE-95, 70.5%). Group 3 and Group 4 were sterilized in different vessels, with steam-in-place at 122-123 degrees Celsius for 30 minutes. Group 5 contained 975 g Thiamine-HCl, 333 g pantothenic acid hemi-calcium salt, and 358 mg of biotin, dissolved and filter sterilized in 5 L distilled water. Groups 3, 4, and 5 were added to the fermentor after the fermentor was cooled down to 22.5 degrees Celsius. The weight in the fermentor volume prior to inoculation was approximately 73,500 kg. After the starting fermentation condition was set (temperature: 22.5° C., pressure: 0.34 bar, airflow: 3000 Nm3/hr, agitation, 40 rpm), the fermentation pH was adjusted to 7 and the dissolved oxygen was spanned to 100%. The weight after inoculation was about 78,000 kg. At the beginning, pH was controlled at 7 utilizing anhydrous ammonia until 550 kg of ammonia was added, and then 30% sodium hydroxide solution was utilized for pH control at a set-point of 7.5. The dissolved oxygen was controlled to maintain a target of 20% during ammonia feed and 10% afterward using agitation from 40 to 100 rpm and airflow from 2000 to 8000 Nm3/hr. Throughout the fermentation, a 65% DE-95 corn syrup solution was fed to maintain a glucose concentration around 35 g/L. In another example [K020], three changes were made from the example K019: 1) pressure was reduced to 0.15 bar, 2) weight after inoculation was reduced to 68,000 kg, 3) airflow was increased to above 5000 Nm3/hr at 60 hrs after inoculation and was maintained high throughout the run regardless of the dissolved oxygen concentration. The above three changes reduced the dissolved carbon dioxide concentration in the broth. The results showed that with the reduced $CO_2$, % DHA/FAME was increased from 38.38% to 43.8%, and % EPA/FAME was reduced from 24.42% to 20.68%. The DHA:EPA ratio was increased from 1.57 to 2.12. The results are presented in Table 11 below.

TABLE 11

K019

| Age Hr | DHA/FAME % | EPA/FAME % | DHA:EPA Ratio |
|---|---|---|---|
| 38 | 56.32 | 11.47 | 4.91 |
| 50 | 51.03 | 13.2 | 3.87 |
| 62 | 43.99 | 16.97 | 2.59 |
| 74 | 34.65 | 19.94 | 1.74 |
| 86 | 32.14 | 22.56 | 1.42 |

TABLE 11-continued

K019

| Age Hr | DHA/FAME % | EPA/FAME % | DHA:EPA Ratio |
|---|---|---|---|
| 98 | 30.05 | 25.2 | 1.19 |
| 134 | 31.45 | 28.36 | 1.11 |
| 146 | 33.54 | 27.43 | 1.22 |
| 158 | 35.48 | 26.29 | 1.35 |
| 170 | 37.16 | 25.47 | 1.46 |
| 182 | 38.38 | 24.42 | 1.57 |

TABLE 12

K020 (Reduced Dissolved $CO_2$)

| Age hr | DHA/FAME % | EPA/FAME % | DHA:EPA Ratio |
|---|---|---|---|
| 12 | 56.3 | 13.03 | 4.32 |
| 28 | 58.12 | 12 | 4.84 |
| 40 | 55.55 | 12.13 | 4.58 |
| 52 | 52.13 | 14.03 | 3.72 |
| 64 | 45.14 | 16.94 | 2.66 |
| 76 | 37.54 | 18.57 | 2.02 |
| 84 | 35.06 | 18.72 | 1.87 |
| 96 | 35.24 | 20.05 | 1.76 |
| 132 | 39.42 | 22.29 | 1.77 |
| 156 | 42.05 | 21.54 | 1.95 |
| 180 | 43.8 | 20.68 | 2.12 |

EXAMPLE 9

In the table below, the maximum dissolved $CO_2$ is calculated for several of the examples using Henry's constant. The first condition, "10 L (NBS4 0719et10) at 0 PSI back pressure and 45.5 mmol/L/hour CER" is the calculated dissolved $CO_2$ for NBS4 in table 8 at a carbon dioxide evolution rate of 45.5 mmol/L/hour, a fermentation volume of 10-liters, an aeration rate of 0.8 vvm, and 0 PSI backpressure. The second condition, "10 L (NBS2 0719et10) at 0 PSI back pressure with 6% $CO_2$ in the inlet gas and 50 mmol/L/hour CER" is the calculated dissolved $CO_2$ for NBS2 in Table 8 at a carbon dioxide evolution rate of 50 mmol/L/hour, a fermentation volume of 10-liters, an aeration rate of 0.8 vvm, at 0 PSI backpressure, and with $CO_2$ supplemented in the inlet stream at 6% of the total gas as measured by mass spectrometry using a Thermo Prima dB mass spectrometer. The third condition, "80-liter (NB5 0614et10) at 2 PSI backpressure and 55 mmol/L/hour CER" is the calculated dissolved $CO_2$ for NB5 in Table 7 at a carbon dioxide evolution rate of 55 mmol/L/hour, a fermentation volume of 80-liters, an aeration rate of 1.0 vvm, and 2 PSI backpressure. The fourth condition, "80-liter (NB6 0614et10) at 15 PSI backpressure and 50 mmol/L/hour CER" is the calculated dissolved $CO_2$ for NB6 in Table 7 at a carbon dioxide evolution rate of 50 mmol/L/hour, a fermentation volume of 80-liters, an aeration rate of 1.0 vvm, and 15 PSI backpressure. The fifth condition, "80-liter (NB7 & NB8 0614et10) at 20 PSI backpressure and 50 mmol/L/hour CER" is the calculated dissolved $CO_2$ for NB7 and NB8 in Table 7 at a carbon dioxide evolution rate of 50 mmol/L/hour, a fermentation volume of 80-liters, an aeration rate of 1.0 vvm, and 20 PSI backpressure. All CER values were calculated using off-gas $CO_2$ data collected with a Thermo Prima dB mass spectrometer. The results of the calculations are provided in Tables 13 and 14 below.

TABLE 13

| | | | |
|---|---|---|---|
| 10 L (NBS4 0719et10) at 0 PSI back pressure and 45.5 mmol/L/hour CER | RV | 10 | L |
| Absolute Pressure | input | 1.01 | bar |
| Airflow | input | 8 | LPM |
| Vvm | | 0.8 | |
| Required $CO_2$ in the air inlet | output | 0.14 | % |
| Delta $CO_2$ in the offgas | | 2.309125 | % |
| $CO_2$ in the offgas | | 2.446301 | % |
| $CO_2$ Partial Pressure | | 0.024708 | bar |
| | dissolved C02 | 0.000785 | mol/L |
| | dissolved C02 | 34.53 | ppm |
| 10 L (NBS2 0719et10) at 0 PSI back pressure with 6% $CO_2$ in the inlet gas and 50 mmol/L/hour CER | RV | 10 | L |
| Absolute Pressure | input | 1.01 | bar |
| Airflow | input | 8 | LPM |
| Vvm | | 0.8 | |
| Required $CO_2$ in the air inlet | output | 7.00 | % |
| Delta $CO_2$ in the offgas | | 2.5375 | % |
| $CO_2$ in the offgas | | 9.534653 | % |
| $CO_2$ Partial Pressure | | 0.0963 | bar |
| | dissolved C02 | 0.003059 | mol/L |
| | dissolved C02 | 134.58 | ppm |
| 80-liter (NB5 0614et10) at 2 PSI backpressure and 55 mmol/L/hour CER | RV | 80 | L |
| Back Pressure | input | 0.138 | bar |
| Total Pressure | | 1.21 | bar |
| Airflow | input | 80 | LPM |
| Vvm | | 1 | |
| Delta $CO_2$ | from CPR | 2.233 | % |
| $CO_2$ in the outlet | | 2.233 | % |
| $CO_2$ Partial Pressure | | 0.026975 | bar |
| | dissolved C02 | 0.000857 | mol/L |
| | dissolved C02 | 37.70 | ppm |
| 80-liter (NB6 0614et10) at 15 PSI backpressure and 50 mmol/L/hour CER | RV | 80 | L |
| Back Pressure | input | 1.0345 | bar |
| Total Pressure | | 2.10 | bar |
| Airflow | input | 80 | LPM |
| Vvm | | 1 | |
| Delta $CO_2$ | from CPR | 2.03 | % |
| $CO_2$ in the outlet | | 2.03 | % |
| $CO_2$ Partial Pressure | | 0.042721 | bar |
| | dissolved C02 | 0.001357 | mol/L |
| | dissolved C02 | 59.71 | ppm |
| 80-liter (NB7 & NB8 0614et10) at 20 PSI backpressure and 50 mmol/L/hour CER | RV | 80 | L |
| Back Pressure | input | 1.38 | bar |
| Total Pressure | | 2.45 | bar |
| Airflow | input | 80 | LPM |
| Vvm | | 1 | |
| Delta $CO_2$ | from CPR | 2.03 | % |
| $CO_2$ in the outlet | | 2.03 | % |
| $CO_2$ Partial Pressure | | 0.049735 | bar |
| | dissolved C02 | 0.00158 | mol/L |
| | dissolved C02 | 69.51 | ppm |

TABLE 14

| | NBS (2 PSI) | NB6 (15 PSI) | NB7 (20 PSI) | NB8 (20 PSI) | NBS2 (+$CO_2$ @ 24 hours) | NBS4 (no $CO_2$ added) |
|---|---|---|---|---|---|---|
| % EPA/FAME | 21.99 | 21.57 | 25.85 | 25.25 | 27.94 | 17.81 |
| % DHA/FAME | 40.35 | 39.22 | 34.14 | 32.42 | 24.36 | 38.81 |
| max dissolved $CO_2$ | 37.70 | 59.71 | 69.51 | 69.51 | 134.58 | 34.53 |

EXAMPLE 10

Experiments were performed to determine the effect of vitamin gradients on performance (dry cell weight of biomass (DW), % DHA, % fat, and % EPA) using ATCC Accession No. PTA-9695 in *Thraustochytrium* Shake Flask Medium (TSFM) under ambient $CO_2$ level.

Materials and Methods: Four vitamins (Thiamine.HCl, B12, Biotin, and Ca-pantothenate) were used in TSFM medium with 0.25 g/L tastone and 0.625 g/L NaCl (see Table 16). Additional MSG and KH2PO4 were added to the media to maintain their total nitrogen and phosphorous contents. The overall vitamin concentrations in the media were, 0, 0.5×, 1×, 5×, 10×, 20×, or 30× the standard amount, depending on the vitamins studied (see Table 17). The gradient study was performed on each vitamin separately. However in the case of biotin and Ca-pantothenate, standard amounts of Thiamine.HCl and B12 were also incorporated in the media, since the concentrations of the latter two were very low in the regular TSFM. Three TSFM controls were also included in the experiment for comparison. These controls were standard TSFM with 2 g/L tastone (see Table 15) and 1× Thiamine.HCl and 1×B12 (Cl); tastone-free TSFM without any vitamins (A); and tastone-free TSFM with 1× Thiamine.HCl and 1×B12 (B). All controls contained 0.625 g/L NaCl. Three-day old culture of PTA-9695 was used to inoculate duplicate 250-ml shake flasks at 0.1 g DW/L. All flasks (flat-bottom, with total of 50 ml media) were incubated aerobically at 22.5+/−1 C on a rotary shaker (200 RPM). All cultures were harvested after 7 days, and FAME analysis was performed on the final freeze-dried biomass samples

TABLE 15

Thraustochytrium Shake Flask Medium (TSFM) with 2 g/L tastone

| Component | Amount per liter (g) | [Stock] (g/l) | mL of stock to use per liter | |
|---|---|---|---|---|
| NaCl | 0.625 | dry | | |
| KCl | 1 | 50 | 20 ml | |
| MgSO4•7H2O | 5 | 227 | 22 ml | |
| (NH4)2SO4 | 0.2 | 190 | 1.05 ml | |
| CaCl2 2H2O | 0.29 | dry | | |
| MSG monohydrate | 2 | dry | | |
| Tastone 154 | 2 | dry | | |
| HEPES (100 mM0 pH 7 | 23.8 | dry | | |
| KH2PO4 | 0.1 | 56.5 | 1.77 ml | add after autoclaving |
| Glucose | 50 | 500 | 100 ml | add after autoclaving |
| Trace Metals | | see below | 1 ml | add after autoclaving |
| Vitamins | | see below | 1 ml | add after autoclaving |
| Trace Metal Solution | | | | |
| FeCl3•6H2O | 2.9 mg | 2.9 | | |
| CuSO4•5H2O | 0.02 mg | 0.02 | | |
| MnCl2•4H2O | 8.6 mg | 8.6 | | |
| CoCl2•6H2O | 0.26 mg | 0.26 | | |
| ZnCl2 | 0.6 mg | 0.6 | | |
| Citric Acid | 12 mg | 12 g (dry) | | |
| Vitamin Solution | | | | |
| Thiamine | 10 ug | 10 mg/l | | |
| Vitamin B12 | 1 ug | 1 mg/L | | |

TABLE 16

Thraustochytrium Shake Flask Medium (TSFM) with 0.25 g/L Tastone

| Component | Amount per liter (g) | [Stock] (g/l) | mL of stock to use per liter | |
|---|---|---|---|---|
| NaCl | 0.625 | dry | | |
| KCl | 1 | 50 | 20 ml | |
| MgSO4•7H2O | 5 | 227 | 22 ml | |
| (NH4)2SO4 | 0.2 | 190 | 1.05 ml | |
| CaCl2 2H2O | 0.29 | dry | | |
| MSG monohydrate | 4.554 | dry | | |
| Tastone GC 7189-1 | 0.25 | dry | | |
| HEPES (100 mM0 pH 7 | 23.8 | dry | | |
| KH2PO4 | 0.1 | 56.5 | 4.28 ml | add after autoclaving |
| Glucose | 50 | 500 | 100 ml | add after autoclaving |
| Trace Metals | | see below | 1 ml | add after autoclaving |
| Vitamins | | see below | 1 ml | add after autoclaving |
| TSFM Trace Metal | | | | |
| FeCl3•6H2O | 2.9 mg | 2.9 | | |
| CuSO4•5H2O | 0.02 mg | 0.02 | | |
| MnCl2•4H2O | 8.6 mg | 8.6 | | |
| CoCl2•6H2O | 0.26 mg | 0.26 | | |
| ZnCl2 | 0.6 mg | 0.6 | | |
| Citric Acid | 12 mg | 12 g (dry) | | |
| Vitamin Solution | | | | |
| Thiamine | 10 ug | 10 mg/l | | |
| Vitamin B12 | 1 ug | 1 mg/L | | |

TABLE 17

Vitamin concentrations used in this study (mg/L):

| vitamin conc. [X] | Thiamine•HCl | B12 | Biotin | Ca-Pantothenate |
|---|---|---|---|---|
| 0 | 0.0 | 0.0 | 0.0 | 0.0 |
| 0.5 | 0.005 | | 0.00234 | |
| 1 | 0.010 | 0.001 | 0.00468 | 3.33 |
| 5 | 0.050 | 0.005 | | 16.65 |
| 10 | 0.100 | 0.010 | 0.0468 | 33.30 |
| 20 | 0.200 | 0.020 | 0.0936 | 66.60 |
| 30 | | | 0.1404 | |

Results: The highest DW and % fat (6.7 g/L and 38.5%, respectively) for the thiamine gradient were achieved when the added amount of this vitamin to the medium was 5 times the standard level (FIG. 1). The % DHA at this level of thiamine was 44.1%. Below and above 5× thiamine, both DW and % fat started declining. % DHA also declined in the media with less than 5× thiamine, and it slightly fluctuated at above 5× thiamine with no significant improvement. % EPA in the thiamine gradient cultures ranged between 8.6 and 11.5. When no tastone or vitamins were added to the medium (FIG. 5, medium A), everything except % DHA declined significantly. The increase in % DHA, however, appeared to be artificial since both the DW and % fat were extremely low for this condition. The 1× concentration of B12 seemed to be optimal for DW, % DHA, % fat, and % EPA (FIG. 2). At this level of vitamin B12, the following were achieved: 7.1 g/L DW, 50.6% DHA, 42.7% fat, and 2.1% EPA. The highest % EPA (11.5) was obtained when no B12 was added to the medium. Tastone-free medium with no added vitamins did not further improve performance of the organism, and the higher % DHA seemed to be artificial, as it was described previously (FIG. 5, medium A).

Similarly, the 1× concentration of biotin was optimal for DW, % DHA, and % fat (FIG. 3). The corresponding values for these parameters were: 6.8 g/L, 47.7%, and 37.9%, respectively. Percent EPA at this point was 1.9. Tastone-free medium with 1× thiamine and 1×B12 (FIG. 5, medium B) significantly compromised the overall performance of PTA-9695.

Ca-pantothenate produced the highest DW, % DHA, and % fat when this vitamin was added to the medium at 10× the standard amount (FIG. 4). The optimal concentrations of these parameters were 7.0 g/L, 47.3%, and 39.1%, accordingly. The EPA content in the entire Ca-pantothenate gradient experiment was less than 2%. Significant reduction in the overall performance of PTA-9695 was noticed when the organism was grown in tastone-free medium with only 1× thiamine and 1×B12 (FIG. 5, medium B).

Results are also shown in the data tables below.

| | Trt ID | | | | | | | | | | | |
|---|---|---|---|---|---|---|---|---|---|---|---|---|
| | 1a | 1b | 2a | 2b | 3a | 3b | 4a | 4b | 5a | 5b | 6a | 6b |
| Thiamine•HCl [x] | 0 | 0 | 0.5 | 0.5 | 1 | 1 | 5 | 5 | 10 | 10 | 20 | 20 |
| B12 [x] | 0 | 0 | 0 | 0 | 0 | 0 | 0 | 0 | 0 | 0 | 0 | 0 |
| Biotin [x] | 0 | 0 | 0 | 0 | 0 | 0 | 0 | 0 | 0 | 0 | 0 | 0 |
| Ca-Pantothenate [x] | 0 | 0 | 0 | 0 | 0 | 0 | 0 | 0 | 0 | 0 | 0 | 0 |
| % DHA | 39.31 | 38.49 | 40.43 | 44.27 | 45.32 | 43.95 | 41.49 | 46.61 | 42.87 | 48.90 | 44.14 | 42.29 |
| average % DHA | | 38.90 | | 42.35 | | 44.63 | | 44.05 | | 45.89 | | 43.21 |
| % Fat | 32.31 | 31.47 | 32.40 | 37.62 | 37.25 | 32.74 | 34.92 | 42.03 | 36.85 | 39.11 | 36.63 | 36.27 |
| average % Fat | | 31.89 | | 35.01 | | 35.00 | | 38.48 | | 37.98 | | 36.45 |
| % EPA | 11.48 | 11.61 | 10.38 | 9.11 | 8.94 | 8.28 | 10.28 | 8.06 | 10.45 | 6.68 | 8.73 | 10.03 |
| average % EPA | | 11.54 | | 9.74 | | 8.61 | | 9.17 | | 8.57 | | 9.38 |
| % 16:0 | 29.58 | 29.48 | 31.34 | 31.19 | 30.38 | 31.87 | 30.15 | 31.04 | 30.20 | 30.97 | 31.59 | 30.00 |
| average % 16:0 | | 29.53 | | 31.26 | | 31.13 | | 30.59 | | 30.58 | | 30.80 |
| % ARA | 1.33 | 1.38 | 1.25 | 1.12 | 1.03 | 0.96 | 1.29 | 1.05 | 1.34 | 0.86 | 1.05 | 1.24 |
| average % ARA | | 1.36 | | 1.18 | | 1.00 | | 1.17 | | 1.10 | | 1.15 |

| vitamin standard conc. | (g/L) |
|---|---|
| Thiamine•HCl [1x] | 1.00E−05 |
| B12 [1x] | 1.00E−06 |
| Biotin [1x] | 4.68E−06 |
| Ca-Pantothenate [1x] | 3.33E−03 |

| | vitamin gradients [x] | | | | | | |
|---|---|---|---|---|---|---|---|
| | 0 | 0.5 | 1 | 5 | 10 | 20 | 30 |
| Thiamine•HCl (g/L) | 0 | 5.00E−06 | 1.00E−05 | 5.00E−05 | 1.00E−04 | 2.00E−04 | 3.00E−04 |
| B12 (g/L) | 0 | 5.00E−07 | 1.00E−06 | 5.00E−06 | 1.00E−05 | 2.00E−05 | 3.00E−05 |
| Biotin (g/L) | 0 | 2.34E−06 | 4.68E−06 | 2.34E−05 | 4.68E−05 | 9.36E−05 | 1.40E−04 |
| Ca-Pantothenate (g/L) | 0 | 1.67E−03 | 3.33E−03 | 1.67E−02 | 3.33E−02 | 6.66E−02 | 9.99E−02 |

Total vitamin concentrations including the carry over from the inoculum:

| | | | | | | | |
|---|---|---|---|---|---|---|---|
| Thiamine•HCl (g/L) | 2.38E−05 | 2.88E−05 | 3.38E−05 | 7.38E−05 | 1.24E−04 | 2.24E−04 | 3.24E−04 |
| B12 (g/L) | 1.37E−08 | 5.14E−07 | 1.01E−06 | 5.01E−06 | 1.00E−05 | 2.00E−05 | 3.00E−05 |
| Biotin (g/L) | 2.49E−04 | 2.51E−04 | 2.53E−04 | 2.72E−04 | 2.96E−04 | 3.42E−04 | 3.89E−04 |
| Ca-Pantothenate (g/L) | 3.10E−05 | 1.70E−03 | 3.36E−03 | 1.67E−02 | 3.33E−02 | 6.66E−02 | 9.99E−02 |

Total vitamin concentrations (mg/L) including the carry over from the inoculum:

| | | | | | | | |
|---|---|---|---|---|---|---|---|
| Thiamine•HCl | 2.38E−02 | 2.88E−02 | 3.38E−02 | 7.38E−02 | 1.24E−01 | 2.24E−01 | 3.24E−01 |
| B12 | 1.37E−05 | 5.14E−04 | 1.01E−03 | 5.01E−03 | 1.00E−02 | 2.00E−02 | 3.00E−02 |
| Biotin | 2.49E−01 | 2.51E−01 | 2.53E−01 | 2.72E−01 | 2.96E−01 | 3.42E−01 | 3.89E−01 |
| Ca-Pantothenate | 3.10E−02 | 1.70E+00 | 3.36E+00 | 1.67E+01 | 3.33E+01 | 6.66E+01 | 9.99E+01 |

| | Trt ID | | | | | | | | | | | |
|---|---|---|---|---|---|---|---|---|---|---|---|---|
| | 7a | 7b | 8a | 8b | 9a | 9b | 10a | 10b | 11a | 11b | 12a | 12b |
| Thiamine•HCl [x] | 0 | 0 | 0 | 0 | 0 | 0 | 0 | 0 | 0 | 0 | 1 | 1 |
| B12 [x] | 0 | 0 | 1 | 1 | 5 | 5 | 10 | 10 | 20 | 20 | 1 | 1 |
| Biotin [x] | 0 | 0 | 0 | 0 | 0 | 0 | 0 | 0 | 0 | 0 | 0 | 0 |
| Ca-Pantothenate [x] | 0 | 0 | 0 | 0 | 0 | 0 | 0 | 0 | 0 | 0 | 0 | 0 |
| % DHA | 39.31 | 38.49 | 50.45 | 50.75 | 50.83 | 50.05 | 45.99 | 46.44 | 46.90 | 44.48 | 42.07 | 42.74 |
| average % DHA | | 38.90 | | 50.60 | | 50.44 | | 46.21 | | 45.69 | | 42.41 |
| % Fat | 32.31 | 31.47 | 42.06 | 43.40 | 44.43 | 38.30 | 36.47 | 34.72 | 34.99 | 33.14 | 32.04 | 28.89 |
| average % Fat | | 31.89 | | 42.73 | | 41.36 | | 35.59 | | 34.06 | | 30.46 |
| % EPA | 11.48 | 11.61 | 2.08 | 2.05 | 2.01 | 2.01 | 2.11 | 2.22 | 2.03 | 2.16 | 1.76 | 2.14 |
| average % EPA | | 11.54 | | 2.06 | | 2.01 | | 2.17 | | 2.10 | | 1.95 |
| % 16:0 | 29.58 | 29.48 | 36.79 | 36.69 | 36.75 | 37.41 | 41.05 | 40.83 | 40.33 | 42.66 | 44.55 | 43.42 |
| average % 16:0 | | 29.53 | | 36.74 | | 37.08 | | 40.94 | | 41.50 | | 43.99 |
| % ARA | 1.33 | 1.38 | 0.16 | 0.15 | 0.17 | 0.14 | 0.14 | 0.00 | 0.00 | 0.00 | 0.00 | 0.00 |
| average % ARA | | 1.36 | | 0.15 | | 0.15 | | 0.07 | | 0.00 | | 0.00 |

| | Trt ID | | | | | | | | | | | |
|---|---|---|---|---|---|---|---|---|---|---|---|---|
| | 13a | 13b | 14a | 14b | 15a | 15b | 16a | 16b | 17a | 17b | 18a | 18b |
| Thiamine•HCl [x] | 1 | 1 | 1 | 1 | 1 | 1 | 1 | 1 | 1 | 1 | 1 | 1 |
| B12 [x] | 1 | 1 | 1 | 1 | 1 | 1 | 1 | 1 | 1 | 1 | 1 | 1 |
| Biotin [x] | 0.5 | 0.5 | 1 | 1 | 10 | 10 | 20 | 20 | 30 | 30 | 0 | 0 |
| Ca-Pantothenate [x] | 0 | 0 | 0 | 0 | 0 | 0 | 0 | 0 | 0 | 0 | 0 | 0 |
| % DHA | 48.32 | 46.94 | 46.13 | 49.18 | 45.43 | 43.63 | 44.37 | 41.79 | 44.36 | 42.19 | 42.07 | 42.74 |
| average % DHA | | 47.63 | | 47.65 | | 44.53 | | 43.08 | | 43.28 | | 42.41 |
| % Fat | 28.16 | 35.67 | 34.34 | 41.39 | 35.67 | 32.04 | 33.84 | 31.41 | 35.51 | 31.11 | 32.04 | 28.89 |
| average % Fat | | 31.92 | | 37.87 | | 33.85 | | 32.63 | | 33.31 | | 30.46 |
| % EPA | 2.36 | 1.83 | 1.92 | 1.91 | 1.81 | 1.77 | 1.82 | 1.84 | 1.94 | 1.88 | 1.76 | 2.14 |
| average % EPA | | 2.09 | | 1.92 | | 1.79 | | 1.83 | | 1.91 | | 1.95 |
| % 16:0 | 38.18 | 40.33 | 40.70 | 38.13 | 41.64 | 43.28 | 42.34 | 44.57 | 42.40 | 44.16 | 44.55 | 43.42 |
| average % 16:0 | | 39.26 | | 39.42 | | 42.46 | | 43.46 | | 43.28 | | 43.99 |
| % ARA | 0.21 | 0.00 | 0.00 | 0.16 | 0.00 | 0.00 | 0.00 | 0.00 | 0.00 | 0.00 | 0.00 | 0.00 |
| average % ARA | | 0.11 | | 0.08 | | 0.00 | | 0.00 | | 0.00 | | 0.00 |

|  | Trt ID | | | | | | | | | |
| --- | --- | --- | --- | --- | --- | --- | --- | --- | --- | --- |
|  | 19a | 19b | 20a | 20b | 21a | 21b | 22a | 22b | C1a (0.625 g/L NaCl) | C1b (0.625 g/L NaCl) |
| Thiamine•HCl [x] | 1 | 1 | 1 | 1 | 1 | 1 | 1 | 1 | 1 | 1 |
| B12 [x] | 1 | 1 | 1 | 1 | 1 | 1 | 1 | 1 | 1 | 1 |
| Biotin [x] | 0 | 0 | 0 | 0 | 0 | 0 | 0 | 0 | 0 | 0 |
| Ca-Pantothenate [x] | 1 | 1 | 5 | 5 | 10 | 10 | 20 | 20 | 0 | 0 |
| % DHA | 45.05 | 41.28 | 44.94 | 46.70 | 50.66 | 43.87 | 44.23 | 38.53 | 56.95 | 56.92 |
| average % DHA |  | 43.16 |  | 45.82 |  | 47.27 |  | 41.38 |  | 56.93 |
| % Fat | 32.05 | 31.10 | 32.32 | 36.07 | 45.61 | 32.51 | 25.50 | 27.42 | 50.11 | 53.39 |
| average % Fat |  | 31.57 |  | 34.20 |  | 39.06 |  | 26.46 |  | 51.75 |
| % EPA | 1.94 | 1.73 | 1.86 | 1.83 | 1.87 | 1.82 | 2.21 | 1.73 | 2.50 | 2.45 |
| average % EPA |  | 1.83 |  | 1.84 |  | 1.85 |  | 1.97 |  | 2.47 |
| % 16:0 | 41.55 | 45.27 | 41.79 | 40.38 | 37.09 | 42.91 | 42.30 | 47.56 | 31.04 | 31.06 |
| average % 16:0 |  | 43.41 |  | 41.09 |  | 40.00 |  | 44.93 |  | 31.05 |
| % ARA | 0.00 | 0.00 | 0.00 | 0.00 | 0.15 | 0.00 | 0.00 | 0.00 | 0.20 | 0.21 |
| average % ARA |  | 0.00 |  | 0.00 |  | 0.08 |  | 0.00 |  | 0.20 |

| Trt ID | Aa | Ab | Ba | Bb |
| --- | --- | --- | --- | --- |
| Thiamine•HCl [x] | 0 | 0 | 0 | 0 |
| B12 [x] | 0 | 0 | 0 | 0 |
| Biotin [x] | 0 | 0 | 0 | 0 |
| Ca-Pantothenate [x] | 0 | 0 | 0 | 0 |
| % DHA | 51.82 | 56.09 | 50.74 | 54.23 |
| average % DHA |  | 53.96 |  | 52.48 |
| % Fat | 9.02 | 7.13 | 20.86 | 26.54 |
| average % Fat |  | 8.07 |  | 23.70 |
| % EPA | 5.91 | 6.63 | 3.71 | 3.38 |
| average % EPA |  | 6.27 |  | 3.54 |
| % 16:0 | 25.07 | 20.69 | 34.01 | 31.44 |
| average % 16:0 |  | 22.88 |  | 32.72 |
| % ARA | 0.00 | 0.00 | 0.00 | 0.23 |
| average % ARA |  | 0.00 |  | 0.11 |

|  | Trt ID | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Thiamine•HCl [x] | 0 | 0.5 | 1 | 5 | 10 | 20 | 0 | 0 | 0 | 0 | 0 |
| B12 [x] | 0 | 0 | 0 | 0 | 0 | 0 | 0 | 1 | 5 | 10 | 20 |
| Biotin [x] | 0 | 0 | 0 | 0 | 0 | 0 | 0 | 0 | 0 | 0 | 0 |
| Ca-Pantothenate [x] | 0 | 0 | 0 | 0 | 0 | 0 | 0 | 0 | 0 | 0 | 0 |
| average % DHA | 38.90 | 42.35 | 44.63 | 44.05 | 45.89 | 43.21 | 38.90 | 50.60 | 50.44 | 46.21 | 45.69 |
| average % Fat | 31.89 | 35.01 | 35.00 | 38.48 | 37.98 | 36.45 | 31.89 | 42.73 | 41.36 | 35.59 | 34.06 |
| average % EPA | 11.54 | 9.74 | 8.61 | 9.17 | 8.57 | 9.38 | 11.54 | 2.06 | 2.01 | 2.17 | 2.10 |
| average % 16:0 | 29.53 | 31.26 | 31.13 | 30.59 | 30.58 | 30.80 | 29.53 | 36.74 | 37.08 | 40.94 | 41.50 |
| average % ARA | 1.36 | 1.18 | 1.00 | 1.17 | 1.10 | 1.15 | 1.36 | 0.15 | 0.15 | 0.07 | 0.00 |

|  | Trt ID | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Thiam/B12/Bio/Ca-Panth. [x] | 0/0/0/0 | 0.5/0/0/0 | 1/0/0/0 | 5/0/0/0 | 10/0/0/0 | 20/0/0/0 | 0/0/0/0 | 0/1/0/0 | 0/5/0/0 | 0/10/0/0 | 0/20/0/0 |
| vitamins conc. (g/L) | 0/0/0/0 | 0.000005/0/0/0 | 0.00001/0/0/0 | 0.00005/0/0/0 | 0.0001/0/0/0 | 0.0002/0/0/0 | 0/0/0/0 | 0/0.000001/0/0 | 0/0.000005/0/0 | 0/0.00001/0/0 | 0/0.00002/0/0 |
| average % DHA | 38.90 | 42.35 | 44.63 | 44.05 | 45.89 | 43.21 | 38.90 | 50.60 | 50.44 | 46.21 | 45.69 |
| average % Fat | 31.89 | 35.01 | 35.00 | 38.48 | 37.98 | 36.45 | 31.89 | 42.73 | 41.36 | 35.59 | 34.06 |
| average % EPA | 11.54 | 9.74 | 8.61 | 9.17 | 8.57 | 9.38 | 11.54 | 2.06 | 2.01 | 2.17 | 2.10 |
| average % 16:0 | 29.53 | 31.26 | 31.13 | 30.59 | 30.58 | 30.80 | 29.53 | 36.74 | 37.08 | 40.94 | 41.50 |
| average % ARA | 1.36 | 1.18 | 1.00 | 1.17 | 1.10 | 1.15 | 1.36 | 0.15 | 0.15 | 0.07 | 0.00 |
| total vitamins conc. (mg/L) | 2.38E-02 | 2.88E-02 | 3.38E-02 | 7.38E-02 | 1.24E-01 | 2.24E-01 | 1.37E-05 | 1.01E-03 | 5.01E-03 | 1.00E-02 | 2.00E-02 |
| average DW (g/L) | 5.863 | 6.214 | 6.112 | 6.658 | 6.355 | 6.277 | 5.863 | 7.079 | 7.001 | 6.505 | 6.442 |

| Trt ID | 12 | 13 | 14 | 15 | 16 |
|---|---|---|---|---|---|
| Thiamine•HCl [x] | 1 | 1 | 1 | 1 | 1 |
| B12 [x] | 1 | 1 | 1 | 1 | 1 |
| Biotin [x] | 0 | 0.5 | 1 | 10 | 20 |
| Ca-Pantothenate [x] | 0 | 0 | 0 | 0 | 0 |
| average % DHA | 42.41 | 47.63 | 47.65 | 44.53 | 43.08 |
| average % Fat | 30.46 | 31.92 | 37.87 | 33.85 | 32.63 |
| average % EPA | 1.95 | 2.09 | 1.92 | 1.79 | 1.83 |
| average % 16:0 | 43.99 | 39.26 | 39.42 | 42.46 | 43.46 |
| average % ARA | 0.00 | 0.11 | 0.08 | 0.00 | 0.00 |

| Trt ID | 12 | 13 | 14 | 15 | 16 |
|---|---|---|---|---|---|
| Thiam/B12/Bio/Ca-Panth.[x] | 1/1/0/0 | 1/1/0.5/0 | 1/1/1/0 | 1/1/10/0 | 1/1/20/0 |
| vitamins conc. (g/L) | 0.00001/0.000001/0/0 | 0.00001/0.000001/0.00000234/0 | 0.00001/0.000001/0.00000468/0 | 0.00001/0.000001/0.0000468/0 | 0.00001/0.000001/0.0000936/0 |
| average % DHA | 42.41 | 47.63 | 47.65 | 44.53 | 43.08 |
| average % Fat | 30.46 | 31.92 | 37.87 | 33.85 | 32.63 |
| average % EPA | 1.95 | 2.09 | 1.92 | 1.79 | 1.83 |
| average % 16:0 | 43.99 | 39.26 | 39.42 | 42.46 | 43.46 |
| average % ARA | 0.00 | 0.11 | 0.08 | 0.00 | 0.00 |
| total vitamins conc. (mg/L) | 2.49E−01 | 2.51E−01 | 2.53E−01 | 2.96E−01 | 3.42E−01 |
| average DW (g/L) | 6.029 | 5.705 | 6.813 | 6.458 | 6.286 |

| Trt ID | 17 | 18 | 19 | 20 | 21 |
|---|---|---|---|---|---|
| Thiamine•HCl [x] | 1 | 1 | 1 | 1 | 1 |
| B12 [x] | 1 | 1 | 1 | 1 | 1 |
| Biotin [x] | 30 | 0 | 0 | 0 | 0 |
| Ca-Pantothenate [x] | 0 | 0 | 1 | 5 | 10 |
| average % DHA | 43.28 | 42.41 | 43.16 | 45.82 | 47.27 |
| average % Fat | 33.31 | 30.46 | 31.57 | 34.20 | 39.06 |
| average % EPA | 1.91 | 1.95 | 1.83 | 1.84 | 1.85 |
| average % 16:0 | 43.28 | 43.99 | 43.41 | 41.09 | 40.00 |
| average % ARA | 0.00 | 0.00 | 0.00 | 0.00 | 0.08 |

| Trt ID | 17 | 18 | 19 | 20 | 21 |
|---|---|---|---|---|---|
| Thiam/B12/Bio/Ca-Panth.[x] | 1/1/30/0 | 1/1/0/0 | 1/1/0/1 | 1/1/0/5 | 1/1/0/10 |
| vitamins conc. (g/L) | 0.00001/0.000001/0.0001404/0 | 0.00001/0.000001/0/0 | 0.00001/0.000001/0/0.00333 | 0.00001/0.000001/0/0.01665 | 0.00001/0.000001/0/0.0333 |
| average % DHA | 43.28 | 42.41 | 43.16 | 45.82 | 47.27 |
| average % Fat | 33.31 | 30.46 | 31.57 | 34.20 | 39.06 |
| average % EPA | 1.91 | 1.95 | 1.83 | 1.84 | 1.85 |
| average % 16:0 | 43.28 | 43.99 | 43.41 | 41.09 | 40.00 |
| average % ARA | 0.00 | 0.00 | 0.00 | 0.00 | 0.08 |
| total vitamins conc. (mg/L) | 3.89E−01 | 3.10E−02 | 3.36E+00 | 1.67E+01 | 3.33E+01 |
| average DW (g/L) | 6.358 | 6.029 | 6.058 | 6.349 | 6.961 |

| | Trt ID | | | |
|---|---|---|---|---|
| | 22 | C1 (0.625 g/L NaCl) | A | B |
| Thiamine•HCl [x] | 1 | 1 | 0 | 1 |
| B12 [x] | 1 | 1 | 0 | 1 |
| Biotin [x] | 0 | 0 | 0 | 0 |
| Ca-Pantothenate [x] | 20 | 0 | 0 | 0 |
| average % DHA | 41.38 | 56.93 | 53.96 | 52.48 |
| average % Fat | 26.46 | 51.75 | 8.07 | 23.70 |
| average % EPA | 1.97 | 2.47 | 6.27 | 3.54 |
| average % 16:0 | 44.93 | 31.05 | 22.88 | 32.72 |
| average % ARA | 0.00 | 0.20 | 0.00 | 0.11 |

| Trt ID | 22 | C1 | A | B |
|---|---|---|---|---|
| Thiam/B12/Bio/Ca-Panth.[x] | 1/1/0/20 | 1/1/0/0 | 0/0/0/0 | 0/0/0/0 |
| vitamins conc. (g/L) | 0.00001/0.000001/0/0.0666 | 0.00001/0.000001/0/0 | 0/0/0/0 | 0.00001/0.000001/0/0 |
| average % DHA | 41.38 | 56.93 | 53.96 | 52.48 |
| average % Fat | 26.46 | 51.75 | 8.07 | 23.70 |
| average % EPA | 1.97 | 2.47 | 6.27 | 3.54 |
| average % 16:0 | 44.93 | 31.05 | 22.88 | 32.72 |
| average % ARA | 0.00 | 0.20 | 0.00 | 0.11 |
| total vitamins conc. (mg/L) | 6.66E+01 | | | |
| average DW (g/L) | 5.492 | 7.651 | 0.428 | 4.809 |

EXAMPLE 11

Experiments were performed to determine the minimum requirement of ATCC Accession No. PTA-9695 for vitamin B12 to achieve maximal performance at 10% $CO_2$, including the minimum amount of vitamin B 12 that is required for PTA-9695 culture to produce maximum dry weight and DHA yield under 10% $CO_2$ conditions.

Temperature: 22.5+/−1 C (@ 10% $CO_2$)
Shaker speed: 200 rpm
Base medium: Defined Scaled-Down Fermentor Medium (DSDFM-B) (Table 20).
Inoculum: 3-day old culture of PTA-9695 grown in DSDFM-B with different concentrations of vitamin B12.

A new cryovial of PTA-9695 was initially thawed in SDFM-B (Table 19), and was subsequently grown and transferred several times in Defined SDFM-B under 10% $CO_2$. A 3-day old culture of PTA-9695 in DSDFM-B was used (at 4%) to prepare the initial inoculum flasks containing DSDFM-B with various concentrations of vitamin B12 (i.e., from 7.68 mg/L to zero mg/L of B12 for treatments A through I, accordingly; see Table 18). The inoculum flasks for each concentration of vitamin B12 were maintained under 10% $CO_2$ and by transferring the cultures into their respective fresh media every 7 days. The weekly transfer of the cultures was essential for washing out any excess vitamin B12 that might have been stored inside the cells, so that the minimum requirement for this vitamin could be more accurately determined. Duplicate shake flasks were inoculated with their respective 3-day old inocula at a theoretical DW of 0.1 g/L, using the Optical Density at 600 nm. Cultures were grown under 10% $CO_2$ for 9 days, prior to being harvested and further analyzed by FAME assay.

Results:
Note: Data points for week 3 are being disregarded in this study, as the supply of $CO_2$ to the incubator had been interrupted, and flasks had to be removed from the incubator for 6 hours during lab renovation.

Prolonged exposure (up to 4 weeks) of PTA-9695 to high concentrations of vitamin B12 (greater than 3.84 mg/L) can adversely impact the dry weight, % fat, and DHA yield, while a concentration of between 1.5 to 768 ug/L vitamin B12 has no significant effect on PTA-9695s' DW, % fat, % EPA, and DHA yield.

An increase in the number of single cells (up to 15, as opposed to 3-4) were noted in cultures that had been grown in the presence of 7 68 mg/L vitamin B12 (treatment A).

Eliminating vitamin B12 from the media recipe, significantly increases % EPA by about 10%, while it slightly decreases both % DHA and % 16:0. FIGS. 6-19 and Table 21 below show the results of the experiments.

Conclusion:
A minimum of about 1.5 ug/L vitamin B12 (1/500th the standard concentration in SDFM-B) is essential for obtaining maximal DW, % DHA, % fat, and DHA yield. While very high concentrations of vitamin B 12 (greater than 3.84 mg/L) can substantially reduce DW, % fat, and DHA yield, a complete deprivation of PTA-9695 from this vitamin can significantly (approximately 10%) increase its % EPA. Very high levels of vitamin B 12 may also play a role in promoting transformation of the "clumpy" culture into "single cells".

TABLE 18

Vitamin B12 Treatments

| | Treatments | | | | | | | | | |
|---|---|---|---|---|---|---|---|---|---|---|
| | A | B | C | D | E | F | G | H | I | J |
| Vit. B12 (ug/L) | 7680 | 3840 | 768 | 384 | 153.6 | 76.8 | 15.36 | 7.68 | 1.536 | 0 |

TABLE 19

Scaled-Down Fermentor Medium for PTA-9695 (SDFM-B), pH 7

| Component | MW | [Stock] (g/L) | mls of stock into 1 L shake flask | grams of dry ingredient in 1 L shake flask | Final concentration (g/L) |
|---|---|---|---|---|---|
| NaCl | 58.44 | | | 0.625 | 0.625 |
| KCl | 74.56 | 56 | 17.9 | | 1.0 |
| MgSO4•7H2O | 246.5 | 227 | 22 | | 5.0 |
| (NH4)2SO4 | 132.14 | 190 | 0.525 | | 0.1 |
| CaCl2•2H2O | 147 | 60 | 4.833 | | 0.290 |

TABLE 19-continued

Scaled-Down Fermentor Medium for PTA-9695 (SDFM-B), pH 7

| Component | MW | [Stock] (g/L) | mls of stock into 1 L shake flask | grams of dry ingredient in 1 L shake flask | Final concentration (g/L) |
|---|---|---|---|---|---|
| MSG (w/1 mole H2O) | 187.1 | | | 1.0 | 1.0 |
| Na2SO4 | 142.04 | | | 6.0 | 6.0 |
| K2SO4 | 174.27 | | | 1.0959 | 1.0959 |
| Tastone (GC9156-1) | | | | 1.0 | 1.0 |
| HEPES (100 mM) pH 7.0 | 195.2 | | | 23.8 | 23.8 |
| KH2PO4 | 136.07 | 56.5 | 0.885 | | 0.05 |
| Glucose | 180 | 500 | 100 | | 50 |
| Trace Metal mix | | | | | |
| FeSO4•7H2O | 278.02 | 1.03 | 10 | | 0.0103 |
| MnCl2•4H2O | 198 | 3.1 | 1 | | 0.0031 |
| ZnSO4•7H2O | 287.4 | 9.3 | 1 | | 0.0093 |
| Na2MoO4•2H2O | 241.95 | 0.04 | 1 | | 0.00004 |
| CuSO4•5H2O | 249.5 | 2.07 | 1 | | 0.00207 |
| NiSO4•6H2O | 262.84 | 2.07 | 1 | | 0.00207 |
| Citric Acid (in FeSO4•7H2O) | | 117.5 | | | 1.175 |
| Vitamin Solution | | | | | |
| Vitamin B12 | 1355.4 | 0.768 | 1 | | 0.000768 |
| Thiamine•HCl | 337.3 | 11.7 | 1 | | 0.0117 |
| Ca-Pantothenate | 476.54 | 3.996 | 1 | | 0.003996 |
| Biotin | 244.3 | 0.002 | 2.17 | | 0.00000434 |

TABLE 20

Defined SDFM-B (DSDFM-B), pH 7

| Component | MW | [Stock] (g/L) | mls of stock into 1 L shake flask | grams of dry ingredient in 1 L shake flask | Final concentration (g/L) |
|---|---|---|---|---|---|
| NaCl | 58.44 | | | 0.625 | 0.625 |
| KCl | 74.56 | 56 | 17.9 | | 1.0 |
| MgSO4•7H2O | 246.5 | 227 | 22 | | 5.0 |
| (NH4)2SO4 | 132.14 | 190 | 1.1483 | | 0.218 |
| CaCl2•2H2O | 147 | 60 | 4.833 | | 0.290 |
| MSG (w/1 mole H2O) | 187.1 | | | 2.188 | 2.188 |
| Na2SO4 | 142.04 | | | 6.0 | 6.0 |
| K2SO4 | 174.27 | | | 1.1240 | 1.1240 |
| Tastone (GC9156-1) | | | | 0.0 | 0.0 |
| HEPES (100 mM) pH 7.0 | 195.2 | | | 23.8 | 23.8 |
| KH2PO4 | 136.07 | 56.5 | 2.475 | | 0.140 |
| Glucose | 180 | 500 | 100 | | 50 |
| Trace Metal mix | | | | | |
| FeSO4•7H2O | 278.02 | 1.03 | 10 | | 0.0103 |
| MnCl2•4H2O | 198 | 3.1 | 1 | | 0.0031 |
| ZnSO4•7H2O | 287.4 | 9.3 | 1 | | 0.0093 |
| Na2MoO4•2H2O | 241.95 | 0.04 | 1 | | 0.00004 |
| CuSO4•5H2O | 249.5 | 2.07 | 1 | | 0.00207 |
| NiSO4•6H2O | 262.84 | 2.07 | 1 | | 0.00207 |
| Citric Acid (in FeSO4•7H2O) | | 117.5 | | | 1.175 |
| Vitamin Solution | | | | | |
| Vitamin B12 | 1355.4 | 0.768 | 1 | | 0.000768 |
| Thiamine•HCl | 337.3 | 11.7 | 1 | | 0.0117 |
| Ca-Pantothenate | 476.54 | 3.996 | 1 | | 0.003996 |
| Biotin | 244.3 | 0.002 | 2.65 | | 0.0000053 |

TABLE 21

Data from Experiments

| | Shake Flask series (SF) | | | | | | | | | |
|---|---|---|---|---|---|---|---|---|---|---|
| | 1 | 1 | 1 | 1 | 1 | 1 | 1 | 1 | 1 | 1 |
| | | | | | Treatment ID | | | | | |
| | A | B | C | D | E | F | G | H | I | J |
| | | | | | Vit. B12 conc. (mg/L) | | | | | |
| | 7680 | 3840 | 768 | 384 | 153.6 | 76.8 | 15.36 | 7.68 | 1.536 | 0 |
| | | | | | Vit. B12 conc. (Log 10-mg/L) | | | | | |
| | 3.885361 | 3.584331 | 2.885361 | 2.584331 | 2.186391 | 1.885361 | 1.186391 | 0.885361 | 0.186391 | 0.001 |
| DW (g/L) | | | | | | | | | | |
| flask 1 | 2.832 | 3.48 | 3.64 | 4.186 | 3.728 | 3.952 | 3.71 | 3.96 | 4.5 | 3.868 |
| flask 2 | 3.03 | 3.324 | 3.88 | 3.412 | 3.626 | 3.746 | 4.024 | 3.682 | 4.17 | 4.094 |
| average | 2.931 | 3.402 | 3.76 | 3.799 | 3.677 | 3.849 | 3.867 | 3.821 | 4.335 | 3.981 |
| % Fat (by area %) | | | | | | | | | | |
| flask 1 | 56.9 | 55.5 | 58.9 | 63.9 | 61.6 | 60.5 | 60.4 | 64.7 | 66.6 | 60.4 |
| flask 2 | 52.4 | 56.7 | 61.6 | 59.8 | 58.7 | 60.7 | 64.1 | 57.9 | 66.3 | 62.9 |
| average | 54.6 | 56.1 | 60.3 | 61.9 | 60.1 | 60.6 | 62.2 | 61.3 | 66.5 | 61.7 |
| % DHA | | | | | | | | | | |
| flask 1 | 45.4 | 45.8 | 46.6 | 48.2 | 45.3 | 46.4 | 47.9 | 47.4 | 48.9 | 46.4 |
| flask 2 | 45.7 | 44.0 | 47.1 | 46.4 | 46.3 | 46.0 | 48.8 | 46.6 | 48.0 | 46.5 |
| average | 45.5 | 44.9 | 46.9 | 47.3 | 45.8 | 46.2 | 48.4 | 47.0 | 48.4 | 46.5 |
| DHA (mg/g) | | | | | | | | | | |
| flask 1 | 260.1 | 256.6 | 277.2 | 310.6 | 281.1 | 283.0 | 291.7 | 309.4 | 328.2 | 283.0 |
| flask 2 | 241.4 | 251.1 | 292.7 | 279.8 | 274.2 | 281.7 | 315.4 | 271.9 | 320.9 | 294.9 |
| average | 250.8 | 253.9 | 285.0 | 295.2 | 277.7 | 282.3 | 303.5 | 290.6 | 324.6 | 289.0 |
| % Fat (by mg/g) | | | | | | | | | | |
| flask 1 | 57.3 | 56.0 | 59.4 | 64.4 | 62.1 | 61.0 | 60.9 | 65.2 | 67.1 | 60.9 |
| flask 2 | 52.8 | 57.1 | 62.1 | 60.3 | 59.2 | 61.2 | 64.6 | 58.4 | 66.9 | 63.4 |
| average | 55.1 | 56.5 | 60.8 | 62.4 | 60.6 | 61.1 | 62.7 | 61.8 | 67.0 | 62.2 |
| Fat (g/L) | | | | | | | | | | |
| flask 1 | 1.6 | 1.9 | 2.2 | 2.7 | 2.3 | 2.4 | 2.3 | 2.6 | 3.0 | 2.4 |
| flask 2 | 1.6 | 1.9 | 2.4 | 2.1 | 2.1 | 2.3 | 2.6 | 2.1 | 2.8 | 2.6 |
| average | 1.6 | 1.9 | 2.3 | 2.4 | 2.2 | 2.4 | 2.4 | 2.4 | 2.9 | 2.5 |
| DHA yield (g/L) | | | | | | | | | | |
| flask 1 | 0.7 | 0.9 | 1.0 | 1.3 | 1.0 | 1.1 | 1.1 | 1.2 | 1.5 | 1.1 |
| flask 2 | 0.7 | 0.8 | 1.1 | 1.0 | 1.0 | 1.1 | 1.3 | 1.0 | 1.3 | 1.2 |
| average | 0.7 | 0.9 | 1.1 | 1.1 | 1.0 | 1.1 | 1.2 | 1.1 | 1.4 | 1.2 |
| % EPA | | | | | | | | | | |
| flask 1 | 19.2 | 20.1 | 18.7 | 16.7 | 20.4 | 19.0 | 16.1 | 17.5 | 15.5 | 19.3 |
| flask 2 | 18.6 | 21.6 | 18.2 | 18.3 | 19.0 | 19.5 | 15.2 | 18.9 | 16.7 | 19.2 |
| average | 18.9 | 20.8 | 18.5 | 17.5 | 19.7 | 19.2 | 15.6 | 18.2 | 16.1 | 19.3 |
| EPA (mg/g) | | | | | | | | | | |
| flask 1 | 108.2 | 110.3 | 109.2 | 105.8 | 124.7 | 113.6 | 96.1 | 112.2 | 102.5 | 115.5 |
| flask 2 | 96.3 | 121.4 | 111.1 | 108.4 | 110.6 | 117.3 | 96.3 | 108.1 | 110.0 | 120.0 |
| average | 102.3 | 115.8 | 110.2 | 107.1 | 117.7 | 115.5 | 96.2 | 110.1 | 106.3 | 117.7 |
| EPA yield (g/L) | | | | | | | | | | |
| flask 1 | 0.3 | 0.4 | 0.4 | 0.5 | 0.5 | 0.5 | 0.4 | 0.5 | 0.5 | 0.5 |
| flask 2 | 0.3 | 0.4 | 0.4 | 0.4 | 0.4 | 0.4 | 0.4 | 0.4 | 0.5 | 0.5 |
| average | 0.3 | 0.4 | 0.4 | 0.4 | 0.4 | 0.5 | 0.4 | 0.4 | 0.5 | 0.5 |
| L-F DW (g/L) | | | | | | | | | | |
| flask 1 | 1.2 | 1.5 | 1.5 | 1.5 | 1.4 | 1.5 | 1.5 | 1.4 | 1.5 | 1.5 |
| flask 2 | 1.4 | 1.4 | 1.5 | 1.4 | 1.5 | 1.5 | 1.4 | 1.5 | 1.4 | 1.5 |
| average | 1.3 | 1.5 | 1.5 | 1.4 | 1.4 | 1.5 | 1.4 | 1.5 | 1.4 | 1.5 |

TABLE 21-continued

Data from Experiments

% 16:0

| | | | | | | | | | | |
|---|---|---|---|---|---|---|---|---|---|---|
| flask 1 | 24.0 | 22.8 | 23.1 | 23.6 | 22.6 | 23.0 | 24.4 | 23.4 | 23.9 | 22.5 |
| flask 2 | 24.2 | 22.7 | 23.1 | 23.8 | 23.1 | 22.8 | 24.5 | 23.0 | 23.6 | 22.5 |
| average | 24.1 | 22.7 | 23.1 | 23.7 | 22.9 | 22.9 | 24.4 | 23.2 | 23.7 | 22.5 |

% DPA n-3

| | | | | | | | | | | |
|---|---|---|---|---|---|---|---|---|---|---|
| flask 1 | 1.1 | 1.0 | 1.2 | 1.0 | 1.2 | 1.1 | 1.1 | 1.1 | 1.0 | 1.1 |
| flask 2 | 1.1 | 1.1 | 1.1 | 1.2 | 1.1 | 1.2 | 1.1 | 1.1 | 1.0 | 1.1 |
| average | 1.1 | 1.1 | 1.1 | 1.1 | 1.2 | 1.2 | 1.1 | 1.1 | 1.0 | 1.1 |

% DPA n-6

| | | | | | | | | | | |
|---|---|---|---|---|---|---|---|---|---|---|
| flask 1 | 2.1 | 2.1 | 2.3 | 2.5 | 2.1 | 2.2 | 2.4 | 2.4 | 2.6 | 2.2 |
| flask 2 | 2.2 | 2.0 | 2.3 | 2.2 | 2.2 | 2.2 | 2.5 | 2.2 | 2.5 | 2.2 |
| average | 2.1 | 2.0 | 2.3 | 2.3 | 2.2 | 2.2 | 2.5 | 2.3 | 2.5 | 2.2 |

% Total omega-3

| | | | | | | | | | | |
|---|---|---|---|---|---|---|---|---|---|---|
| flask 1 | 65.7 | 66.9 | 66.5 | 66.0 | 66.9 | 66.5 | 65.1 | 66.0 | 65.4 | 66.9 |
| flask 2 | 65.4 | 66.7 | 66.5 | 65.9 | 66.5 | 66.7 | 65.1 | 66.5 | 65.8 | 66.9 |
| average | 65.6 | 66.8 | 66.5 | 65.9 | 66.7 | 66.6 | 65.1 | 66.3 | 65.6 | 66.9 | pH

| | | | | | | | | | | |
|---|---|---|---|---|---|---|---|---|---|---|
| flask 1 | 6.81 | 6.83 | 6.84 | 6.83 | 6.82 | 6.82 | 6.83 | 6.83 | 6.82 | 6.81 |
| flask 2 | 6.81 | 6.83 | 6.81 | 6.82 | 6.83 | 6.82 | 6.82 | 6.82 | 6.82 | 6.81 |
| average | 6.81 | 6.83 | 6.83 | 6.83 | 6.83 | 6.82 | 6.83 | 6.83 | 6.82 | 6.81 |

| Shake Flask series (SF) | | | | | | | | | | |
|---|---|---|---|---|---|---|---|---|---|---|
| | 2 | 2 | 2 | 2 | 2 | 2 | 2 | 2 | 2 | 2 |
| Treatment ID | | | | | | | | | | |
| | A | B | C | D | E | F | G | H | I | J |
| Vit. B12 conc. (mg/L) | | | | | | | | | | |
| | 7680 | 3840 | 768 | 384 | 153.6 | 76.8 | 15.36 | 7.68 | 1.536 | 0 |
| Vit. B12 conc. (Log 10-mg/L) | | | | | | | | | | |
| | 3.885361 | 3.584331 | 2.885361 | 2.584331 | 2.186391 | 1.885361 | 1.186391 | 0.885361 | 0.186391 | 0.001 |

DW (g/L)

| | | | | | | | | | | |
|---|---|---|---|---|---|---|---|---|---|---|
| flask 1 | 2.01 | 4.17 | 4.176 | 3.764 | 4.276 | 4.218 | 3.916 | 4.44 | 4.59 | 3.676 |
| flask 2 | 2.574 | 3.354 | 4.106 | 3.824 | 3.922 | 4.21 | 4.046 | 4.352 | 4.518 | 3.174 |
| average | 2.292 | 3.762 | 4.141 | 3.794 | 4.099 | 4.214 | 3.981 | 4.396 | 4.554 | 3.425 |

% Fat (by area %)

| | | | | | | | | | | |
|---|---|---|---|---|---|---|---|---|---|---|
| flask 1 | 28.8 | 62.2 | 64.4 | 60.5 | 65.3 | 58.8 | 58.2 | 66.4 | 63.0 | 61.4 |
| flask 2 | 39.2 | 55.6 | 65.0 | 55.9 | 62.6 | 62.2 | 65.4 | 62.0 | 66.3 | 53.0 |
| average | 34.0 | 58.9 | 64.7 | 58.2 | 63.9 | 60.5 | 61.8 | 64.2 | 64.7 | 57.2 |

% DHA

| | | | | | | | | | | |
|---|---|---|---|---|---|---|---|---|---|---|
| flask 1 | 38.9 | 46.4 | 47.5 | 46.1 | 48.0 | 45.7 | 43.2 | 47.7 | 47.9 | 38.5 |
| flask 2 | 40.9 | 41.3 | 46.9 | 43.6 | 46.3 | 47.1 | 45.2 | 47.6 | 47.5 | 35.3 |
| average | 39.9 | 43.9 | 47.2 | 44.9 | 47.1 | 46.4 | 44.2 | 47.6 | 47.7 | 36.9 |

DHA (mg/g)

| | | | | | | | | | | |
|---|---|---|---|---|---|---|---|---|---|---|
| flask 1 | 109.7 | 283.1 | 300.1 | 273.9 | 307.2 | 263.4 | 246.7 | 310.6 | 296.0 | 232.1 |
| flask 2 | 157.3 | 225.4 | 299.0 | 239.5 | 284.4 | 287.8 | 290.3 | 289.4 | 309.4 | 183.6 |
| average | 133.5 | 254.3 | 299.6 | 256.7 | 295.8 | 275.6 | 268.5 | 300.0 | 302.7 | 207.8 |

% Fat (by mg/g)

| | | | | | | | | | | |
|---|---|---|---|---|---|---|---|---|---|---|
| | 28.8 | 62.2 | 64.4 | 60.5 | 65.3 | 58.8 | 58.2 | 66.4 | 63.0 | 61.4 |
| flask 1 | 28.2 | 61.0 | 63.1 | 59.4 | 64.0 | 57.7 | 57.1 | 65.1 | 61.9 | 60.2 |
| flask 2 | 38.5 | 54.5 | 63.7 | 54.9 | 61.4 | 61.1 | 64.2 | 60.8 | 65.1 | 52.0 |
| average | 33.3 | 57.8 | 63.4 | 57.2 | 62.7 | 59.4 | 60.6 | 63.0 | 63.5 | 56.1 |

Fat (g/L)

| | | | | | | | | | | |
|---|---|---|---|---|---|---|---|---|---|---|
| flask 1 | 0.6 | 2.5 | 2.6 | 2.2 | 2.7 | 2.4 | 2.2 | 2.9 | 2.8 | 2.2 |
| flask 2 | 1.0 | 1.8 | 2.6 | 2.1 | 2.4 | 2.6 | 2.6 | 2.6 | 2.9 | 1.7 |
| average | 0.8 | 2.2 | 2.6 | 2.2 | 2.6 | 2.5 | 2.4 | 2.8 | 2.9 | 1.9 |

DHA yield (g/L)

| | | | | | | | | | | |
|---|---|---|---|---|---|---|---|---|---|---|
| flask 1 | 0.2 | 1.2 | 1.3 | 1.0 | 1.3 | 1.1 | 1.0 | 1.4 | 1.4 | 0.9 |
| flask 2 | 0.4 | 0.8 | 1.2 | 0.9 | 1.1 | 1.2 | 1.2 | 1.3 | 1.4 | 0.6 |
| average | 0.3 | 1.0 | 1.2 | 1.0 | 1.2 | 1.2 | 1.1 | 1.3 | 1.4 | 0.7 |

TABLE 21-continued

| Data from Experiments | | | | | | | | | | |
|---|---|---|---|---|---|---|---|---|---|---|
| % EPA | | | | | | | | | | |
| flask 1 | 22.9 | 19.0 | 18.8 | 17.4 | 17.1 | 18.8 | 21.6 | 18.0 | 16.4 | 28.3 |
| flask 2 | 20.8 | 24.5 | 18.8 | 19.6 | 18.8 | 17.0 | 20.0 | 16.1 | 16.8 | 31.4 |
| average | 21.8 | 21.8 | 18.8 | 18.5 | 17.9 | 17.9 | 20.8 | 17.0 | 16.6 | 29.8 |
| EPA (mg/g) | | | | | | | | | | |
| flask 1 | 63.9 | 114.9 | 117.4 | 102.4 | 108.3 | 107.6 | 122.1 | 115.8 | 100.5 | 168.9 |
| flask 2 | 79.1 | 132.4 | 118.6 | 106.6 | 114.4 | 102.8 | 127.0 | 96.9 | 108.3 | 161.6 |
| average | 71.5 | 123.6 | 118.0 | 104.5 | 111.4 | 105.2 | 124.5 | 106.4 | 104.4 | 165.2 |
| EPA yield (g/L) | | | | | | | | | | |
| flask 1 | 0.1 | 0.5 | 0.5 | 0.4 | 0.5 | 0.5 | 0.5 | 0.5 | 0.5 | 0.6 |
| flask 2 | 0.2 | 0.4 | 0.5 | 0.4 | 0.5 | 0.4 | 0.5 | 0.4 | 0.5 | 0.5 |
| average | 0.2 | 0.5 | 0.5 | 0.4 | 0.5 | 0.4 | 0.5 | 0.5 | 0.5 | 0.6 |
| L-F DW (g/L) | | | | | | | | | | |
| flask 1 | 1.4 | 1.6 | 1.5 | 1.5 | 1.5 | 1.8 | 1.7 | 1.5 | 1.8 | 1.5 |
| flask 2 | 1.6 | 1.5 | 1.5 | 1.7 | 1.5 | 1.6 | 1.5 | 1.7 | 1.6 | 1.5 |
| average | 1.5 | 1.6 | 1.5 | 1.6 | 1.5 | 1.7 | 1.6 | 1.6 | 1.7 | 1.5 |
| % 16:0 | | | | | | | | | | |
| flask 1 | 26.0 | 22.5 | 21.7 | 24.3 | 22.5 | 23.1 | 23.0 | 22.0 | 23.2 | 20.2 |
| flask 2 | 25.9 | 22.1 | 21.9 | 24.2 | 22.6 | 23.3 | 22.5 | 23.5 | 23.1 | 19.9 |
| average | 26.0 | 22.3 | 21.8 | 24.3 | 22.5 | 23.2 | 22.7 | 22.8 | 23.2 | 20.0 |
| % DPA n-3 | | | | | | | | | | |
| flask 1 | 1.5 | 1.0 | 1.1 | 1.0 | 1.0 | 1.0 | 1.0 | 0.9 | 1.0 | 1.4 |
| flask 2 | 1.2 | 1.1 | 1.0 | 1.0 | 1.0 | 1.0 | 0.9 | 1.0 | 0.9 | 1.4 |
| average | 1.4 | 1.0 | 1.1 | 1.0 | 1.0 | 1.0 | 1.0 | 1.0 | 0.9 | 1.4 |
| % DPA n-6 | | | | | | | | | | |
| flask 1 | 1.3 | 2.3 | 2.3 | 2.3 | 2.5 | 2.3 | 1.9 | 2.4 | 2.6 | 1.3 |
| flask 2 | 1.7 | 1.6 | 2.3 | 2.1 | 2.3 | 2.5 | 2.1 | 2.6 | 2.5 | 1.1 |
| average | 1.5 | 1.9 | 2.3 | 2.2 | 2.4 | 2.4 | 2.0 | 2.5 | 2.6 | 1.2 |
| % Total omega-3 | | | | | | | | | | |
| flask 1 | 63.2 | 66.4 | 67.4 | 64.5 | 66.1 | 65.5 | 65.8 | 66.6 | 65.2 | 68.2 |
| flask 2 | 62.9 | 66.9 | 66.7 | 64.2 | 66.1 | 65.1 | 66.1 | 64.6 | 65.2 | 68.1 |
| average | 63.1 | 66.7 | 67.0 | 64.4 | 66.1 | 65.3 | 66.0 | 65.6 | 65.2 | 68.1 |
| pH | | | | | | | | | | |
| flask 1 | 6.70 | 6.69 | 6.72 | 6.71 | 6.71 | 6.72 | 6.71 | 6.71 | 6.72 | 6.71 |
| flask 2 | 6.67 | 6.71 | 6.72 | 6.71 | 6.72 | 6.72 | 6.71 | 6.71 | 6.72 | 6.71 |
| average | 6.69 | 6.70 | 6.72 | 6.71 | 6.72 | 6.72 | 6.71 | 6.71 | 6.72 | 6.71 |
| Shake Flask series (SF) | | | | | | | | | | |
| | 3 | 3 | 3 | 3 | 3 | 3 | 3 | 3 | 3 | 3 |
| Treatment ID | | | | | | | | | | |
| | A | B | C | D | E | F | G | H | I | J |
| Vit. B12 conc. (mg/L) | | | | | | | | | | |
| | 7680 | 3840 | 768 | 384 | 153.6 | 76.8 | 15.36 | 7.68 | 1.536 | 0 |
| Vit. B12 conc. (Log 10-mg/L) | | | | | | | | | | |
| | 3.885361 | 3.584331 | 2.885361 | 2.584331 | 2.186391 | 1.885361 | 1.186391 | 0.885361 | 0.186391 | 0.001 |
| DW (g/L) | | | | | | | | | | |
| flask 1 | 2.786 | 2.92 | 4.108 | 3.258 | 3.524 | 4.258 | 3.974 | 3.794 | 3.74 | 3.902 |
| flask 2 | 2.868 | 3.106 | 2.87 | 3.376 | 3.234 | 4.39 | 4.834 | 3.374 | 4.434 | 3.82 |
| average | 2.827 | 3.013 | 3.489 | 3.317 | 3.379 | 4.324 | 4.404 | 3.584 | 4.087 | 3.861 |
| % Fat (by area %) | | | | | | | | | | |
| flask 1 | 42.6 | 41.0 | 54.5 | 46.5 | 50.7 | 59.8 | 57.0 | 51.0 | 55.9 | 62.3 |
| flask 2 | 44.0 | 43.1 | 48.4 | 49.8 | 49.3 | 56.8 | 62.2 | 52.3 | 56.4 | 56.5 |
| average | 43.3 | 42.0 | 51.4 | 48.1 | 50.0 | 58.3 | 59.6 | 51.7 | 56.2 | 59.4 |

TABLE 21-continued

Data from Experiments

% DHA

| | | | | | | | | | | |
|---|---|---|---|---|---|---|---|---|---|---|
| flask 1 | 42.0 | 39.8 | 43.0 | 43.1 | 43.1 | 44.8 | 45.4 | 44.0 | 43.4 | 45.4 |
| flask 2 | 41.9 | 39.9 | 40.5 | 42.8 | 42.5 | 44.2 | 46.3 | 43.8 | 37.7 | 38.3 |
| average | 41.9 | 39.9 | 41.8 | 42.9 | 42.8 | 44.5 | 45.9 | 43.9 | 40.6 | 41.9 |

DHA (mg/g)

| | | | | | | | | | | |
|---|---|---|---|---|---|---|---|---|---|---|
| flask 1 | 177.2 | 161.7 | 232.4 | 198.4 | 216.2 | 265.6 | 256.5 | 222.5 | 240.8 | 280.2 |
| flask 2 | 182.6 | 170.3 | 194.2 | 210.9 | 207.6 | 248.8 | 285.6 | 227.2 | 211.0 | 214.4 |
| average | 179.9 | 166.0 | 213.3 | 204.6 | 211.9 | 257.2 | 271.1 | 224.8 | 225.9 | 247.3 |

% Fat (by mg/g)

| | | | | | | | | | | |
|---|---|---|---|---|---|---|---|---|---|---|
| flask 1 | 42.2 | 40.6 | 54.0 | 46.1 | 50.2 | 59.2 | 56.4 | 50.5 | 55.4 | 61.7 |
| flask 2 | 43.6 | 42.7 | 47.9 | 49.3 | 48.9 | 56.3 | 61.7 | 51.9 | 55.9 | 56.0 |
| average | 42.9 | 41.7 | 51.0 | 47.7 | 49.5 | 57.8 | 59.1 | 51.2 | 55.7 | 58.8 |

Fat (g/L)

| | | | | | | | | | | |
|---|---|---|---|---|---|---|---|---|---|---|
| flask 1 | 1.2 | 1.2 | 2.2 | 1.5 | 1.8 | 2.5 | 2.2 | 1.9 | 2.1 | 2.4 |
| flask 2 | 1.2 | 1.3 | 1.4 | 1.7 | 1.6 | 2.5 | 3.0 | 1.7 | 2.5 | 2.1 |
| average | 1.2 | 1.3 | 1.8 | 1.6 | 1.7 | 2.5 | 2.6 | 1.8 | 2.3 | 2.3 |

DHA yield (g/L)

| | | | | | | | | | | |
|---|---|---|---|---|---|---|---|---|---|---|
| flask 1 | 0.5 | 0.5 | 1.0 | 0.6 | 0.8 | 1.1 | 1.0 | 0.8 | 0.9 | 1.1 |
| flask 2 | 0.5 | 0.5 | 0.6 | 0.7 | 0.7 | 1.1 | 1.4 | 0.8 | 0.9 | 0.8 |
| average | 0.5 | 0.5 | 0.8 | 0.7 | 0.7 | 1.1 | 1.2 | 0.8 | 0.9 | 1.0 |

% EPA

| | | | | | | | | | | |
|---|---|---|---|---|---|---|---|---|---|---|
| flask 1 | 22.4 | 24.7 | 23.9 | 22.0 | 23.5 | 22.1 | 20.9 | 22.3 | 23.8 | 21.3 |
| flask 2 | 23.0 | 24.9 | 25.7 | 22.8 | 24.4 | 23.0 | 20.1 | 22.6 | 31.3 | 30.9 |
| average | 22.7 | 24.8 | 24.8 | 22.4 | 24.0 | 22.6 | 20.5 | 22.4 | 27.5 | 26.1 |

EPA (mg/g)

| | | | | | | | | | | |
|---|---|---|---|---|---|---|---|---|---|---|
| flask 1 | 93.6 | 99.2 | 127.3 | 100.4 | 116.5 | 129.6 | 116.7 | 111.3 | 130.2 | 129.9 |
| flask 2 | 98.9 | 105.2 | 121.5 | 111.2 | 118.0 | 128.1 | 122.6 | 115.5 | 173.1 | 170.7 |
| average | 96.2 | 102.2 | 124.4 | 105.8 | 117.2 | 128.8 | 119.7 | 113.4 | 151.6 | 150.3 |

EPA yield (g/L)

| | | | | | | | | | | |
|---|---|---|---|---|---|---|---|---|---|---|
| flask 1 | 0.3 | 0.3 | 0.5 | 0.3 | 0.4 | 0.6 | 0.5 | 0.4 | 0.5 | 0.5 |
| flask 2 | 0.3 | 0.3 | 0.4 | 0.4 | 0.4 | 0.6 | 0.6 | 0.4 | 0.8 | 0.7 |
| average | 0.3 | 0.3 | 0.4 | 0.4 | 0.4 | 0.6 | 0.5 | 0.4 | 0.6 | 0.6 |

L-F DW (g/L)

| | | | | | | | | | | |
|---|---|---|---|---|---|---|---|---|---|---|
| flask 1 | 1.6 | 1.7 | 1.9 | 1.8 | 1.8 | 1.7 | 1.7 | 1.9 | 1.7 | 1.5 |
| flask 2 | 1.6 | 1.8 | 1.5 | 1.7 | 1.7 | 1.9 | 1.9 | 1.6 | 2.0 | 1.7 |
| average | 1.6 | 1.8 | 1.7 | 1.7 | 1.7 | 1.8 | 1.8 | 1.8 | 1.8 | 1.6 |

% 16:0

| | | | | | | | | | | |
|---|---|---|---|---|---|---|---|---|---|---|
| flask 1 | 24.0 | 23.8 | 21.4 | 23.1 | 21.7 | 21.3 | 21.9 | 22.0 | 21.0 | 21.6 |
| flask 2 | 23.5 | 23.5 | 21.7 | 22.8 | 21.4 | 21.0 | 21.5 | 22.0 | 18.2 | 18.0 |
| average | 23.7 | 23.6 | 21.5 | 23.0 | 21.6 | 21.1 | 21.7 | 22.0 | 19.6 | 19.8 |

% DPA n-3

| | | | | | | | | | | |
|---|---|---|---|---|---|---|---|---|---|---|
| flask 1 | 1.2 | 1.2 | 1.0 | 1.2 | 1.2 | 1.0 | 1.0 | 1.1 | 1.0 | 0.9 |
| flask 2 | 1.2 | 1.2 | 1.1 | 1.2 | 1.2 | 1.0 | 1.0 | 1.1 | 1.3 | 1.4 |
| average | 1.2 | 1.2 | 1.1 | 1.2 | 1.2 | 1.0 | 1.0 | 1.1 | 1.2 | 1.1 |

% DPA n-6

| | | | | | | | | | | |
|---|---|---|---|---|---|---|---|---|---|---|
| flask 1 | 1.7 | 1.4 | 1.8 | 1.8 | 1.8 | 2.0 | 2.1 | 1.9 | 1.8 | 2.1 |
| flask 2 | 1.7 | 1.5 | 1.5 | 1.8 | 1.7 | 2.0 | 2.3 | 1.9 | 1.2 | 1.3 |
| average | 1.7 | 1.5 | 1.7 | 1.8 | 1.8 | 2.0 | 2.2 | 1.9 | 1.5 | 1.7 |

% Total omega-3

| | | | | | | | | | | |
|---|---|---|---|---|---|---|---|---|---|---|
| flask 1 | 65.6 | 65.8 | 67.9 | 66.3 | 67.7 | 67.9 | 67.4 | 67.4 | 68.2 | 67.6 |
| flask 2 | 66.0 | 66.0 | 67.3 | 66.8 | 68.1 | 68.3 | 67.4 | 67.5 | 70.4 | 70.5 |
| average | 65.8 | 65.9 | 67.6 | 66.6 | 67.9 | 68.1 | 67.4 | 67.5 | 69.3 | 69.1 | pH

| | | | | | | | | | | |
|---|---|---|---|---|---|---|---|---|---|---|
| flask 1 | 6.85 | 6.89 | 6.89 | 6.88 | 6.88 | 6.88 | 6.87 | 6.88 | 6.88 | 6.87 |
| flask 2 | 6.86 | 6.89 | 6.89 | 6.88 | 6.88 | 6.89 | 6.86 | 6.87 | 6.88 | 6.86 |
| average | 6.86 | 6.89 | 6.89 | 6.88 | 6.88 | 6.89 | 6.87 | 6.88 | 6.88 | 6.87 |

TABLE 21-continued

Data from Experiments

| | \multicolumn{10}{c}{Shake Flask series (SF)} |
|---|---|---|---|---|---|---|---|---|---|---|
| | 4 | 4 | 4 | 4 | 4 | 4 | 4 | 4 | 4 | 4 |
| | \multicolumn{10}{c}{Treatment ID} |
| | A | B | C | D | E | F | G | H | I | J |
| | \multicolumn{10}{c}{Vit. B12 conc. (mg/L)} |
| | 7680 | 3840 | 768 | 384 | 153.6 | 76.8 | 15.36 | 7.68 | 1.536 | 0 |
| | \multicolumn{10}{c}{Vit. B12 conc. (Log 10-mg/L)} |
| | 3.885361 | 3.584331 | 2.885361 | 2.584331 | 2.186391 | 1.885361 | 1.186391 | 0.885361 | 0.186391 | 0.001 |
| DW (g/L) | | | | | | | | | | |
| flask 1 | 2.538 | 2.512 | 4.242 | 4.528 | 2.498 | 3.796 | 3.79 | 3.87 | 3.676 | 3.972 |
| flask 2 | 2.646 | 3.162 | 2.86 | 4.368 | 2.744 | 3.774 | 3.81 | 4.002 | 4.202 | 4.35 |
| average | 2.592 | 2.837 | 3.551 | 4.448 | 2.621 | 3.785 | 3.8 | 3.936 | 3.939 | 4.161 |
| % Fat (by area %) | | | | | | | | | | |
| flask 1 | 42.5 | 41.9 | 57.5 | 66.7 | 43.6 | 58.1 | 58.2 | 60.0 | 57.1 | 59.2 |
| flask 2 | 44.6 | 32.9 | 45.4 | 63.0 | 43.9 | 57.3 | 57.7 | 59.9 | 60.4 | 62.0 |
| average | 43.5 | 37.4 | 51.5 | 64.9 | 43.8 | 57.7 | 57.9 | 59.9 | 58.8 | 60.6 |
| % DHA | | | | | | | | | | |
| flask 1 | 41.1 | 38.0 | 47.6 | 47.1 | 36.6 | 45.1 | 46.0 | 44.6 | 43.8 | 38.0 |
| flask 2 | 40.2 | 40.8 | 40.0 | 46.7 | 39.0 | 45.5 | 45.1 | 45.9 | 46.7 | 40.2 |
| average | 40.7 | 39.4 | 43.8 | 46.9 | 37.8 | 45.3 | 45.5 | 45.2 | 45.2 | 39.1 |
| DHA (mg/g) | | | | | | | | | | |
| flask 1 | 172.7 | 157.5 | 270.6 | 311.0 | 157.7 | 259.4 | 264.6 | 264.2 | 247.3 | 222.3 |
| flask 2 | 177.2 | 132.8 | 179.6 | 290.9 | 169.2 | 257.3 | 257.1 | 271.7 | 278.5 | 246.0 |
| average | 175.0 | 145.2 | 225.1 | 300.9 | 163.5 | 258.4 | 260.9 | 267.9 | 262.9 | 234.2 |
| % Fat (by mg/g) | | | | | | | | | | |
| flask 1 | 42.0 | 41.4 | 56.9 | 66.0 | 43.1 | 57.5 | 57.5 | 59.3 | 56.5 | 58.5 |
| flask 2 | 44.1 | 32.5 | 44.9 | 62.3 | 43.4 | 56.6 | 57.0 | 59.2 | 59.7 | 61.3 |
| average | 43.0 | 37.0 | 50.9 | 64.1 | 43.2 | 57.0 | 57.3 | 59.3 | 58.1 | 59.9 |
| Fat (g/L) | | | | | | | | | | |
| flask 1 | 1.1 | 1.0 | 2.4 | 3.0 | 1.1 | 2.2 | 2.2 | 2.3 | 2.1 | 2.3 |
| flask 2 | 1.2 | 1.0 | 1.3 | 2.7 | 1.2 | 2.1 | 2.2 | 2.4 | 2.5 | 2.7 |
| average | 1.1 | 1.0 | 1.8 | 2.9 | 1.1 | 2.2 | 2.2 | 2.3 | 2.3 | 2.5 |
| DHA yield (g/L) | | | | | | | | | | |
| flask 1 | 0.4 | 0.4 | 1.1 | 1.4 | 0.4 | 1.0 | 1.0 | 1.0 | 0.9 | 0.9 |
| flask 2 | 0.5 | 0.4 | 0.5 | 1.3 | 0.5 | 1.0 | 1.0 | 1.1 | 1.2 | 1.1 |
| average | 0.5 | 0.4 | 0.8 | 1.3 | 0.4 | 1.0 | 1.0 | 1.1 | 1.0 | 1.0 |
| % EPA | | | | | | | | | | |
| flask 1 | 22.8 | 27.1 | 17.8 | 16.7 | 29.2 | 21.6 | 20.0 | 21.9 | 22.2 | 31.3 |
| flask 2 | 24.5 | 24.4 | 26.7 | 19.5 | 26.3 | 21.0 | 20.9 | 20.5 | 19.2 | 28.5 |
| average | 23.6 | 25.7 | 22.3 | 18.1 | 27.7 | 21.3 | 20.4 | 21.2 | 20.7 | 29.9 |
| EPA (mg/g) | | | | | | | | | | |
| flask 1 | 94.9 | 111.3 | 100.5 | 109.1 | 124.9 | 123.0 | 114.1 | 128.8 | 124.1 | 181.9 |
| flask 2 | 106.9 | 78.5 | 118.8 | 120.4 | 113.0 | 118.1 | 117.9 | 120.4 | 113.7 | 173.2 |
| average | 100.9 | 94.9 | 109.7 | 114.7 | 119.0 | 120.5 | 116.0 | 124.6 | 118.9 | 177.6 |
| EPA yield (g/L) | | | | | | | | | | |
| flask 1 | 0.2 | 0.3 | 0.4 | 0.5 | 0.3 | 0.5 | 0.4 | 0.5 | 0.5 | 0.7 |
| flask 2 | 0.3 | 0.3 | 0.3 | 0.5 | 0.3 | 0.4 | 0.5 | 0.5 | 0.5 | 0.8 |
| average | 0.3 | 0.3 | 0.4 | 0.5 | 0.3 | 0.5 | 0.4 | 0.5 | 0.5 | 0.7 |
| L-F DW (g/L) | | | | | | | | | | |
| flask 1 | 1.5 | 1.5 | 1.8 | 1.5 | 1.4 | 1.6 | 1.6 | 1.6 | 1.6 | 1.6 |
| flask 2 | 1.5 | 2.1 | 1.6 | 1.6 | 1.6 | 1.6 | 1.6 | 1.6 | 1.7 | 1.7 |
| average | 1.5 | 1.8 | 1.7 | 1.6 | 1.5 | 1.6 | 1.6 | 1.6 | 1.6 | 1.7 |

TABLE 21-continued

Data from Experiments

% 16:0

| | | | | | | | | | | |
|---|---|---|---|---|---|---|---|---|---|---|
| flask 1 | 24.1 | 23.1 | 22.7 | 24.5 | 22.4 | 21.6 | 22.3 | 21.7 | 22.3 | 17.8 |
| flask 2 | 23.6 | 23.1 | 21.6 | 22.0 | 22.9 | 21.8 | 22.5 | 21.9 | 22.2 | 18.4 |
| average | 23.9 | 23.1 | 22.1 | 23.3 | 22.7 | 21.7 | 22.4 | 21.8 | 22.2 | 18.1 |

% DPA n-3

| | | | | | | | | | | |
|---|---|---|---|---|---|---|---|---|---|---|
| flask 1 | 1.5 | 1.4 | 1.2 | 1.2 | 1.5 | 1.1 | 1.2 | 1.1 | 1.1 | 1.4 |
| flask 2 | 1.5 | 1.3 | 1.5 | 1.1 | 1.4 | 1.1 | 1.1 | 1.1 | 1.2 | 1.3 |
| average | 1.5 | 1.4 | 1.4 | 1.2 | 1.5 | 1.1 | 1.2 | 1.1 | 1.1 | 1.3 |

% DPA n-6

| | | | | | | | | | | |
|---|---|---|---|---|---|---|---|---|---|---|
| flask 1 | 1.6 | 1.2 | 2.4 | 2.3 | 1.1 | 2.1 | 2.2 | 2.0 | 1.9 | 1.2 |
| flask 2 | 1.5 | 1.6 | 1.4 | 2.2 | 1.3 | 2.1 | 2.1 | 2.2 | 2.2 | 1.4 |
| average | 1.5 | 1.4 | 1.9 | 2.3 | 1.2 | 2.1 | 2.1 | 2.1 | 2.1 | 1.3 |

% Total omega-3

| | | | | | | | | | | |
|---|---|---|---|---|---|---|---|---|---|---|
| flask 1 | 65.4 | 66.6 | 66.6 | 65.0 | 67.3 | 67.8 | 67.2 | 67.6 | 67.0 | 70.7 |
| flask 2 | 66.2 | 66.5 | 68.2 | 67.3 | 66.8 | 67.6 | 67.0 | 67.5 | 67.1 | 70.0 |
| average | 65.8 | 66.5 | 67.4 | 66.2 | 67.0 | 67.7 | 67.1 | 67.5 | 67.0 | 70.3 | pH

| | | | | | | | | | | |
|---|---|---|---|---|---|---|---|---|---|---|
| flask 1 | 6.83 | 6.84 | 6.82 | 6.84 | 6.83 | 6.84 | 6.84 | 6.84 | 6.86 | 6.85 |
| flask 2 | 6.82 | 6.84 | 6.81 | 6.84 | 6.83 | 6.84 | 6.84 | 6.84 | 6.84 | 6.85 |
| average | 6.83 | 6.84 | 6.82 | 6.84 | 6.83 | 6.84 | 6.84 | 6.84 | 6.85 | 6.85 |

EXAMPLE 12

ATCC Accession No. PTA-10208 Vitamin B12 Gradients at 10% CO2

Experiments performed to determine the concentration of Vitamin B12 that provides optimum PTA-10208 growth and EPA productivity.

Temperature: 23° C.
Shaker Speed: 200 rpm
Base Medium: Defined SDFM-O (DSDFM-O)
Inoculum: Thawed a vial of PTA-10208 into SDFM-O at ambient conditions.

Transferred 2 mL of culture into 48 mL of DSDFM-O at 10% $CO_2$. Transferred culture into fresh DSDFM-O (10% $CO_2$) (see Table 22). Transferred culture into fresh DSDFM-O (10% CO2). Used culture to inoculate Vitamin B12 gradient experiment Week #1 (2 mL/flask) (10% CO2).

Experimental Set-Up:

All cultures were grown in 50 mL shake flasks and duplicate flasks were grown for each condition. PTA-10208 was inoculated into nine day Vitamin B12 gradients in DSDFM-O (no tastone) every seven days. Inocula for each concentration of Vitamin B12 were maintained throughout the course of the experiment. By continuing to transfer PTA-10208 in reduced concentrations of Vitamin B12, excess Vitamin B12 was effectively washed out of the cells. Inocula for each concentration of Vitamin B12 were transferred every seven days. Four day old inocula were used to start each nine day Vitamin B12 gradient. Each nine day gradient is consecutively labeled as Experiment Set A, B, C, D, E, F, G, H, I, J, and K below in Table 23. Before each gradient inoculation, optical density was measured for each concentration of Vitamin B 12 in order to transfer approximately the same amount of cells. After nine days of growth, all cultures were harvested to measure pH, dry weight, and fatty acid profile. The experiment was ended once dry weights at each concentration of Vitamin B 12 were found to have stabilized for at least three consecutive nine day gradients.

TABLE 22

Defined Scaled Down Fermentor Medium for Orca (DSDFM-O)

| Component | Amount per liter (g) | [Stock] (g/l) | mL of stock to use per liter | | g/l | | | | | mg/l | | | | |
|---|---|---|---|---|---|---|---|---|---|---|---|---|---|---|
| | | | | | Na | K | Mg | Ca | Cl | Fe | Cu | Mn | Co | Zn |
| NaCl | 0.625 | dry | | | 0.25 | | | | 0.38 | | | | | |
| Na2SO4 | 7.52 | dry | | | | | | | | | | | | |
| K2SO4 | 0.1 | 50 | 2 ml | | | 0.04 | | | | | | | | |
| KCl | 1 | 50 | 20 ml | | | 0.52 | | | 0.48 | | | | | |
| MgSO4•7H2O | 5 | 227 | 22 ml | | | | 0.47 | | | | | | | |
| (NH4)2SO4 | 0.217 | 190 | 1.14 ml | | | | | | | | | | | |
| CaCl2 2H2O | 0.29 | dry | | | | | | 0.08 | 0.14 | | | | | |
| MSG monohydrate | 2.16 | dry | | | | | | | | | | | | |
| HEPES (100 mM) pH 7 | 23.8 | dry | | | | | | | | | | | | |
| KH2PO4 | 0.136 | 56.5 | 2.4 | add after autoclaving | | 0.04 | | | | | | | | |
| Glucose | 50 | 500 | 100 ml | add after autoclaving | | | | | | | | | | |

TABLE 22-continued

Defined Scaled Down Fermentor Medium for Orca (DSDFM-O)

| Component | Amount per liter (g) | [Stock] (g/l) | mL of stock to use per liter | | g/l Na | K | Mg | Ca | Cl | mg/l Fe | Cu | Mn | Co | Zn |
|---|---|---|---|---|---|---|---|---|---|---|---|---|---|---|
| Citrate-Fe Solution | | see below | 10 ml | add after autoclaving | | | | | | | | | | |
| Trace Metals | | see below | 1 ml | add after autoclaving | | | | | | | | | | |
| Vitamins | | see below | 1 ml | add after autoclaving | | | | | | | | | | |
| Citrate-Fe Solution | | | | | | | | | | | | | | |
| Citric Acid | 1175 mg | 117.5 | | | | | | | | | | | | |
| $FeSO_4 \cdot 7H_2O$ | 10.3 mg | 1.03 | | | | | | | | 2.07 | | | | |
| Trace Metal Solution | | | | | | | | | | | | | | |
| $MnCl_2 \cdot 4H_2O$ | 3.1 mg | 3.1 | | | | | | | | | | 0.86 | | |
| $ZnSO_4 \cdot 7H_2O$ | 9.3 mg | 9.3 | | | | | | | | | | | | 2.12 |
| $Na_2MoO_4 \cdot 2H_2O$ | 0.04 mg | 0.04 | | | | | | | | | | | | |
| $CuSO_4 \cdot 5H_2O$ | 2.07 mg | 2.07 | | | | | | | | | 0.53 | | | |
| $NiSO_4 \cdot 6H_2O$ | 2.07 mg | 2.07 | | | | | | | | | | | | |
| pH to 2.5 with HCl | | | | | | | | | | | | | | |
| Vitamin Solution | | | | | | | | | | | | | | |
| Vitamin B12 | 0.768 mg | 0.768 | | | | | | | | | | | | |
| Thiamine | 11.7 mg | 11.7 | | | | | | | | | | | | |
| CaPantothenate | 3.996 mg | 3.996 | | | | | | | | | | | | |
| Biotin | 0.00434 mg | 4.34 mg | | | | | | | | | | | | |
| Ion Totals (ppm) | | | | | 607.32 | | | | 995.8536 | | | | | |

TABLE 23

| [ ] Vitamin B12 | mg/L Vitamin B12 |
|---|---|
| 5x | 3.84 |
| 1x | 0.77 |
| 1/2x | 0.38 |
| 1/5x | 0.15 |
| 1/10x | 0.077 |
| 1/20x | 0.038 |
| 1/50x | 0.015 |
| 1/1000x | 0.0077 |
| 1/500x | 0.0015 |
| 0x | 0 |

Seven consecutive 5× to 1/500× Vitamin B12 gradients were carried out. At the end of the last experiment, a new experiment was started comparing PTA-10208 growth and EPA production at 1/500× (0.0015 mg/L) and 0× (0 mg/L Vitamin B12). Four consecutive 1/500× vs 0× Vitamin B12 experiments were carried out.

Results:

(For 5×->1/500× Vitamin B12): For seven consecutive nine day experiments, PAT-10208 dry weight, % EPA, % DHA, % fat, and EPA yield did not change in Vitamin B12 concentrations ranging from 5×(3.84 mg/L) to 1/500× (0.0015 mg/L).

(For 1/500× and 0× Vitamin B12): Results over the course of four consecutive nine day experiments show that PTA-10208 grown in DSDFM-O containing 0 mg/L Vitamin B12 has much higher % EPA than when grown with just 1/500× (0.0015 mg/L) Vitamin B12. While % EPA increases from about 18% with 1/500× (0.0015 mg/L) Vitamin B12 to about 27% without any Vitamin B12, % DHA decreases from about 45% with 1/500× (0.0015 mg/L) Vitamin B12 to about 36% without any Vitamin B12. PTA-10208 dry weight and % fat increase slightly when Vitamin B12 is completely removed from DSDFM-O. As a result of the increase in % EPA and the slight increases in dry weight and % fat, PTA-10208 EPA yield increases by about 60% when Vitamin B12 is removed from DSDFM-O.

Results are also shown in FIGS. 20-49 and in the tables below.

| Experiment Set | SAMPLE | 600 nm Inoc. O.D. | mg/L Vit B12 | pH | Tare (g) | Out wt (g) | dry pellet wt (g) | g/L Biomass |
|---|---|---|---|---|---|---|---|---|
| A | 5x (1) | | 3.84 | 6.80 | 10.4757 | 10.723 | 0.2473 | 4.95 |
| | 5x (2) | | 3.84 | 6.80 | 10.4534 | 10.689 | 0.2356 | 4.71 |
| | 1x (1) | | 0.77 | 6.80 | 10.5142 | 10.7449 | 0.2307 | 4.61 |
| | 1x (2) | | 0.77 | 6.81 | 10.431 | 10.6512 | 0.2202 | 4.40 |
| | 1/2x (1) | | 0.38 | 6.82 | 10.5684 | 10.7882 | 0.2198 | 4.40 |
| | 1/2x (2) | | 0.38 | 6.82 | 10.6373 | 10.8691 | 0.2318 | 4.64 |
| | 1/5x (1) | | 0.15 | 6.81 | 10.5044 | 10.7348 | 0.2304 | 4.61 |
| | 1/5x (2) | | 0.15 | 6.82 | 10.5219 | 10.747 | 0.2251 | 4.50 |
| | 1/10x (1) | | 0.077 | 6.83 | 10.5221 | 10.7481 | 0.226 | 4.52 |
| | 1/10x (2) | | 0.077 | 6.83 | 10.4705 | 10.6979 | 0.2274 | 4.55 |
| | 1/20x (1) | | 0.038 | 6.83 | 10.4743 | 10.6988 | 0.2245 | 4.49 |
| | 1/20x (2) | | 0.038 | 6.83 | 10.7322 | 10.9646 | 0.2324 | 4.65 |

| | | | | | | | |
|---|---|---|---|---|---|---|---|
| | 1/50x (1) | | 0.015 | 6.84 | 10.4777 | 10.6945 | 0.2168 | 4.34 |
| | 1/50x (2) | | 0.015 | 6.85 | 10.4766 | 10.7018 | 0.2252 | 4.50 |
| | 1/100x (1) | | 0.0077 | 6.84 | 10.4543 | 10.6863 | 0.232 | 4.64 |
| | 1/100x (2) | | 0.0077 | 6.85 | 10.5041 | 10.7452 | 0.2411 | 4.82 |
| | 1/500x (1) | | 0.0015 | 6.86 | 10.5152 | 10.7563 | 0.2411 | 4.82 |
| | 1/500x (2) | | 0.0015 | 6.85 | 10.574 | 10.8081 | 0.2341 | 4.68 |
| B | 5x (1) | 4.0445 | 3.84 | 6.63 | 10.5021 | 10.7338 | 0.2317 | 4.63 |
| | 5x (2) | 4.0445 | 3.84 | 6.65 | 10.4735 | 10.7152 | 0.2417 | 4.83 |
| | 1x (1) | 4.3024 | 0.77 | 6.64 | 10.5011 | 10.7394 | 0.2383 | 4.77 |
| | 1x (2) | 4.3024 | 0.77 | 6.65 | 10.4004 | 10.6362 | 0.2358 | 4.72 |
| | 1/2x (1) | 4.1648 | 0.38 | 6.64 | 10.4599 | 10.71 | 0.2501 | 5.00 |
| | 1/2x (2) | 4.1648 | 0.38 | 6.64 | 10.5630 | 10.804 | 0.241 | 4.82 |
| | 1/5x (1) | 4.1600 | 0.15 | 6.63 | 10.6521 | 10.889 | 0.2369 | 4.74 |
| | 1/5x (2) | 4.1600 | 0.15 | 6.63 | 10.5032 | 10.7341 | 0.2309 | 4.62 |
| | 1/10x (1) | 4.4997 | 0.077 | 6.65 | 10.4726 | 10.6998 | 0.2272 | 4.54 |
| | 1/10x (2) | 4.4997 | 0.077 | 6.64 | 10.4841 | 10.7279 | 0.2438 | 4.88 |
| | 1/20x (1) | 4.9716 | 0.038 | 6.64 | 10.3785 | 10.6112 | 0.2327 | 4.65 |
| | 1/20x (2) | 4.9716 | 0.038 | 6.64 | 10.3832 | 10.6154 | 0.2322 | 4.64 |
| | 1/50x (1) | 4.3049 | 0.015 | 6.65 | 10.3782 | 10.612 | 0.2338 | 4.68 |
| | 1/50x (2) | 4.3049 | 0.015 | 6.65 | 10.5546 | 10.7877 | 0.2331 | 4.66 |
| | 1/100x (1) | 4.6035 | 0.0077 | 6.65 | 10.4858 | 10.7172 | 0.2314 | 4.63 |
| | 1/100x (2) | 4.6035 | 0.0077 | 6.66 | 10.4771 | 10.7122 | 0.2351 | 4.70 |
| | 1/500x (1) | 4.4494 | 0.0015 | 6.65 | 10.6083 | 10.8163 | 0.208 | 4.16 |
| | 1/500x (2) | 4.4494 | 0.0015 | 6.65 | 10.5722 | 10.7896 | 0.2174 | 4.35 |
| C | 5x (1) | 4.1784 | 3.84 | 6.77 | 10.4842 | 10.7237 | 0.2395 | 4.79 |
| | 5x (2) | 4.1784 | 3.84 | 6.80 | 10.5261 | 10.7553 | 0.2292 | 4.58 |
| | 1x (1) | 4.2842 | 0.77 | 6.80 | 10.3785 | 10.6194 | 0.2409 | 4.82 |
| | 1x (2) | 4.2842 | 0.77 | 6.77 | 10.6083 | 10.8459 | 0.2376 | 4.75 |
| | 1/2x (1) | 4.8865 | 0.38 | 6.81 | 10.5274 | 10.7183 | 0.1909 | 3.82 |
| | 1/2x (2) | 4.8865 | 0.38 | 6.81 | 10.4713 | 10.6853 | 0.214 | 4.28 |
| | 1/5x (1) | 4.5411 | 0.15 | 6.81 | 10.3831 | 10.5997 | 0.2166 | 4.33 |
| | 1/5x (2) | 4.5411 | 0.15 | 6.84 | 10.5444 | 10.7666 | 0.2222 | 4.44 |
| | 1/10x (1) | 5.2960 | 0.077 | 6.80 | 10.501 | 10.7181 | 0.2171 | 4.34 |
| | 1/10x (2) | 5.2960 | 0.077 | 6.82 | 10.3783 | 10.5978 | 0.2195 | 4.39 |
| | 1/20x (1) | 5.2480 | 0.038 | 6.82 | 10.4521 | 10.6539 | 0.2018 | 4.04 |
| | 1/20x (2) | 5.2480 | 0.038 | 6.83 | 10.4018 | 10.5881 | 0.1863 | 3.73 |
| | 1/50x (1) | 5.6680 | 0.015 | 6.82 | 10.5049 | 10.7248 | 0.2199 | 4.40 |
| | 1/50x (2) | 5.6680 | 0.015 | 6.83 | 10.4197 | 10.6441 | 0.2244 | 4.49 |
| | 1/100x (1) | 4.9024 | 0.0077 | 6.83 | 10.5531 | 10.7847 | 0.2316 | 4.63 |
| | 1/100x (2) | 4.9024 | 0.0077 | 6.83 | 10.7098 | 10.9412 | 0.2314 | 4.63 |
| | 1/500x (1) | 4.6011 | 0.0015 | 6.83 | 10.5543 | 10.7942 | 0.2399 | 4.80 |
| | 1/500x (2) | 4.6011 | 0.0015 | 6.83 | 10.3382 | 10.5746 | 0.2364 | 4.73 |
| D | 5x (1) | 4.3297 | 3.84 | 6.85 | 10.3415 | 10.5976 | 0.2561 | 5.12 |
| | 5x (2) | 4.3297 | 3.84 | 6.85 | 10.4549 | 10.698 | 0.2431 | 4.86 |
| | 1x (1) | 5.3731 | 0.77 | 6.85 | 10.3785 | 10.6143 | 0.2358 | 4.72 |
| | 1x (2) | 5.3731 | 0.77 | 6.85 | 10.6117 | 10.8401 | 0.2284 | 4.57 |
| | 1/2x (1) | 4.9040 | 0.38 | 6.85 | 10.4318 | 10.6573 | 0.2255 | 4.51 |
| | 1/2x (2) | 4.9040 | 0.38 | 6.85 | 10.6572 | 10.8742 | 0.217 | 4.34 |
| | 1/5x (1) | 4.7084 | 0.15 | 6.85 | 10.552 | 10.7791 | 0.2271 | 4.54 |
| | 1/5x (2) | 4.7084 | 0.15 | 6.85 | 10.7118 | 10.9623 | 0.2505 | 5.01 |
| | 1/10x (1) | 4.9843 | 0.077 | 6.85 | 10.6174 | 10.8589 | 0.2415 | 4.83 |
| | 1/10x (2) | 4.9843 | 0.077 | 6.86 | 10.5229 | 10.7614 | 0.2385 | 4.77 |
| | 1/20x (1) | 4.7533 | 0.038 | 6.84 | 10.5045 | 10.7446 | 0.2401 | 4.80 |
| | 1/20x (2) | 4.7533 | 0.038 | 6.84 | 10.5049 | 10.7281 | 0.2232 | 4.46 |
| | 1/50x (1) | 4.3732 | 0.015 | 6.86 | 10.5161 | 10.7566 | 0.2405 | 4.81 |
| | 1/50x (2) | 4.3732 | 0.015 | 6.85 | 10.5234 | 10.7574 | 0.234 | 4.68 |
| | 1/100x (1) | 4.0902 | 0.0077 | 6.86 | 10.4858 | 10.7193 | 0.2335 | 4.67 |
| | 1/100x (2) | 4.0902 | 0.0077 | 6.86 | 10.5523 | 10.7856 | 0.2333 | 4.67 |
| | 1/500x (1) | 4.2472 | 0.0015 | 6.86 | 10.553 | 10.8032 | 0.2502 | 5.00 |
| | 1/500x (2) | 4.2472 | 0.0015 | 6.86 | 10.4488 | 10.6976 | 0.2488 | 4.98 |

-continued

| | | | | | | | | |
|---|---|---|---|---|---|---|---|---|
| E | 5x (1) | 4.5635 | 3.84 | 6.79 | 10.3613 | 10.6103 | 0.249 | 4.98 |
| | 5x (2) | 4.5635 | 3.84 | 6.80 | 10.5311 | 10.7546 | 0.2235 | 4.47 |
| | 1x (1) | 4.2673 | 0.77 | 6.80 | 10.3311 | 10.5651 | 0.234 | 4.68 |
| | 1x (2) | 4.2673 | 0.77 | 6.80 | 10.466 | 10.7162 | 0.2502 | 5.00 |
| | 1/2x (1) | 5.1989 | 0.38 | 6.79 | 10.6796 | 10.9054 | 0.2258 | 4.52 |
| | 1/2x (2) | 5.1989 | 0.38 | 6.80 | 10.5552 | 10.7836 | 0.2284 | 4.57 |
| | 1/5x (1) | 5.0275 | 0.15 | 6.80 | 10.4877 | 10.721 | 0.2333 | 4.67 |
| | 1/5x (2) | 5.0275 | 0.15 | 6.80 | 10.5061 | 10.7331 | 0.227 | 4.54 |
| | 1/10x (1) | 5.6680 | 0.077 | 6.81 | 10.3585 | 10.5946 | 0.2361 | 4.72 |
| | 1/10x (2) | 5.6680 | 0.077 | 6.80 | 10.6807 | 10.9116 | 0.2309 | 4.62 |
| | 1/20x (1) | 5.2891 | 0.038 | 6.81 | 10.3664 | 10.6143 | 0.2479 | 4.96 |
| | 1/20x (2) | 5.2891 | 0.038 | 6.81 | 10.3745 | 10.6253 | 0.2508 | 5.02 |
| | 1/50x (1) | 5.0356 | 0.015 | 6.81 | 10.4285 | 10.682 | 0.2535 | 5.07 |
| | 1/50x (2) | 5.0356 | 0.015 | 6.80 | 10.4022 | 10.6524 | 0.2502 | 5.00 |
| | 1/100x (1) | 5.7271 | 0.0077 | 6.81 | 10.3332 | 10.5937 | 0.2605 | 5.21 |
| | 1/100x (2) | 5.7271 | 0.0077 | 6.81 | 10.525 | 10.7782 | 0.2532 | 5.06 |
| | 1/500x (1) | 5.1000 | 0.0015 | 6.81 | 10.4192 | 10.6785 | 0.2593 | 5.19 |
| | 1/500x (2) | 5.1000 | 0.0015 | 6.81 | 10.3991 | 10.6668 | 0.2677 | 5.70 |
| F | 5x (1) | 4.5635 | 3.84 | 6.75 | 10.524 | 10.7696 | 0.2456 | 5.23 |
| | 5x (2) | 4.5635 | 3.84 | 6.75 | 10.3291 | 10.5729 | 0.2438 | 4.88 |
| | 1x (1) | 4.2673 | 0.77 | 6.75 | 10.4927 | 10.7424 | 0.2497 | 4.99 |
| | 1x (2) | 4.2673 | 0.77 | 6.76 | 10.5257 | 10.7652 | 0.2395 | 4.79 |
| | 1/2x (1) | 5.1989 | 0.38 | 6.75 | 10.463 | 10.6908 | 0.2278 | 4.56 |
| | 1/2x (2) | 5.1989 | 0.38 | 6.76 | 10.3756 | 10.6003 | 0.2247 | 4.49 |
| | 1/5x (1) | 5.0275 | 0.15 | 6.76 | 10.4212 | 10.6704 | 0.2492 | 4.98 |
| | 1/5x (2) | 5.0275 | 0.15 | 6.76 | 10.5061 | 10.7509 | 0.2448 | 4.90 |
| | 1/10x (1) | 5.6680 | 0.077 | 6.76 | 10.3829 | 10.6062 | 0.2233 | 4.47 |
| | 1/10x (2) | 5.6680 | 0.077 | 6.76 | 10.3651 | 10.6068 | 0.2417 | 4.83 |
| | 1/20x (1) | 5.2891 | 0.038 | 6.75 | 10.5096 | 10.7442 | 0.2346 | 4.69 |
| | 1/20x (2) | 5.2891 | 0.038 | 6.77 | 10.3875 | 10.6226 | 0.2351 | 4.70 |
| | 1/50x (1) | 5.0356 | 0.015 | 6.78 | 10.3584 | 10.6063 | 0.2479 | 4.96 |
| | 1/50x (2) | 5.0356 | 0.015 | 6.76 | 10.5235 | 10.7671 | 0.2436 | 4.87 |
| | 1/100x (1) | 5.7271 | 0.0077 | 6.77 | 10.3664 | 10.6148 | 0.2484 | 4.97 |
| | 1/100x (2) | 5.7271 | 0.0077 | 6.78 | 10.5055 | 10.7441 | 0.2386 | 4.77 |
| | 1/500x (1) | 5.1000 | 0.0015 | 6.79 | 10.3322 | 10.5868 | 0.2546 | 5.09 |
| | 1/500x (2) | 5.1000 | 0.0015 | 6.80 | 10.3279 | 10.591 | 0.2631 | 5.26 |
| G | 5x (1) | 3.7017 | 3.84 | 6.83 | 10.362 | 10.6077 | 0.2457 | 4.91 |
| | 5x (2) | 3.7017 | 3.84 | 6.82 | 10.3595 | 10.6145 | 0.255 | 5.10 |
| | 1x (1) | 4.2905 | 0.77 | 6.84 | 10.3648 | 10.6151 | 0.2503 | 5.01 |
| | 1x (2) | 4.2905 | 0.77 | 6.85 | 10.3356 | 10.5972 | 0.2616 | 5.23 |
| | 1/2x (1) | 4.4548 | 0.38 | 6.84 | 10.5096 | 10.7683 | 0.2587 | 5.17 |
| | 1/2x (2) | 4.4508 | 0.38 | 6.84 | 10.435 | 10.6889 | 0.2539 | 5.08 |
| | 1/5x (1) | 4.6844 | 0.15 | 6.84 | 10.3305 | 10.5868 | 0.2563 | 5.13 |
| | 1/5x (2) | 4.6844 | 0.15 | 6.85 | 10.4964 | 10.7476 | 0.2512 | 5.02 |
| | 1/10x (1) | 5.8389 | 0.077 | 6.85 | 10.3637 | 10.6173 | 0.2536 | 5.07 |
| | 1/10x (2) | 5.8389 | 0.077 | 6.85 | 10.3351 | 10.5881 | 0.253 | 5.06 |
| | 1/20x (1) | 4.4483 | 0.038 | 6.85 | 10.4393 | 10.6958 | 0.2565 | 5.13 |
| | 1/20x (2) | 4.4483 | 0.038 | 6.86 | 10.3798 | 10.6416 | 0.2618 | 5.24 |
| | 1/50x (1) | 3.9821 | 0.015 | 6.86 | 10.3619 | 10.619 | 0.2571 | 5.14 |
| | 1/50x (2) | 3.9821 | 0.015 | 6.87 | 10.5179 | 10.7721 | 0.2542 | 5.08 |
| | 1/100x (1) | 5.0043 | 0.0077 | 6.87 | 10.4756 | 10.7288 | 0.2532 | 5.06 |
| | 1/100x (2) | 5.0043 | 0.0077 | 6.87 | 10.4993 | 10.7561 | 0.2568 | 5.14 |
| | 1/500x (1) | 5.0108 | 0.0015 | 6.88 | 10.434 | 10.6941 | 0.2601 | 5.20 |
| | 1/500x (2) | 5.0108 | 0.0015 | 6.87 | 10.3896 | 10.6446 | 0.255 | 5.10 |
| H | 1/500x (1) | 4.6921 | 0.0015 | 6.85 | 10.3599 | 10.5954 | 0.2355 | 4.71 |
| | 1/500x (2) | 4.6921 | 0.0015 | 6.85 | 10.3720 | 10.6254 | 0.2534 | 5.07 |
| | 0x (1) | 4.8144 | 0.0000 | 6.85 | 10.3624 | 10.6052 | 0.2428 | 4.86 |
| | 0x (2) | 4.8144 | 0.0000 | 6.86 | 10.3585 | 10.6093 | 0.2508 | 5.02 |
| I | 1/500x (1) | 4.7906 | 0.0015 | 6.89 | 10.5492 | 10.7920 | 0.2428 | 4.86 |
| | 1/500x (2) | 4.7906 | 0.0015 | 6.90 | 10.5958 | 10.8508 | 0.255 | 5.10 |
| | 0x (1) | 4.7063 | 0.0000 | 6.89 | 10.5505 | 10.8037 | 0.2532 | 5.06 |
| | 0x (2) | 4.7063 | 0.0000 | 6.89 | 10.5120 | 10.7693 | 0.2573 | 5.15 |

-continued

| | | | | | | | | |
|---|---|---|---|---|---|---|---|---|
| J | 1/500x (1) | 5.8805 | 0.0015 | 6.99 | 10.5433 | 10.8089 | 0.2656 | 5.31 |
| | 1/500x (2) | 5.8805 | 0.0015 | 7.00 | 10.5974 | 10.8714 | 0.274 | 5.48 |
| | 0x (1) | 4.6385 | 0.0000 | 7.00 | 10.5509 | 10.8145 | 0.2636 | 5.27 |
| | 0x (2) | 4.6385 | 0.0000 | 6.98 | 10.5462 | 10.8252 | 0.279 | 5.58 |
| K | 1/500x (1) | 4.7133 | 0.0015 | 6.87 | 10.5424 | 10.8085 | 0.2661 | 5.32 |
| | 1/500x (2) | 4.7133 | 0.0015 | 6.88 | 10.3444 | 10.6111 | 0.2667 | 5.33 |
| | 0x (1) | 4.2141 | 0.0000 | 6.86 | 10.3873 | 10.6587 | 0.2714 | 5.43 |
| | 0x (2) | 4.2141 | 0.0000 | 6.86 | 10.4188 | 10.6866 | 0.2678 | 5.36 |

| Experiment Set | SAMPLE | % 16:0 | % ARA | % EPA | (n-6) DPA | (n-3) DPA | % DHA | % Fat |
|---|---|---|---|---|---|---|---|---|
| A | 5x (1) | 27.53 | 1.67 | 16.01 | 2.22 | 2.33 | 41.72 | 67.22 |
| | 5x (2) | 27.65 | 1.71 | 16.02 | 2.16 | 2.41 | 41.17 | 66.07 |
| | 1x (1) | 27.73 | 1.72 | 16.00 | 2.15 | 2.44 | 41.06 | 66.25 |
| | 1x (2) | 27.72 | 1.75 | 16.32 | 2.10 | 2.48 | 40.46 | 65.42 |
| | 1/2x (1) | 27.86 | 1.74 | 16.36 | 2.09 | 2.49 | 40.54 | 65.45 |
| | 1/2x (2) | 27.73 | 1.77 | 16.53 | 2.14 | 2.32 | 40.93 | 66.57 |
| | 1/5x (1) | 27.60 | 1.73 | 16.33 | 2.13 | 2.38 | 41.03 | 66.59 |
| | 1/5x (2) | 27.88 | 1.74 | 15.94 | 2.17 | 2.43 | 41.04 | 66.28 |
| | 1/10x (1) | 27.87 | 1.75 | 16.28 | 2.09 | 2.56 | 40.66 | 65.14 |
| | 1/10x (2) | 27.81 | 1.74 | 16.07 | 2.13 | 2.48 | 40.96 | 65.39 |
| | 1/20x (1) | 27.70 | 1.75 | 16.36 | 2.08 | 2.52 | 40.53 | 65.64 |
| | 1/20x (2) | 27.63 | 1.75 | 16.42 | 2.13 | 2.36 | 40.93 | 66.30 |
| | 1/50x (1) | 27.83 | 1.76 | 16.61 | 2.07 | 2.43 | 40.60 | 66.02 |
| | 1/50x (2) | 27.82 | 1.69 | 16.35 | 2.11 | 2.49 | 40.84 | 64.97 |
| | 1/100x (1) | 27.50 | 1.72 | 16.13 | 2.16 | 2.50 | 41.19 | 66.21 |
| | 1/100x (2) | 27.60 | 1.69 | 15.64 | 2.24 | 2.34 | 41.72 | 66.56 |
| | 1/500x (1) | 27.58 | 1.70 | 15.63 | 2.24 | 2.28 | 41.74 | 66.99 |
| | 1/500x (2) | 27.57 | 1.75 | 16.86 | 2.06 | 2.41 | 40.59 | 64.91 |
| B | 5x (1) | 28.30 | 1.75 | 16.44 | 2.32 | 2.35 | 42.35 | 64.09 |
| | 5x (2) | 28.45 | 1.74 | 15.96 | 2.36 | 2.36 | 42.62 | 62.46 |
| | 1x (1) | 28.55 | 1.74 | 16.10 | 2.32 | 2.43 | 42.35 | 62.96 |
| | 1x (2) | 28.47 | 1.78 | 16.33 | 2.33 | 2.44 | 42.26 | 63.13 |
| | 1/2x (1) | 28.21 | 1.71 | 15.90 | 2.39 | 2.34 | 42.95 | 64.75 |
| | 1/2x (2) | 28.15 | 1.75 | 16.65 | 2.29 | 2.33 | 42.32 | 63.50 |
| | 1/5x (1) | 28.51 | 1.74 | 16.34 | 2.29 | 2.37 | 42.23 | 62.02 |
| | 1/5x (2) | 28.43 | 1.75 | 16.35 | 2.29 | 2.48 | 42.24 | 63.88 |
| | 1/10x (1) | 28.66 | 1.77 | 15.85 | 2.37 | 2.45 | 42.45 | 62.47 |
| | 1/10x (2) | 28.52 | 1.74 | 15.74 | 2.40 | 2.39 | 42.70 | 63.14 |
| | 1/20x (1) | 28.67 | 1.75 | 15.86 | 2.33 | 2.37 | 42.55 | 63.10 |
| | 1/20x (2) | 28.36 | 1.75 | 16.13 | 2.35 | 2.26 | 42.62 | 63.90 |
| | 1/50x (1) | 28.36 | 1.79 | 16.64 | 2.29 | 2.42 | 42.04 | 62.31 |
| | 1/50x (2) | 28.43 | 1.77 | 15.92 | 2.40 | 2.42 | 42.57 | 62.77 |
| | 1/100x (1) | 28.81 | 1.75 | 16.01 | 2.30 | 2.49 | 42.16 | 61.70 |
| | 1/100x (2) | 28.61 | 1.73 | 15.93 | 2.35 | 2.40 | 42.51 | 63.60 |
| | 1/500x (1) | 28.62 | 1.85 | 17.15 | 2.17 | 2.59 | 41.19 | 60.91 |
| | 1/500x (2) | 28.30 | 1.84 | 17.39 | 2.20 | 2.43 | 41.40 | 61.56 |
| C | 5x (1) | 27.97 | 1.95 | 16.08 | 2.60 | 2.43 | 42.37 | 67.30 |
| | 5x (2) | 28.24 | 1.96 | 15.99 | 2.55 | 2.54 | 42.02 | 66.72 |
| | 1x (1) | 28.20 | 1.94 | 15.96 | 2.60 | 2.61 | 42.06 | 66.98 |
| | 1x (2) | 28.10 | 1.98 | 16.39 | 2.54 | 2.64 | 41.73 | 66.30 |
| | 1/2x (1) | 27.77 | 2.14 | 17.67 | 2.40 | 2.85 | 40.46 | 64.53 |
| | 1/2x (2) | 27.84 | 2.10 | 17.27 | 2.50 | 2.62 | 40.85 | 65.79 |
| | 1/5x (1) | 27.57 | 2.06 | 17.37 | 2.46 | 2.64 | 41.17 | 66.69 |
| | 1/5x (2) | 27.71 | 2.05 | 17.05 | 2.50 | 2.70 | 41.31 | 65.86 |
| | 1/10x (1) | 28.02 | 2.06 | 16.89 | 2.48 | 2.70 | 41.27 | 65.53 |
| | 1/10x (2) | 27.66 | 2.05 | 16.76 | 2.55 | 2.64 | 41.66 | 65.85 |
| | 1/20x (1) | 27.64 | 2.13 | 17.27 | 2.52 | 2.74 | 41.03 | 65.00 |
| | 1/20x (2) | 27.56 | 2.19 | 18.62 | 2.27 | 2.88 | 39.82 | 64.23 |
| | 1/50x (1) | 27.78 | 2.02 | 16.98 | 2.51 | 2.52 | 41.61 | 66.22 |

-continued

| | | | | | | | | |
|---|---|---|---|---|---|---|---|---|
| | 1/50x (2) | 27.82 | 2.01 | 16.92 | 2.53 | 2.65 | 41.47 | 65.85 |
| | 1/100x (1) | 27.85 | 2.01 | 16.77 | 2.54 | 2.67 | 41.50 | 65.23 |
| | 1/100x (2) | 27.91 | 2.01 | 16.61 | 2.58 | 2.59 | 41.72 | 66.87 |
| | 1/500x (1) | 27.73 | 2.02 | 17.42 | 2.41 | 2.58 | 41.10 | 65.60 |
| | 1/500x (2) | 27.48 | 2.05 | 17.93 | 2.39 | 2.54 | 40.85 | 65.85 |
| D | 5x (1) | 27.80 | 1.85 | 15.97 | 2.59 | 2.32 | 42.99 | 67.08 |
| | 5x (2) | 27.89 | 1.86 | 16.27 | 2.52 | 2.42 | 42.60 | 66.60 |
| | 1x (1) | 27.60 | 1.92 | 16.59 | 2.54 | 2.53 | 42.42 | 66.32 |
| | 1x (2) | 27.75 | 1.89 | 16.40 | 2.53 | 2.48 | 42.60 | 66.35 |
| | 1/2x (1) | 27.35 | 1.98 | 17.19 | 2.52 | 2.53 | 41.97 | 65.19 |
| | 1/2x (2) | 27.26 | 2.01 | 17.65 | 2.45 | 2.45 | 41.58 | 66.67 |
| | 1/5x (1) | 27.42 | 1.97 | 17.53 | 2.42 | 2.55 | 41.72 | 66.69 |
| | 1/5x (2) | 27.46 | 1.91 | 16.60 | 2.60 | 2.45 | 42.44 | 66.58 |
| | 1/10x (1) | 27.45 | 1.97 | 17.03 | 2.50 | 2.61 | 42.04 | 66.06 |
| | 1/10x (2) | 27.45 | 1.90 | 16.66 | 2.52 | 2.46 | 42.46 | 66.91 |
| | 1/20x (1) | 27.45 | 1.96 | 16.95 | 2.58 | 2.41 | 42.11 | 66.10 |
| | 1/20x (2) | 27.30 | 2.00 | 17.94 | 2.42 | 2.45 | 41.50 | 65.30 |
| | 1/50x (1) | 27.58 | 1.87 | 16.65 | 2.55 | 2.33 | 42.61 | 66.84 |
| | 1/50x (2) | 27.69 | 1.89 | 16.85 | 2.50 | 2.44 | 42.27 | 65.40 |
| | 1/100x (1) | 27.44 | 1.92 | 16.88 | 2.51 | 2.51 | 42.38 | 65.88 |
| | 1/100x (2) | 27.47 | 1.92 | 16.67 | 2.58 | 2.43 | 42.56 | 65.83 |
| | 1/500x (1) | 26.91 | 1.98 | 18.05 | 2.40 | 2.47 | 41.66 | 66.18 |
| | 1/500x (2) | 27.03 | 1.99 | 18.08 | 2.40 | 2.36 | 41.69 | 65.80 |
| E | 5x (1) | 27.46 | 1.89 | 16.02 | 2.60 | 2.30 | 43.33 | 66.12 |
| | 5x (2) | 27.86 | 1.93 | 16.05 | 2.50 | 2.38 | 43.02 | 63.64 |
| | 1x (1) | 27.75 | 1.95 | 15.91 | 2.58 | 2.39 | 43.09 | 65.41 |
| | 1x (2) | 27.51 | 1.94 | 15.59 | 2.72 | 2.29 | 43.52 | 67.35 |
| | 1/2x (1) | 27.07 | 2.04 | 16.99 | 2.52 | 2.42 | 42.64 | 65.01 |
| | 1/2x (2) | 26.86 | 2.05 | 17.23 | 2.48 | 2.35 | 42.59 | 65.00 |
| | 1/5x (1) | 27.05 | 1.96 | 16.65 | 2.55 | 2.29 | 43.21 | 65.66 |
| | 1/5x (2) | 27.12 | 1.98 | 16.69 | 2.52 | 2.41 | 43.08 | 63.58 |
| | 1/10x (1) | 27.35 | 1.95 | 16.45 | 2.55 | 2.48 | 42.94 | 64.34 |
| | 1/10x (2) | 27.31 | 1.92 | 16.22 | 2.60 | 2.41 | 43.24 | 64.49 |
| | 1/20x (1) | 26.72 | 1.93 | 16.73 | 2.64 | 2.31 | 43.21 | 65.83 |
| | 1/20x (2) | 26.47 | 1.94 | 17.11 | 2.65 | 2.21 | 43.14 | 66.13 |
| | 1/50x (1) | 26.63 | 1.86 | 16.30 | 2.72 | 2.19 | 43.84 | 65.30 |
| | 1/50x (2) | 26.68 | 1.86 | 16.33 | 2.69 | 2.26 | 43.76 | 65.67 |
| | 1/100x (1) | 26.47 | 1.87 | 16.39 | 2.69 | 2.28 | 43.89 | 63.98 |
| | 1/100x (2) | 26.45 | 1.89 | 16.78 | 2.62 | 2.38 | 43.49 | 65.21 |
| | 1/500x (1) | 26.06 | 1.88 | 17.13 | 2.60 | 2.23 | 43.73 | 66.13 |
| | 1/500x (2) | 25.95 | 1.88 | 17.58 | 2.57 | 2.10 | 43.40 | 65.46 |
| F | 5x (1) | 25.71 | 1.96 | 17.50 | 2.46 | 2.34 | 43.56 | 65.46 |
| | 5x (2) | 25.91 | 1.93 | 17.26 | 2.47 | 2.38 | 43.73 | 65.71 |
| | 1x (1) | 25.93 | 1.90 | 16.70 | 2.54 | 2.43 | 43.93 | 66.05 |
| | 1x (2) | 26.03 | 1.94 | 17.17 | 2.48 | 2.39 | 43.41 | 65.34 |
| | 1/2x (1) | 25.76 | 2.03 | 18.11 | 2.43 | 2.38 | 42.76 | 65.27 |
| | 1/2x (2) | 25.74 | 2.05 | 18.52 | 2.37 | 2.31 | 42.52 | 65.75 |
| | 1/5x (1) | 25.44 | 1.95 | 17.62 | 2.49 | 2.27 | 43.73 | 65.80 |
| | 1/5x (2) | 25.41 | 1.94 | 17.35 | 2.52 | 2.32 | 43.99 | 65.88 |
| | 1/10x (1) | 26.13 | 2.04 | 18.06 | 2.36 | 2.55 | 42.43 | 64.10 |
| | 1/10x (2) | 25.62 | 1.98 | 17.53 | 2.48 | 2.44 | 43.52 | 65.51 |
| | 1/20x (1) | 25.77 | 2.01 | 17.97 | 2.45 | 2.34 | 42.94 | 65.21 |
| | 1/20x (2) | 25.55 | 2.03 | 18.45 | 2.42 | 2.24 | 42.78 | 66.05 |
| | 1/50x (1) | 25.26 | 1.96 | 17.54 | 2.55 | 2.18 | 44.07 | 66.41 |
| | 1/50x (2) | 25.48 | 1.95 | 17.58 | 2.50 | 2.30 | 43.72 | 65.93 |
| | 1/100x (1) | 25.50 | 1.93 | 17.00 | 2.62 | 2.23 | 44.36 | 65.37 |
| | 1/100x (2) | 25.59 | 1.96 | 17.37 | 2.56 | 2.26 | 43.80 | 65.18 |
| | 1/500x (1) | 25.54 | 1.99 | 18.11 | 2.45 | 2.20 | 43.08 | 65.05 |
| | 1/500x (2) | 25.55 | 2.00 | 18.59 | 2.36 | 2.18 | 42.66 | 64.57 |
| G | 5x (1) | 25.74 | 1.95 | 17.58 | 2.37 | 2.08 | 43.04 | 63.68 |
| | 5x (2) | 25.79 | 1.89 | 16.83 | 2.51 | 2.04 | 43.69 | 63.67 |
| | 1x (1) | 26.01 | 1.90 | 16.69 | 2.52 | 2.08 | 43.42 | 64.95 |
| | 1x (2) | 25.71 | 1.91 | 16.74 | 2.57 | 1.98 | 43.85 | 65.37 |

-continued

|   |          |       |      |       |      |      |       |       |
|---|----------|-------|------|-------|------|------|-------|-------|
|   | 1/2x (1) | 25.47 | 1.93 | 17.14 | 2.52 | 1.97 | 43.69 | 64.28 |
|   | 1/2x (2) | 25.68 | 1.95 | 17.80 | 2.42 | 1.94 | 42.76 | 64.15 |
|   | 1/5x (1) | 25.63 | 1.94 | 17.43 | 2.46 | 2.02 | 43.21 | 63.70 |
|   | 1/5x (2) | 25.86 | 1.91 | 17.03 | 2.47 | 2.04 | 43.16 | 64.14 |
|   | 1/10x (1) | 26.34 | 1.95 | 17.09 | 2.48 | 2.14 | 42.35 | 63.27 |
|   | 1/10x (2) | 26.24 | 1.93 | 16.79 | 2.52 | 2.04 | 42.93 | 64.71 |
|   | 1/20x (1) | 25.47 | 1.97 | 18.06 | 2.37 | 2.12 | 42.62 | 63.38 |
|   | 1/20x (2) | 25.38 | 1.98 | 18.16 | 2.40 | 1.95 | 42.73 | 62.81 |
|   | 1/50x (1) | 25.46 | 1.94 | 18.06 | 2.37 | 2.02 | 42.72 | 63.38 |
|   | 1/50x (2) | 25.50 | 1.94 | 17.46 | 2.46 | 2.04 | 43.15 | 63.66 |
|   | 1/100x (1) | 25.52 | 1.92 | 16.69 | 2.60 | 1.81 | 44.16 | 65.74 |
|   | 1/100x (2) | 25.96 | 1.92 | 17.11 | 2.48 | 1.96 | 43.00 | 63.89 |
|   | 1/500x (1) | 25.71 | 1.95 | 17.78 | 2.41 | 1.97 | 42.83 | 64.61 |
|   | 1/500x (2) | 25.56 | 2.02 | 18.25 | 2.37 | 1.90 | 42.63 | 64.80 |
| H | 1/500x (1) | 25.19 | 2.03 | 19.36 | 2.14 | 2.02 | 41.86 | 65.21 |
|   | 1/500x (2) | 25.41 | 1.94 | 17.85 | 2.37 | 1.83 | 43.31 | 65.75 |
|   | 0x (1) | 21.45 | 2.62 | 27.54 | 1.31 | 2.50 | 35.78 | 67.83 |
|   | 0x (2) | 21.79 | 2.63 | 27.33 | 1.30 | 2.51 | 35.66 | 67.07 |
| I | 1/500x (1) | 25.21 | 2.02 | 19.89 | 2.15 | 2.10 | 41.48 | 64.17 |
|   | 1/500x (2) | 25.00 | 2.02 | 20.00 | 2.11 | 2.09 | 41.63 | 64.04 |
|   | 0x (1) | 21.82 | 2.62 | 28.55 | 1.20 | 2.61 | 34.16 | 67.22 |
|   | 0x (2) | 21.66 | 2.64 | 28.83 | 1.18 | 2.55 | 34.20 | 66.93 |
| J | 1/500x (1) | 24.44 | 1.81 | 16.75 | 2.49 | 2.22 | 45.20 | 63.43 |
|   | 1/500x (2) | 24.34 | 1.82 | 17.73 | 2.39 | 1.95 | 44.71 | 63.88 |
|   | 0x (1) | 21.56 | 2.58 | 26.96 | 1.30 | 2.60 | 36.04 | 66.74 |
|   | 0x (2) | 21.53 | 2.61 | 27.30 | 1.31 | 2.43 | 35.96 | 65.71 |
| K | 1/500x (1) | 23.87 | 1.82 | 17.33 | 2.46 | 2.00 | 45.45 | 64.67 |
|   | 1/500x (2) | 24.07 | 1.82 | 17.67 | 2.42 | 1.93 | 45.06 | 64.30 |
|   | 0x (1) | 21.77 | 2.63 | 26.13 | 1.39 | 2.81 | 36.49 | 66.14 |
|   | 0x (2) | 21.91 | 2.63 | 27.19 | 1.29 | 2.63 | 35.60 | 66.81 |

| Experiment Set | SAMPLE | (g/L) EPA Yield | mg/g EPA | DHA Yield | (g/L) mg/g DHA | (g/L) LFDW | g B12/ g LFDW | g/L Fat |
|---|---|---|---|---|---|---|---|---|
| A | 5x (1) | 0.53 | 107.64 | 1.39 | 291.68 | 1.62 | 0.0024 | 3.32 |
|   | 5x (2) | 0.50 | 105.83 | 1.28 | 282.95 | 1.60 | 0.0024 | 3.11 |
|   | 1x (1) | 0.49 | 105.99 | 1.26 | 282.93 | 1.56 | 0.00049 | 3.06 |
|   | 1x (2) | 0.47 | 106.77 | 1.17 | 275.34 | 1.52 | 0.00051 | 2.88 |
|   | 1/2x (1) | 0.47 | 107.06 | 1.17 | 275.98 | 1.52 | 0.00025 | 2.88 |
|   | 1/2x (2) | 0.51 | 110.04 | 1.26 | 283.39 | 1.55 | 0.00025 | 3.09 |
|   | 1/5x (1) | 0.50 | 108.74 | 1.26 | 284.18 | 1.54 | 0.00010 | 3.07 |
|   | 1/5x (2) | 0.48 | 105.63 | 1.22 | 282.95 | 1.52 | 0.00010 | 2.98 |
|   | 1/10x (1) | 0.48 | 106.01 | 1.20 | 275.47 | 1.58 | 0.000049 | 2.94 |
|   | 1/10x (2) | 0.48 | 105.07 | 1.22 | 278.58 | 1.57 | 0.000049 | 2.97 |
|   | 1/20x (1) | 0.48 | 107.36 | 1.19 | 276.71 | 1.54 | 0.000025 | 2.95 |
|   | 1/20x (2) | 0.51 | 108.87 | 1.26 | 282.24 | 1.57 | 0.000024 | 3.08 |
|   | 1/50x (1) | 0.48 | 109.67 | 1.16 | 278.77 | 1.47 | 0.000010 | 2.86 |
|   | 1/50x (2) | 0.48 | 106.19 | 1.19 | 275.96 | 1.58 | 0.000010 | 2.93 |
|   | 1/100x (1) | 0.50 | 106.81 | 1.27 | 283.69 | 1.57 | 0.0000049 | 3.07 |
|   | 1/100x (2) | 0.50 | 104.11 | 1.34 | 288.86 | 1.61 | 0.0000048 | 3.21 |
|   | 1/500x (1) | 0.50 | 104.68 | 1.35 | 290.83 | 1.59 | 0.00000094 | 3.23 |
|   | 1/500x (2) | 0.51 | 109.46 | 1.23 | 274.01 | 1.64 | 0.00000091 | 3.04 |
| B | 5x (1) | 0.49 | 105.34 | 1.26 | 279.16 | 1.66 | 0.0023 | 2.97 |
|   | 5x (2) | 0.48 | 99.71 | 1.29 | 273.81 | 1.81 | 0.0021 | 3.02 |
|   | 1x (1) | 0.48 | 101.34 | 1.27 | 274.22 | 1.77 | 0.00044 | 3.00 |
|   | 1x (2) | 0.49 | 103.10 | 1.26 | 274.39 | 1.74 | 0.00044 | 2.98 |
|   | 1/2x (1) | 0.52 | 102.99 | 1.39 | 286.04 | 1.76 | 0.00022 | 3.24 |
|   | 1/2x (2) | 0.51 | 105.75 | 1.30 | 276.38 | 1.76 | 0.00022 | 3.06 |
|   | 1/5x (1) | 0.48 | 101.36 | 1.24 | 269.37 | 1.80 | 0.000083 | 2.94 |
|   | 1/5x (2) | 0.48 | 104.41 | 1.25 | 277.49 | 1.67 | 0.000090 | 2.95 |
|   | 1/10x (1) | 0.45 | 98.98 | 1.20 | 272.75 | 1.71 | 0.000045 | 2.84 |
|   | 1/10x (2) | 0.48 | 99.38 | 1.31 | 277.29 | 1.80 | 0.000043 | 3.08 |

-continued

|   |          |      |        |      |        |      |           |      |
|---|----------|------|--------|------|--------|------|-----------|------|
|   | 1/20x (1) | 0.47 | 100.10 | 1.25 | 276.16 | 1.72 | 0.000022  | 2.94 |
|   | 1/20x (2) | 0.48 | 103.06 | 1.26 | 280.15 | 1.68 | 0.000023  | 2.97 |
|   | 1/50x (1) | 0.48 | 103.67 | 1.22 | 269.42 | 1.76 | 0.0000085 | 2.91 |
|   | 1/50x (2) | 0.47 | 99.90  | 1.25 | 274.84 | 1.74 | 0.0000086 | 2.93 |
|   | 1/100x (1) | 0.46 | 98.77 | 1.20 | 267.53 | 1.77 | 0.0000043 | 2.86 |
|   | 1/100x (2) | 0.48 | 101.29 | 1.27 | 278.11 | 1.71 | 0.0000045 | 2.99 |
|   | 1/500x (1) | 0.43 | 104.49 | 1.04 | 258.03 | 1.63 | 0.00000092 | 2.53 |
|   | 1/500x (2) | 0.47 | 107.03 | 1.11 | 262.14 | 1.67 | 0.00000090 | 2.68 |
| C | 5x (1)   | 0.52 | 108.25 | 1.37 | 292.82 | 1.57 | 0.0025    | 3.22 |
|   | 5x (2)   | 0.49 | 106.70 | 1.29 | 287.91 | 1.53 | 0.0025    | 3.06 |
|   | 1x (1)   | 0.51 | 106.88 | 1.36 | 289.31 | 1.59 | 0.00048   | 3.23 |
|   | 1x (2)   | 0.52 | 108.67 | 1.31 | 284.09 | 1.60 | 0.00048   | 3.15 |
|   | 1/2x (1) | 0.44 | 114.02 | 1.00 | 268.13 | 1.35 | 0.00028   | 2.46 |
|   | 1/2x (2) | 0.49 | 113.61 | 1.15 | 275.95 | 1.46 | 0.00026   | 2.82 |
|   | 1/5x (1) | 0.50 | 115.85 | 1.19 | 281.94 | 1.44 | 0.00010   | 2.89 |
|   | 1/5x (2) | 0.50 | 112.29 | 1.21 | 279.43 | 1.52 | 0.00010   | 2.93 |
|   | 1/10x (1) | 0.48 | 110.70 | 1.17 | 277.71 | 1.50 | 0.000051  | 2.85 |
|   | 1/10x (2) | 0.48 | 110.39 | 1.20 | 281.73 | 1.50 | 0.000051  | 2.89 |
|   | 1/20x (1) | 0.45 | 112.23 | 1.08 | 273.88 | 1.41 | 0.000027  | 2.62 |
|   | 1/20x (2) | 0.45 | 119.57 | 0.95 | 262.65 | 1.33 | 0.000029  | 2.39 |
|   | 1/50x (1) | 0.49 | 112.42 | 1.21 | 282.97 | 1.49 | 0.000010  | 2.91 |
|   | 1/50x (2) | 0.50 | 111.40 | 1.23 | 280.41 | 1.53 | 0.000010  | 2.96 |
|   | 1/100x (1) | 0.51 | 109.40 | 1.25 | 278.02 | 1.61 | 0.0000048 | 3.02 |
|   | 1/100x (2) | 0.51 | 111.08 | 1.29 | 286.49 | 1.53 | 0.0000050 | 3.09 |
|   | 1/500x (1) | 0.55 | 114.30 | 1.29 | 276.88 | 1.65 | 0.00000091 | 3.15 |
|   | 1/500x (2) | 0.56 | 118.05 | 1.27 | 276.25 | 1.61 | 0.00000093 | 3.11 |
| D | 5x (1)   | 0.55 | 107.16 | 1.48 | 296.16 | 1.69 | 0.0023    | 3.44 |
|   | 5x (2)   | 0.53 | 108.39 | 1.38 | 291.37 | 1.62 | 0.0024    | 3.24 |
|   | 1x (1)   | 0.52 | 110.03 | 1.33 | 288.89 | 1.59 | 0.00048   | 3.13 |
|   | 1x (2)   | 0.50 | 108.83 | 1.29 | 290.26 | 1.54 | 0.00050   | 3.03 |
|   | 1/2x (1) | 0.51 | 112.05 | 1.23 | 281.00 | 1.57 | 0.00024   | 2.94 |
|   | 1/2x (2) | 0.51 | 117.67 | 1.20 | 284.69 | 1.45 | 0.00026   | 2.89 |
|   | 1/5x (1) | 0.53 | 116.92 | 1.26 | 285.74 | 1.51 | 0.00010   | 3.03 |
|   | 1/5x (2) | 0.55 | 110.50 | 1.42 | 290.20 | 1.67 | 0.000090  | 3.34 |
|   | 1/10x (1) | 0.54 | 112.52 | 1.34 | 285.20 | 1.64 | 0.000047  | 3.19 |
|   | 1/10x (2) | 0.53 | 111.48 | 1.36 | 291.77 | 1.58 | 0.000049  | 3.19 |
|   | 1/20x (1) | 0.54 | 112.02 | 1.34 | 285.86 | 1.63 | 0.000023  | 3.17 |
|   | 1/20x (2) | 0.52 | 117.18 | 1.21 | 278.32 | 1.55 | 0.000025  | 2.91 |
|   | 1/50x (1) | 0.54 | 111.32 | 1.37 | 292.53 | 1.59 | 0.0000094 | 3.22 |
|   | 1/50x (2) | 0.52 | 110.19 | 1.29 | 283.91 | 1.62 | 0.0000093 | 3.06 |
|   | 1/100x (1) | 0.52 | 111.21 | 1.30 | 286.73 | 1.59 | 0.0000048 | 3.08 |
|   | 1/100x (2) | 0.51 | 109.75 | 1.31 | 287.74 | 1.59 | 0.0000048 | 3.07 |
|   | 1/500x (1) | 0.60 | 119.41 | 1.38 | 283.11 | 1.69 | 0.00000089 | 3.31 |
|   | 1/500x (2) | 0.59 | 118.98 | 1.37 | 281.74 | 1.70 | 0.00000088 | 3.27 |
| E | 5x (1)   | 0.53 | 105.94 | 1.43 | 294.23 | 1.69 | 0.0023    | 3.29 |
|   | 5x (2)   | 0.46 | 102.13 | 1.22 | 281.16 | 1.63 | 0.0024    | 2.84 |
|   | 1x (1)   | 0.49 | 104.07 | 1.32 | 289.48 | 1.62 | 0.00048   | 3.06 |
|   | 1x (2)   | 0.53 | 104.97 | 1.47 | 301.01 | 1.63 | 0.00047   | 3.37 |
|   | 1/2x (1) | 0.50 | 110.46 | 1.25 | 284.65 | 1.58 | 0.00024   | 2.94 |
|   | 1/2x (2) | 0.51 | 112.01 | 1.26 | 284.34 | 1.60 | 0.00024   | 2.97 |
|   | 1/5x (1) | 0.51 | 109.31 | 1.32 | 291.38 | 1.60 | 0.000094  | 3.06 |
|   | 1/5x (2) | 0.48 | 106.13 | 1.24 | 281.31 | 1.65 | 0.000091  | 2.89 |
|   | 1/10x (1) | 0.50 | 105.82 | 1.30 | 283.74 | 1.68 | 0.000046  | 3.04 |
|   | 1/10x (2) | 0.48 | 104.57 | 1.29 | 286.39 | 1.64 | 0.000047  | 2.98 |
|   | 1/20x (1) | 0.55 | 110.12 | 1.41 | 292.12 | 1.69 | 0.000022  | 3.26 |
|   | 1/20x (2) | 0.57 | 113.13 | 1.43 | 293.02 | 1.70 | 0.000022  | 3.32 |
|   | 1/50x (1) | 0.54 | 106.44 | 1.45 | 294.03 | 1.76 | 0.0000085 | 3.31 |
|   | 1/50x (2) | 0.54 | 107.21 | 1.44 | 295.14 | 1.72 | 0.0000087 | 3.29 |
|   | 1/100x (1) | 0.55 | 104.88 | 1.46 | 288.40 | 1.88 | 0.0000041 | 3.33 |
|   | 1/100x (2) | 0.55 | 109.40 | 1.44 | 291.26 | 1.76 | 0.0000044 | 3.30 |
|   | 1/500x (1) | 0.59 | 113.27 | 1.50 | 296.97 | 1.76 | 0.00000085 | 3.43 |
|   | 1/500x (2) | 0.66 | 115.09 | 1.62 | 291.79 | 1.97 | 0.00000076 | 3.73 |

-continued

| | | | | | | | | |
|---|---|---|---|---|---|---|---|---|
| F | 5x (1) | 0.60 | 114.57 | 1.49 | 292.02 | 1.80 | 0.00212779 | 3.42 |
| | 5x (2) | 0.55 | 113.41 | 1.40 | 294.25 | 1.67 | 0.00229687 | 3.20 |
| | 1x (1) | 0.55 | 110.28 | 1.45 | 297.11 | 1.70 | 0.00045415 | 3.30 |
| | 1x (2) | 0.54 | 112.21 | 1.36 | 290.41 | 1.66 | 0.00046376 | 3.13 |
| | 1/2x (1) | 0.54 | 118.20 | 1.27 | 285.84 | 1.58 | 0.00024017 | 2.97 |
| | 1/2x (2) | 0.55 | 121.79 | 1.26 | 286.25 | 1.54 | 0.00024686 | 2.95 |
| | 1/5x (1) | 0.58 | 115.91 | 1.43 | 294.66 | 1.70 | 0.00008801 | 3.28 |
| | 1/5x (2) | 0.56 | 114.29 | 1.42 | 296.75 | 1.67 | 0.00008979 | 3.23 |
| | 1/10x (1) | 0.52 | 115.79 | 1.21 | 278.51 | 1.60 | 0.00004803 | 2.86 |
| | 1/10x (2) | 0.56 | 114.86 | 1.38 | 291.97 | 1.67 | 0.00004619 | 3.17 |
| | 1/20x (1) | 0.55 | 117.21 | 1.31 | 286.75 | 1.63 | 0.00002328 | 3.06 |
| | 1/20x (2) | 0.57 | 121.84 | 1.33 | 289.39 | 1.60 | 0.00002381 | 3.11 |
| | 1/50x (1) | 0.58 | 116.45 | 1.45 | 299.69 | 1.67 | 0.00000901 | 3.29 |
| | 1/50x (2) | 0.56 | 115.90 | 1.40 | 295.17 | 1.66 | 0.00000904 | 3.21 |
| | 1/100x (1) | 0.55 | 111.13 | 1.44 | 296.95 | 1.72 | 0.00000448 | 3.25 |
| | 1/100x (2) | 0.54 | 113.25 | 1.36 | 292.35 | 1.66 | 0.00000463 | 3.11 |
| | 1/500x (1) | 0.60 | 117.81 | 1.43 | 286.97 | 1.78 | 0.00000084 | 3.31 |
| | 1/500x (2) | 0.63 | 120.03 | 1.45 | 282.05 | 1.86 | 0.00000080 | 3.40 |
| G | 5x (1) | 0.55 | 111.96 | 1.35 | 279.27 | 1.78 | 0.00215168 | 3.13 |
| | 5x (2) | 0.55 | 107.14 | 1.42 | 283.43 | 1.85 | 0.00207251 | 3.25 |
| | 1x (1) | 0.54 | 108.42 | 1.41 | 287.31 | 1.75 | 0.00043883 | 3.25 |
| | 1x (2) | 0.57 | 109.44 | 1.50 | 292.04 | 1.81 | 0.00042495 | 3.42 |
| | 1/2x (1) | 0.57 | 110.17 | 1.45 | 286.10 | 1.85 | 0.00020558 | 3.33 |
| | 1/2x (2) | 0.58 | 114.19 | 1.39 | 279.49 | 1.82 | 0.00020874 | 3.26 |
| | 1/5x (1) | 0.57 | 111.03 | 1.41 | 280.46 | 1.86 | 0.00008062 | 3.27 |
| | 1/5x (2) | 0.55 | 109.25 | 1.39 | 282.05 | 1.80 | 0.00008326 | 3.22 |
| | 1/10x (1) | 0.55 | 108.14 | 1.36 | 273.02 | 1.86 | 0.00004134 | 3.21 |
| | 1/10x (2) | 0.55 | 108.66 | 1.41 | 283.05 | 1.79 | 0.00004313 | 3.27 |
| | 1/20x (1) | 0.59 | 114.48 | 1.39 | 275.22 | 1.88 | 0.00002023 | 3.25 |
| | 1/20x (2) | 0.60 | 114.04 | 1.41 | 273.40 | 1.95 | 0.00001951 | 3.29 |
| | 1/50x (1) | 0.59 | 114.46 | 1.39 | 275.82 | 1.88 | 0.00000797 | 3.26 |
| | 1/50x (2) | 0.57 | 111.16 | 1.40 | 279.89 | 1.85 | 0.00000812 | 3.24 |
| | 1/100x (1) | 0.56 | 109.75 | 1.47 | 295.79 | 1.73 | 0.00000444 | 3.33 |
| | 1/100x (2) | 0.56 | 109.31 | 1.41 | 279.92 | 1.85 | 0.00000415 | 3.28 |
| | 1/500x (1) | 0.60 | 114.86 | 1.44 | 281.92 | 1.84 | 0.00000081 | 3.36 |
| | 1/500x (2) | 0.60 | 118.27 | 1.41 | 281.47 | 1.79 | 0.00000084 | 3.31 |
| H | 1/500x (1) | 0.59 | 126.25 | 1.29 | 279.17 | 1.64 | 0.00000092 | 3.07 |
| | 1/500x (2) | 0.59 | 117.35 | 1.44 | 291.28 | 1.74 | 0.00000086 | 3.33 |
| | 0x (1) | 0.91 | 186.81 | 1.18 | 248.20 | 1.56 | 0.00000000 | 3.29 |
| | 0x (2) | 0.92 | 183.32 | 1.20 | 244.63 | 1.65 | 0.00000000 | 3.36 |
| I | 1/500x (1) | 0.62 | 127.64 | 1.29 | 272.24 | 1.74 | 0.00000086 | 3.12 |
| | 1/500x (2) | 0.65 | 128.06 | 1.36 | 272.66 | 1.83 | 0.00000082 | 3.27 |
| | 0x (1) | 0.97 | 191.93 | 1.16 | 234.87 | 1.66 | 0.00000000 | 3.40 |
| | 0x (2) | 0.99 | 192.97 | 1.18 | 234.10 | 1.70 | 0.00000000 | 3.44 |
| J | 1/500x (1) | 0.56 | 106.22 | 1.52 | 292.66 | 1.94 | 0.00000077 | 3.37 |
| | 1/500x (2) | 0.62 | 113.25 | 1.57 | 291.57 | 1.98 | 0.00000076 | 3.50 |
| | 0x (1) | 0.95 | 179.92 | 1.27 | 245.50 | 1.75 | 0.00000000 | 3.52 |
| | 0x (2) | 1.00 | 179.38 | 1.32 | 241.17 | 1.91 | 0.00000000 | 3.67 |
| K | 1/500x (1) | 0.60 | 112.09 | 1.56 | 298.08 | 1.88 | 0.00000080 | 3.44 |
| | 1/500x (2) | 0.61 | 113.60 | 1.55 | 293.84 | 1.90 | 0.00000079 | 3.43 |
| | 0x (1) | 0.94 | 172.82 | 1.31 | 244.79 | 1.84 | 0.00000000 | 3.59 |
| | 0x (2) | 0.97 | 181.66 | 1.27 | 241.23 | 1.78 | 0.00000000 | 3.58 |

Conclusion: PTA-10208 growth and EPA productivity does not change at Vitamin B12 concentrations ranging between 5×(3.84 mg/L) and 1/500× (0.0015 mg/L) in DSDFM-O at 10% CO2. However, when Vitamin B12 is completely removed from DSDFM-O, % EPA increases by about 50%, while dry weight and % fat also increase slightly, resulting in a 60% increase in EPA productivity.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed:

1. A method of making a biomass of a microorganism having fatty acids and a concentration of EPA, comprising:
   (a) fermenting the microorganism in a fermentor vessel to produce a fermentation broth having an aqueous phase and biomass wherein the aqueous phase has a dissolved gas wherein the microorganism comprises a Thraustochytrid that produces a biomass having at least 3% EPA of the total weight of the fatty acids; and
   (b) attaining a desired EPA level in the biomass by (i) adjusting the dissolved $CO_2$ to >2% of the dissolved gas, (ii) optionally adjusting the pressure on the biomass, and (iii) optionally adjusting the temperature in the broth.

2. A method of increasing the concentration of EPA in a biomass of a microorganism having fatty acids and a concentration of EPA, comprising:
   (a) fermenting the microorganism in a fermentor vessel to produce biomass; and
   (b) providing a pressure on the biomass of greater than or equal to 0.5 psi above atmospheric pressure for a time sufficient to increase the concentration of EPA in the biomass.

3. A biomass made according to claim 1 or claim 2.

* * * * *

SEQUENCE LISTING

<160> NUMBER OF SEQ ID NOS: 2

<210> SEQ ID NO 1
<211> LENGTH: 1705
<212> TYPE: DNA
<213> ORGANISM: Thraustochytrium sp.

<400> SEQUENCE: 1

```
aagatacctg gttgatcctg ccagtagtca tacgctcgtc tcaaagatta agccatgcat      60
gtgtcagtat aaatactttt actttgaaac tgcgaacggc tcattaaatc agtaattatc     120
tacatggtaa cgaaaattat atggataacc gtagtaattc tagggctaat acatgcgtaa     180
aatctgggta actggatgca tttattggat tgaagccaac attaaaaggt gattcacgat     240
aactaagcgg agcgttttag gacgctgaat cattcgagtt tctgccctat cagctgtcga     300
tggtaaggta ttggcttacc atggcgttaa cgggtaacgg agaattaggg ttcgattccg     360
gagagggagc ctgagagacg gctaccacat ccaaggaagg cagcaggcgc gtaaattgcc     420
caatgagaac ttctcgaggc agtgacaaga aatatcaaag tgatgccgtt aggtattgca     480
tttgaaatga gaacgatgta caacttctaa cgatgatcaa ttggagggca agtctggtgc     540
cagcagccgc ggtaattcca gctccaatag cgtatactaa cgttgctgca gttaaaacgc     600
ccgtagttga attagtatca tggtatttta accttattcg atgaatttga gttgaaagct     660
aggatatata ggaagcgatt cctcatttac tgtaaaaaaa ttagagtgtt tcacacagat     720
cgtaagatcg ggatatatta gtatggaata ataagatagg actttggtgc tattttgttg     780
gtttgcacac caaagtaatg attaataggg acagttgggg gtattcgtat ttaattgtca     840
gaggtgaaat tcttggattt atgaaagacg aactactgcg aaagcattta ccaaggatgt     900
tttcattaat caaggacgaa agttagggga tcgaagatga ttagatacca tcgtagtctt     960
aaccataaac tatgccgact gaggattctt gaaatttgta aatgaattta agagcactcc    1020
atgagaaatc aaagtctttg ggttccgggg ggagtatggt cgcaagtctg aaacttaaag    1080
gaattgacgg aagggcacca ccaggagtgg agcctgcggc ttaatttgac tcaacacggg    1140
aaaacttacc aggtccagac atagtgagga ttgacagatt gatagctctt tcttgattct    1200
atgggtggtg gtgcatggcc gttcttagtt ggtggtttga actgtctgct taattgcgtt    1260
aacgaacgag acctcagcct actaaatagt atgttgttta gtaataaatg atatgacttc    1320
ttagagggac atttcgggtt taccggaagg aagtttgagg caataacagg tctgtgatgc    1380
ccttagatgt tctgggccgc acgcgcgcta cactgacgag ctcaacaagt aatatttggt    1440
tgtctggaag gattgcctaa tcttttaaat actcgtcgtg atgggctag attcttgtaa     1500
ttattaatct ccaacgagga attcctagta aacgcaagtc atcagcttgc attgattacg    1560
tccctgccct tgtacacac cgcccgtcgc acctaccgat tggatggtcc ggtgaaatct    1620
tcggatgttt ttttacaata gtagagagac aaaagttgag taaaccttac catctagagg    1680
aaggtgaagt cgtaacaagg atctt                                           1705
```

<210> SEQ ID NO 2
<211> LENGTH: 1713
<212> TYPE: DNA
<213> ORGANISM: Schizochytrium sp.

<400> SEQUENCE: 2

| | | | | | |
|---|---|---|---|---|---|
| acctggttga | tcctgccagc | tgtcatttgc | tcgtctaaaa | gattaagcca | tgcatgtcta       60 |
| agtataaaca | aattatacgg | tgaaactgcg | aacggctcat | tatatcagtt | atagtttctt      120 |
| tgatagtgta | tttctatatc | tatttggata | actgtggcaa | ttctagagct | aacacatgct      180 |
| ttcgagtggg | acttttggt  | accactgcat | ttattagatt | ttgaagccaa | cgtaaaattg      240 |
| gtgattcatg | ataactttgc | gaatcgcagt | agcgtcttgt | acgcggcgat | gaatcattca      300 |
| agtttctgcc | ccatcagctg | tcgatggtac | ggtattggcc | taccatggct | ttcacgggtg      360 |
| acggagaatt | agggtttgat | tccggagagg | acgcttgaga | gacggcgacc | acatccaagg      420 |
| aaggcagcag | gcgcgtaaat | tacccaatgg | ggactccccg | aggtagtgac | aagaaataaa      480 |
| aatgaggagc | gctttgcgtt | tttcaatttg | aatgagagaa | tcgtacaatc | ctcatcgagg      540 |
| atcaattgga | gggcaagtct | ggtgccagca | gccgcggtaa | ctccagctcc | aatagcaaat      600 |
| attagagttg | ttgcagttaa | aaagctcgta | gttgaatttc | cgatagtctt | tggccgtgtc      660 |
| cttggtctcg | tatcatgggt | ttattgtgcc | aagatgatcg | tcctctatgg | ttagtgatag      720 |
| tcatagtcgt | ttactgtaaa | aaaactggag | tgtttaaagc | atttctttgg | gaaaggtaca      780 |
| tattagtata | ggataattag | ataggacctg | tgattcttat | ttggttggtt | tgtgagtcat      840 |
| ggtaatgatt | aatagggaca | tcggggta   | ttcgaattta | attgtcagag | gtgaaattct      900 |
| tggatttaag | aaagtcgaac | tactgcgaag | gcatttacca | aggatgtttt | cattaataaa      960 |
| gaacgaaagt | taggggatcg | aagatgatta | gataccatcg | tagtcttaac | tgtaaactat     1020 |
| gccgacttgc | gattgtccgt | cgttgttttt | tcaaaaaaga | gacctgggca | gcagcacatg     1080 |
| agaaatcaaa | gttttgggt  | tccggggga  | gtatggtcgc | aaggctgaaa | cttaaaggaa     1140 |
| ttgacggaag | ggcaccacca | ggagtggagc | ctgcggctta | attcgactca | acacgggaaa     1200 |
| acttaccagg | tccagacata | gtaaggattg | acagattgag | agctctttct | tgattctatg     1260 |
| ggtggtggtg | catggccgtt | cttagttggt | ggagtgattt | gtctggttaa | ttccgttaac     1320 |
| gaacgagacc | tcagcctact | aaatagtggt | gcatattgtg | agatatgtga | caaaaatcgc     1380 |
| ttcttagagg | gacatttcgg | gtttaccgga | aggaagtttg | aggcaataac | aggtctgtga     1440 |
| tgcccctaga | tgttctgggc | cgcacgcgcg | ctacaatgac | agattcaaca | agtccggtag     1500 |
| tggagctttt | gcttctctat | tattactttt | ccgagaggaa | tggttaatct | tctaaatgtc     1560 |
| tgtcgtgatg | gggctagatt | tttgcaatta | ttaatctcca | acgaggaatt | cctagtaaac     1620 |
| gcaagtcatc | agcttgcatt | gattacgtcc | ctgcccttg  | tacacaccgc | ccgtcgcacc     1680 |
| taccgattga | acggtcctat | gaaatcttcg | gat        |            |                1713 |